(12) United States Patent
Lorman et al.

(10) Patent No.: US 12,097,361 B2
(45) Date of Patent: Sep. 24, 2024

(54) FLUID MANAGEMENT SYSTEMS AND METHODS

(71) Applicant: Thermedx, LLC, Solon, OH (US)

(72) Inventors: Benjamin T. Lorman, Solon, OH (US); Matthew R. Biats, Chardon, OH (US); Paul A. Marijan, Parma Heights, OH (US); Jeffrey P. Minnich, Elyria, OH (US)

(73) Assignee: Stryker Corporation, Kalamazoo, MI (US)

( * ) Notice: Subject to any disclaimer, the term of this patent is extended or adjusted under 35 U.S.C. 154(b) by 685 days.

(21) Appl. No.: 17/091,670

(22) Filed: Nov. 6, 2020

(65) Prior Publication Data

US 2021/0138125 A1   May 13, 2021

Related U.S. Application Data

(60) Provisional application No. 62/932,921, filed on Nov. 8, 2019.

(51) Int. Cl.
*A61M 5/44*     (2006.01)
*A61M 1/00*     (2006.01)
(Continued)

(52) U.S. Cl.
CPC ............ *A61M 5/445* (2013.01); *A61M 1/73* (2021.05); *A61M 1/743* (2021.05); *A61M 1/80* (2021.05);
(Continued)

(58) Field of Classification Search
CPC ...... A61M 1/73; A61M 1/743; A61M 3/0258; F16K 15/14
See application file for complete search history.

(56) References Cited

U.S. PATENT DOCUMENTS 3,475,590 A   10/1969   Pins
3,515,137 A   6/1970    Santomieri
(Continued)

FOREIGN PATENT DOCUMENTS

DE   102010005745 A1   7/2011
EP   0575512 B1        5/1998
(Continued)

OTHER PUBLICATIONS

International Search Report and Written Opinion from PCT/US20/59463 dated Mar. 30, 2021.
(Continued)

*Primary Examiner* — Philip R Wiest
*Assistant Examiner* — Matthew Wrubleski
(74) *Attorney, Agent, or Firm* — Morrison & Foerster LLP

(57) ABSTRACT

Fluid management systems are disclosed that include software-controlled, electro-mechanical devices used in combination with single-use or multi-use tubing sets. Functions of the fluid management systems can include fluid pressurization, fluid warming, fluid deficit monitoring (including flow-based and weight-based), suction, fluid collection, and fluid evacuation (including indirect-to-drain and direct-to-drain options). The systems can be configured based on the surgical environment (e.g., operating room or physician office) as well as other user needs and/or preferences.

14 Claims, 86 Drawing Sheets

(51) Int. Cl.
*A61M 3/02* (2006.01)
*A61M 39/08* (2006.01)
*A61M 39/22* (2006.01)

(52) U.S. Cl.
CPC .......... *A61M 3/0258* (2013.01); *A61M 39/08* (2013.01); *A61M 39/227* (2013.01); *A61M 2205/02* (2013.01); *A61M 2205/3317* (2013.01); *A61M 2205/3331* (2013.01); *A61M 2205/3344* (2013.01); *A61M 2205/3368* (2013.01); *A61M 2205/3379* (2013.01); *A61M 2205/3393* (2013.01); *A61M 2205/368* (2013.01); *A61M 2205/502* (2013.01); *A61M 2205/505* (2013.01); *A61M 2205/52* (2013.01)

(56) References Cited

U.S. PATENT DOCUMENTS

| | | |
|---|---|---|
| 4,180,074 A | 12/1979 | Murry et al. |
| 4,278,078 A | 7/1981 | Smith |
| 4,388,922 A | 6/1983 | Telang |
| 4,464,563 A | 8/1984 | Jewett |
| 4,574,876 A | 3/1986 | Aid |
| 4,759,749 A | 7/1988 | Verkaart |
| 4,819,682 A | 4/1989 | Van |
| 4,844,074 A | 7/1989 | Kurucz |
| 4,898,518 A | 2/1990 | Hubbard et al. |
| 4,911,691 A | 3/1990 | Aniuk et al. |
| 4,933,843 A | 6/1990 | Scheller et al. |
| 5,013,303 A | 5/1991 | Tamari et al. |
| 5,050,266 A | 9/1991 | Schneider |
| 5,106,373 A | 4/1992 | Augustine et al. |
| 5,125,069 A | 6/1992 | O'Boyle |
| 5,137,509 A | 8/1992 | Freitas |
| 5,178,606 A | 1/1993 | Ognier et al. |
| 5,195,958 A | 3/1993 | Phillips |
| 5,224,929 A | 7/1993 | Remiszewski |
| 5,228,646 A | 7/1993 | Raines |
| 5,245,693 A | 9/1993 | Ford et al. |
| 5,250,032 A | 10/1993 | Carter, Jr. et al. |
| 5,254,094 A | 10/1993 | Starkey et al. |
| 5,271,086 A | 12/1993 | Kamiyama et al. |
| 5,303,735 A | 4/1994 | Cerola et al. |
| D350,822 S | 9/1994 | Lanigan |
| 5,347,992 A | 9/1994 | Pearlman et al. |
| 5,368,569 A | 11/1994 | Sanese |
| 5,381,510 A | 1/1995 | Ford et al. |
| 5,382,805 A | 1/1995 | Fannon et al. |
| 5,388,612 A | 2/1995 | Cerola et al. |
| 5,391,145 A | 2/1995 | Dorsey, III |
| D357,312 S | 4/1995 | Riquier et al. |
| 5,420,962 A | 5/1995 | Bakke |
| 5,427,144 A | 6/1995 | Teets et al. |
| 5,447,494 A | 9/1995 | Dorsey, III |
| 5,449,145 A | 9/1995 | Wortrich |
| 5,460,490 A | 10/1995 | Carr et al. |
| 5,496,314 A | 3/1996 | Eggers |
| 5,503,626 A | 4/1996 | Goldrath |
| 5,505,710 A | 4/1996 | Dorsey, III |
| 5,520,638 A | 5/1996 | O'Quinn et al. |
| 5,522,796 A | 6/1996 | Dorsey, III |
| 5,522,805 A | 6/1996 | Vancaillie et al. |
| 5,551,448 A | 9/1996 | Matula et al. |
| 5,559,924 A | 9/1996 | Kadotani et al. |
| 5,562,640 A | 10/1996 | McCabe et al. |
| 5,573,504 A | 11/1996 | Dorsey, III |
| 5,586,977 A | 12/1996 | Dorsey, III |
| 5,607,391 A | 3/1997 | Klinger et al. |
| 5,626,563 A | 5/1997 | Dodge et al. |
| 5,643,203 A | 7/1997 | Beiser et al. |
| 5,683,381 A | 11/1997 | Carr et al. |
| 5,690,614 A | 11/1997 | Carr et al. |
| 5,733,263 A | 1/1998 | Wheatman |
| 5,729,653 A | 3/1998 | Magliochetti et al. |
| D398,051 S | 9/1998 | Lanigan et al. |
| 5,800,383 A | 9/1998 | Chandler et al. |
| 5,800,387 A | 9/1998 | Duffy et al. |
| 5,803,510 A | 9/1998 | Dorsey, III |
| 5,807,313 A | 9/1998 | Delk et al. |
| 5,807,332 A | 9/1998 | Augustine et al. |
| 5,810,770 A | 9/1998 | Chin et al. |
| 5,814,009 A | 9/1998 | Wheatman |
| 5,830,180 A | 11/1998 | Chandler et al. |
| 5,836,909 A | 11/1998 | Cosmescu |
| 5,875,282 A | 2/1999 | Jordan et al. |
| D409,748 S | 5/1999 | Lanigan et al. |
| 5,914,047 A | 6/1999 | Griffiths |
| 5,989,423 A | 11/1999 | Kamen et al. |
| 5,993,410 A | 11/1999 | Vincent et al. |
| 6,024,720 A | 2/2000 | Chandler et al. |
| 6,047,108 A | 4/2000 | Sword et al. |
| 6,074,363 A | 6/2000 | Beran et al. |
| 6,106,494 A | 8/2000 | Saravia et al. |
| 6,139,528 A | 10/2000 | Kistner et al. |
| 6,139,571 A | 10/2000 | Fuller et al. |
| 6,142,974 A | 11/2000 | Kistner et al. |
| 6,146,359 A | 11/2000 | Carr et al. |
| 6,149,622 A | 11/2000 | Marie |
| 6,149,674 A | 11/2000 | Borders |
| 6,175,688 B1 | 1/2001 | Cassidy et al. |
| 6,176,847 B1 | 1/2001 | Humphreys, Jr. et al. |
| 6,213,970 B1 | 4/2001 | Nelson et al. |
| 6,234,205 B1 | 5/2001 | D'Amelio et al. |
| 6,236,809 B1 | 5/2001 | Cassidy et al. |
| 6,238,366 B1 | 5/2001 | Savage et al. |
| 6,246,831 B1 | 6/2001 | Seitz et al. |
| 6,257,265 B1 | 7/2001 | Brunner et al. |
| 6,259,074 B1 | 7/2001 | Brunner et al. |
| 6,261,261 B1 | 7/2001 | Gordon |
| 6,336,003 B1 | 1/2002 | Mitsunaga et al. |
| 6,358,224 B1 | 3/2002 | Tims et al. |
| 6,406,470 B1 | 7/2002 | Kierce |
| 6,413,233 B1 | 7/2002 | Sites et al. |
| 6,464,666 B1 | 10/2002 | Augustine et al. |
| 6,527,743 B1 | 3/2003 | Fowler et al. |
| 6,535,689 B2 | 3/2003 | Augustine et al. |
| 6,572,641 B2 | 6/2003 | Brugger et al. |
| 6,572,689 B2 | 6/2003 | Cosby, II et al. |
| 6,585,708 B1 | 7/2003 | Maaskamp |
| 6,595,957 B1 | 7/2003 | Griffiths et al. |
| 6,602,221 B1 | 8/2003 | Saravia et al. |
| 6,620,130 B1 | 9/2003 | Ginsburg |
| 6,635,031 B2 | 10/2003 | Fowler et al. |
| 6,635,034 B1 | 10/2003 | Cosmescu |
| 6,641,556 B1 | 11/2003 | Shigezawa |
| 6,645,232 B2 | 11/2003 | Carson |
| 6,648,906 B2 | 11/2003 | Lasheras et al. |
| 6,652,488 B1 | 11/2003 | Cover et al. |
| 6,685,667 B1 | 2/2004 | Delk et al. |
| 6,699,184 B2 | 3/2004 | Felix et al. |
| 6,699,267 B2 | 3/2004 | Voorhees |
| 6,722,782 B2 | 4/2004 | Faries, Jr. et al. |
| 6,743,201 B1 | 6/2004 | Dönig |
| 6,775,473 B2 | 8/2004 | Augustine et al. |
| 6,780,322 B1 | 8/2004 | Bissler et al. |
| 6,788,885 B2 | 9/2004 | Mitsunaga et al. |
| 6,824,528 B1 | 11/2004 | Faries, Jr. et al. |
| 6,875,198 B2 | 4/2005 | Foley |
| 6,882,797 B2 | 4/2005 | Stewart et al. |
| 6,899,697 B2 | 5/2005 | Fowler et al. |
| 6,901,216 B2 | 5/2005 | Jusiak et al. |
| 6,918,902 B2 | 7/2005 | French et al. |
| 6,958,058 B1 | 10/2005 | Hunter, Sr. et al. |
| 6,997,942 B2 | 2/2006 | Machold et al. |
| 7,004,960 B2 | 2/2006 | Daoud |
| 7,010,221 B2 | 3/2006 | Augustine et al. |
| 7,031,602 B2 | 4/2006 | Faries, Jr. et al. |
| 7,083,601 B1 | 8/2006 | Cosmescu et al. |
| 7,094,219 B2 | 8/2006 | Noice et al. |
| 7,153,285 B2 | 12/2006 | Aumn et al. |
| 7,158,719 B2 | 1/2007 | Cassidy |
| 7,164,852 B2 | 1/2007 | Cazzini et al. |
| 7,207,966 B2 | 4/2007 | Savare et al. |
| 7,232,457 B2 | 6/2007 | Schmidt et al. |

(56) References Cited

U.S. PATENT DOCUMENTS

| | | | |
|---|---|---|---|
| 7,236,694 B1 | 6/2007 | Chammas |
| 7,238,170 B2 | 7/2007 | Park |
| 7,258,711 B2 | 8/2007 | Dunn et al. |
| 7,261,557 B2 | 8/2007 | Gill et al. |
| 7,273,359 B2 | 9/2007 | Blight et al. |
| 7,297,133 B2 | 11/2007 | Nelson et al. |
| 7,316,666 B1 | 1/2008 | Entenman et al. |
| 7,394,976 B2 | 6/2008 | Entenman et al. |
| 7,410,475 B2 | 8/2008 | Krensky et al. |
| 7,458,951 B2 | 12/2008 | Lauman et al. |
| 7,604,610 B2 | 10/2009 | Shener et al. |
| 7,621,898 B2 | 11/2009 | Lalomia et al. |
| 7,678,070 B2 | 3/2010 | Kumar et al. |
| D615,191 S | 5/2010 | McGill et al. |
| D616,539 S | 5/2010 | McGill et al. |
| 7,753,880 B2 | 7/2010 | Malackowski |
| 7,762,989 B2 | 7/2010 | Simpson |
| D650,896 S | 12/2011 | McGill et al. |
| 8,123,731 B2 | 2/2012 | Ryan |
| 8,138,925 B2 | 3/2012 | Downie et al. |
| 8,225,643 B2 | 7/2012 | Abboud et al. |
| 8,262,603 B2 | 9/2012 | Shener et al. |
| 8,388,570 B2 | 3/2013 | Kumar et al. |
| 8,562,577 B2 | 10/2013 | Michaels et al. |
| 8,652,089 B2 | 2/2014 | Kumar et al. |
| 8,979,798 B2 | 3/2015 | Shener et al. |
| 9,289,110 B2 | 3/2016 | Woolford et al. |
| 9,474,848 B2 | 10/2016 | Williams et al. |
| 9,855,383 B2 | 1/2018 | Shener et al. |
| 10,080,554 B2 | 9/2018 | Hamel et al. |
| 10,105,470 B2 | 10/2018 | Reasoner et al. |
| 10,201,647 B2 | 2/2019 | Norris et al. |
| 10,253,792 B2 | 4/2019 | Schmidt et al. |
| 10,368,912 B2 | 8/2019 | Truckai et al. |
| 10,369,267 B2 | 8/2019 | Norman et al. |
| 10,881,778 B2 | 1/2021 | Scarpaci et al. |
| 10,954,975 B2 | 3/2021 | Schmidt et al. |
| 11,547,815 B2 | 1/2023 | Minahan |
| 2002/0032403 A1 | 3/2002 | Savagle et al. |
| 2002/0096984 A1 | 7/2002 | Konishi et al. |
| 2003/0004470 A1 | 1/2003 | Hickerson et al. |
| 2003/0109826 A1 | 6/2003 | Fowler et al. |
| 2003/0176833 A1 | 9/2003 | Libermann |
| 2003/0212363 A1 | 11/2003 | Shipp |
| 2003/0216689 A1 | 11/2003 | Bouhuijs et al. |
| 2004/0097872 A1 | 5/2004 | Delk et al. |
| 2004/0190884 A1 | 9/2004 | Stewart et al. |
| 2004/0204679 A1 | 10/2004 | Visconti et al. |
| 2005/0055074 A1 | 3/2005 | Tak et al. |
| 2005/0095155 A1 | 5/2005 | Blight et al. |
| 2005/0142013 A1 | 6/2005 | Faries, Jr. et al. |
| 2005/0148934 A1 | 7/2005 | Martens et al. |
| 2006/0122576 A1 | 6/2006 | Raja et al. |
| 2006/0148279 A1 | 7/2006 | German et al. |
| 2006/0210255 A1 | 9/2006 | Cassidy |
| 2006/0222350 A1 | 10/2006 | Cassidy |
| 2006/0253075 A1 | 11/2006 | Faries, Jr. et al. |
| 2007/0045272 A1 | 3/2007 | French et al. |
| 2007/0129707 A1 | 6/2007 | Blott et al. |
| 2007/0142773 A1 | 6/2007 | Rosiello et al. |
| 2007/0142775 A1 | 6/2007 | Visconti et al. |
| 2007/0161978 A1 | 6/2007 | Fedenia et al. |
| 2007/0159337 A1 | 7/2007 | Tethrake et al. |
| 2007/0217948 A1 | 9/2007 | Ghelli et al. |
| 2007/0233003 A1 | 10/2007 | Radgowski et al. |
| 2007/0242934 A1 | 10/2007 | Entenman et al. |
| 2007/0265689 A1 | 11/2007 | Frey |
| 2007/0278155 A1 | 12/2007 | Lo et al. |
| 2008/0015504 A1* | 1/2008 | Boehringer ............. A61M 1/78 137/557 |
| 2008/0031773 A1 | 2/2008 | Eccleston |
| 2008/0039815 A1 | 2/2008 | Ogawa |
| 2008/0077087 A1 | 3/2008 | Martens |
| 2008/0093276 A1 | 4/2008 | Roger et al. |
| 2008/0145249 A1 | 6/2008 | Smisson et al. |
| 2008/0146996 A1 | 6/2008 | Smisson et al. |
| 2008/0154095 A1 | 6/2008 | Stubkjaer et al. |
| 2009/0009290 A1 | 1/2009 | Kneip et al. |
| 2010/0151785 A1 | 6/2010 | Steeger et al. |
| 2010/0228222 A1 | 9/2010 | Williams et al. |
| 2010/0228224 A1 | 9/2010 | Pyles et al. |
| 2010/0280435 A1* | 11/2010 | Raney ............. A61M 1/76 604/35 |
| 2011/0034866 A1 | 2/2011 | Zhang et al. |
| 2011/0144812 A1 | 6/2011 | Davis et al. |
| 2011/0162333 A1 | 7/2011 | Cook et al. |
| 2013/0079702 A1 | 3/2013 | Klein et al. |
| 2013/0261530 A1* | 10/2013 | Yalamanchili ........ F16K 15/031 604/9 |
| 2013/0317413 A1* | 11/2013 | Field ................ A61M 5/14276 604/9 |
| 2014/0350511 A1 | 11/2014 | Carlisle et al. |
| 2015/0094673 A1 | 4/2015 | Pratt et al. |
| 2015/0265768 A1 | 9/2015 | Vazquez et al. |
| 2016/0101227 A1 | 4/2016 | Norris et al. |
| 2016/0115557 A1 | 4/2016 | Khatib |
| 2017/0087016 A1* | 3/2017 | Camras ............... A61F 9/00781 |
| 2018/0344949 A1 | 12/2018 | Haddad et al. |
| 2018/0361055 A1 | 12/2018 | Pereira et al. |
| 2019/0143010 A1 | 5/2019 | Gaspredes et al. |
| 2019/0201083 A1 | 7/2019 | Shelton, IV et al. |
| 2019/0201086 A1 | 7/2019 | Shelton, IV et al. |
| 2019/0234437 A1 | 8/2019 | Schmidt et al. |
| 2019/0321535 A1 | 10/2019 | Beavers et al. |
| 2019/0366017 A1 | 12/2019 | Minahan |
| 2020/0033897 A1 | 1/2020 | Jensen et al. |
| 2020/0297900 A1 | 9/2020 | Holigan et al. |
| 2020/0315640 A1 | 10/2020 | Germain et al. |
| 2020/0405953 A1 | 12/2020 | Toth |
| 2020/0405955 A1 | 12/2020 | Shah et al. |
| 2021/0100710 A1 | 4/2021 | Augustine et al. |
| 2021/0128815 A1 | 5/2021 | Byrne et al. |
| 2021/0138124 A1 | 5/2021 | Lorman |
| 2021/0138146 A1 | 5/2021 | Sutter et al. |
| 2021/0138163 A1 | 5/2021 | Sutter et al. |
| 2021/0205507 A1 | 7/2021 | Heeren |
| 2021/0268182 A1 | 9/2021 | O'donnell et al. |
| 2022/0143278 A1 | 5/2022 | Lorman et al. |
| 2022/0143279 A1 | 5/2022 | Lorman et al. |
| 2022/0143299 A1 | 5/2022 | Sutter et al. |
| 2023/0124591 A1 | 4/2023 | Minahan |

FOREIGN PATENT DOCUMENTS

| | | |
|---|---|---|
| EP | 0776670 B1 | 9/2001 |
| GB | 2242367 B | 3/1992 |
| WO | 9217040 | 10/1992 |
| WO | 0047283 | 8/2000 |
| WO | 2010104878 A1 | 9/2010 |
| WO | 2020033209 A1 | 2/2020 |
| WO | 2022234448 A1 | 11/2022 |

OTHER PUBLICATIONS

International Preliminary Report on Patentability dated May 10, 2022, directed to International Application No. PCT/US2020/059463; 8 pages.

Lorman et al., U.S. Notice of Allowance and Fee(s) due mailed Aug. 23, 2023, directed to U.S. Appl. No. 17/168,829; 10 pages.

Lorman et al., U.S. Restriction Requirement dated Mar. 8, 2024, directed to U.S. Appl. No. 17/091,662; 7 pages.

Lorman, U.S. Office Action dated Mar. 10, 2023, directed to U.S. Appl. No. 17/168,829; 6 pages.

Office Action dated Apr. 30, 2024, directed to EP Application No. 20 816 809.6; 4 pages.

Sutter et al., U.S. Advisory Action dated Jul. 11, 2023, directed to U.S. Appl. No. 17/091,328; 3 pages.

Sutter et al., U.S. Election of Species Requirement dated Jan. 12, 2024, directed to U.S. Appl. No. 17/091,651; 6 pages.

Sutter et al., U.S. Office Action dated Apr. 21, 2023, directed to U.S. Appl. No. 17/168,817; 17 pages.

(56) References Cited

OTHER PUBLICATIONS

Sutter et al., U.S. Office Action dated Aug. 12, 2022, directed to U.S. Appl. No. 17/091,328; 19 pages.
Sutter et al., U.S. Office Action dated Dec. 28, 2023, directed to U.S. Appl. No. 17/168,817; 18 pages.
Sutter et al., U.S. Office Action dated Dec. 6, 2023, directed to U.S. Appl. No. 17/091,328; 19 pages.
Sutter et al., U.S. Office Action dated Mar. 22, 2024, directed to U.S. Appl. No. 17/091,651; 14 pages.
Sutter et al., U.S. Office Action dated Mar. 8, 2023, directed to U.S. Appl. No. 17/091,328; 20 pages.
Sutter et al., U.S. Office Action dated Sep. 13, 2022, directed to U.S. Appl. No. 17/168,817; 17 pages.

* cited by examiner

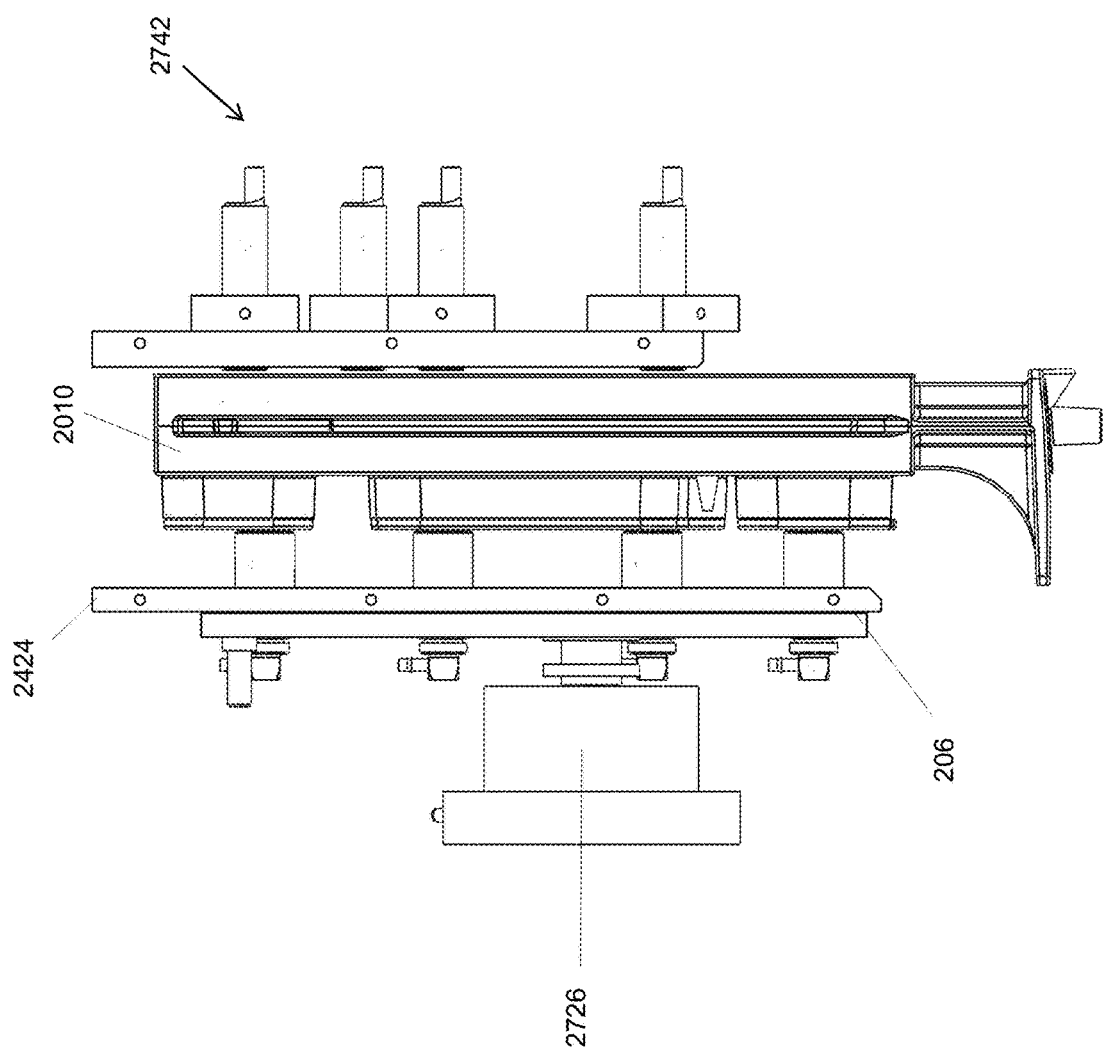

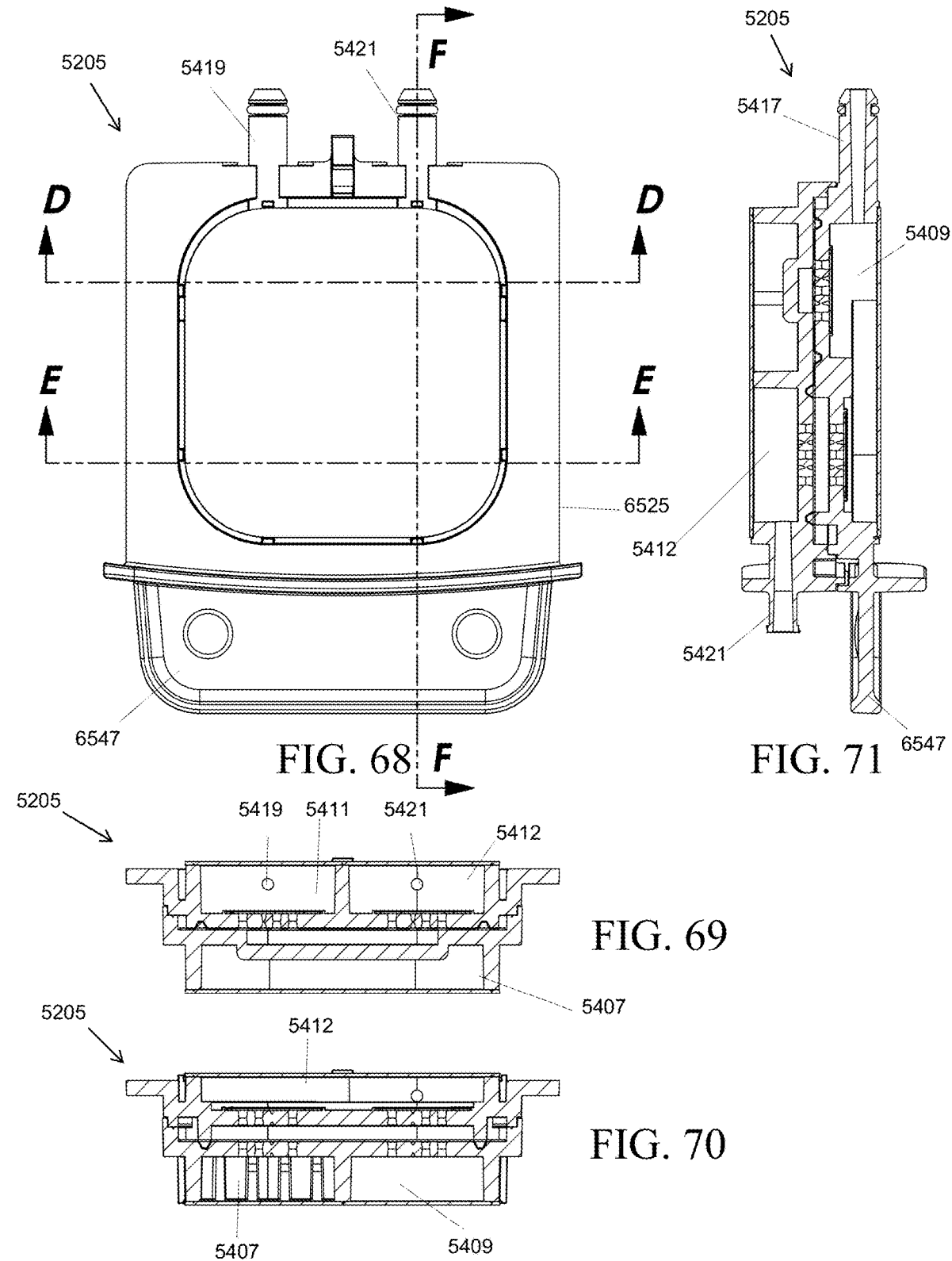

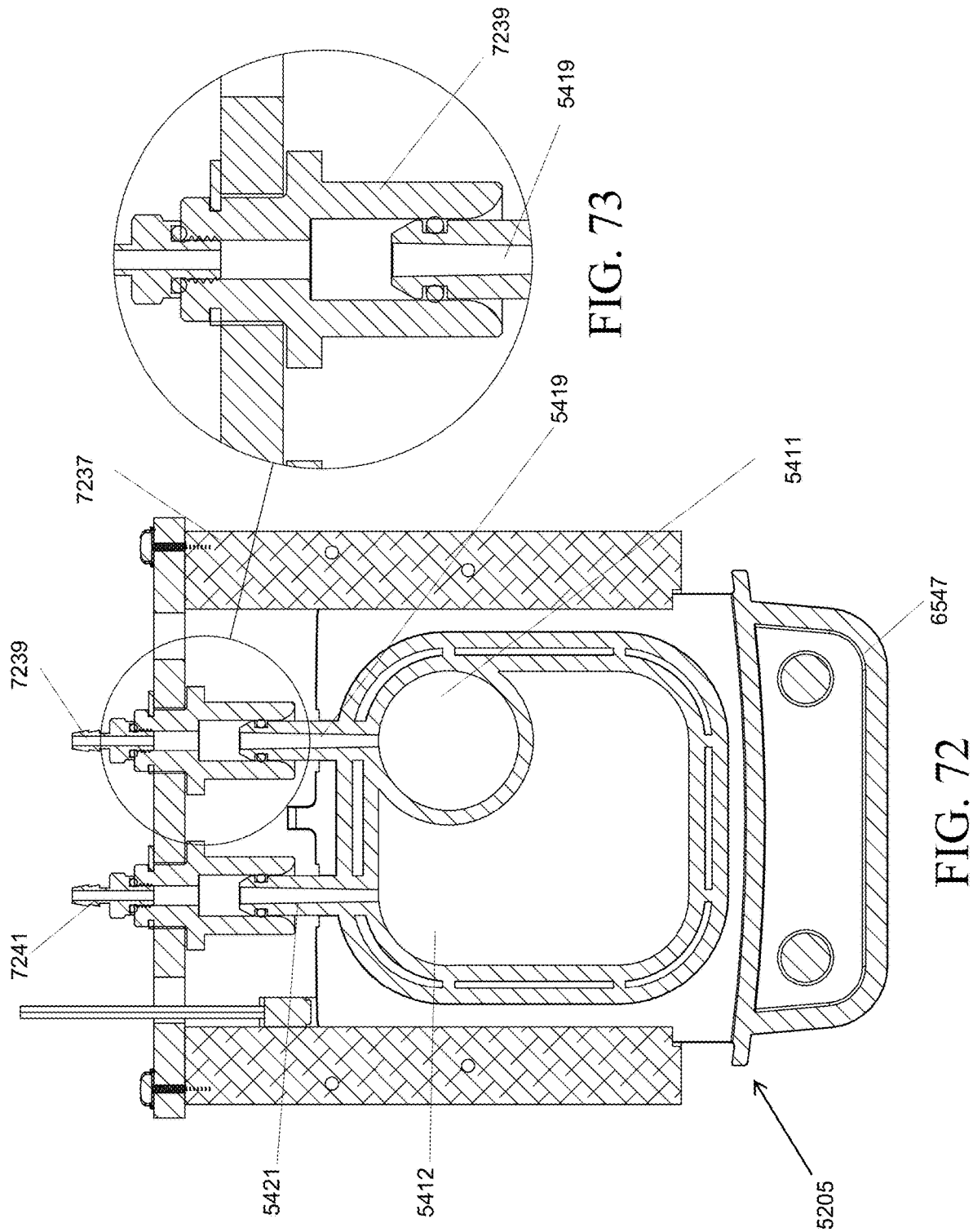

FLUID MANAGEMENT SYSTEMS AND METHODS

TECHNICAL FIELD

The present application is directed to fluid management systems and, more particularly, to fluid management systems and methods for surgical procedures.

BACKGROUND

Surgical fluid management systems are used in endoscopic procedures to pressurize and deliver fluid to a surgical site for distending and continually flushing the surgical site to keep it free of blood and debris for visualization purposes.

Fluid management systems may pressurize the fluid by manipulating the height from which fluid supply bags are hung relative to the height of the surgical site, controlling the air pressure in pressure cuffs or pressure chambers surrounding the fluid supply bags, or by pumping the fluid, typically with a peristaltic pump. Gravity provides non-pulsatile fluid flow, but poor fluid pressure control. Similarly, pressure cuffs or chambers provide non-pulsatile fluid flow, but poor fluid pressure control, unless the pressure in the cuffs or chambers is constantly adjusted to account for the fluid volume exiting the fluid supply bags. Peristaltic pumps can provide good pressure control, but the pulsatile nature of the fluid flow may impair distention and visualization at the surgical site.

Fluid management systems may warm the fluid in order to assist in the mitigation or prevention of intraoperative hypothermia which can result in adverse outcomes. Such systems, however, may lack precise fluid temperature control, the ability to adequately warm fluid at the high fluid flow rates required for many procedures, and/or other capabilities required for certain surgical procedures (e.g., fluid deficit monitoring which is required for operative hysteroscopy). In facilities that lack fluid management systems with fluid warming capabilities, fluid bags may be pre-warmed in warming cabinets prior to use during a surgical procedure. However, use of such warming cabinets can result in dangerously hot fluid or, if the pre-warmed fluid is not used shortly after the pre-warming process has been completed, fluid that has cooled to room temperature and may contribute to intraoperative hypothermia.

Fluid management systems may include a deficit monitoring system for calculating a deficit between an amount of a fluid supplied to a surgical site and an amount of fluid returned from a surgical site. Currently, fluid deficit monitoring is accomplished by subtracting the volume of fluid supplied to the surgical site from the volume of fluid returned from the surgical site into fluid collection canisters, bags, or vessels. The volume of fluid supplied is determined by monitoring the weight of the fluid source bags, counting the rotations of a peristaltic pump, and/or manually recording the number and volume of fluid bags utilized during the surgical procedure. The volume of fluid returned is determined by monitoring the weight of the canisters, bags, or vessels and/or manually viewing and recording the fluid levels in such canisters, bags, or vessels using graduation marks. In order for the returned fluid from the surgical site to move into the fluid collection canisters, the canisters are interconnected with tandem tubing and then connected to the surgical site and a suction source. If the fluid collection canisters become full during the surgical procedure, the procedure must be interrupted so that such canisters can be replaced. This process typically involves suspending suction, disconnecting the canisters from the surgical site and suction source, disconnecting the tandem tubing, replacing the full canisters with new canisters, interconnecting the new canisters with tandem tubing, reconnecting the new canisters to the surgical site and suction source, and resuming suction. Due to the blood, tissue, and contaminated bodily fluids collected, full fluid collection canisters require regulated "red bag" disposal unless treated with solidifiers that, in most states, allow non-regulated "white bag" disposal.

Fluid management systems may be connected to an internal or external suction source to pull fluid from a surgical site. As external suction sources are often set to high suction levels in an operating room environment, down-regulation may be necessary for proper operation of certain fluid outflow regulation, deficit monitoring, and/or collection functions. Down-regulation of an external suction source to provide desired suction levels may be accomplished via a manually or electronically controlled regulator. In order to isolate the regulator from biohazardous fluid, fluid collection canisters, bags, or vessels are typically placed between the regulator and the surgical site. These canisters, bags, or vessels must be removed and replaced after they become full during a surgical procedure.

During endoscopic surgical procedures, a temporary increase in the fluid pressure and/or flow rate may be necessary to maintain or increase distention and/or to maintain or increase fluid flow for procedural and/or visualization purposes. To provide such a temporary increase, the user may manually operate a syringe, bulb, or similar device that is connected to the fluid inflow line of a surgical scope or instrument. As the duration of any increase in the fluid pressure and/or flow rate provided by these manual methods is limited to the volume of fluid contained in the syringe, bulb, or similar device, the necessary increase in the fluid pressure and/or flow rate may be interrupted while the syringe, bulb, or similar device is refilled with fluid. In other instances, the user may increase the fluid pressure by raising the height of the fluid supply bag, manually squeezing the fluid supply bag, or manually pumping up the pressure in a pressure bag or cuff surrounding the fluid supply bag. Alternatively, in some instances, the user may increase the setpoint fluid pressure of a fluid management system via a user interface such that the setpoint fluid pressure is set at a higher setpoint fluid pressure, and then the user decreases the setpoint fluid pressure to the original setpoint fluid pressure or other desired setpoint fluid pressure when the increase in pressure or flow is no longer necessary.

SUMMARY

An exemplary embodiment of a pressure regulator includes a first chamber, a second chamber, a third chamber, and a flexible membrane. The first chamber has an inlet opening for fluidly connecting to an external pressure source, the second chamber has an outlet opening for supplying a regulated pressure to a regulated source, and the third chamber has a pressure opening for connection to a pressure source. The flexible membrane fluidly isolates the third chamber from both of the first and second chambers, and the flexible membrane is movable by the pressure source between a first position in which the flexible membrane fluidly isolates the first chamber from the second chamber and a second position in which the first and second chambers are fluidly connected.

An exemplary embodiment of a pressure regulator includes a first chamber, a second chamber, a third chamber, a fourth chamber, and a flexible membrane. The first chamber has an inlet opening for fluidly connecting to an external pressure source, and the second chamber has an outlet opening for supplying a regulated pressure to a regulated source. The third chamber has a pressure opening for connection to a pressure source, and the fourth chamber has a sensing opening for connecting to a pressure sensor that senses a pressure in the fourth chamber. The flexible membrane fluidly isolates the third and fourth chambers from both of the first and second chambers. The flexible membrane is movable by a vacuum pressure applied to the first chamber such that the third and fourth chambers are fluidly connected, and the flexible membrane is movable by a pressure applied by the pressure source such that the first and second chambers are fluidly connected.

An exemplary embodiment of a fluid management system includes a pump and a disposable pressure regulator. The pump delivers fluid from a fluid supply container to a surgical site. The disposable pressure regulator is positioned between the surgical site and an external vacuum source. The disposable pressure regulator regulates a vacuum pressure provided by the external vacuum source to the surgical site, and the fluid from the surgical site passes through the pressure regulator prior to being evacuated by the fluid management system.

An exemplary embodiment of a fluid management system includes a pump and an aspiration module assembly. The pump delivers fluid from a fluid supply container to a surgical site. The aspiration module assembly connects to an external vacuum source and is positioned between the surgical site and the vacuum source. The aspiration module assembly includes an aspiration module and a pressure regulator. The aspiration module has a pressure source and a pressure sensor. The pressure regulator removably connects to the aspiration module and includes a first chamber, a second chamber, a third chamber, and a flexible membrane. The first chamber has an inlet opening for fluidly connecting to an external vacuum source, the second chamber has an outlet opening for supplying a regulated pressure to a regulated source, and the third chamber has a one or more openings for connection to the pressure source and pressure sensor of the aspiration module. The flexible membrane fluidly isolates the third chamber from both of the first and second chambers, and the flexible membrane is movable by the pressure source between a first position in which the flexible membrane fluidly isolates the first chamber from the second chamber and a second position in which the first and second chambers are fluidly connected.

An exemplary embodiment of a fluid management system includes a pump and an aspiration module assembly. The pump delivers fluid from a fluid supply container to a surgical site. The aspiration module assembly connects to an external vacuum source and is positioned between the surgical site and the vacuum source. The aspiration module assembly includes an aspiration module and a pressure regulator. The aspiration module has a pressure source and a pressure sensor. The pressure regulator removably connects to the aspiration module and includes a first chamber, a second chamber, a third chamber, a fourth chamber, and a flexible membrane. The first chamber has an inlet opening for fluidly connecting to an external vacuum source, and the second chamber has an outlet opening for supplying a regulated pressure to a regulated source. The third chamber has a pressure opening for connection to the pressure source of the aspiration module, and the fourth chamber has a sensing opening for connecting to the pressure sensor of the aspiration module. The flexible membrane fluidly isolates the third and fourth chambers from both of the first and second chambers. The flexible membrane is movable by the external vacuum source such that the third and fourth chambers are fluidly connected, and the flexible membrane is movable by a pressure applied by the pressure source such that the first and second chambers are fluidly connected.

An exemplary method of regulating a vacuum pressure supplied to a surgical site with a fluid management system includes configuring a control system of the fluid management system to provide a first vacuum pressure from the pressure source to a pressure regulator of the fluid management system to move a flexible membrane disposed within the pressure regulator form a first position in which the flexible membrane fluidly isolates an external vacuum source from a surgical site to a second position in which the vacuum source and the surgical site are fluidly connected. Movement of the flexible membrane to the second position causes the vacuum pressure supplied to the surgical site to pull fluid from the surgical site and through the disposable pressure regulator prior to being evacuated by the fluid management system.

An exemplary method of regulating a vacuum pressure supplied to a surgical site with a fluid management system includes configuring a control system of the fluid management system to provide a first vacuum pressure from the pressure source to a pressure regulator of the fluid management system to move a flexible membrane disposed within the pressure regulator form a first position in which the flexible membrane fluidly isolates an external vacuum source from a surgical site to a second position in which the vacuum source and the surgical site are fluidly connected. Movement of the flexible membrane to the second position causes the vacuum pressure supplied to the surgical site to pull fluid from the surgical site and into a fluid collection canister that is disposed between the surgical site and the pressure regulator.

BRIEF DESCRIPTION OF THE DRAWINGS

FIG. 28 illustrates the deficit cartridge of FIG. 20 aligned with a moveable manifold of the deficit module of FIG. 20, where the movable manifold is in a closed position relative to the deficit cartridge such that connections are made between the deficit cartridge and the deficit module;

FIG. 68 illustrates a top view of the pressure regulator shown in FIG. 65;

FIG. 69 illustrates a cross-sectional view of the pressure regulator shown in FIG. 65 taken along the lines D-D shown in FIG. 68;

FIG. 70 illustrates a cross-sectional view of the pressure regulator shown in FIG. 65 taken along the lines E-E shown in FIG. 68;

FIG. 71 illustrates a cross-sectional view of the pressure regulator shown in FIG. 65 taken along the lines F-F shown in FIG. 68;

FIG. 72 illustrates a top cross-sectional view of an exemplary connection between the pressure regulator shown in FIG. 65 and an exemplary receiving mechanism for the aspiration module shown in FIG. 52;

FIG. 73 illustrates a partial view of the exemplary connection between the pressure regulator and receiving mechanism shown in FIG. 72 showing a connection between a port of the pressure regulator and a port of the aspiration module;

DETAILED DESCRIPTION

The Detailed Description describes exemplary embodiments of the invention and is not intended to limit the scope of the claims in any way. Indeed, the invention is broader than and unlimited by the exemplary embodiments, and the terms used in the claims have their full ordinary meaning, unless otherwise noted in the application. Features and components of one exemplary embodiment may be incorporated into the other exemplary embodiments. Inventions within the scope of this application may include additional features, or may have less features, than those shown in the exemplary embodiments.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

In endoscopic surgical procedures, steady distention and clear visibility are important to procedural efficacy and efficiency. Fluid management systems are used to provide fluid to a surgical site such that a surgeon has the desired distention and visualization while performing a surgical procedure. Fluid management systems can also be used to remove fluid from the surgical site. The various embodiments of fluid management systems described herein relate to modular systems that include software-controlled, electro-mechanical devices or modules that may be used in combination with single or multiuse tubing sets. The modular, surgical fluid management systems described herein are fully configurable to meet user needs based on, for example, the types of surgical procedures being performed and the surgical environment. Exemplary functions of the fluid management systems described herein include fluid pressurization, fluid warming, fluid deficit monitoring, suction, suction regulation, fluid collection, and/or fluid evacuation into a facility's waste disposal system. The fluid management systems can be configured based on surgical discipline (e.g., gynecological, urological, and/or orthopedic procedures) and environment (e.g., operating room or physician's office), as well as based on other needs and/or preferences of the user and/or facility. The fluid management systems may be capable of integrated suction and fluid collection and/or may be compatible with third-party suction and fluid collection devices, as well as central suction systems of facilities where the fluid management systems are used.

Figure 1:
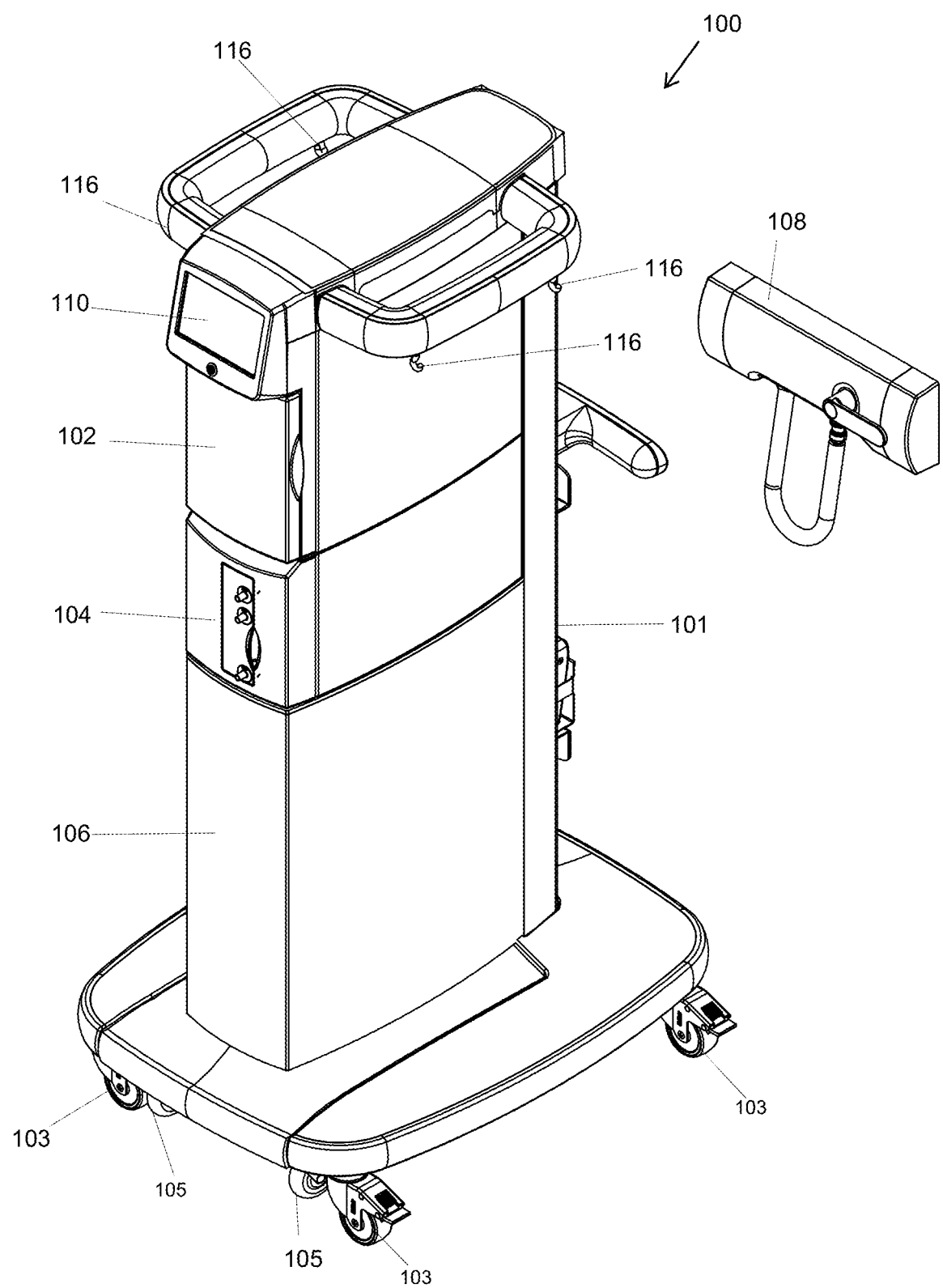
FIG. 1 illustrates an exemplary embodiment of a fluid management system for an operating room environment.
Figure 51:
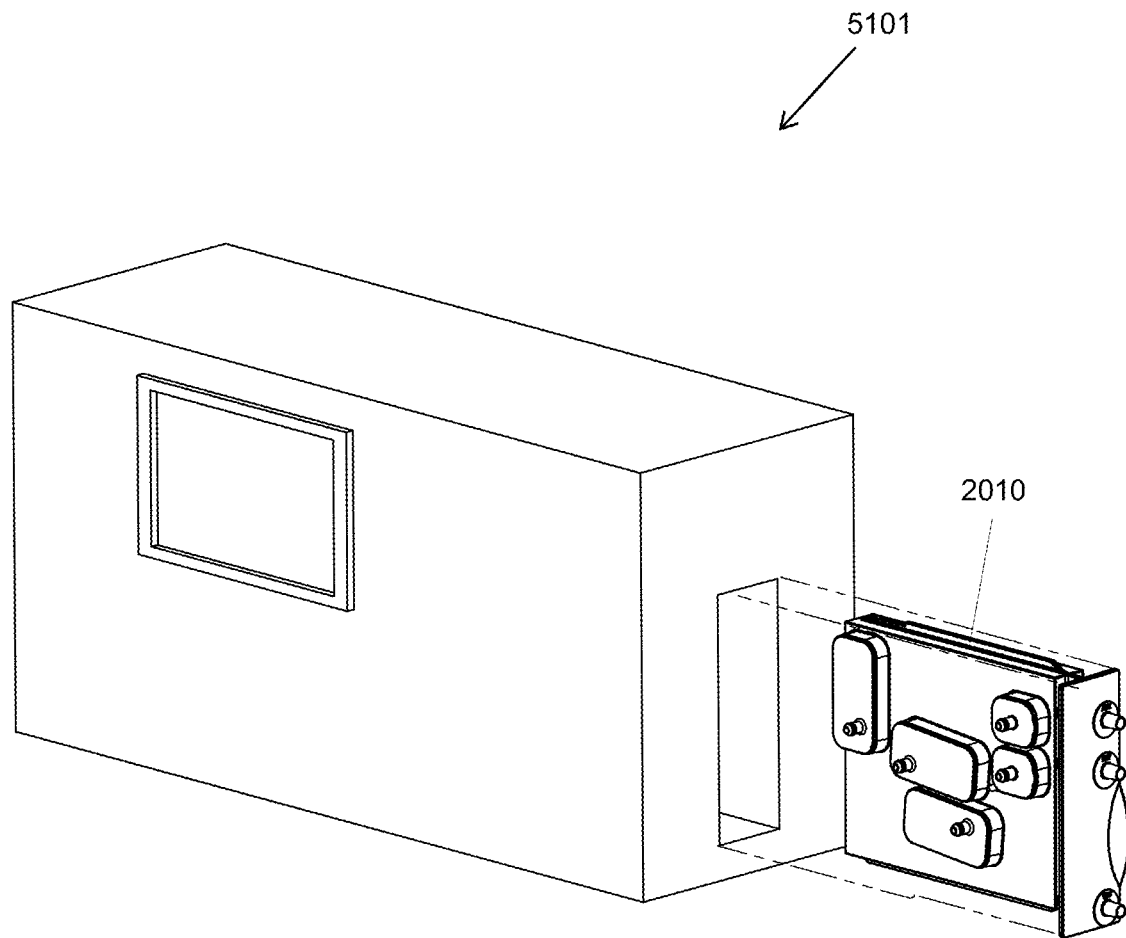
FIG. 51 illustrates an exemplary embodiment of a fluid flow monitoring and evacuation module for the fluid management system of FIG. 50.

Referring to FIG. 1, an exemplary embodiment of a fluid management system 100 for an operating room environment where gynecological, urological, and orthopedic procedures are performed is shown. The system 100 includes an elevated structure 101, a main unit 102, a deficit module 104, a fluid collection module 106, and a fluid evacuation module 108. The system 100 may also include an aspiration module 5201 (FIG. 52), and/or a fluid flow and evacuation module 5101 (FIG. 51). In some embodiments, the elevated structure 101 includes wheels 103 such that the system 100 can be moved to a desired location within the operating room or to a storage area. The system 100 may be modular, such that the system 100 described above can be configured as desired by the user.

The main unit 102 may have a control system that includes one or more processors (not shown) for controlling and/or communicating with the various modules and components of the system 100 or other facility equipment. The various modules and components may also have one or more processors (not shown) for performing designated functions and/or communicating with the control system of main unit 102 or other facility equipment. The processor(s) may execute instructions (e.g., software code) stored in memory (not shown) of the system 100 and/or execute instructions inputted into the system by a user. In some embodiments, the control system may have "Bluetooth" capability for connecting to remotely located components or modules of the system 100 or other facility equipment and "Wi-Fi" capability for connecting to the internet. The control system may include a touch-screen graphical user interface 110 for receiving one or more inputs from a user and displaying information of the system 100 (e.g., information regarding fluid pressure, fluid volume, fluid temperature, fluid deficit, etc.).

Figure 2:
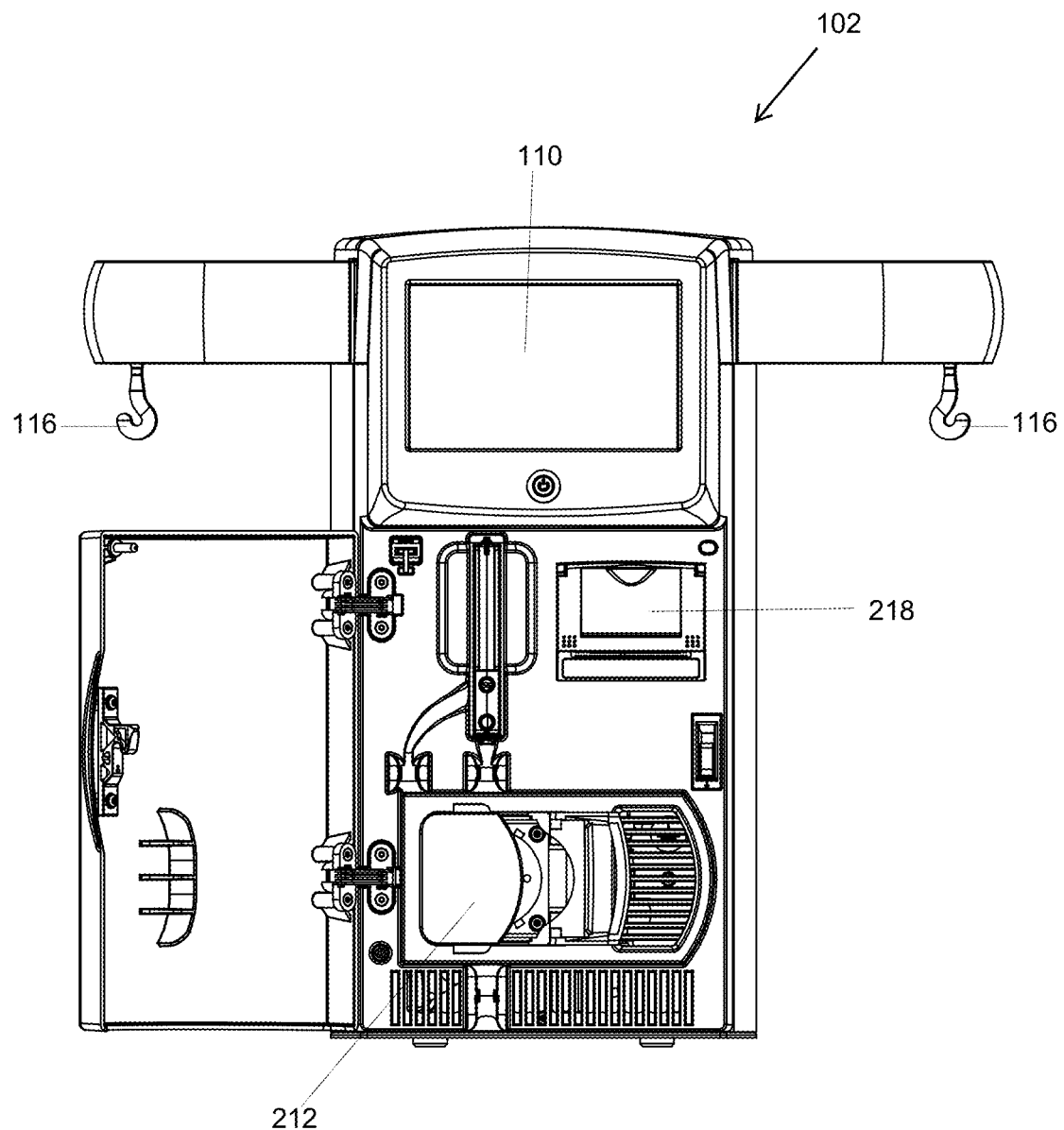
FIG. 2 illustrates an exemplary embodiment of a main unit of the fluid management system of FIG. 1.
Figure 3:
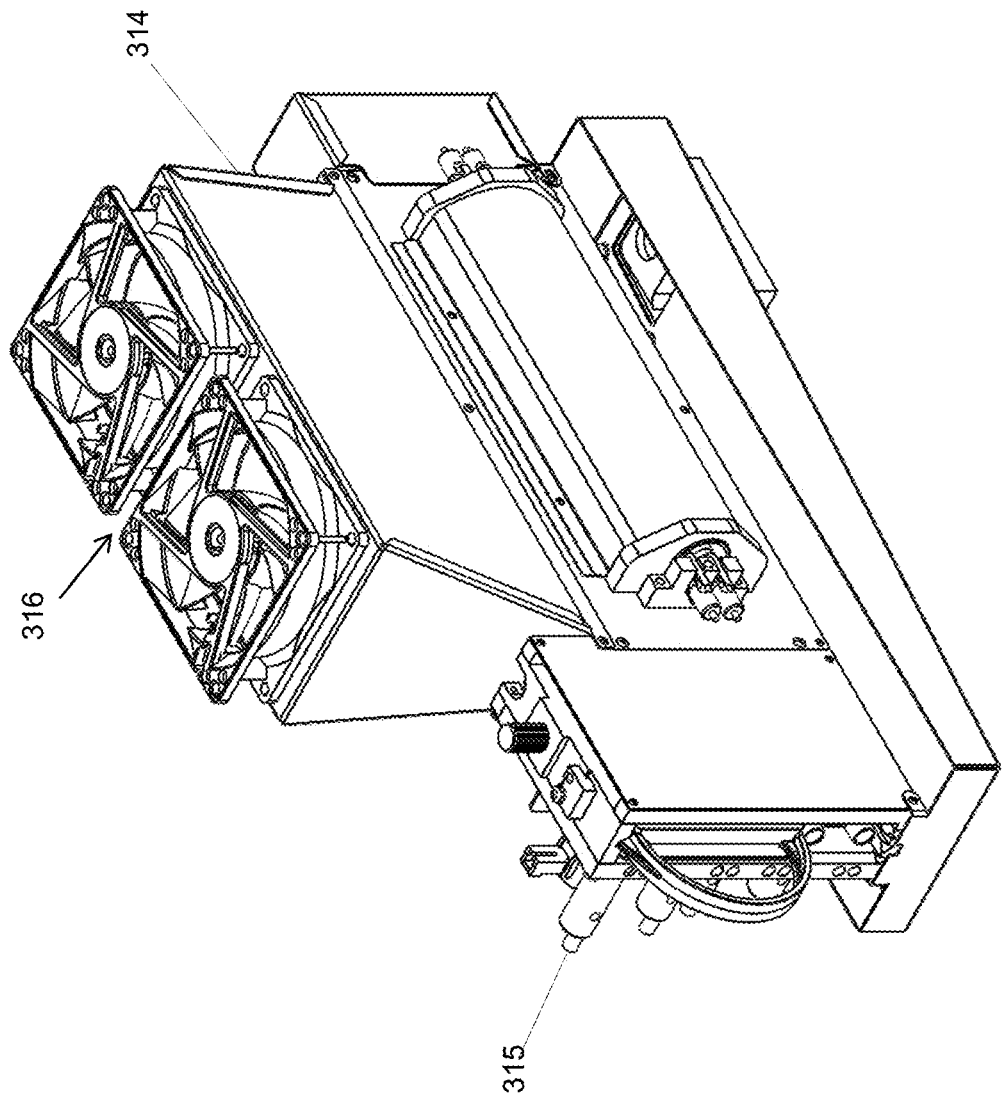
FIG. 3 illustrates an exemplary embodiment of a heater and fluid conditioner assembly of the main unit of FIG. 2.

Referring to FIGS. 1 through 3, the main unit 102 may also include a pump 212 (e.g., a peristaltic pump) for fluid pressurization, a heater assembly 314 for fluid warming, a fluid conditioning assembly 315 for sensing one or more fluid characteristics (e.g., fluid presence, temperature, etc.), hanging members 116 (e.g., hooks) for hanging fluid supply and/or return containers (e.g., bags, canisters, vessels, etc.), and a printer 218 for printing out pertinent procedure information (e.g., information regarding procedure type, procedure start time, procedure end time, total fluid volume, average fluid pressure, total fluid deficit, deficit by fluid type, average fluid temperature, etc.) during or after the surgical procedure. The processor of the control system can be in communication with the pump 212, heater assembly 314, fluid conditioning assembly 315, pressure sensors 949 (FIG. 9), solenoid valve 951 (FIG. 9), hanging members 116, printer 218, deficit module 104, fluid collection module 106, fluid evacuation module 108, aspiration module 5201 (FIG. 52), fluid flow and evacuation module 5101 (FIG. 51), and/or any other component of the system 100.

The pump 212 may be fluidly connected to the fluid container(s) that are hanging on the hanging members 116 such that the pump can pump fluid through a tubing set to a surgical scope or instrument (e.g., hysteroscope, cystoscope, ureteroscope, nephroscope, etc.) at a surgical site. The tubing set may include a fluid conditioner (e.g., fluid conditioner 420 shown in FIG. 4 and described in the present application) that works in combination with one or more non-contact sensors (e.g., non-contact sensors of the fluid conditioning assembly 315 or any other non-contact sensors in the system 100) such that the system 100 can monitor one or more characteristics of the fluid that is moving to the surgical site. The tubing set may also include a fluid warming cartridge (e.g., fluid warming cartridge 422 shown in FIG. 4 and described in the present application) that works in combination with the heater assembly 314 such that the system 100 can warm fluid that is moving to the surgical site.

A suction source pulls fluid from the surgical site, through a tubing set, and either into a collection container of the collection module 106, into a third-party fluid collection system, or into the waste disposal system of the facility in which the system 100 is being used. In certain embodiments, the suction source is a vacuum pump that is integral to main unit 102 or the fluid collection module 106. In some embodiments, fluid collection module also includes a pump and one or more filters such that the fluid collection module can evacuate and filter surgical smoke to eliminate potentially hazardous byproducts of electrosurgical procedures.

Figure 50:
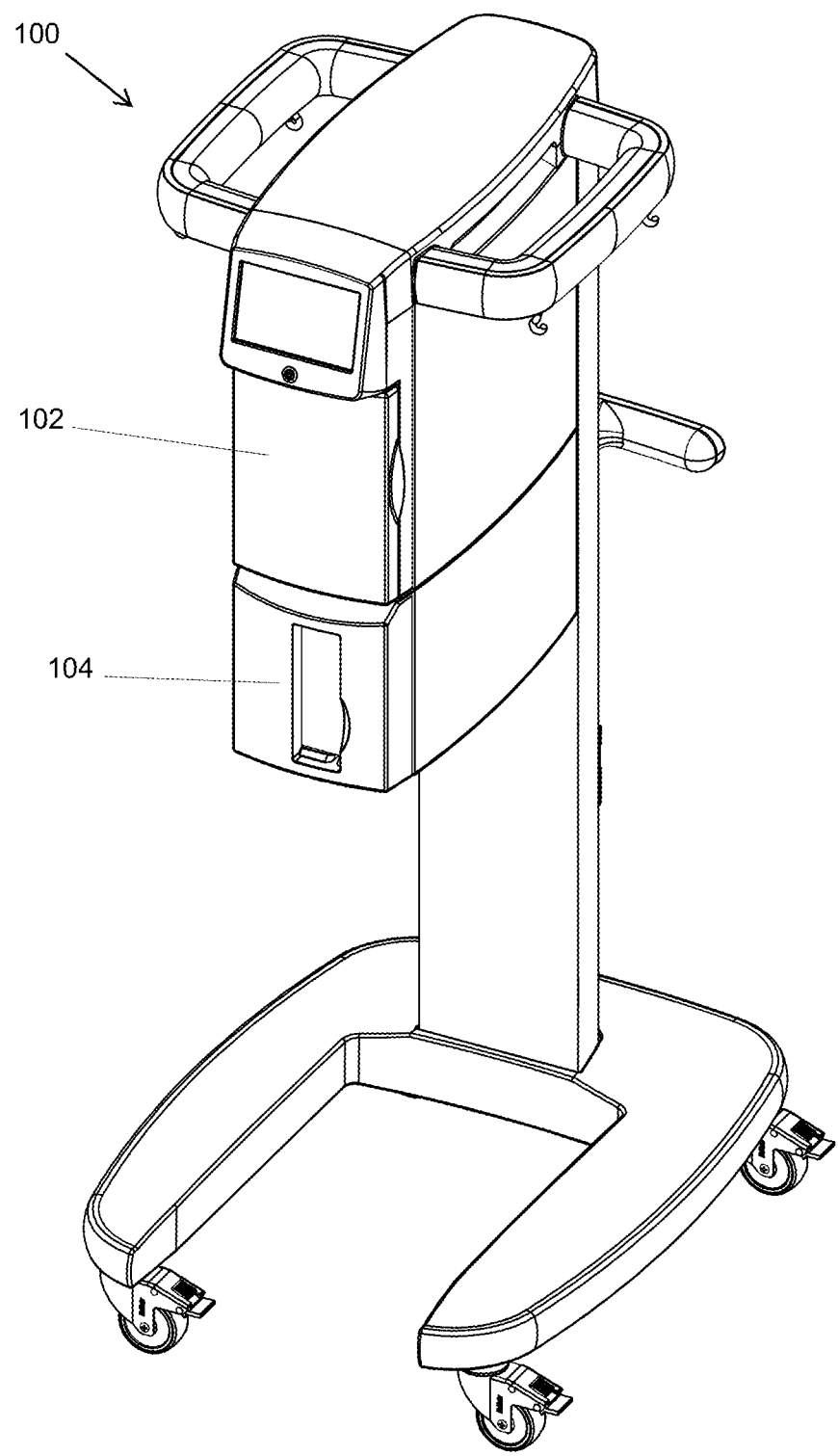
FIG. 50 illustrates another exemplary embodiment of the fluid management system shown in FIG. 1.

Referring to FIG. 1, the fluid collection module 106 may be independently mobile and removably coupled to the elevated structure 101 such that the module 106 can be removed from the elevated structure 101 and transported to a waste disposal area or room for disposal of the collected fluid. In some embodiments, the collection container of the collection module 106 may include disposable liners that can easily be replaced after the fluid has been evacuated from the suction and collection module 106 and into the facility's waste disposal system. In some embodiments, the suction source is external to the system 100 and pulls fluid to either the collection container of the collection module 106, a third party-fluid collection system, or the waste disposal system of the facility. In embodiments in which the fluid is pulled directly into the waste disposal system of the facility, the collection module 106 may be bypassed or removed from the system 100 during use (e.g., as shown in FIG. 50). The fluid collection module 106 may include a processor that communicates with the main unit 102, the deficit module 104, the aspiration module 5201 (FIG. 52), other components of the system 100, and/or other facility equipment. In some embodiments, the fluid collection module 106 may include a weight measuring mechanism (e.g., a scale) that allows the fluid management system 100 to determine a volume of fluid returning from the surgical site for fluid outflow and/or deficit monitoring purposes.

Figure 25:
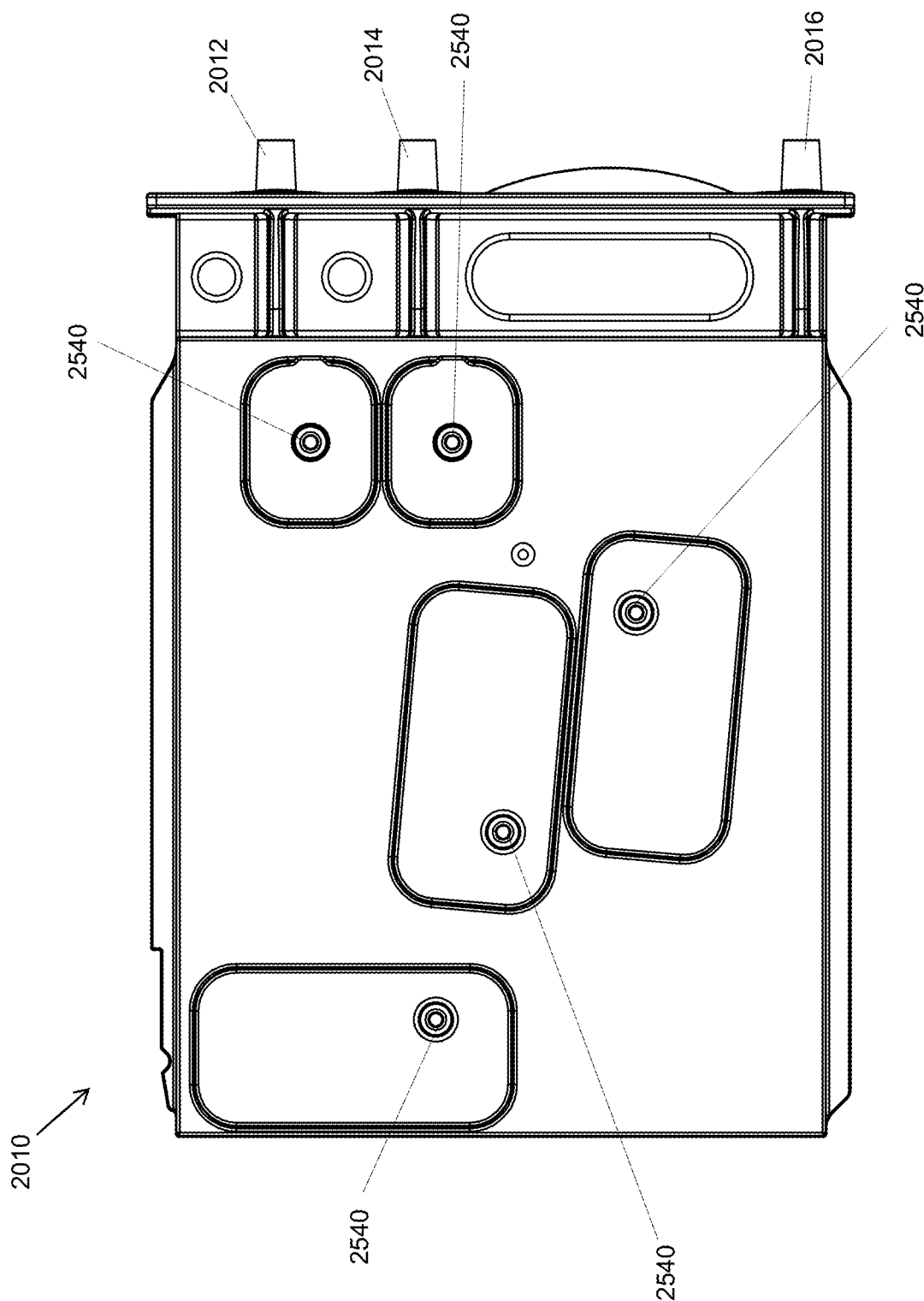
FIG. 25 illustrates a side view of the deficit cartridge of FIG. 20.
Figure 26:
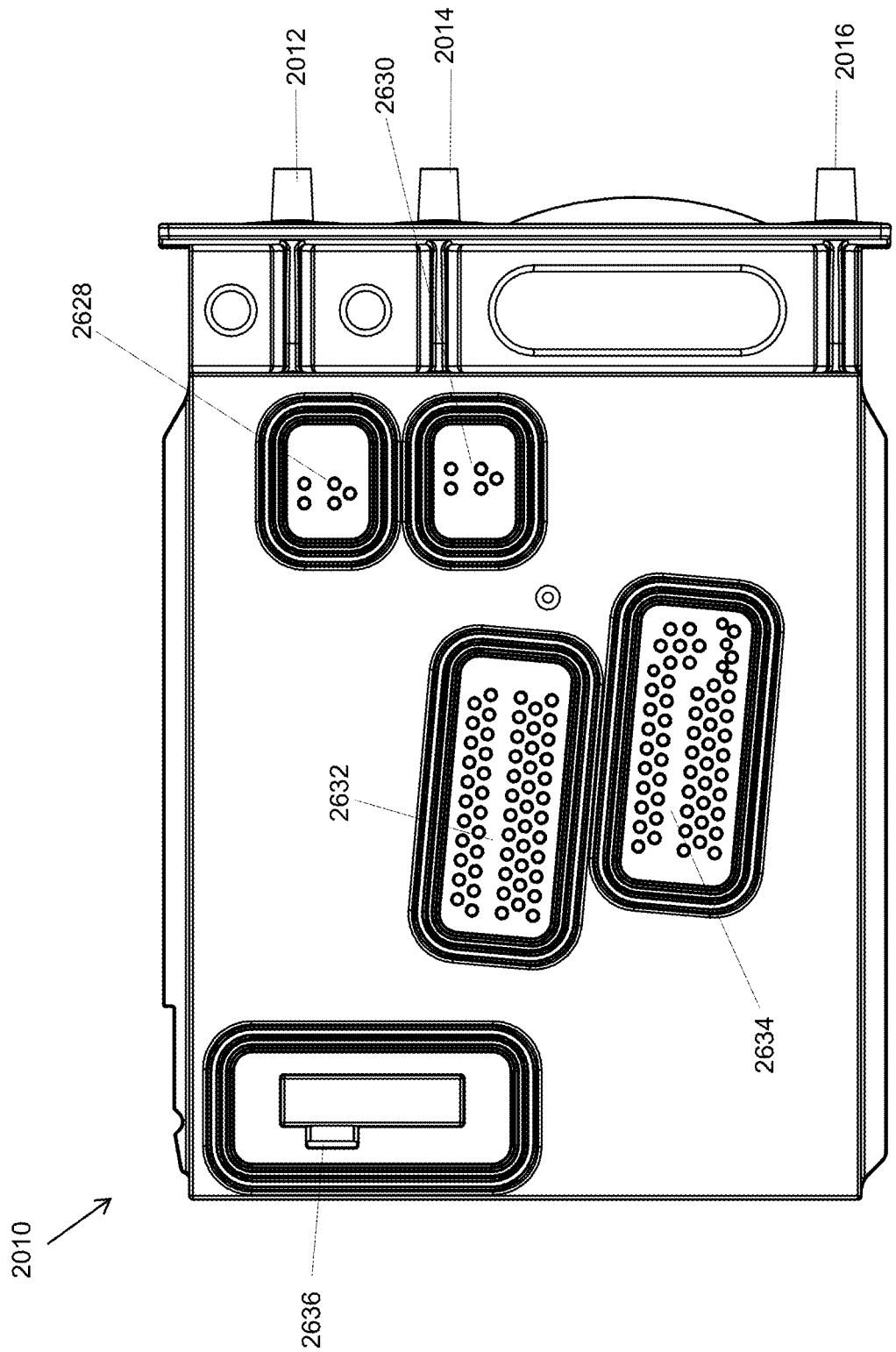
FIG. 26 illustrates a side view of the deficit cartridge of FIG. 20 with valve and port covers removed.

Prior to the fluid moving into the collection module 106, a third-party fluid collection system, or a waste disposal system of the facility, the fluid may move through a single or multiuse deficit cartridge (e.g., deficit cartridge 2010 shown in FIG. 25 and described in the present application) such that the system 100 can calculate and monitor a fluid deficit between fluid being provided to the surgical site and fluid being returned from the surgical site. The deficit cartridge may work in combination with the deficit module 104 (or the fluid flow and evacuation module 5101 shown in FIG. 51 and described in the present application) and the main unit 102 to allow the system 100 to calculate and monitor the fluid deficit.

In certain embodiments, system 100 includes an aspiration module (e.g., aspiration module 5201 shown in FIG. 52 and described in the present application), and a single or multiuse pressure regulator (e.g., the pressure regulators 5205 shown in FIGS. 52-73 and described in the present application) that is fluidly connected to the tubing set and the suction source. The pressure regulator and aspiration module may work in combination with each other and the main unit 102 to regulate a vacuum pressure provided to the surgical site by the suction source to pull fluid from the surgical site.

Figure 4:
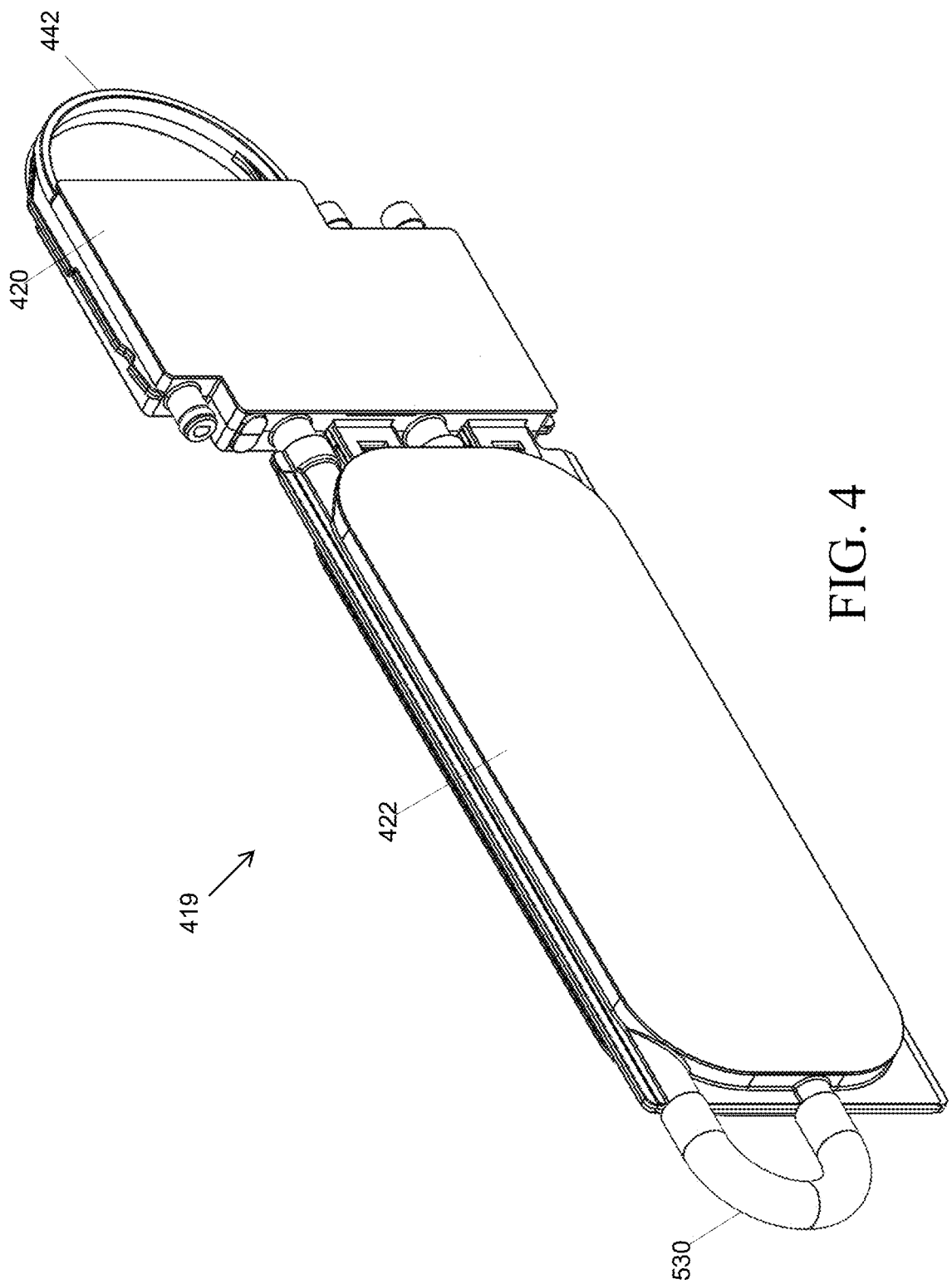
FIG. 4 illustrates an exemplary cartridge assembly for insertion into the heater and fluid conditioner assembly of FIG. 3.
Figure 5:
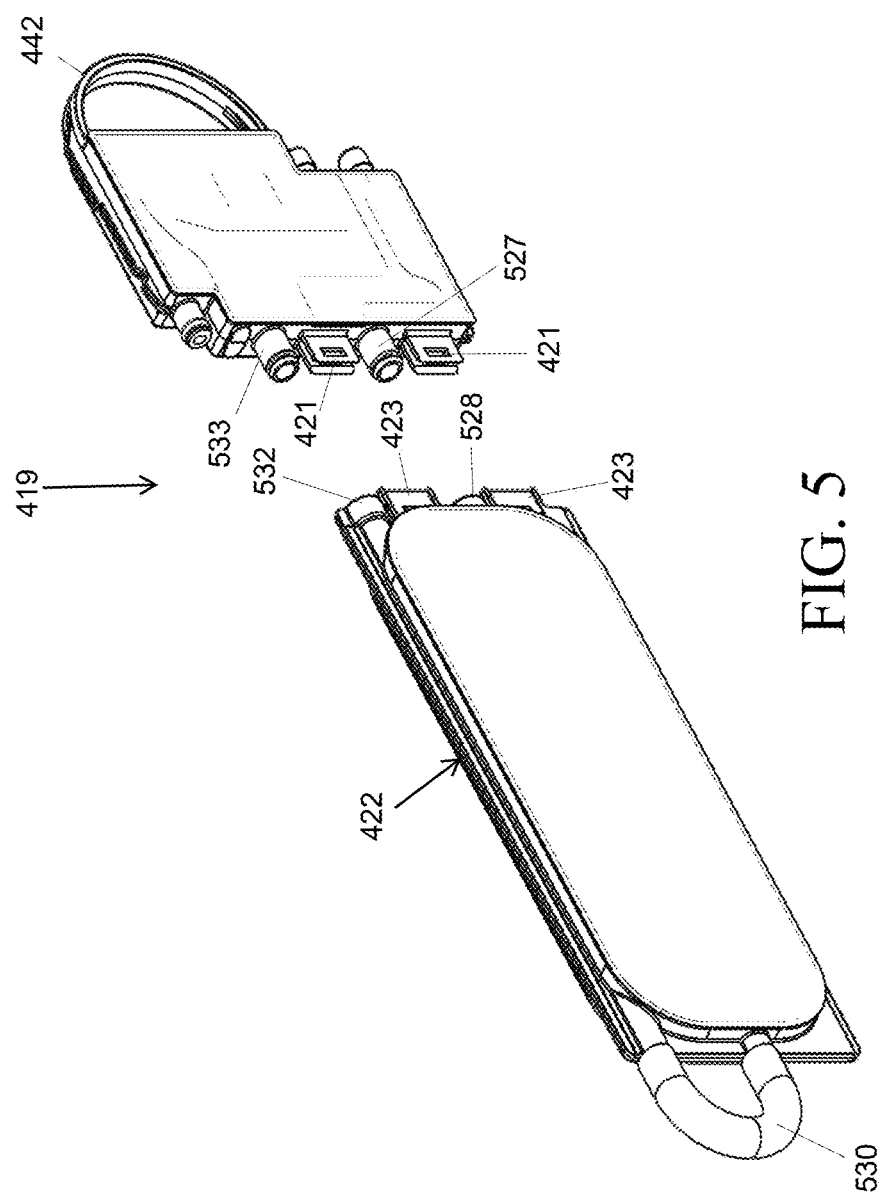
FIG. 5 illustrates an exemplary fluid conditioner and fluid warming cartridge of the cartridge assembly of FIG. 4 disconnected from each other.
Figure 6:
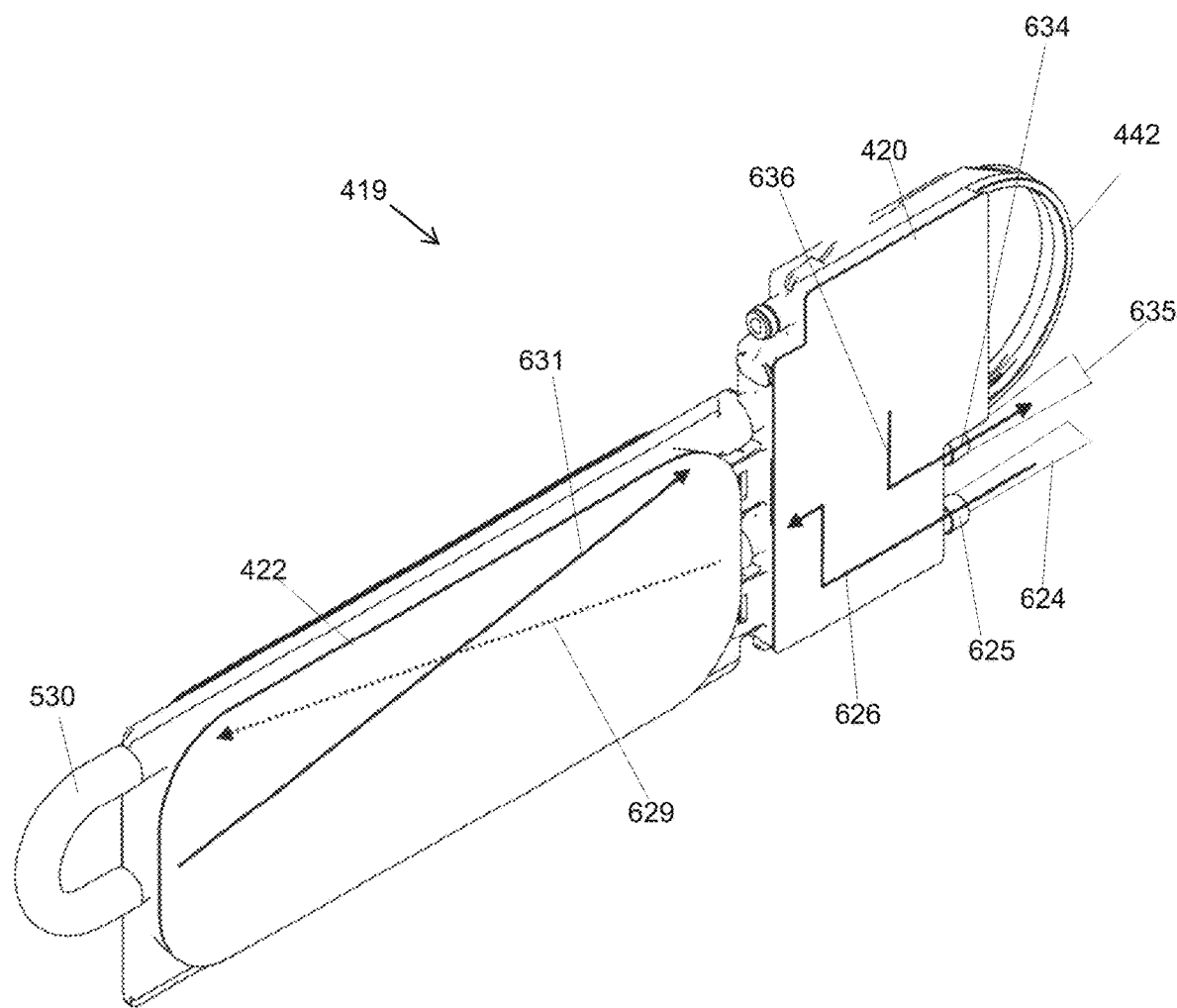
FIG. 6 illustrates an exemplary fluid path through the cartridge assembly of FIG. 4.

FIGS. 4 through 6 illustrate an exemplary embodiment of a cartridge assembly 419 for a single or multiuse disposable tubing set of the system 100, where the cartridge assembly 419 includes a fluid conditioner 420 and a fluid warming cartridge 422. The fluid conditioner 420 is configured to connect to the warming cartridge 422 to form the cartridge assembly 419 (as shown in FIG. 4). For example, referring to FIG. 5, the fluid conditioner 420 may have one or more connection members 421 that are configured to connect to one or more connection members 423 of the fluid warming cartridge 422. The connection members 421, 423 of the fluid conditioner 420 and the fluid warming cartridge 422 may be connected by, for example, a snap-fit connection, a friction fit connection, etc. In other embodiments, the fluid conditioner 420 and the fluid warming cartridge 422 may be connected by gluing, ultrasonically welding, or any other suitable means of joining the fluid conditioner and the fluid warming cartridge. In certain embodiments, the cartridge assembly 419 is a single, fully integrated component with combined fluid conditioning and fluid warming functions. In these embodiments, the single, fully integrated component of the cartridge assembly 419 can be, for example, a single injection molded component. In certain embodiments, the cartridge assembly 419 is provided as a fully assembled component of a single or multiuse tubing set. In some embodiments, the fluid conditioner 420 is provided as a fully assembled component of a single or multiuse tubing set (e.g., including the fluid conditioner 420 and tube 841 assembly shown in FIG. 8), and the warming cartridge 422 is provided as an accessory component that can be attached to the fluid conditioner 420 if desired. In such embodiments, the user may configure the tubing set for fluid warming by removing tube 841 (FIG. 8) from the fluid conditioner 420 and connecting the warming cartridge 422 to the fluid conditioner 420.

In certain embodiments, the main unit 102 can sense whether the fluid conditioner 420 has been inserted alone (e.g., without the warming cartridge 422) into the system 100 or the cartridge assembly 419 (that includes the fluid conditioner 420 and warming cartridge 422) has been inserted into the system. For example, the main unit 102 may include one or more sensors (e.g., proximity sensors, mechanical sensors, optical sensors, laser sensors, etc.) that can detect whether the fluid conditioner 420 alone or the cartridge assembly 419 was inserted into the system 100. The control system of the system 100 can then enable the fluid warming function of the system 100 (e.g., the heater assembly 314 shown in FIG. 3) when a warming cartridge 422 is inserted into the system 100 and disable the warming function when a warming cartridge 422 is not inserted into the system 100.

Referring to FIG. 6, during use of the system 100, fluid may be pumped through a first tube 624 of the tubing set and into an inlet port 625 of the fluid conditioner 420. The fluid then flows along a first flow path 626 through an inlet chamber 1053 (FIG. 10) of the fluid conditioner, moves through an outlet port 527 (FIG. 5) of the fluid conditioner 420, and through an inlet opening 528 (FIG. 5) of the fluid warming cartridge 422. The fluid then moves along a first side 1671 (FIGS. 16-18) of the warming cartridge 422 along a fluid path 629, moves through a connector or tube 530, and into a second side 1670 (FIGS. 16-18) of the fluid warming cartridge 422 along a path 631. Subsequently, the fluid exits an outlet opening 532 (FIG. 5) and moves through inlet port 533 (FIG. 5) of an outlet chamber 1054 (FIG. 10) of the fluid conditioner 420, where the fluid moves along a path 636 such that the fluid exits outlet 634 of the fluid conditioner 422 and moves through a tube 635 of the disposable tubing set to a surgical instrument at a surgical site. The connector or tube 530 is shown as having a U-shape, but the connector or tube can take any suitable form that causes the first and second sides of the warming cartridge 422 to be fluidly connected. While the first and second sides of the fluid warming cartridge are shown being fluidly connected by the connector or tube 530, it should be understood that the first and second sides can be fluidly connected without the need for the connector or tube 530. For example, the warming cartridge 422 can have a channel that fluidly connects the first and second sides.

In the illustrated embodiment. the fluid enters the fluid path 629 through the inlet opening 528 (FIG. 5) of the warming cartridge 422 at a lower position relative to the exit of the fluid path 629 at the inlet of the connector or tube 530, and the fluid enters the fluid path 631 at the exit of the connector or tube 530 at a lower position relative to the outlet opening 532 (FIG. 5) of the warming cartridge 422. The enter low, exit high configuration for each of the fluid paths 629, 631 promotes a more uniform, controlled warming by reducing Eddy currents and areas of stagnant flow. While the fluid is shown taking the fluid paths 629, 631 through the warming cartridge 422, it should be understood that the fluid can take any suitable path through the warming cartridge 422.

Inserting the cartridge assembly 419 into the main unit 102 of the system 100 aligns the fluid conditioner 420 with the fluid conditioning assembly 315 (FIG. 3) and the fluid warming cartridge 422 with the heater assembly 314 (FIG. 3). The fluid conditioner 420 may have a handle 442 that allows a user to easily insert the cartridge assembly 419 into the main unit 102.

Figure 7:
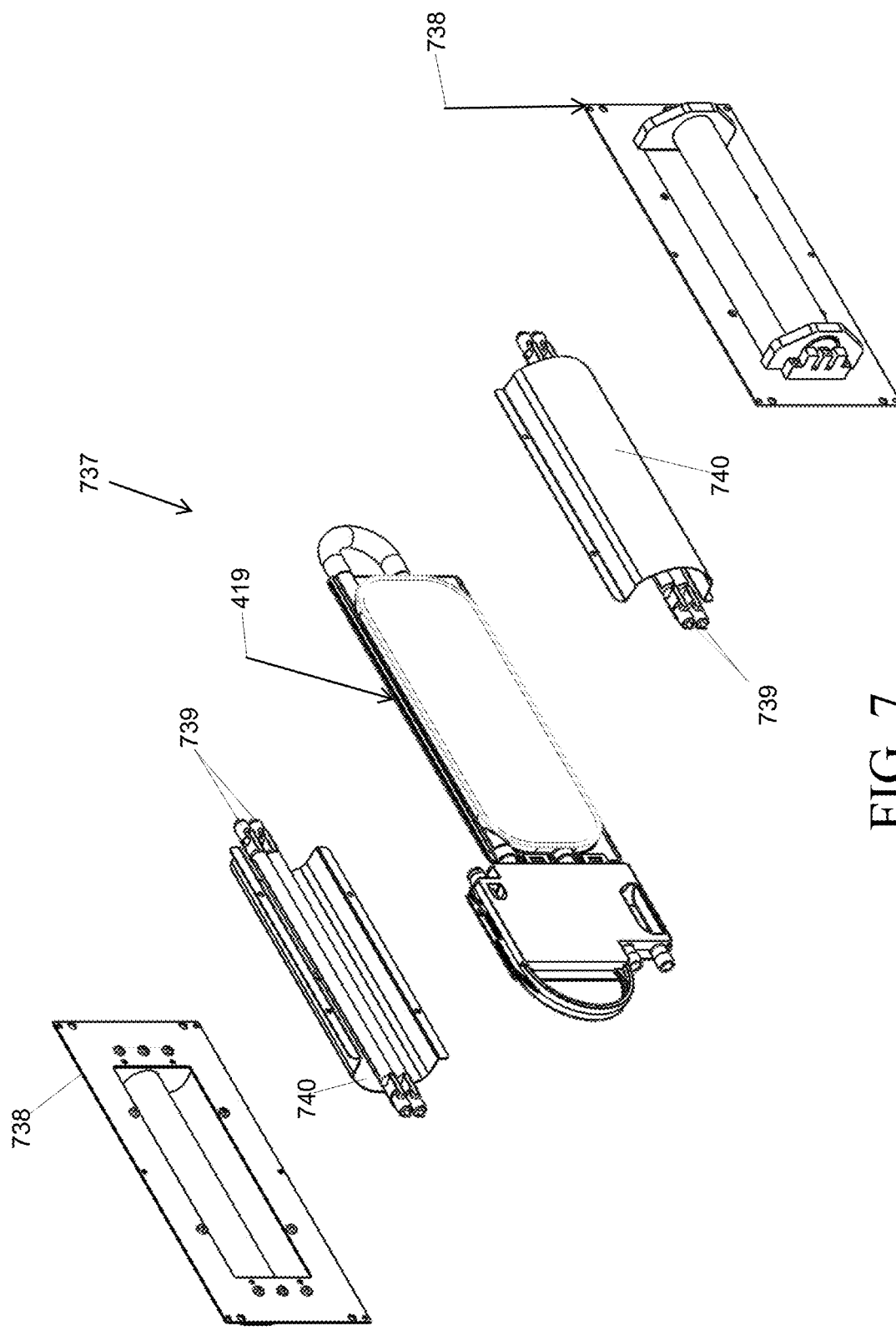
FIG. 7 illustrates an exploded view of an IR lamp subassembly of the heater assembly of FIG. 3 with the cartridge assembly of FIG. 4.

Referring to FIG. 7, the heater assembly 314 (FIG. 3) may include an IR lamp assembly 737 used to warm the fluid moving along the fluid paths 629, 631 (FIG. 6) of the warming cartridge 422. The IR lamp assembly 737 may include a support structure 738, one or more elongated IR lamps with IR reflective coatings 739 disposed on each side of the warming cartridge 422, and a parabolic reflector 740 disposed on each side of the warming cartridge 422 such that the parabolic reflector 740 focuses the IR energy on the fluid paths. The heater assembly 314 may, however, utilize other types of IR lamps such as bulbs, rings, panels, circular modules, or any other suitable forms that are capable of warming fluid moving through the warming cartridge 422 or any other cartridge, tube, or vessel capable of exposing the fluid to IR lamps.

Figure 8:
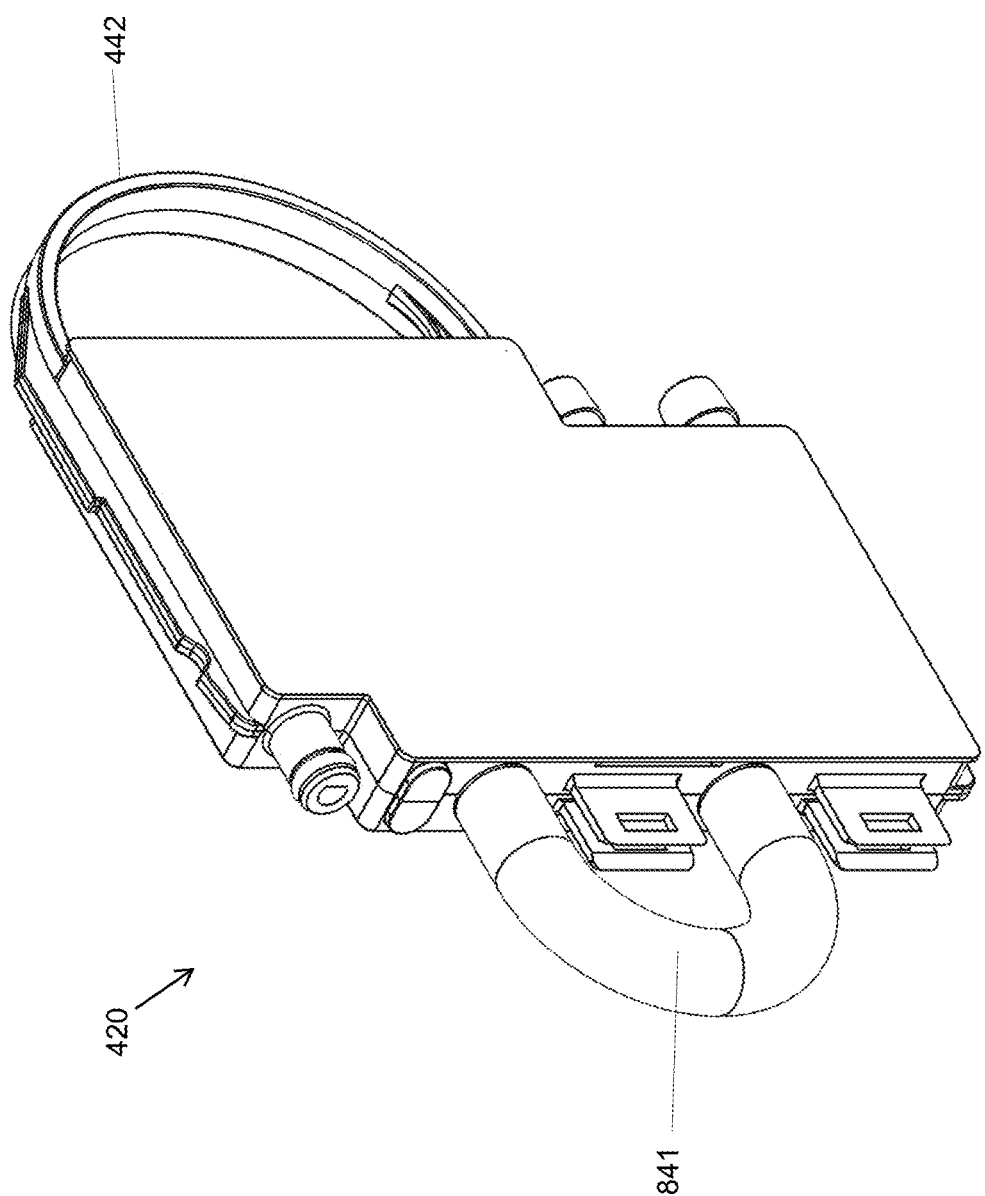
FIG. 8 illustrates another exemplary embodiment of a fluid conditioner for insertion into a fluid conditioning assembly of a fluid management system.

Referring to FIG. 8, in some embodiments, fluid warming may not be desired or necessary during a procedure. In these embodiments where fluid warming cartridge 422 is not necessary, a connector or tube 841 is used to connect the inlet chamber 1053 (FIG. 10) and the outlet chamber 1054 (FIG. 10) of the fluid conditioner 420. While the inlet and outlet chambers are shown being fluidly connected by the connector or tube 841, it should be understood that the inlet and outlet chambers can be fluidly connected without the need for the connector or tube 841. For example, the fluid conditioner 420 can have a channel that fluidly connects the inlet and outlet chambers.

In an alternative embodiment, rather than utilizing the connector or tube 841, the fluid conditioner 420 may be included in a cartridge assembly that has a pulse damping component (not shown) that is similar in construction to the warming cartridge 422 described below with reference to FIGS. 14-18, but the fluid damping component is not used for fluid warming. For example, the pulse damping component may include a rigid body (e.g., similar to rigid body 1472 shown in FIGS. 14-18) and flexible side sheets (e.g., similar to flexible side sheets 1473, 1474 shown in FIGS. 14-18), where the rigid body and flexible side sheets at least partially define a fluid path that connects the inlet chamber 1053 (FIG. 10) of the fluid conditioner 420 to the outlet chamber 1054 (FIG. 10) of the fluid conditioner 420. In alternative embodiments, the pulse damping component may comprise a flexible vessel or channel without a rigid body, in which the flexible vessel or channel defines a fluid path that fluidly connects to the inlet chamber 1053 (FIG. 10) and the outlet chamber 1054 (FIG. 10) of the fluid conditioner 420. In any of the embodiments described above, the flexible vessel or channel is capable of expanding and contracting to dampen the fluid pulsations. That is, the flexible vessel or flexible side sheets can expand and contract to reduce pulsations of the fluid as pressure of the fluid moving through the conduit fluctuates. This damping of the fluid pulsations facilitates steady distention and good visualization during a surgical procedure. The fluid conditioner 420 and pulse damping component can be connected by any suitable means, such as, for example, any means discussed in the present application regarding the connection of the fluid conditioner 420 and the fluid warming cartridge 422. In certain embodiments, the fluid conditioner and pulse damping component can be included in an integrated cartridge assembly where the fluid conditioner 420 and fluid damping component are included in a single cartridge. In certain embodiments, the pulse damping component with a rigid body and flexible side sheets or the flexible vessel or channel used for pulse damping may not be connected to fluid conditioner 420, but instead be connected in the tubing set between the outlet port 634 (FIG. 10) and the surgical site.

Figure 9:
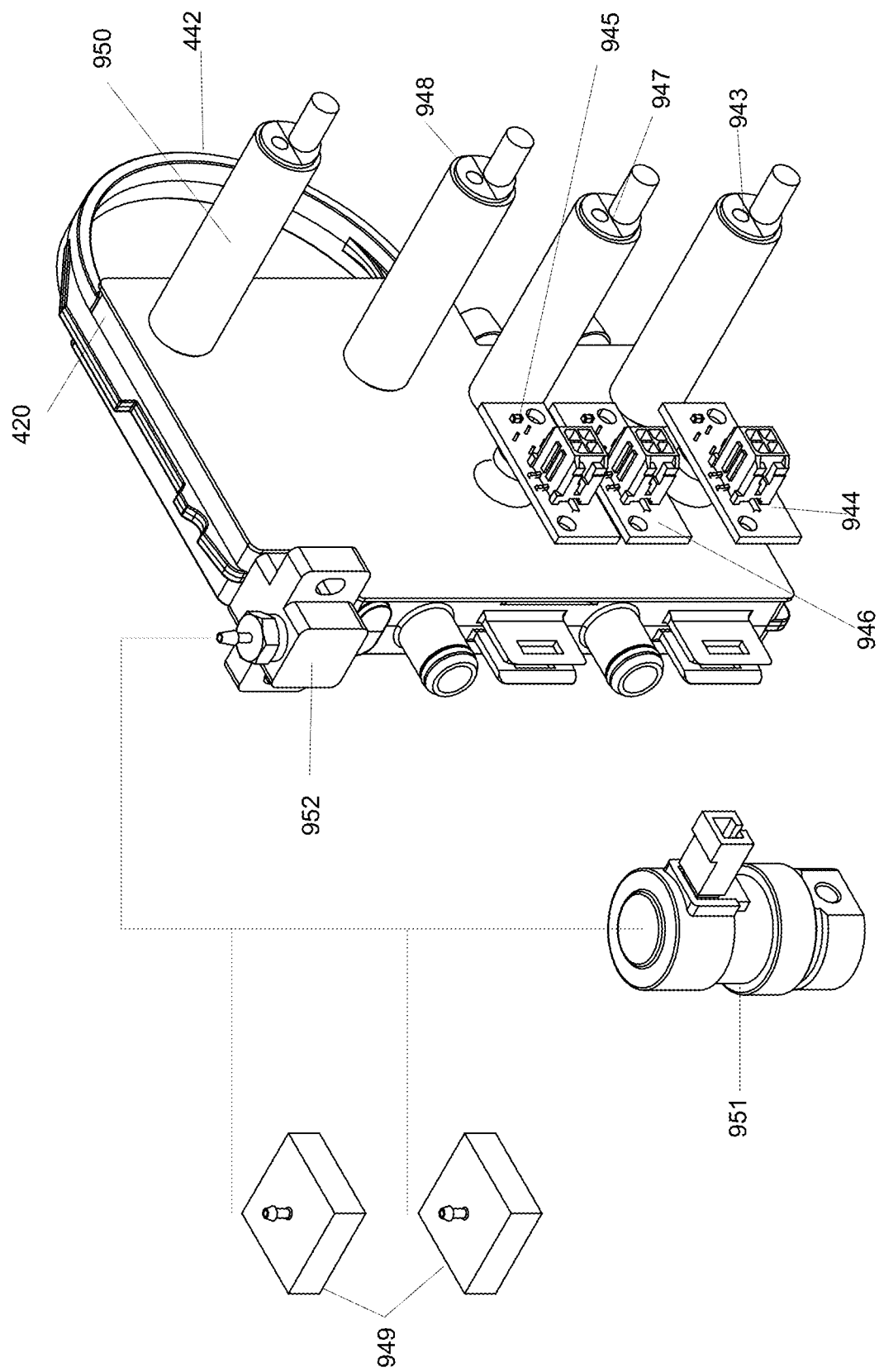
FIG. 9 illustrates an exemplary alignment between the fluid conditioner of FIG. 5 and the fluid conditioning assembly of FIG. 3.

Referring to FIG. 9, the fluid conditioner 420 is configured to connect or align with one or more non-contact sensors (e.g., sensors 943-950) of the fluid conditioning assembly 315 such that the sensors can sense one or more characteristics of the fluid without contacting the fluid. For example, the fluid conditioning assembly 315 may include one or more fluid presence sensors (943, 947, 948, 950), one or more fluid temperature sensors (944, 945, 946), and a port 1062 (FIG. 10) that connects to one or more pressure sensors 949 located in the main unit 102. The port 1062 (FIG. 10) that connects to one or more pressure sensors 949 may also connect to a solenoid valve 951 for expelling excess air that has accumulated in the fluid conditioner 420. The pressure sensors 949 and the solenoid valve 951 may be connected to the port 1062 by one or more tubes or conduits and connection component 952. The control system of the fluid management system 100 may be configured to at least partially control the pressurization of the fluid by pump 212, the warming of fluid by the heater assembly 314, and the expelling of air from the fluid conditioner 420 based on the interface between the fluid conditioning assembly 315 (FIG. 3) and the fluid conditioner 420.

Figure 10:
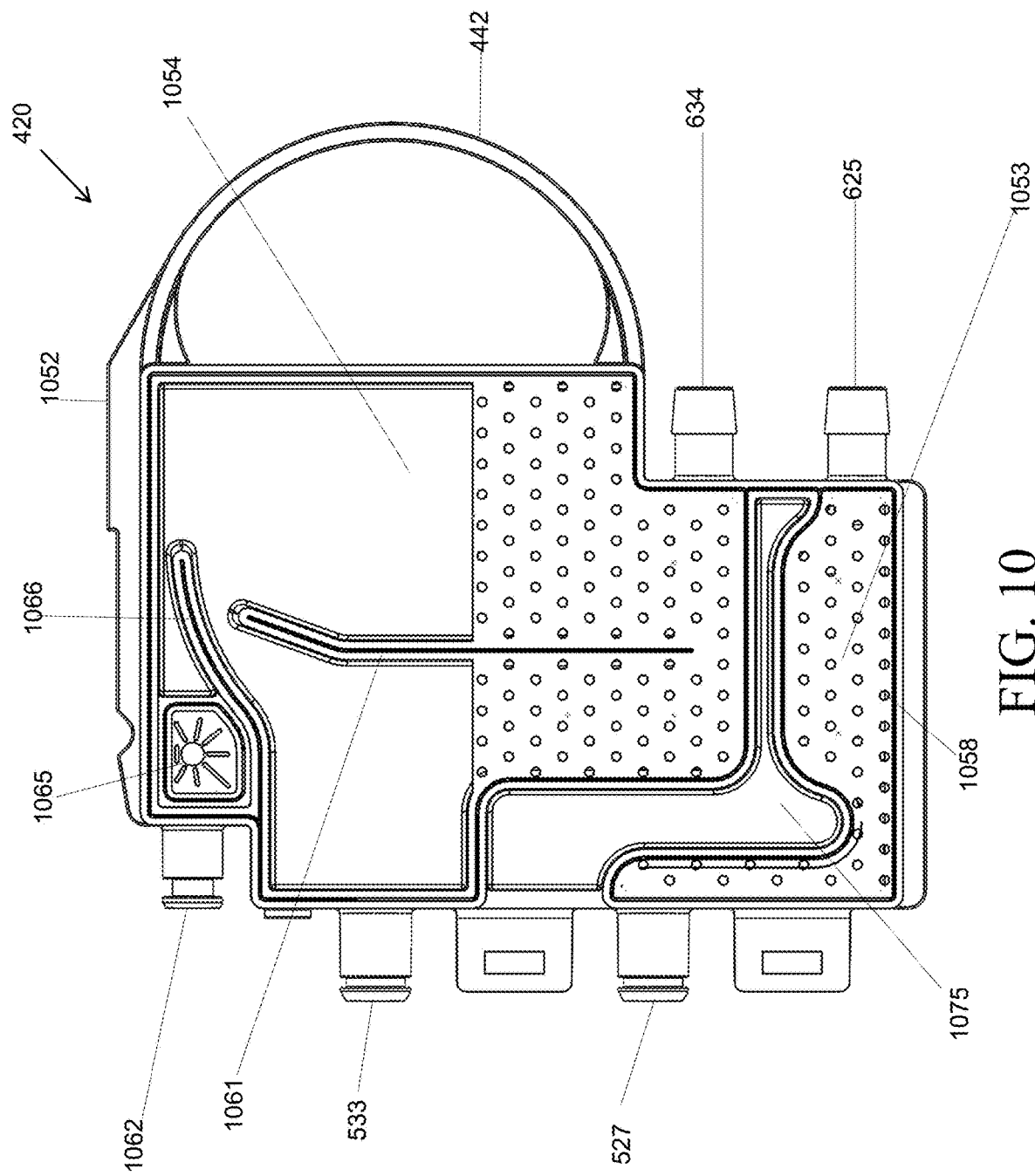
FIG. 10 illustrates a cross-sectional view of an exemplary embodiment of a fluid conditioner for the cartridge assembly of FIG. 4.
Figure 11:
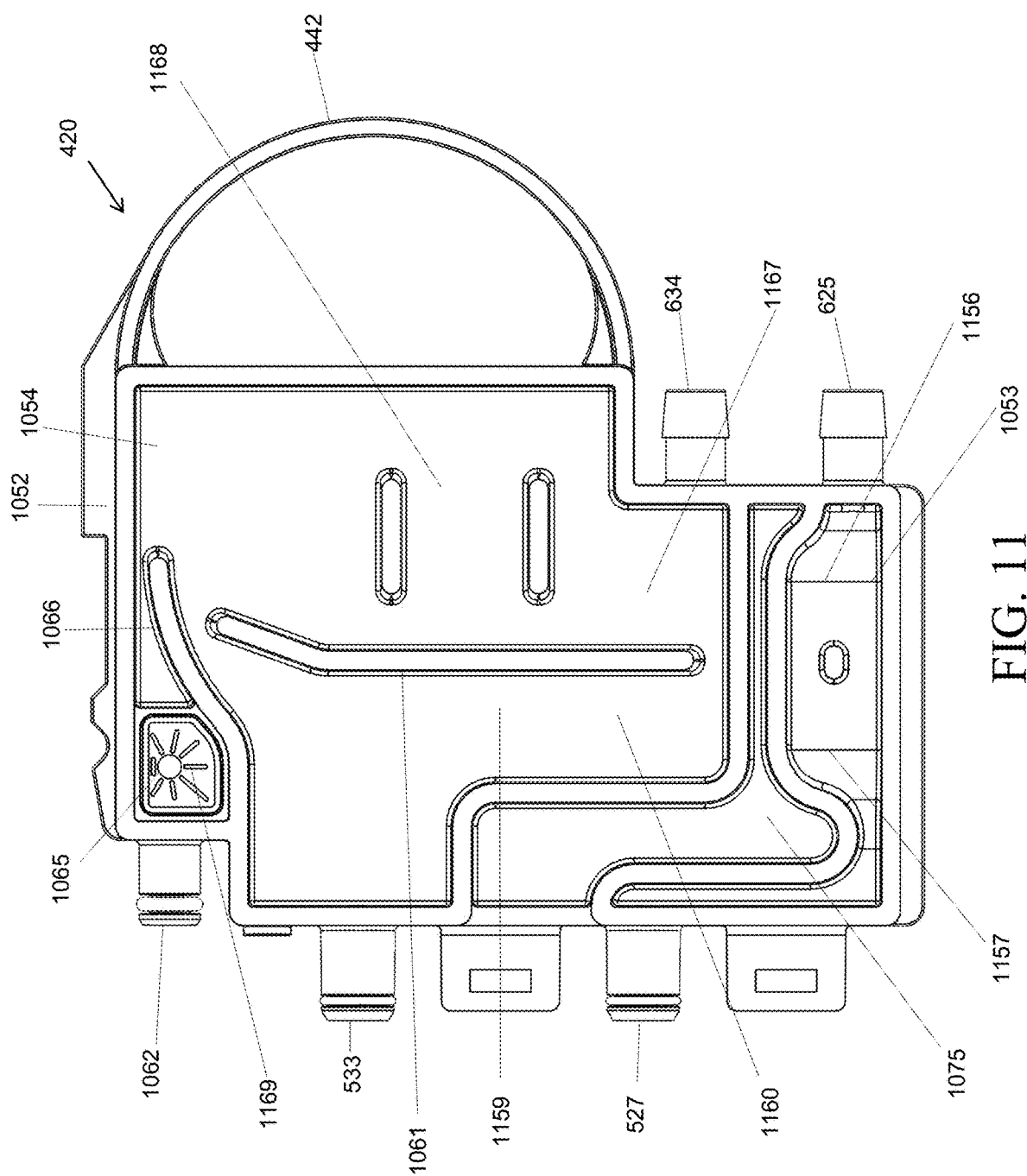
FIG. 11 illustrates the fluid conditioner of FIG. 10 showing locations of the fluid conditioner that are aligned with sensors of the fluid conditioning assembly of FIG. 3.
Figure 12:
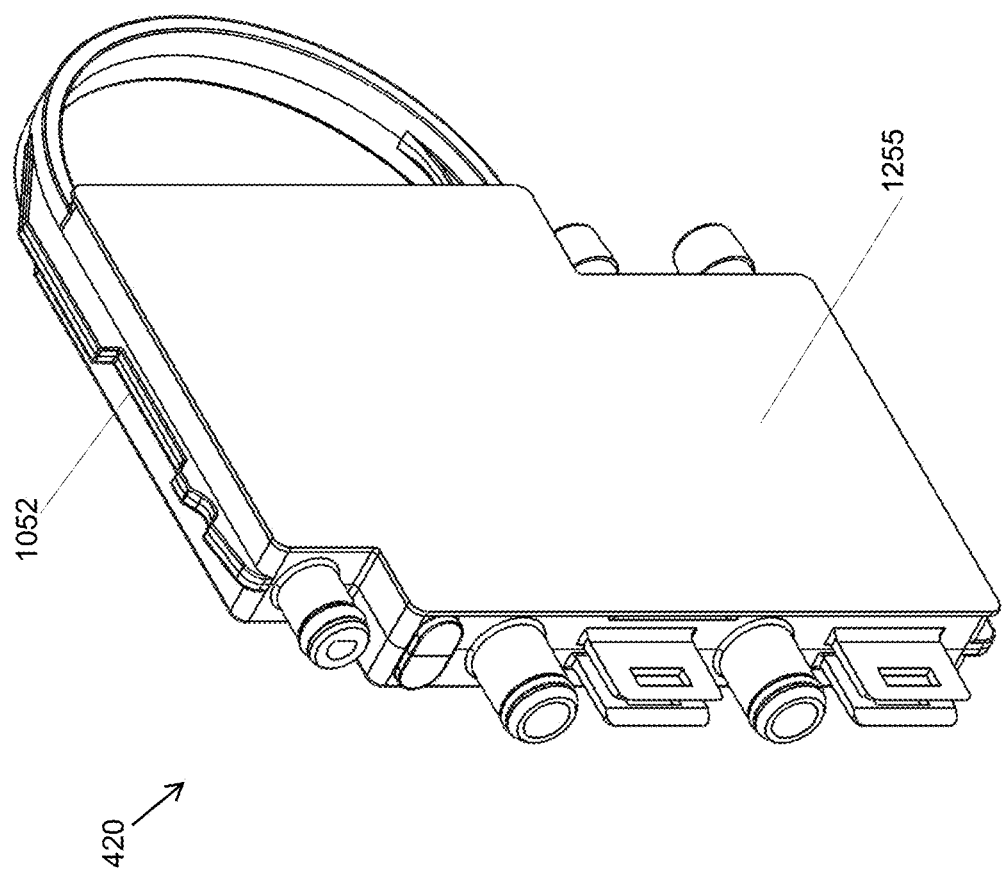
FIG. 12 illustrates a perspective view of the fluid conditioner of FIG. 10.
Figure 13:
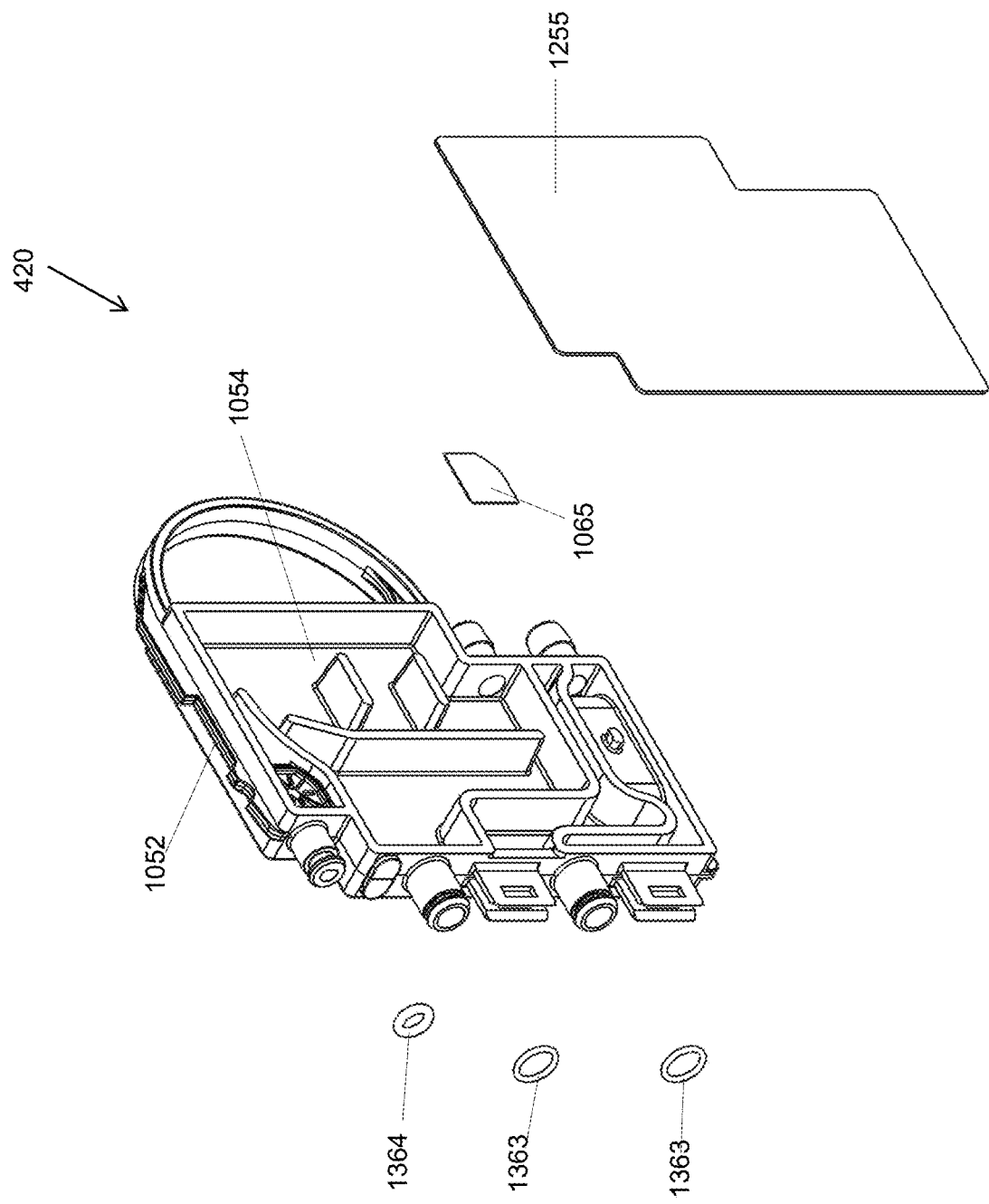
FIG. 13 illustrates an exploded perspective view of the fluid conditioner of FIG. 10.

Referring to FIGS. 10 through 13, an exemplary embodiment of the fluid conditioner 420 may include a rigid body 1052 that defines a first or inlet chamber 1053 and a second or outlet chamber 1054. In some embodiments, fluid conditioner 420 may include a fully or partially enclosed middle chamber 1075 located between the inlet chamber 1053 and the outlet chamber 1054 to provide a separation gap between walls of the inlet and outlet chambers. This separation gap created by the middle chamber 1075 prevents heat transfer between incoming and outgoing fluid that would occur if the inlet chamber 1053 shared a common wall with the outlet chamber 1054. The rigid body 1052 can be, for example, an injection molded body. Referring to FIGS. 12 and 13, the fluid conditioner 420 may also include a film 1255 that is connected to the rigid body 1052 to further define and enclose the chambers 1053, 1054 to create flow paths. The film 1255 can be connected to the rigid body 1052 by gluing, laser welding, ultrasonic welding, or any other suitable means. The film 1255 is configured to allow one or more sensors of the sensing assembly 315 (FIG. 3) to sense one or more characteristics of the fluid moving through the inlet and outlet chambers 1053, 1054 without contacting the fluid. The film 1255 can be, for example, a plastic film. In alternative embodiments, the fluid conditioner 420 does not include the film 1255, but rather the fluid conditioner 420 is a rigid vessel that is configured to allow one or more sensors of the sensing assembly 315 (FIG. 3) to sense one or more characteristics of the fluid without contacting the fluid. In some of these embodiments, a portion of the rigid vessel that aligns with the sensors of the sensing assembly can have a reduced thickness relative to the remainder of the fluid vessel that allows the sensors to sense characteristics of the fluid. In the embodiments mentioned above, the inlet chamber 1053 may have an inlet port 625 and an outlet port 527, and the outlet chamber 1054 may have an inlet port 533 and an outlet port 634. Outlet port 527 and inlet port 533 can have O-rings (e.g., O-rings 1363 shown in FIG. 13) for making water-tight connections. In certain embodiments, the inlet port 625 and outlet port 634 can have barbed and/or glued portions for connecting to fluid tubing.

Referring to FIGS. 9 through 11, the fluid inlet chamber 1053 is aligned with a fluid presence sensor 943 that targets area 1156 and a fluid inlet temperature sensor 944 that targets area 1157. Operation of the pump 212 (FIG. 2) causes fluid to flow from a fluid supply bag or container through inlet port 625 into the inlet chamber 1053. The inlet chamber 1053 may have a protruding wall 1058 that causes a section of the chamber to become thin or shallow, which mitigates air bubble stagnation by causing laminar flow through this section. The fluid presence sensor 943 verifies that fluid is present in the inlet chamber 1053 and, therefore, can be used by the system 100 to monitor performance and identify any problems. For example, if the pump is operating, but fluid presence sensor 943 is not detecting fluid, the control system may notify the user to check for a disconnected tubing line or possible occlusions of the fluid path between the fluid containers and the fluid conditioner 420, such as, for example, kinked tubing or closed clamps.

The fluid temperature sensor 944 may have several functions. For example, in embodiments in which the heater assembly 314 is used to warm the fluid to a desired temperature (e.g., a temperature inputted by the user or a default system temperature), fluid temperature sensor 944 allows the control system to monitor the temperature of the fluid entering the warming cartridge 422 such that the control system can adjust the amount of IR energy provided by the heater assembly 314 to cause the fluid entering the outlet chamber 1054 of the fluid conditioner 420 to be at the desired temperature. In addition, if the user has hung pre-warmed fluid bags with fluid temperatures at high, potentially unsafe levels, the control system may disable the pump 212 and/or the heater assembly 314, and then notify the user that such operations will remain disabled until the fluid temperature has sufficiently cooled or the fluid supply bags or containers have been changed. Alternatively, the control system may continue operation while increasing air flow through the heater assembly 314 to sufficiently cool the fluid before it reaches the outlet chamber 1054 of the fluid conditioner 420. If such attempt fails, the fluid outlet temperature sensor 945 that targets area 1159 and/or fluid high-limit or thermal cutoff temperature sensor ("TCO Sensor") 946 that targets area 1160 will cause the control system to disable the fluid pumping and warming operations until the temperature of the fluid has sufficiently cooled. Additionally, assuming an operating room environment where the user has enabled the fluid warming function, the temperature sensor 944 can be used to notify the user if the temperature of the fluid entering the fluid conditioner 420 may be too cool to achieve the desired fluid temperature. Finally, the control system can also determine if there is a problem with heater assembly 314. For example, if the temperature sensor 944 detects that the temperature entering inlet chamber 1053 is acceptable, but sensor 945 detects that the temperature of the fluid did not achieve the desired fluid temperature, the control system will notify the user that there may be a problem with the heater assembly 314.

Still referring to FIGS. 9 through 11, the outlet chamber 1054 of the fluid conditioner 420 may be designed to separate air bubbles from the fluid being delivered to the surgical site that may have been caused by fluid bag changes or the fluid warming process. For example, the fluid outlet chamber 1054 may have a substantially vertical wall or baffle 1061 (FIGS. 10-11) that causes air bubbles to separate from the fluid when the fluid engages the wall. As shown in the illustrated embodiment, the baffle 1061 may not be connected to a perimeter of the outlet chamber 1054.

In certain embodiments, the outlet chamber 1054 is designed to facilitate fluid pressure monitoring and control via pressure sensors 949 located in the main unit 102. For example, insertion of the fluid conditioner 420 may cause a connection between the outlet chamber 1054 of the fluid conditioner 420 with pressure sensors 949 located in main unit 102 via pressure port 1062 and one or more tubes or conduits (not shown). As the pressure of the pocket of air trapped between the fluid in outlet chamber 1054 and the pressure sensors 949 is indicative of the fluid pressure, the control system monitors the fluid pressure being read by the pressure sensors 949 in relation to the setpoint fluid pressure, and the control system adjusts the speed of the pump 212 to achieve and maintain the setpoint fluid pressure. To ensure pressure monitoring accuracy and guard against over pressure conditions, the control system constantly compares the readings of the pressure sensors 949 to ensure they are the same excepting normal tolerances for such sensors. Independent of software, the control system may employ redundant hardware circuits that disable or reverse the pump 212 if the fluid pressure exceeds the maximum allowable pressure for the procedure.

To ensure that the pressure sensors 949 remain isolated from the fluid, the outlet chamber 1054 is designed not only to maintain a pocket of air between the pressure sensors 949 and the fluid, but also to include a hydrophobic filter 1065 that acts as a fluid barrier. Such hydrophobic filter 1065 may also act as a bacterial barrier to preserve the sterility of the fluid. To protect the hydrophobic filter 1065 from coming into contact with fluid entering the outlet chamber 1054 under turbulent or high flow conditions, outlet chamber 1054 may include an arcing wall or barrier 1066 that, in combination with the baffle 1061, ensures that any fluid going over the top of the baffle 1061 is directed away from the hydrophobic filter. The pressure port 1062 may also include an O-ring 1364 (FIG. 13) for making a fluid tight connection.

In addition to the presence sensor 943 for the inlet chamber 1053, there may be at least three additional fluid presence sensors (947, 948, 950) that are aligned with the outlet chamber 1054. The fluid presence sensor 947 ("fluid outlet sensor") located at the outlet port 634 of the outlet chamber 1054 targets area 1167 and is used to ensure proper flow of fluid through the fluid conditioner 420. For example, if the control system detects that the pump 212 is pumping fluid, but the fluid outlet sensor 947 is not detecting fluid, the control system may disable the pump 212 and/or notify the user of a problem with the system 100. In addition, if the fluid warming function is present and enabled, the fluid outlet sensor 947 ensures that the fluid warming cartridge 422 is full of fluid before the fluid warming function is commenced or continued.

The fluid presence sensor 948 located at the midpoint of the outlet chamber 1054 targets area 1168 and is used to control the amount of air that has accumulated in the outlet chamber 1054. During normal operation, the fluid level in the outlet chamber 1054 should be maintained proximate the midpoint of the outlet chamber. If fluid is not detected by the fluid midpoint sensor 948, and the pressure sensors 949 are reading a positive pressure, the control system opens the solenoid valve 951 to expel excess air that has accumulated in the outlet chamber 1054 until the fluid midpoint sensor 948 detects fluid (i.e., until the fluid level has increased to the midpoint of the outlet chamber 1054). To avoid materially impacting the pressure monitoring and control function of the system 100, the solenoid valve 951 may have a small orifice or restriction so that the excess air in the outlet chamber 1054 bleeds off at a low, controlled rate. Alternatively, the system 100 can average the fluid pressure readings so that the effects of any minor pressure decreases associated with the air expelling function are mitigated, or the system 100 can ignore the fluid pressure readings while the solenoid valve 951 remains open.

The fluid presence sensor 950 located proximate the pressure port 1062 of the outlet chamber 1054 targets area 1169 to ensure proper operation of the pressure sensing function of the system 100, which requires that a pocket of air be maintained between the fluid in the outlet chamber 1054 and the pressure sensors 949 of the sensing assembly 315. The pressure of this pocket of air, which is monitored by the pressure sensors 949, increases and decreases as a result of increases and decreases in the fluid pressure. If the fluid level reaches the hydrophobic filter 1065 that protects the pressure port 1062, the control system may lose the ability to accurately monitor the fluid pressure. Accordingly, if the fluid pressure port sensor 950 senses fluid, the control system may disable pump 212.

Referring to FIGS. 6 and 14 through 18, if the system 100 includes a main unit 102 with fluid warming capability, for example when configured for an operating room environment, the fluid conditioner 420 will generally be connected to the fluid warming cartridge component 422. Joining the fluid conditioner 420 and fluid warming cartridge 422 together form cartridge assembly 419 and causes fluid connections to be made between the inlet chamber 1053 (FIG. 10) of the fluid conditioner 420 and the first fluid path 629 (FIG. 6) on a first side 1671 (FIGS. 16-18) of the warming cartridge 422. This connection also causes fluid connections between the second fluid path 631 (FIG. 6) on the second side 1670 (FIGS. 16-18) of the warming cartridge 422 and the outlet chamber 1054 (FIG. 10) of the fluid conditioner 420.

Figure 14:
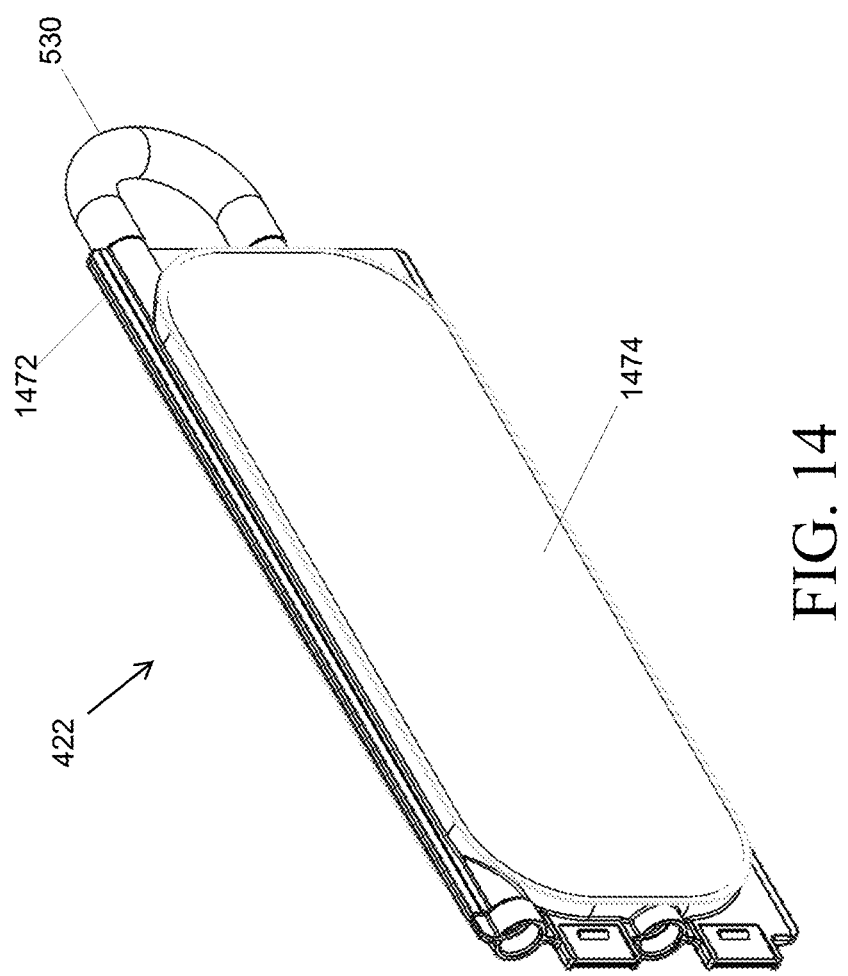
FIG. 14 illustrates a perspective view of an exemplary fluid warming cartridge of the cartridge assembly of FIG. 4.
Figure 15:
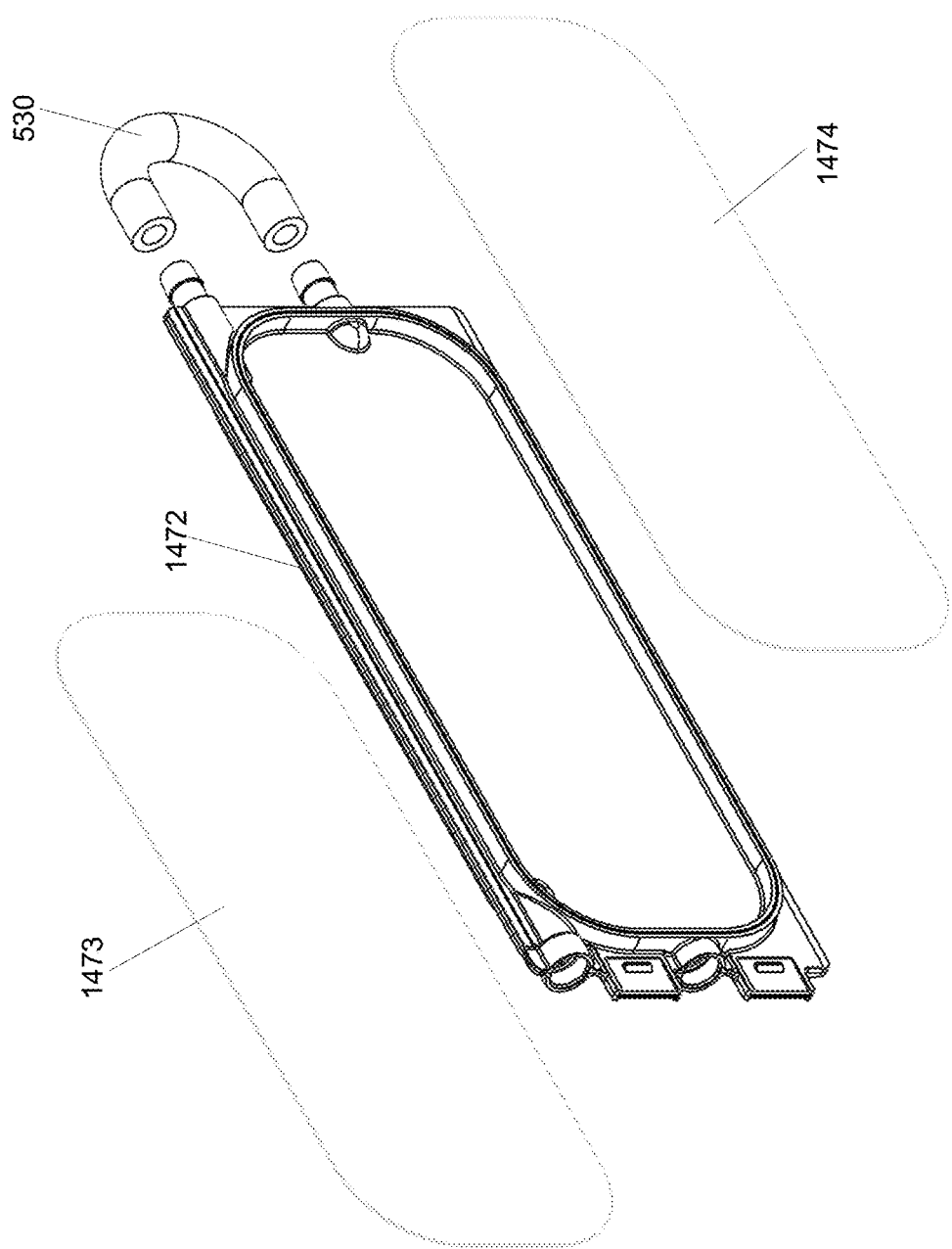
FIG. 15 illustrates an exploded perspective view of the fluid warming cartridge of FIG. 14.
Figure 16:
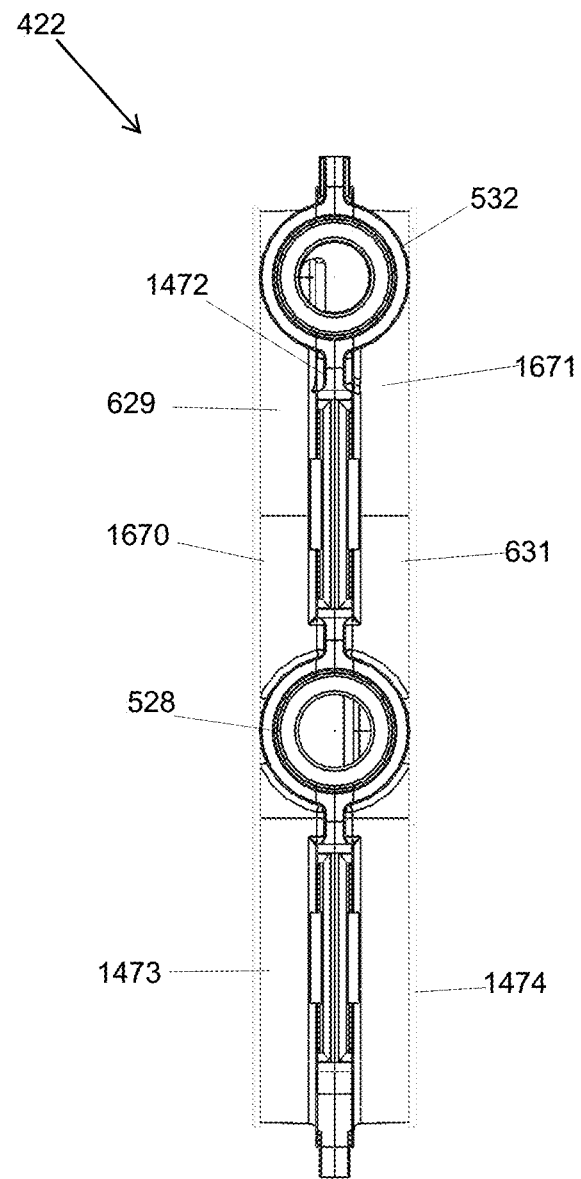
FIG. 16 illustrates a front view of the fluid warming cartridge of FIG. 14 when fluid moving through it is at a low pressure.
Figure 17:
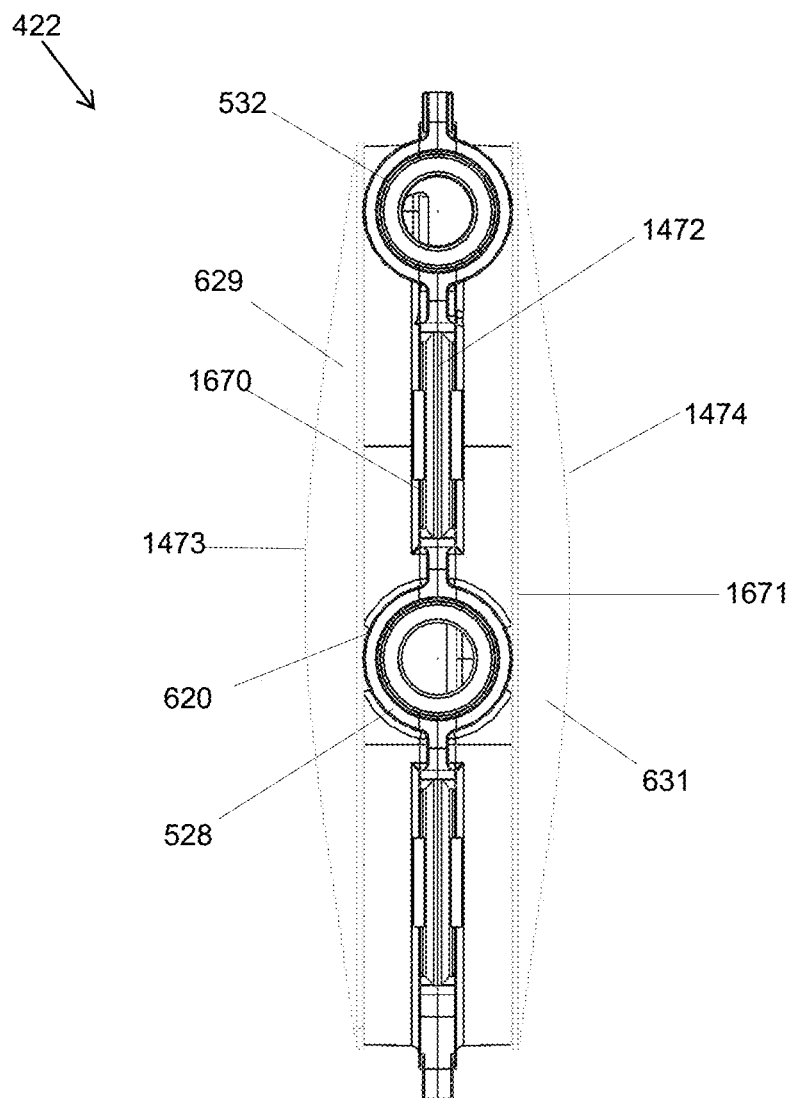
FIG. 17 illustrates a front view of the fluid warming cartridge of FIG. 14 when fluid moving through it is at a high pressure.
Figure 18:
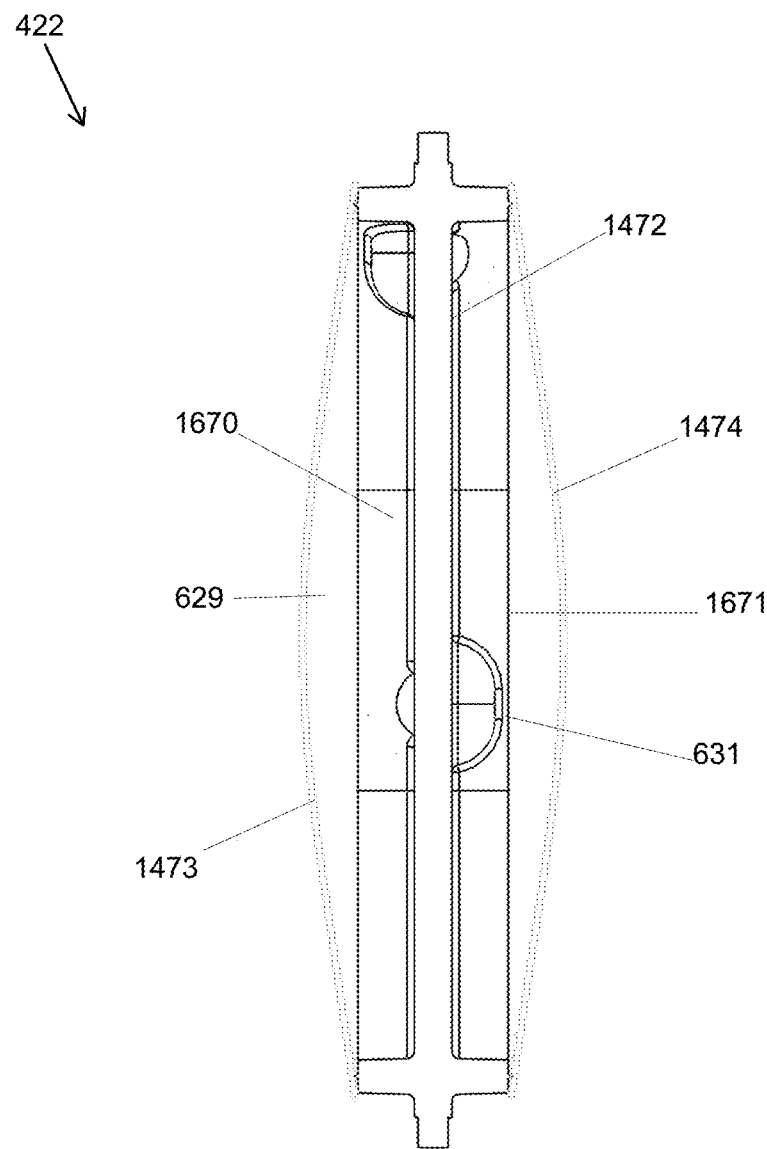
FIG. 18 illustrates a cross-sectional front view of the fluid warming cartridge of FIG. 14 when fluid moving through it is at a high pressure.

The fluid warming cartridge 422 may include a rigid body 1472 (FIGS. 14-18), a first thin flexible sheet 1473 (FIGS. 15-18), and a second thin flexible sheet 1474 (FIGS. 15-18). Referring to FIGS. 16-18, the first flexible sheet 1474 is connected to a first side 1671 of the rigid body 1472 to define the first fluid flow path 629, and the second flexible sheet 1473 is connected to a second side 1670 of the rigid body 1472 to define the second fluid flow path 631. In the illustrated embodiment, the first and second fluid flow paths 629, 631 are connected by a connector or tube 530 (FIGS. 14-15). In other embodiments, the first and second flow paths may be connected by a channel that is integral to the warming cartridge 422. The rigid body 1472 can be, for example, an injection molded body. The flexible side sheets 1473, 1474 can be made of, for example, plastic which is highly transmissive to IR to facilitate the fluid warming function. The rigid body 1472 and the flexible side sheets may be connected by gluing, laser welding, ultrasonic welding, or any other suitable means.

The flexible side sheets 1473, 1474 may be configured to expand and contract to effectively dampen fluid pulsations generated by the pump 212, which allows the fluid delivered to the surgical site to be non-pulsatile. That is, although the system 100 may utilize a peristaltic pump which generates a pulsatile fluid flow, the fluid warming cartridge 422, which is downstream of the peristaltic pump, may include thin, flexible side sheets 1473, 1474 to at least partially define the fluid paths and expand and contract as the pressure of the fluid moving through the warming cartridge fluctuates to dampen the fluid pulsations. This damping of the fluid pulsations facilitates steady distention and good visualization during a surgical procedure.

Referring to FIG. 6, in operation, fluid from the fluid supply bags or containers enters the fluid inlet chamber 1053 (FIG. 10) of the fluid conditioner 420 via port 625, enters the fluid warming cartridge 422, flows through the first elongated section of the fluid path 629 on a first side 1671 (FIGS. 16-18) of fluid warming cartridge 422, exits the first elongated section of the fluid path and enters the second elongated section of the fluid path 631 on a second side 1670 of the fluid warming cartridge via connector 530, exits the fluid warming cartridge 422 and enters fluid outlet chamber 1054 of the fluid conditioner 420, and then exits the fluid outlet chamber 1054 for delivery to the surgical site via port 634.

The system 100 can control fluid temperature by monitoring the difference between the setpoint fluid temperature and the actual outlet fluid temperature sensed by temperature sensor 945 (FIG. 9) to adjust power to the IR lamp assemblies 737 (FIG. 7) in accordance with proportional integral control and scaling, which is based on the actual fluid flow rate and/or the difference between the actual fluid temperature sensed by the temperature sensor 944 aligned with the inlet chamber 1053 of the fluid conditioner 420 and the actual fluid temperature sensed by the temperature sensor 945 aligned with the outlet chamber 1054 of the fluid conditioner 420. Alternatively, other suitable open-loop and closed-loop control systems can be employed, such as, for example, proportional control, integral control, proportion-integral-derivative control, mathematical modelling, predictive function control, error squared control, and bang-bang control.

In addition to the control scheme, the fluid warming efficiency can be enhanced by utilization of thin, flexible side sheets 1473, 1474 (FIG. 15) of the fluid warming cartridge 422, which may be highly transmissive to IR energy and an injection molded rigid body 1472 (e.g., a black injection molded body) that absorbs IR energy from the IR lamp assemblies 737 (FIG. 7) and radiates the IR energy back to the fluid. Additionally, the fluid warming efficiency can be enhanced by the elongated sections of the fluid warming cartridge 422 that define fluid paths 629, 631. The elongated sections of the fluid warming cartridge 422 can facilitate uniform heat distribution by introducing fluid into each section at or below the centerline and exiting fluid from each section at the top of the opposite end such that the fluid moves from a lower position to a higher position as it moves along each of the fluid paths 629, 631.

Figure 19:
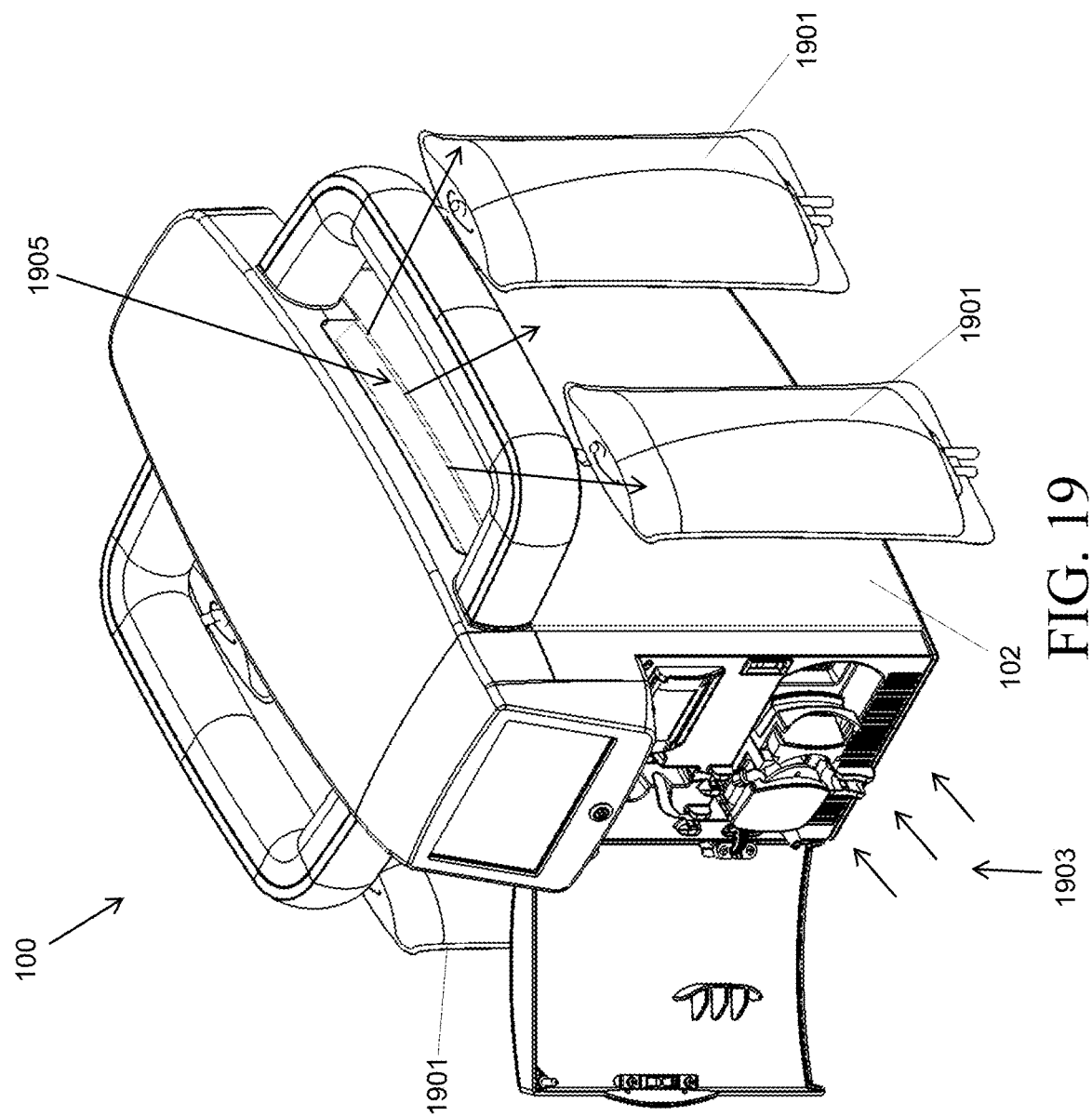
FIG. 19 illustrates an exemplary embodiment of a main unit for the fluid management system of FIG. 1, where the main unit includes an opening to draw air through the heater assembly of the main unit for cooling purposes and another opening to exhaust the resulting warm air onto or near one or more of the fluid supply bags or containers that are hanging from the fluid management system in order to pre-warm the fluid.
Figure 20:
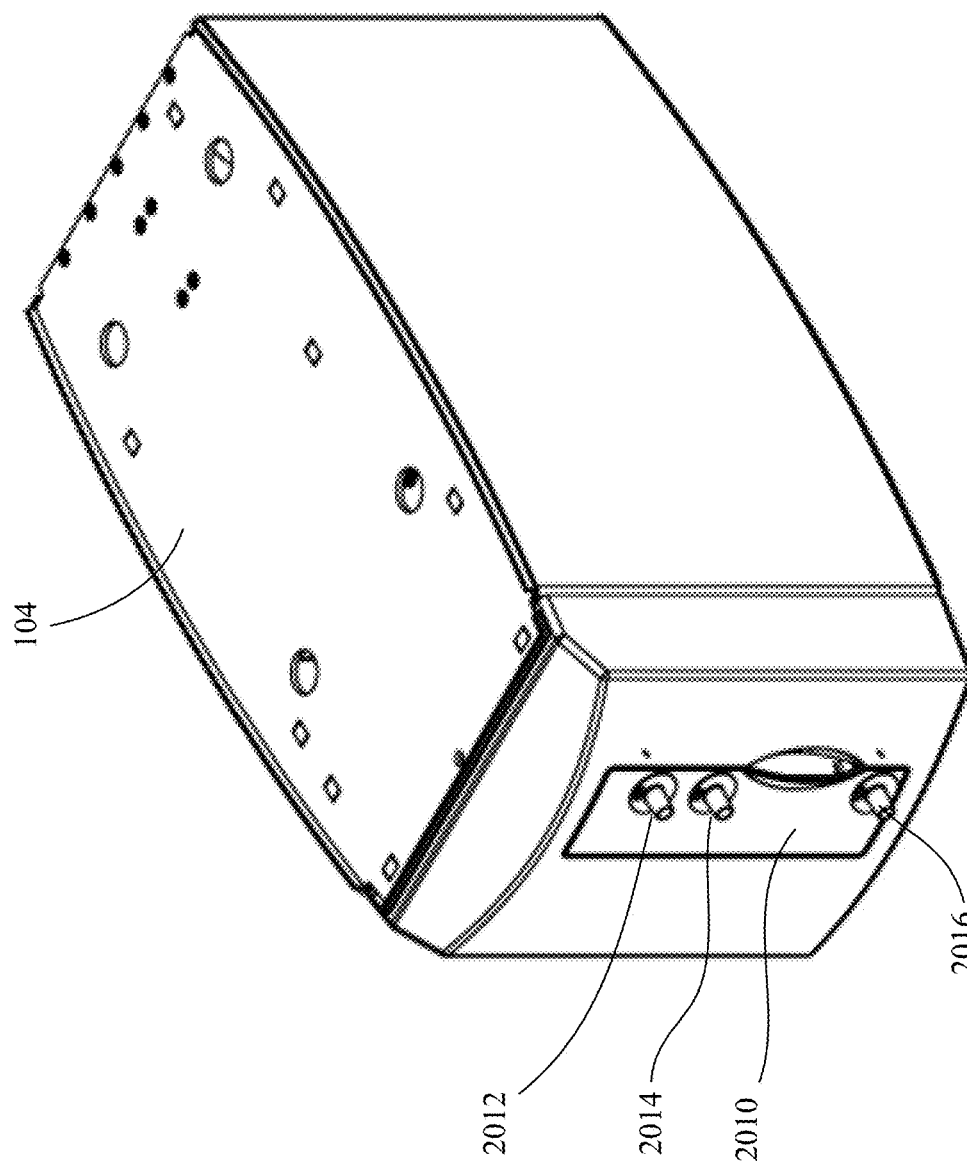
FIG. 20 illustrates a perspective view of an exemplary embodiment of a deficit module and a deficit cartridge for the fluid management system of FIG. 1, where the deficit cartridge is inserted in the deficit module.
Figure 21:
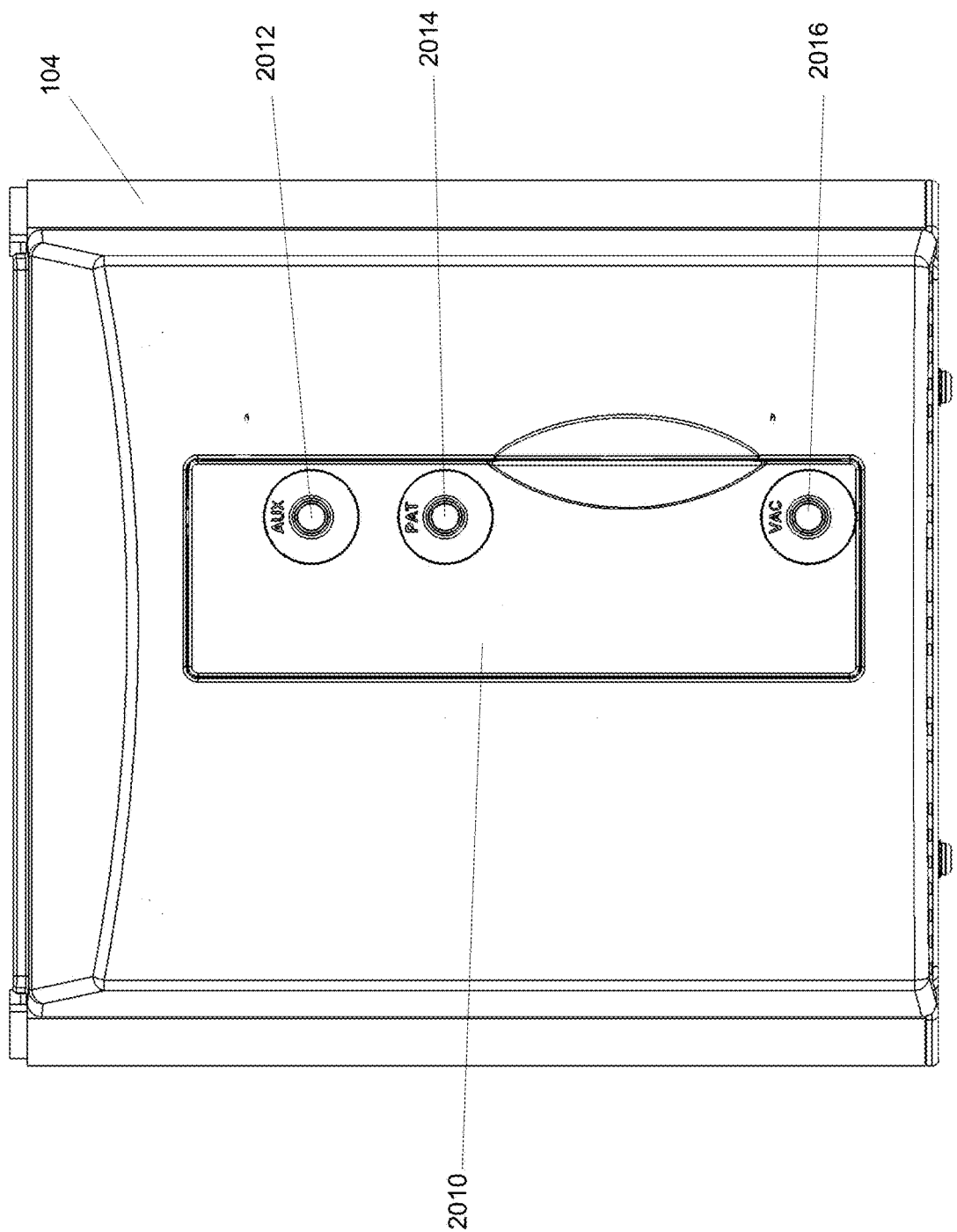
FIG. 21 illustrates a front view of the deficit module and deficit cartridge of FIG. 20.
Figure 22:
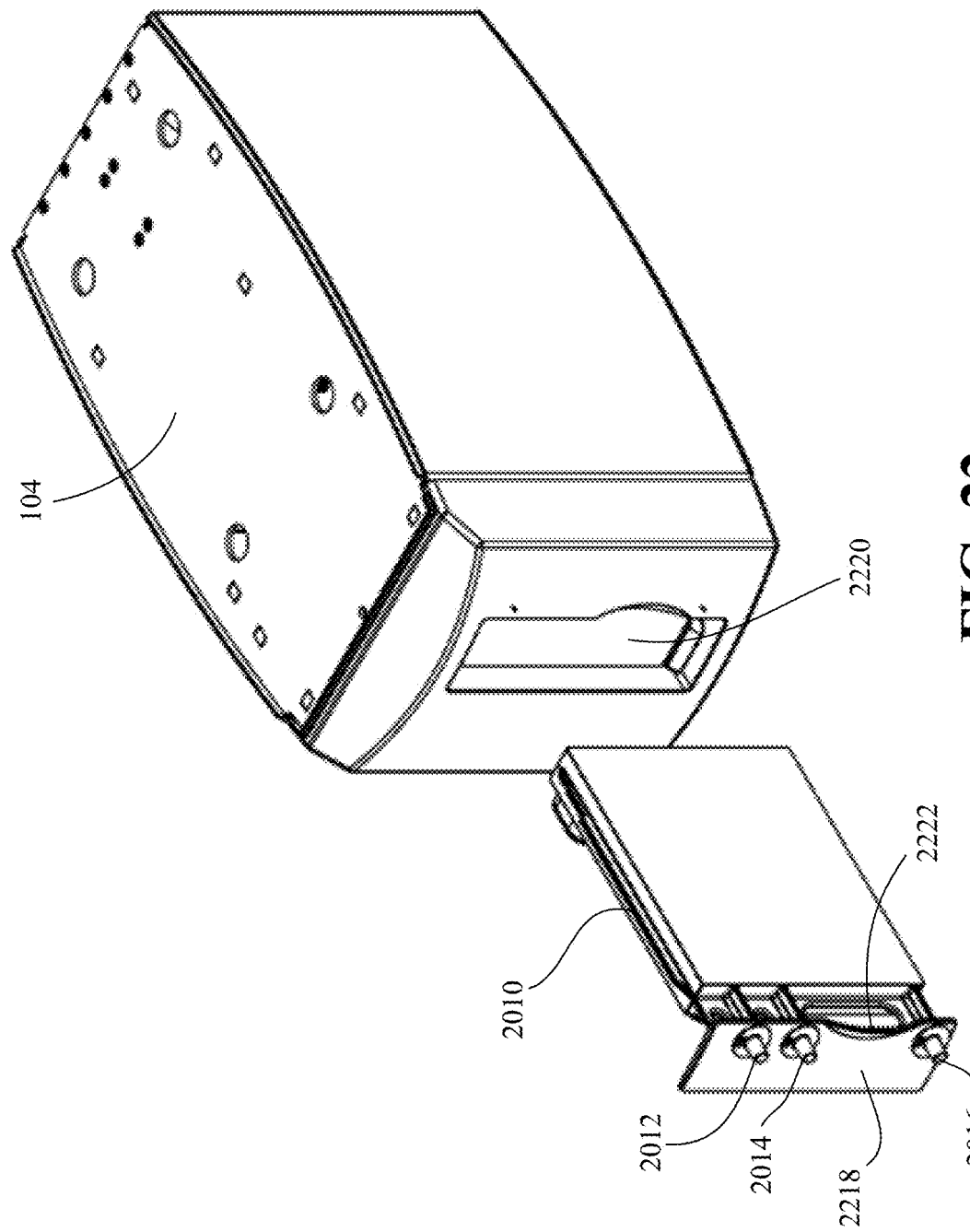
FIG. 22 illustrates a right-side perspective view of the deficit module and deficit cartridge of FIG. 20, where the deficit cartridge is removed from the deficit module.
Figure 23:
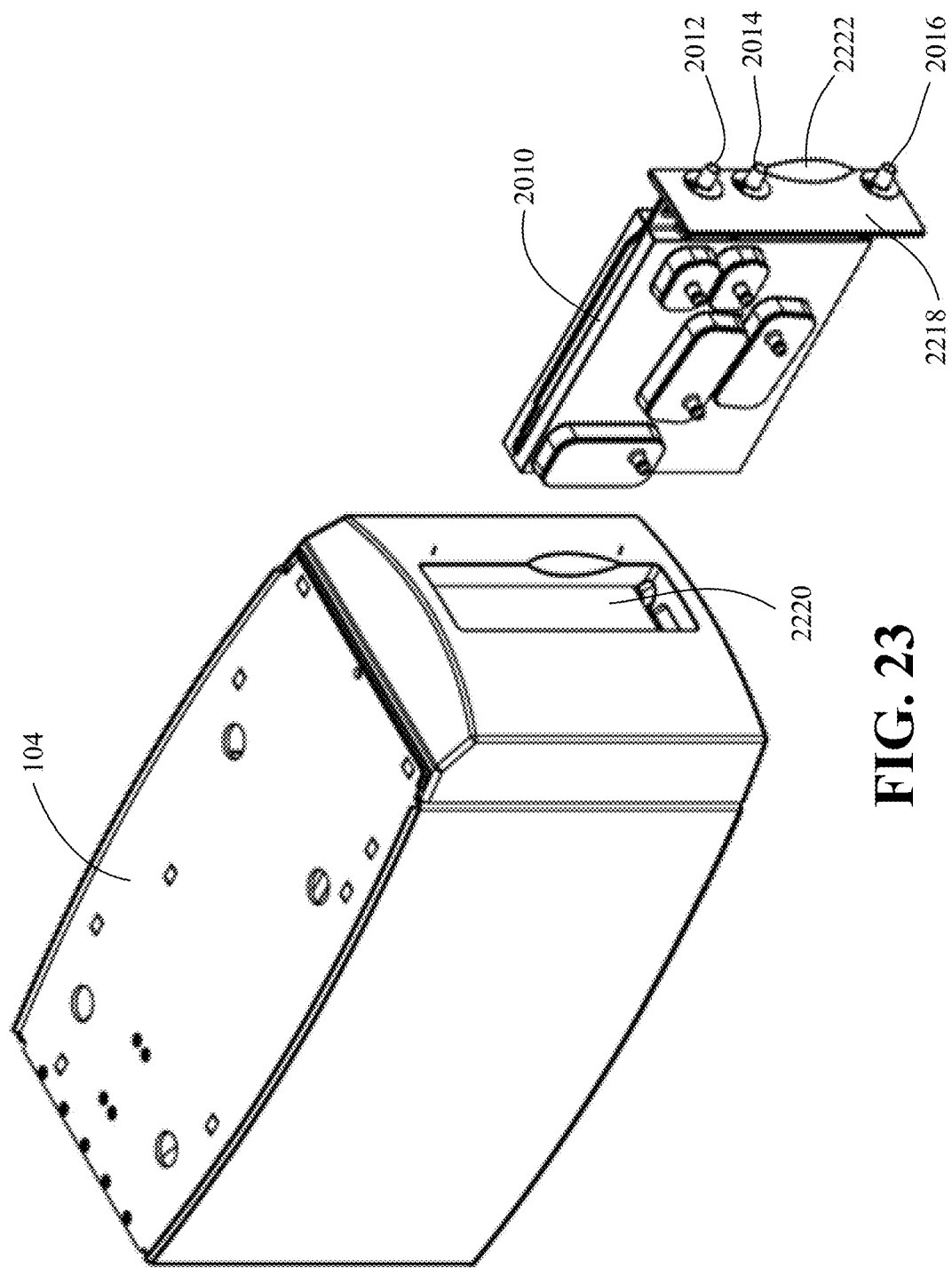
FIG. 23 illustrates a left side perspective view of the deficit module and the deficit cartridge of FIG. 20, where the deficit cartridge is removed from the deficit module.
Figure 24:
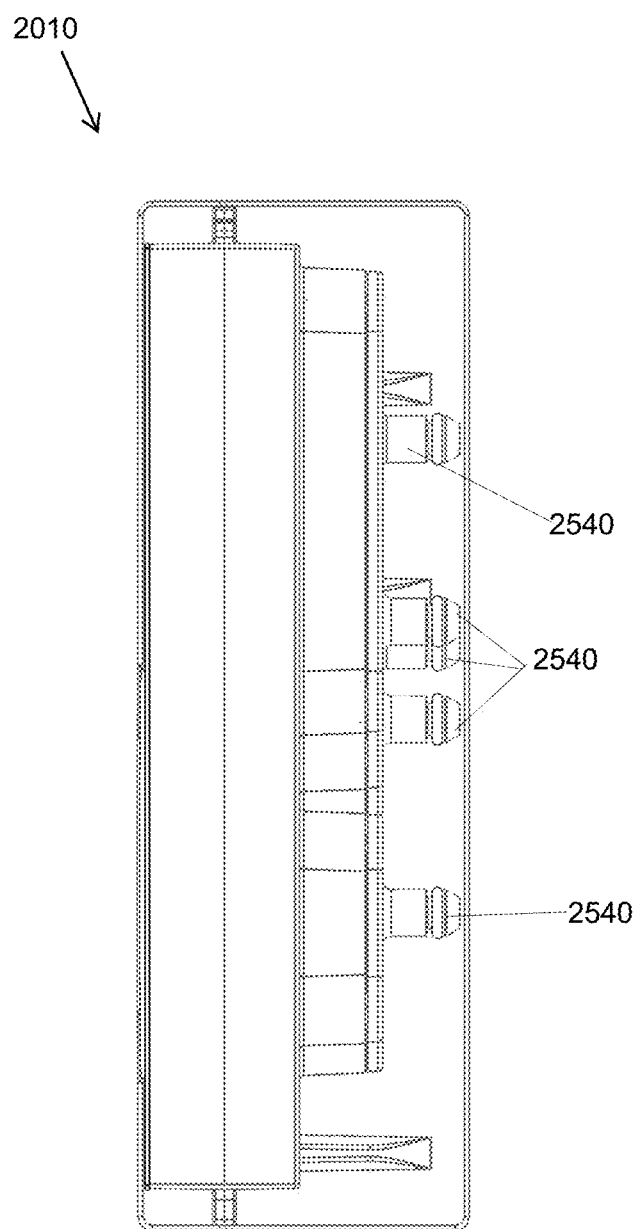
FIG. 24 illustrates a rear view of the deficit cartridge of FIG. 20.

Referring to FIG. 19, in certain embodiments, the fluid warming efficiency of system 100 can also be enhanced by pre-warming of the fluid containers 1901. That is, air intake 1903 allows air to be drawn by fans 316 (FIG. 3) of heater assembly 314 (FIG. 3) into the main unit 102 to cool the heater assembly 314 and the main unit 102 during the fluid warming process, and this air becomes heated as a result of interacting with the heater assembly 314. The heated air is then exhausted by the main unit 102 through exhaust openings 1905 and directed towards the fluid containers 1901 on each side of main unit 102 such that the fluid within the fluid containers is pre-warmed prior to being pumped through the fluid conditioner 420 (FIG. 6) and fluid warming cartridge 422 (FIG. 6).

To guard against overtemperature conditions, the system 100 has low and high limits that disable the IR lamps 739 (FIG. 7) if the fluid temperature exceeds a low safety limit, and disables the IR lamps 739 and the pump 212 if the fluid temperature exceeds a high safety limit. In some embodiments, independent of software, the system 100 employs a hardware circuit that includes the thermal cutoff sensor ("TCO") 946 (FIG. 9) to disable the IR lamps and the pump in an overtemperature condition exceeding the high limit. In some embodiments, the system 100 employs a cooling fan to remove heat to help prevent and/or mitigate overtemperature conditions. The cooling fan may be electronically controlled based on thermistor or other temperature sensor inputs and/or heating algorithm conditions that could lead to overtemperature (e.g. a rapid decrease in flow rate where full heating was required at maximum flow rates).

Figure 7A:
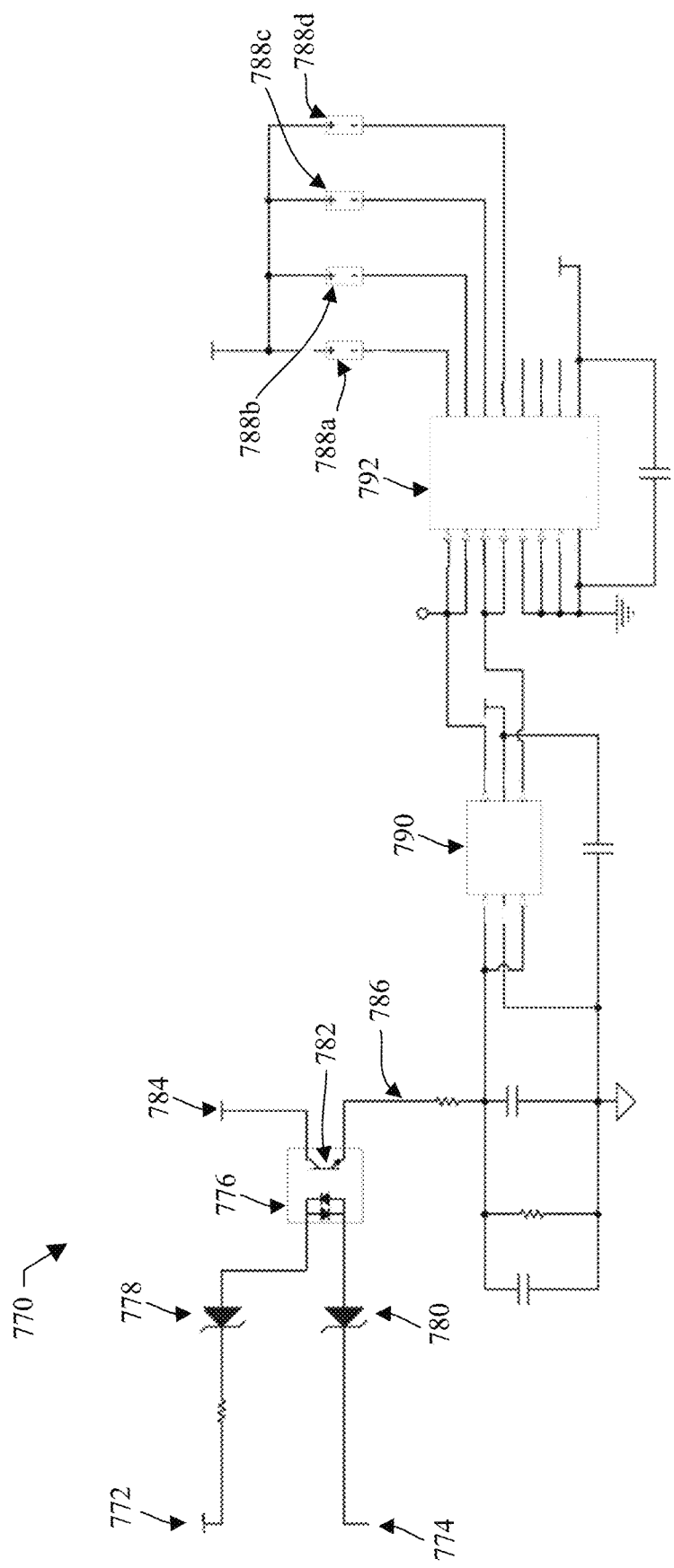
FIG. 7A illustrates an exemplary embodiment of a threshold detector for a crossover circuit.
Figure 7B:
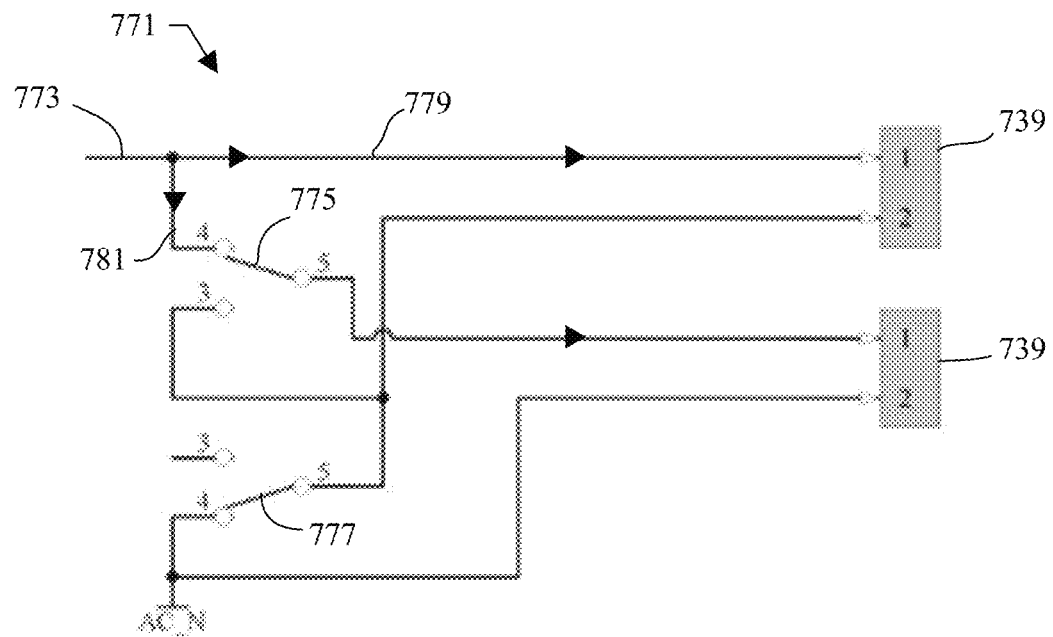
FIG. 7B illustrates an exemplary embodiment of a relay bank for interacting with the crossover circuit of FIG. 7A, where the switches of the relay bank are in a first position.
Figure 7C:
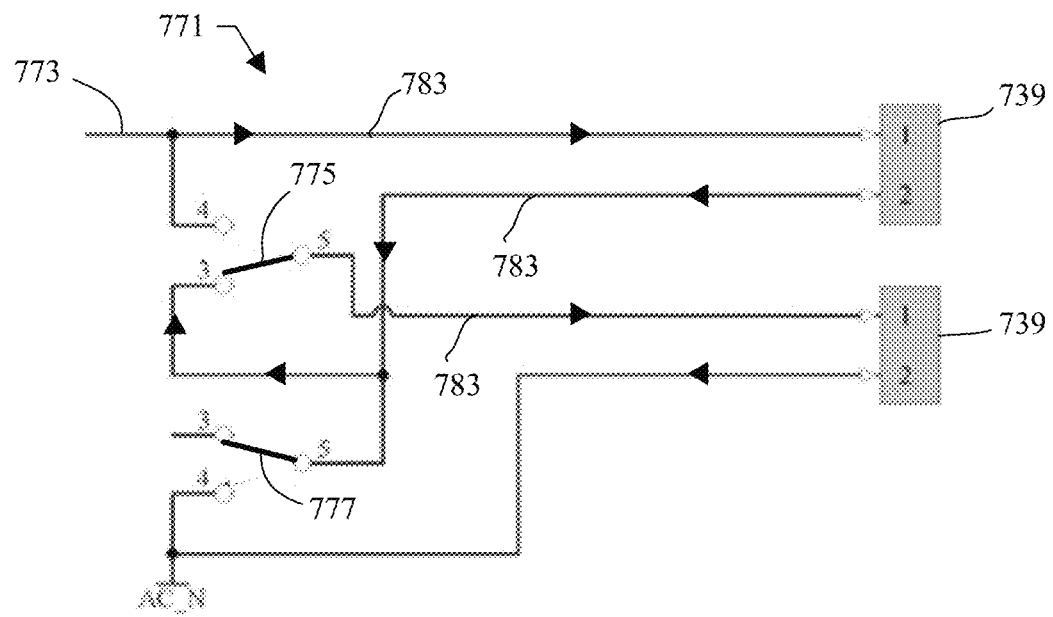
FIG. 7C illustrates the relay bank of FIG. 7B, where the switches of the relay bank are in a second position.

Due in large part to the fluid warming function of the system 100, which is intended to rapidly warm fluid up to the setpoint fluid temperature and to maintain the setpoint fluid temperature at high flow rates, the system 100, for markets where the nominal supply voltage is 120V, must be connected to a dedicated 20-amp circuit. However, the system 100 can be configured for connection to a standard 15-amp circuit by utilizing lower wattage lamps and/or current limiting power to the lamps. In certain embodiments, fluid management system 100 is configured to operate on nominal supply voltage of 120 v or 240 v without requiring a change in lamps. For example, the system 100 can include a crossover circuit that includes a threshold detector 770 (FIG. 7A) and a relay bank 771 (FIGS. 7B-7C). Referring to FIG. 7, in certain embodiments, the lamp assembly 737 includes four lamps 739 (e.g., two lamps on each side of the cartridge 419). FIG. 7B shows a circuit of a relay bank 771 for two lamps 739 of the lamp assembly 737 (e.g., two lamps 739 positioned on the same side of the cartridge 419) with relay contacts 775, 777 in a first position in which the lamps 739 are placed into a parallel configuration. FIG. 7A shows a circuit for a threshold detector 770 that can cause the relay contacts 775, 777 (FIGS. 7B-7C) to move to a second position (as shown in FIG. 7C) in which the lamps 739 are placed into a series configuration. While FIGS. 7B and 7C show a circuit for a relay bank 771 of two lamps 739 that are disposed on one side of the cartridge 719 shown in FIG. 7, it should be understood that the circuit for the other two lamps 739 on the other side of the cartridge may be identical to the circuit shown in FIGS. 7B and 7C.

Referring to FIG. 7A, the threshold detector 770 has an AC line input 772 and an AC line input 774 that each connect to the input side of bi-directional photocoupler 776, where the voltage being supplied to the heating assembly 314 is also applied to the inputs 772, 774. A first Zener diode 778 is positioned between the line input 772 and an input of the photocoupler 776, and a second Zener diode 780 is positioned between the line input 774 and the input of the photocoupler 776. The Zener diodes 778, 780 prevent current flow from the inputs 772, 774 through the photocoupler 776 until the peak voltage applied to the inputs 772, 774 is greater than or equal to a predetermined amount. The photocoupler 776 includes a transistor output element 782 connected to voltage source 784, where the transistor output element 782 is configured to operate between an "On" position and "Off" position with a line 786 that generates a control signal used to energize relay coils 788 that operate the relay bank 771. The transistor output element 782 remains off when current is not moving through the input of the photocoupler 776, and the transistor output element 782 turns on when the current flows through Zener diodes 778, 780 and enters the input of the photocoupler 776. When the transistor output element 782 turns on, current from the voltage source 784 energizes line 786 to generate the control signal to activate the coils 788a-d and move corresponding contacts (e.g., contacts 775, 777) of the relay bank 771 from the first position (as shown in FIG. 7B) to the second position (as shown in FIG. 7C). In some embodiments, the control signal is applied to a Schmitt trigger 790 and transistor array 792 prior to energizing the coils 788a-d. The Schmitt trigger 790 ensures that the voltage on line 786 is stable and exceeds a predetermined limit prior to being connected to the transistor array. The transistor array 792 energizes coils 788a-d and moves the relay contacts 775, 777 from the first position to the second position.

Referring to FIG. 7B, in the illustrated embodiment, the contacts 775, 777 are in the first position when the lamps 739 are in a parallel configuration. When in the first position, the contacts 775, 777 are connected at points 4 and 5 such that both lamps 739 are in communication with the inlet 773 of the circuit. This allows half the current moving through inlet 773 to move along a first path 779 into one lamp 739 and half the current to move through the second path 781 (through the contact 775) and into the second lamp 739. In this configuration, the same voltage applied to the inlet 773 is individually applied across both of the lamps 739 such that each lamp 739 receives the voltage entering the circuit. For example, if 120 v is applied to inlet 773, the 120 v is connected to both the first path 779 and the second path 781 such that each lamp receives 120 v.

Referring to FIG. 7C, when the threshold detector 770 (FIG. 7A) causes the contacts 775, 777 to move to the second position, an electrical connection is made between points 3 and 5 such that the lamps 739 are connected in a series configuration. In this configuration, all the current applied to the inlet 773 moves along a single path 783 (because the disconnection between points 4 and 5 prevents the current from moving directly through the contact 775 after entering the inlet 773) such that the current moves through one lamp 739, continues to move along the path 783 such that the current moves through the contact 775 at points 3 and 5, and the current then moves into the second lamp 739. Because both lamps 739 are disposed along a single path 783, the voltage applied to the lamps 739 is split between the number of lamps disposed on the path 783. As the illustrated embodiment includes two lamps 739, each lamp 739 receives half of the voltage entering the inlet 773. For example, if 240 v is applied to inlet 773, all the current flows along the single path 783 such that the voltage drop across one lamp 739 is 120 v and this dropped voltage is applied along the single path 783 such that the other lamp receives 120 v.

The fluid management system 100 may be configured to provide accurate and reliable flow-based deficit monitoring for surgical procedures performed in an operating room environment. For example, FIGS. 20 through 49 illustrate an exemplary embodiment of a deficit module 104 and a single or multiuse deficit cartridge 2010 for the fluid management system shown in FIG. 1. The use of the deficit cartridge 2010 negates the need for canisters and avoids exposing the sensors and other durable components of fluid management system 100 to the fluid returning from the surgical site. The deficit module 104 works in combination with the control system of the main unit 102 and a single or multiuse tubing set that includes the deficit cartridge 2010 to measure and record the fluid volume being returned from the surgical site as it moves through deficit cartridge 2010. The fluid is pulled from the surgical site and both into and out of the deficit cartridge 2010 by a suction source (e.g., a vacuum pump integral or external to the system 100). In an alternative embodiment, fluid may be pulled from the surgical site and pushed into the deficit cartridge 2010 by a more positive pressure than present inside deficit cartridge 2010 (e.g., a peristaltic pump integral or external to the system 100 inserted in-line between the surgical site and the deficit cartridge 2010 and configured to create suction at the surgical site and positive pressure at the inlet to the deficit cartridge 2010) and pulled from the deficit cartridge 2010 by a more negative pressure than present inside deficit cartridge 2010 (e.g., a vacuum pump integral to or external to the system 100 or a sufficiently positive pressure inside the deficit cartridge 2010 due to the positive pressure created by the peristaltic pump to push the fluid out of the deficit cartridge 2010 to ambient pressure).

Referring to FIGS. 20 through 23, the deficit cartridge 2010 is inserted into the deficit module 104. The deficit cartridge 2010 may include a front section 2218 that aligns with an opening 2220 (FIGS. 22-23) of the deficit module 104 and a raised portion 2222 (FIGS. 22-23) that allows for a user to easily grasp the deficit cartridge 2010 to remove the cartridge from the deficit module 104. The deficit cartridge 2010 includes one or more inlet openings 2012, 2014 that are configured to connect to one or more fluid return tubes of the tubing set such that fluid can move from the surgical site and into the deficit cartridge 2010. The deficit cartridge also includes at least one vacuum opening 2016 that is configured to connect to an evacuation tube such that fluid moves through the evacuation tube after moving through the deficit cartridge 2010. The evacuation tube is connected to the suction source such that a vacuum pressure is supplied to the deficit cartridge to pull fluid from the surgical site into and out of the deficit cartridge 2010. The fluid return and evacuation tubes may be manually connected to the deficit cartridge 2010 after insertion of the deficit cartridge into the deficit module 104.

The control system of the main unit 102 is configured to determine a deficit of fluid provided to the surgical site and returned from the surgical site by comparing the volume of fluid moving through the deficit cartridge 2010 to the volume of fluid being supplied to the surgical site. The control system may calculate the volume of fluid being supplied to the surgical site by, for example, monitoring the weight of the fluid supply bags or containers (e.g., by using the hanging members 116 that are operatively connected to load cells), and/or counting the rotations of a peristaltic pump.

Figure 27:
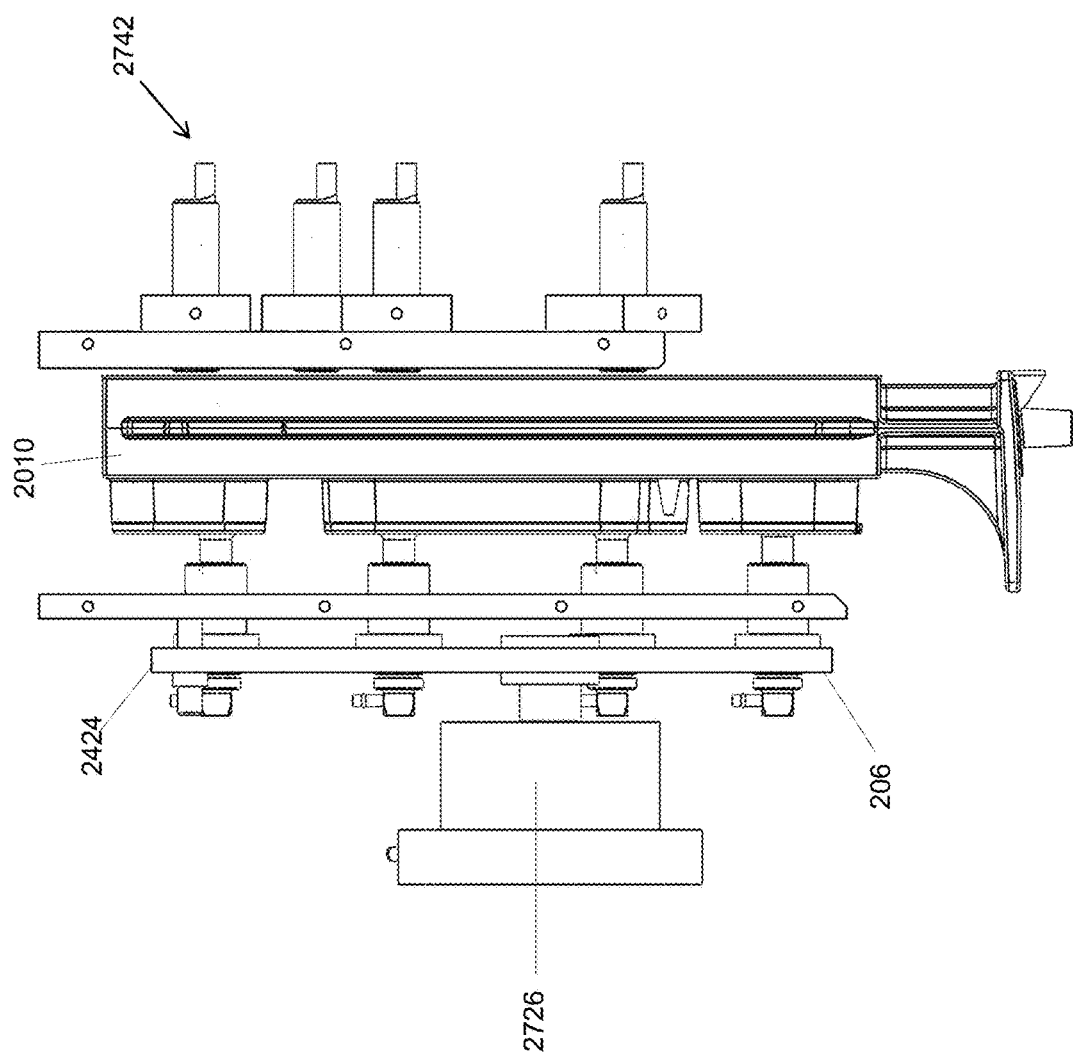
FIG. 27 illustrates the deficit cartridge of FIG. 20 aligned with a moveable manifold of the deficit module of FIG. 20, wherein the movable manifold is in an open position relative to the deficit cartridge.

Referring to FIGS. 24 through 28, insertion of the deficit cartridge 2010 into the deficit module 104 causes a manifold connection assembly 2424 (FIGS. 27-28) to engage the deficit cartridge 2010 and connect, via a pump manifold assembly (e.g., pump manifold assembly 3513 shown in FIG. 37), positive and negative pressure pumps (3515 and 3517, respectively, of FIGS. 35-36) and a pressure sensor (not shown) of the deficit module 104 to pneumatically operated diaphragm regulators/valves (e.g., regulators/valves 2628, 2630, 2632, 2634 shown in FIG. 26) and a pressure sensing area 2636 (FIG. 26) of the deficit cartridge 2010. The manifold connection assembly 2424 has a plurality of connectors (e.g., connectors 4510, 4511, 4512, 4513 shown in FIGS. 45 and 49) for receiving corresponding ports 2540 for each of the regulators/valves and the pressure sensing area of the deficit cartridge 2010. Referring to FIGS. 27-28 (and FIGS. 42-49), the connectors of the manifold connection assembly 2424 can be configured to be moved between an engaged or connected state and a disengaged or disconnected state relative to the ports 2540 by a mechanical or electromechanical mechanism 2726 (e.g., a manual lever, a Pancake cylinder, or other type of pneumatic, mechanical, or electromechanical actuator). The ports 2540 of the deficit cartridge 2010 may include an O-ring that allows for a hermetically sealed connection between the manifold connection assembly 2424 and the deficit cartridge 2010. Insertion of the deficit cartridge 2010 into the deficit module 104 also causes one or more non-contact fluid sensors 2742 (FIGS. 30-31) of the deficit module 104 to align with desired locations of the deficit cartridge 2010.

The connectors (e.g., connectors 4510, 4511, 4512, 4513 shown in FIGS. 45 and 49) of the manifold connection assembly 2424 may be configured to account for any manufacturing or assembly tolerances in the ports 2540 of the deficit cartridge 2010. That is, the connectors may be configured to move to ensure alignment with the corresponding ports 2540 of the deficit cartridge 2010 to account for minor differences in the location of the ports 2540 resulting from manufacturing and assembly of the deficit cartridge 2010. For example, referring to FIGS. 28A-28C, in certain embodiments, a connector 4512 (also shown in FIGS. 45 and 49) of the manifold assembly 2424 may be a separate component that is connected to the manifold assembly 2424 by an attachment element 2815 (e.g., an E-clip), and a receiving assembly 3511 (also shown in FIGS. 38-39) of the system 100 may include an opening 3828 (also shown in FIGS. 38-39) that is larger than the diameter of the connector 4512 for receiving the connector 4512 such that the connector 4512 can move within the opening 3828.

Figure 28C:
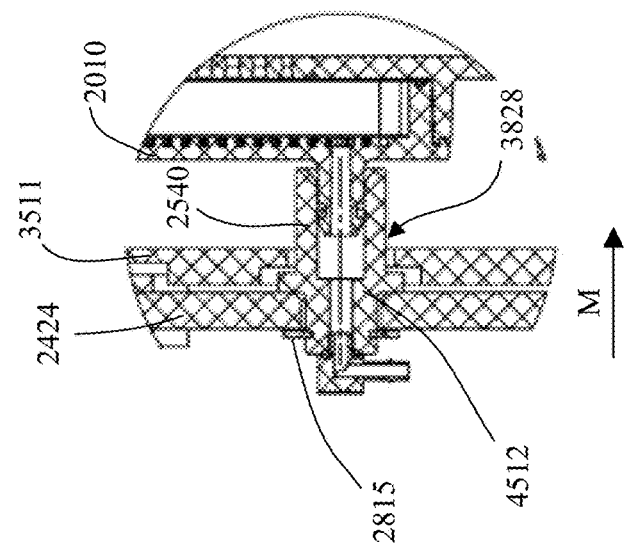
FIGS. 28A-28C illustrate an exemplary connection between a port of the deficit cartridge of FIG. 20 and a connector of the movable manifold of the deficit module of FIG. 20.
Figure 28B:
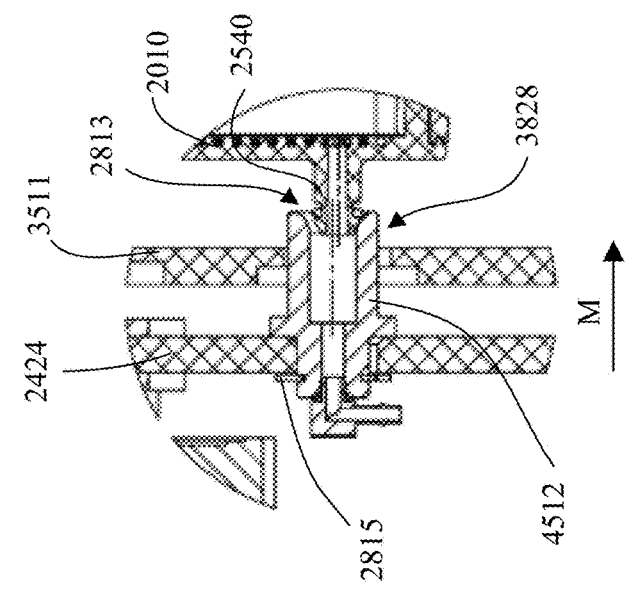
Figure 28A:
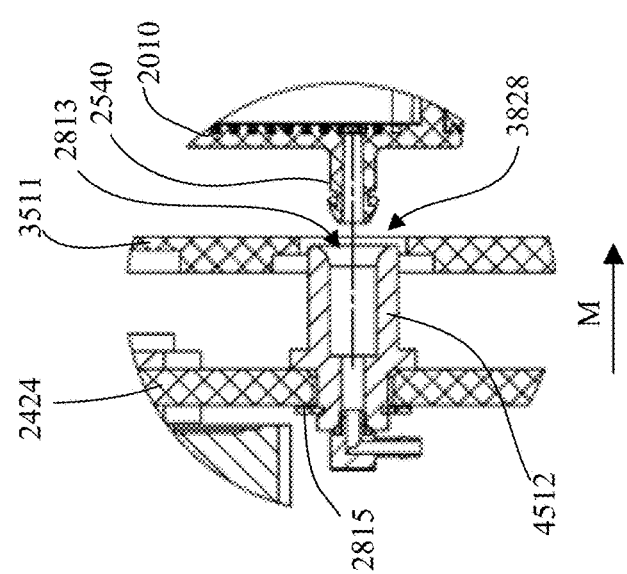

Referring to FIG. 28A, the manifold connection assembly 2424 is shown in a disengaged position with the port 2540 of the deficit cartridge 2010. Activation of the mechanism 2726 (FIG. 28) causes the manifold connection assembly 2424 to move in the direction M such that the connector 4512 engages the port 2540 of the deficit cartridge 2010. FIG. 28B shows the initial engagement between the connector 4512 and the port 2540, and FIG. 28C shows the completed engagement between the connector 4512 and the port 2540. Referring to FIG. 28B, the port 2540 of the deficit cartridge 2010 is not centered with the connector 4512, which causes the port 2540 to engage an edge of an inlet 2813 of the connector 4512. The large opening 3828 of the receiving assembly 3511 allows for the connector 4512 to move within the opening 3828 and align with the port 2540. That is, referring to FIG. 28C, continued movement of the manifold connection assembly 2424 in the direction M causes the port 2540 to align with and move into the connector 4512. In certain embodiments, the inlet 2813 of the connector 4512 is tapered to facilitate movement of the port 2540 into the connector 4512. The connection described above between the connector 4512 and the port 2540 allows for an easy and automatic connection between the deficit cartridge 2010 and the system 100 (e.g., via the deficit module 104). While FIGS. 28A-28C only show the connection between connector 4512 and a port 2540 of the deficit cartridge 2010, it should be understood that the other connectors (e.g., connectors 4510, 4511, 4512, 4513 shown in FIGS. 45 and 49) may be configured to connect to the ports 2540 of the deficit cartridge 2010 in the same manner described in FIGS. 28A-28C.

Referring to FIGS. 29-34, the deficit cartridge 2010 may include a single chamber 2944 with three sections 2946, 2948, 2950 that are fluidically connected. The three sections include a fill section 2946, a measure section 2948, and an evacuation section 2950 that are fluidly connected at all times as the system 100 alternates between "Fill/Measure" and "Fill/Evacuation" Cycles, which allows the pressure gradient across the three sections to be minimized or substantially equal.

The fill section 2946 is fluidly connected to the inlet openings 2012, 2014 such that fluid returning from a surgical site can move into the fill section 2946 through the inlet openings 2012, 2014. The evacuation section 2950 is fluidly connected to the vacuum port 2016 such that a suction source can supply a vacuum pressure to the deficit cartridge 2010 that causes fluid to move from the surgical site, into the deficit cartridge 2010 through the inlet openings 2012, 2014, and exit the deficit cartridge 2010 through the vacuum port 2016. In other embodiments, a pump in-line between the surgical site and port 2012 and/or port 2014 (e.g., a peristaltic pump) may pull fluid from the surgical site and push the fluid through the inlet openings 2012 and/or 2014 and out of the deficit cartridge 2010 through the vacuum port 2016. Alternatively, a pump in-line between the surgical site and port 2012 and/or port 2014 (e.g., a peristaltic pump) may pull fluid from the surgical site and push the fluid through the inlet openings 2012 and/or 2014 while a separate suction source supplies vacuum pressure to pull fluid out of the deficit cartridge 2010 through the vacuum port 2016.

One or more inlet valves 2628, 2630 may be positioned at the inlet openings 2012, 2014 and configured to close to prevent fluid from entering chamber 2944 to avoid overfill conditions. In certain embodiments, the valves 2628, 2630 are pneumatically-operated diaphragm valves that are connected to a pump assembly (e.g., an assembly including positive pressure pump 3515 and negative pressure pump 3517 shown in FIGS. 35-36) of the deficit module 104 such that the pump assembly can move the valves 2628, 2630 between the open and closed positions. In certain embodiments, a negative pressure pump of the pump assembly opens the diaphragm valves and a positive pressure pump of the pump assembly assists closing of the diaphragm valves with positive back pressure.

Figure 35:
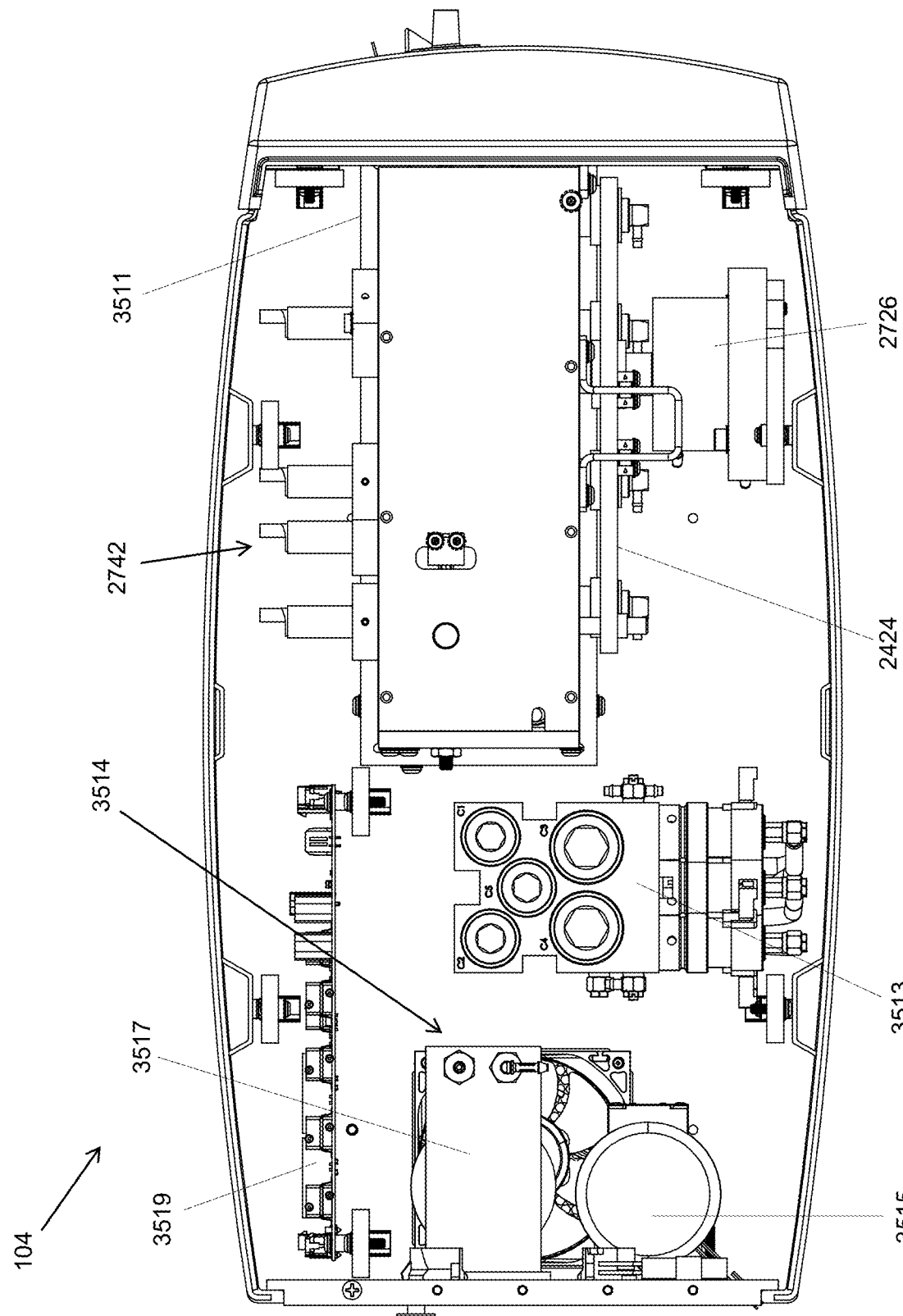
FIG. 35 illustrates a cross-sectional top view of the deficit module of FIG. 20.
Figure 36:
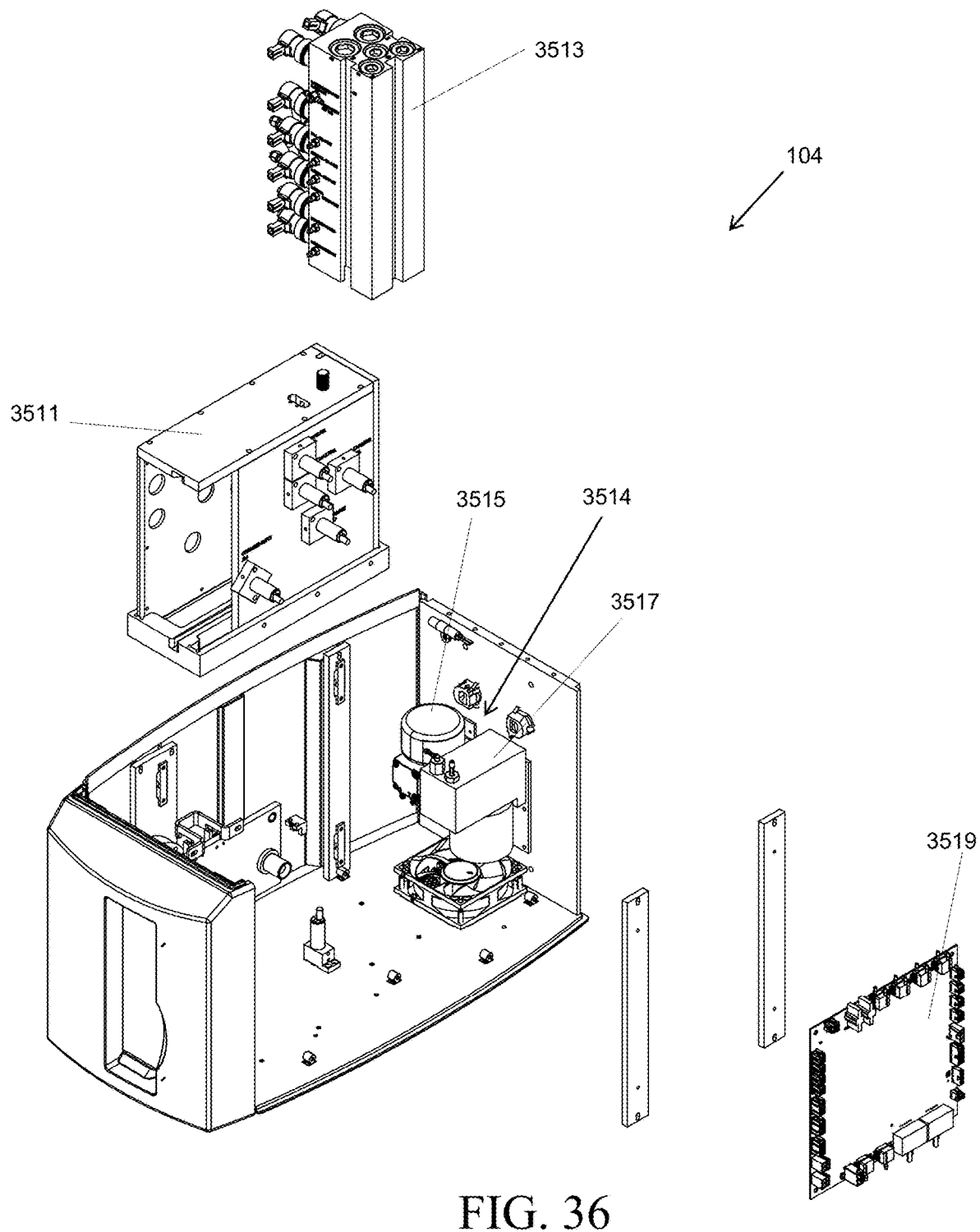
FIG. 36 illustrates an exploded perspective view of the deficit module of FIG. 20.

The pneumatically-operated diaphragm valves 2628, 2630 may also work in combination with the pump assembly (e.g., an assembly including positive pressure pump 3515 and negative pressure pump 3517 shown in FIGS. 35-36) to act as a pressure regulator that regulates the vacuum pressure being supplied to the surgical site. That is, the control system of the fluid management system 100 may be configured to adjust the amount of pressure applied to the valves 2628, 2630 by the pump assembly, which adjusts the threshold pressure required to displace flexible membrane 2956 and allow fluid to flow through 2628, 2630, and thereby allows the control system to control the amount of vacuum pressure supplied to the surgical site via the suction source that is connected to the vacuum port 2016. For example, referring to FIG. 29, the valves 2628, 2630 may each include a housing component 2958 that defines a chamber 2959, where the chamber 2959 is connected to the pump assembly of the deficit cartridge. A flexible membrane 2956 is disposed in the chamber 2959 and movable within the chamber 2959 by the pressure pumps. When the valves 2628, 2630 are in the closed position, the membrane 2956 engages the chamber 2944 of the deficit cartridge 2010 to fluidly isolate the fill section 2946 from the inlet openings 2012, 2014. The pressure pumps are configured to move the flexible membrane 2956 within the chamber to open the valves 2628, 2630, and the pump assembly can adjust the size of the opening by creating a desired pressure differential between the pressure supplied by the pump assembly and the vacuum level within the chamber 2944 of the deficit cartridge 2010. The membrane 2956 can be made of, for example, neoprene, silicone, natural rubber, nitrile, EPDM, or any other suitable material. The valves 2628, 2630 may also have a hydrophobic filter 2960 to prevent fluid from traveling to the pump assembly in case of a tear or other failure of the flexible membrane. In other words, the valves 2628, 2630 work similar to the pressure regulator described with respect to FIGS. 52-73 of the present application to regulate the vacuum pressure supplied to the surgical site.

In the illustrated embodiment, the fill section 2946 is positioned at a top portion of the chamber 2944, and the measure section 2948 is positioned below the fill section 2946. A valve 2632 is positioned in an opening between the fill and measure sections 2946, 2948 and is movable between an open position and a closed position. When the valve 2632 is in the open position, the fill section 2946 and the measure section 2948 are fluidly connected such that fluid in the fill section 2946 can move into the measure section 2948 via gravity. One or more sensors of the deficit module 104 are used to measure the fluid within the measure section 2948. In certain embodiments, the measure section includes a main area 3276 (FIG. 32) and a narrow area 3277 (FIG. 32) positioned above the main area 3276, where the volume of fluid capable of being disposed in these areas 3276, 3777 are known by the system 100 such that the system can determine the volume of fluid moving through the measure section 2948. The measuring of fluid within the measure section 2946 will be described in more detail below. The evacuation section 2950 is positioned below the measure section 2948, and a valve 2634 is positioned in an opening between the measure and evacuation sections and is movable between an open position and a closed position. When the valve 2634 is in the open position, the measure section 2948 and the evacuation section 2950 are fluidly connected such that fluid in the measure section 2948 can move into the evacuation section 2950 via gravity. In the illustrated embodiment, the valves 2632, 2634 are pneumatically-operated diaphragm valves that are connected to a pump assembly (e.g., an assembly including pumps 3515, 3517 shown in FIGS. 35-36) of the deficit module 104 such that the pump assembly moves the valves 2632, 2634 between the open and closed positions.

Figure 32:
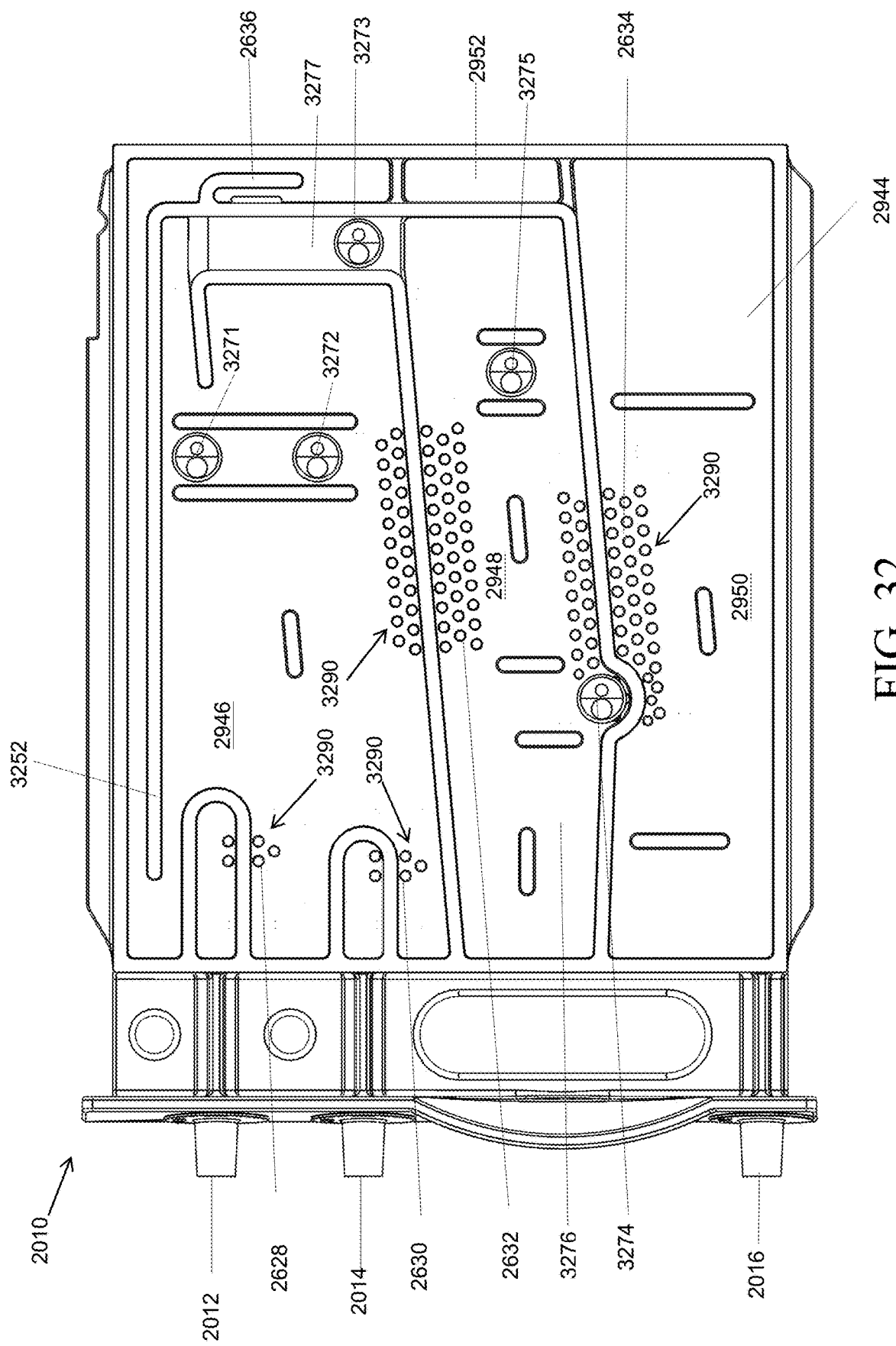
FIG. 32 illustrates a side view of the deficit cartridge of FIG. 20.

Referring to FIG. 32, the valves 2628, 2630, 2632, 2634 may include a flexible membrane (e.g., flexible membrane 2956 shown in FIG. 29) that is movable between an engaged position and a disengaged position with openings 3290 of the deficit cartridge 2010. That is, a portion of the openings 3290 fluidly connect the inlets 2012, 2014 to the fill section 2946, another portion of the openings 3290 fluidly connect the fill section 2946 to the measure section 2948, and another portion of the openings 3290 fluidly connect the measure section 2948 to the evacuation section 2950. The flexible membranes of the valves 2628, 2630, 2632, 2634 engage the openings 3290 to prevent movement of fluid between the inlets/sections, and disengage at least a portion of the openings 3290 to allow movement of flow between the inlets/sections. The size and spacing of the openings 3290 may be configured to prevent extrusion of the flexible membranes through the openings 3290 when positive pressure is applied to the valves 2628, 2630, 2632, 2634. The size and spacing of the openings 3290 may vary based on the elasticity and/or thickness of the material of the flexible membrane. The number of openings 3290 associated with each valve 2628, 2630, 2632, 2634 are configured to ensure adequate flow of fluid through the deficit cartridge 2010. In certain embodiments, the combined surface area of the openings on each side of the valves 2628, 2630, 2632, 2634 is substantially equal to an inner cross-sectional area of tubing that is attached to the inlet ports 2012, 2014 of the deficit cartridge 2010. Because gravity is the dominant force acting on the fluid to cause the fluid to move between the sections 2946, 2948, 2950 of the chamber 2944, in some embodiments, the number of openings 3290 corresponding to the valves 2632, 2634 is configured to be large enough to allow sufficient flow through the valves 2632, 2634 to achieve high flow rates. For example, the number of openings 3290 corresponding to each valve 2632, 2634 may be configured to achieve a target flow rate of greater than or equal to 1200 ml/min through the chamber 2944 without stopping flow from the surgical site. In certain embodiments, because the measure section 2948 of the chamber 2944 may be both filled and emptied while fluid continuously flows from the surgical site, the fluid flow rate through the valves 2632, 2634 may be at least twice the target flow rate through the chamber 2944.

In the illustrated embodiment, the chamber 2944 includes a channel 2952 that fluidly connects the fill section 2946 to the evacuation section 2950 and a narrow portion 3277 that fluidly connects the fill section 2946 to the measure section 2948. The channel 2952 and narrow portion 3277 allow the fill, measure, and evacuation sections 2946, 2948, and 2950 to be fluidly connected at all times, including when one or both of the valves 2632, 2634 are in the closed position. This fluid connection between the fill, measure, and evacuation sections 2946, 2948, and 2950 via the channel 2952 and narrow portion 3277 allows the pressure gradient across the three sections of the chamber 2944 to be minimized or substantially equal such that the fluid is not caused to move within the chamber 2944 by a pressure source, but rather the fluid can move within the chamber 2944 due to gravity. In certain embodiments, the deficit cartridge includes a wall 3252 that is positioned to prevent fluid from entering the channel 2952 and bypassing the measure section 2948. In an alternative embodiment, rather than the chamber 2944 including the channel 2952, the deficit cartridge 2010 can include a connector or tube (e.g., similar to tube 841 shown in FIG. 8 for the fluid conditioner 420) that fluidly connects the fill section 2946 to the evacuation section 2950 such that the fill, measure, and evacuation sections 2946, 2948, and 2950 are fluidly connected at all times. While the illustrated embodiment shows the three sections 2946, 2948, 2950 being in a stacked configuration, in an alternative embodiment, these three sections can be in a side-by-side configuration, as long as the fluid can travel from the fill section 2946 to the measure section 2948 to the evacuation section 2950 via gravity.

Figure 29:
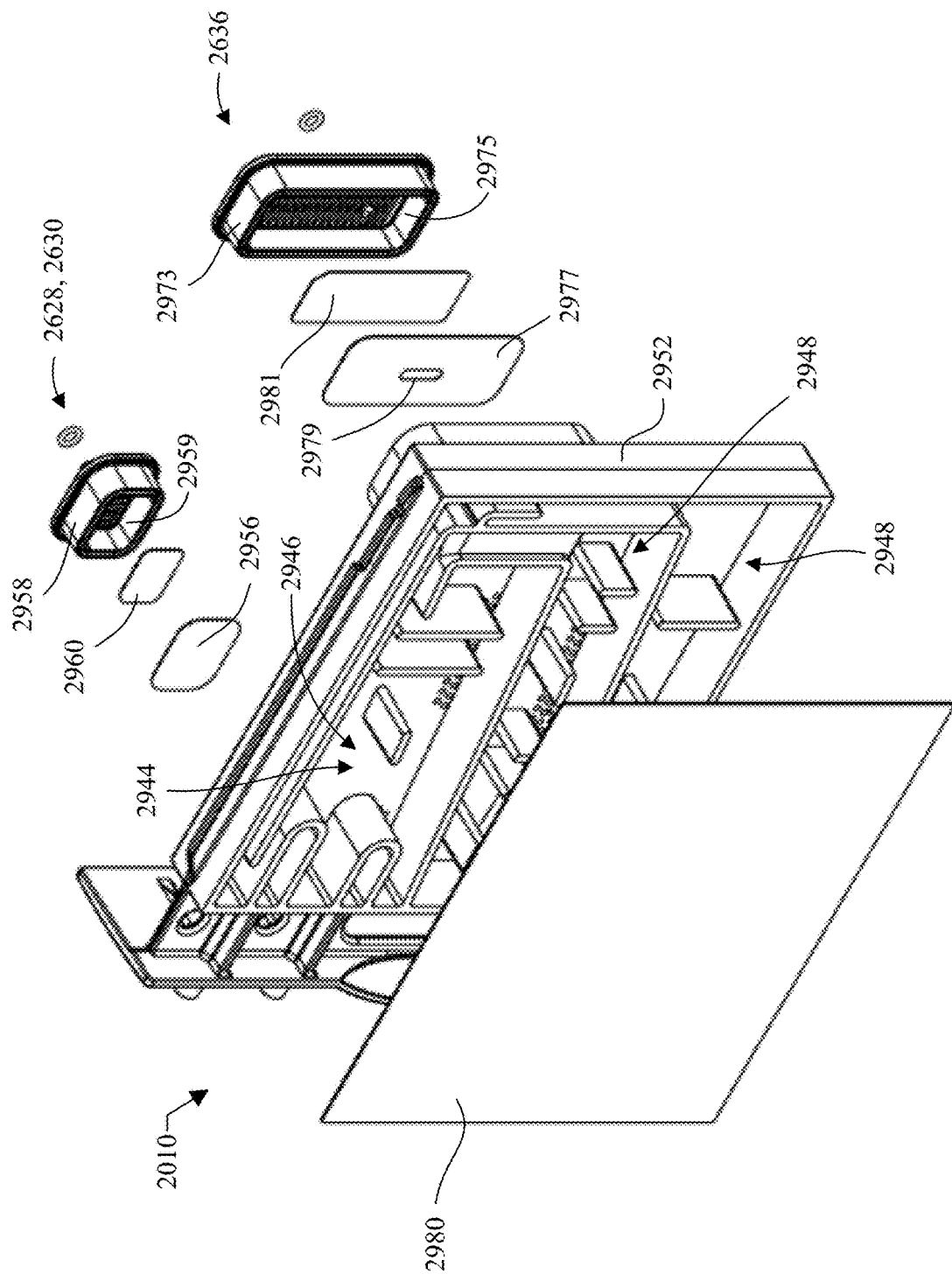
FIG. 29 illustrates an exploded perspective view of the deficit cartridge of FIG. 20.

In various embodiments, the deficit cartridge 2010 includes a waste vacuum level sensing and regulation port 2636 for connecting to a solenoid valve which is open to ambient on one side and a pressure sensor of the deficit module 104. The control system of the fluid management system 100 is capable of sensing the vacuum level of the chamber 2944 via the pressure sensor of the deficit module 104 and opening the solenoid valve to atmospheric pressure to down regulate the vacuum pressure being supplied to the deficit cartridge 2010 via the suction source. Referring to FIG. 29, the port 2636 may include a housing component 2973 that defines a chamber 2975, where the chamber 2975 is connected to the solenoid valve and pressure sensor of the deficit module 104. A flexible membrane 2977 is disposed in the chamber 2975 and has an opening 2979 that enables pressure measurement of the pressure in chamber 2944 and exposes chamber 2944 to ambient when the solenoid valve is open. The membrane 2977 can be made of, for example, neoprene, silicone, natural rubber, nitrile, EPDM, or any other suitable material. The port 2971 may also have a hydrophobic filter 2981.

Figure 30:
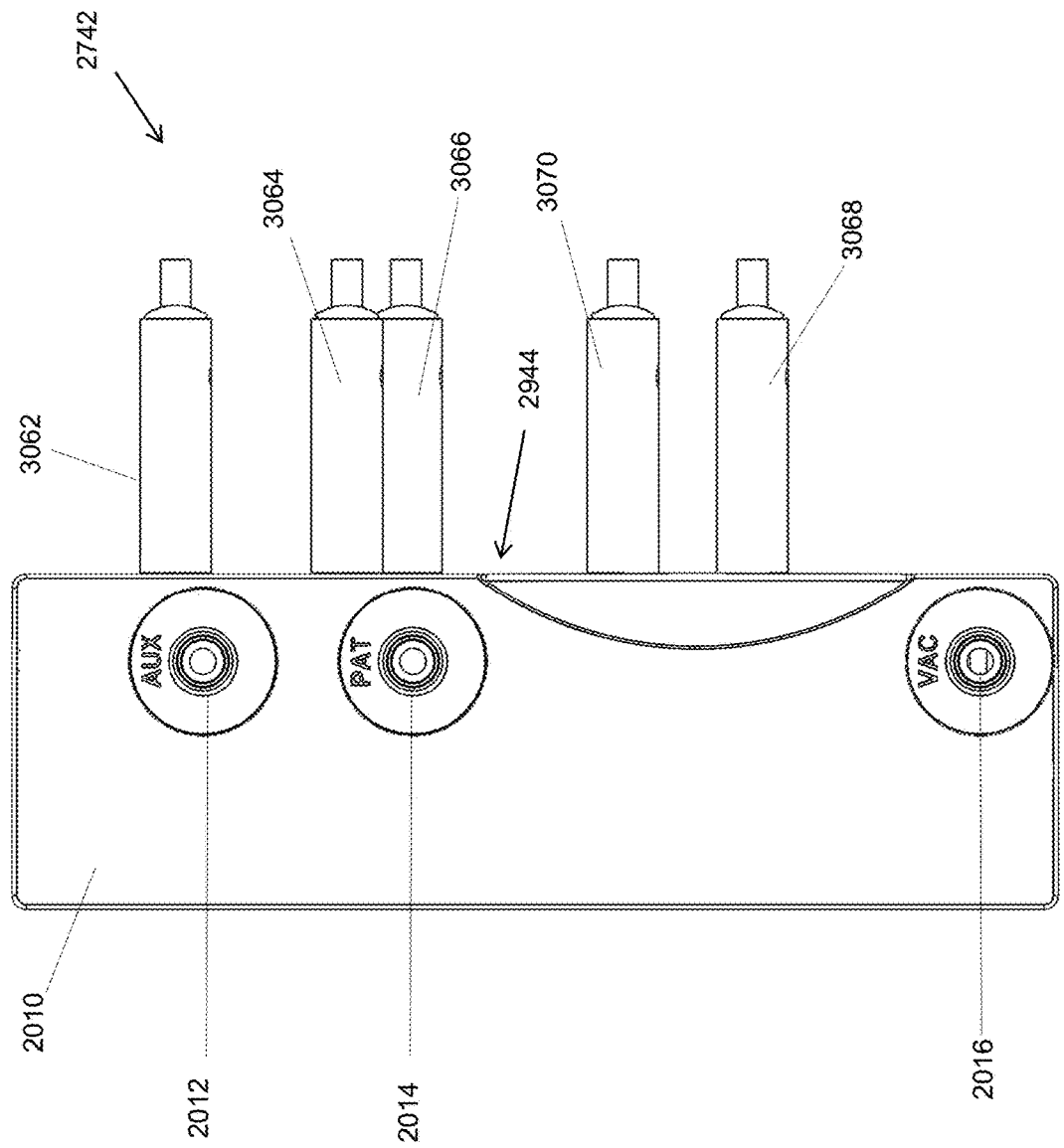
FIG. 30 illustrates a front view of the deficit cartridge of FIG. 20 aligned with non-contact fluid presence sensors of the deficit module of FIG. 20.
Figure 31:
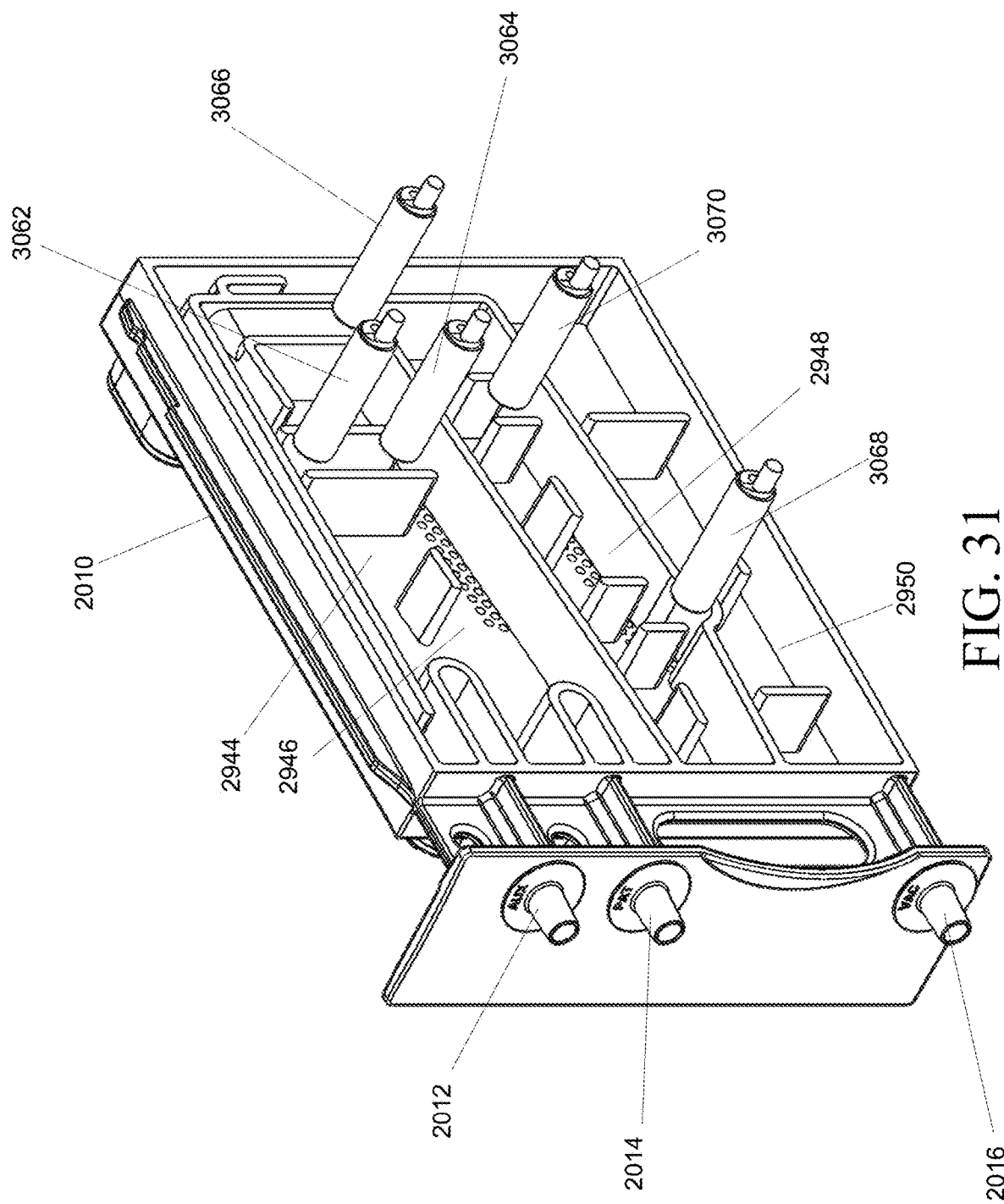
FIG. 31 illustrates a perspective view of the deficit cartridge of FIG. 20 aligned with non-contact fluid presence sensors of the deficit module of FIG. 20.
Figure 33:
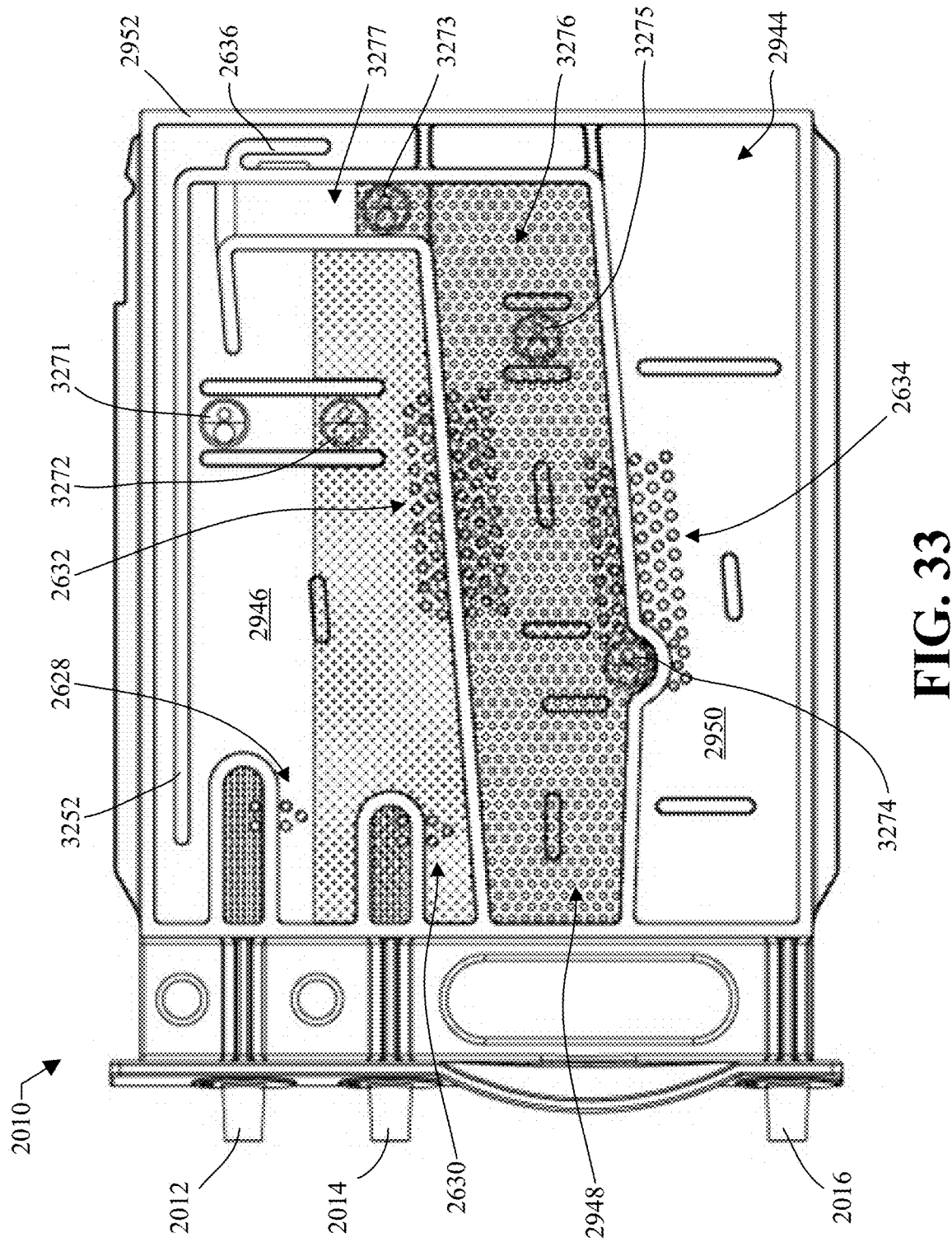
FIG. 33 illustrates a side view of the deficit cartridge of FIG. 20 when the deficit monitoring feature of the fluid management system is in a fill/measure cycle.
Figure 34:
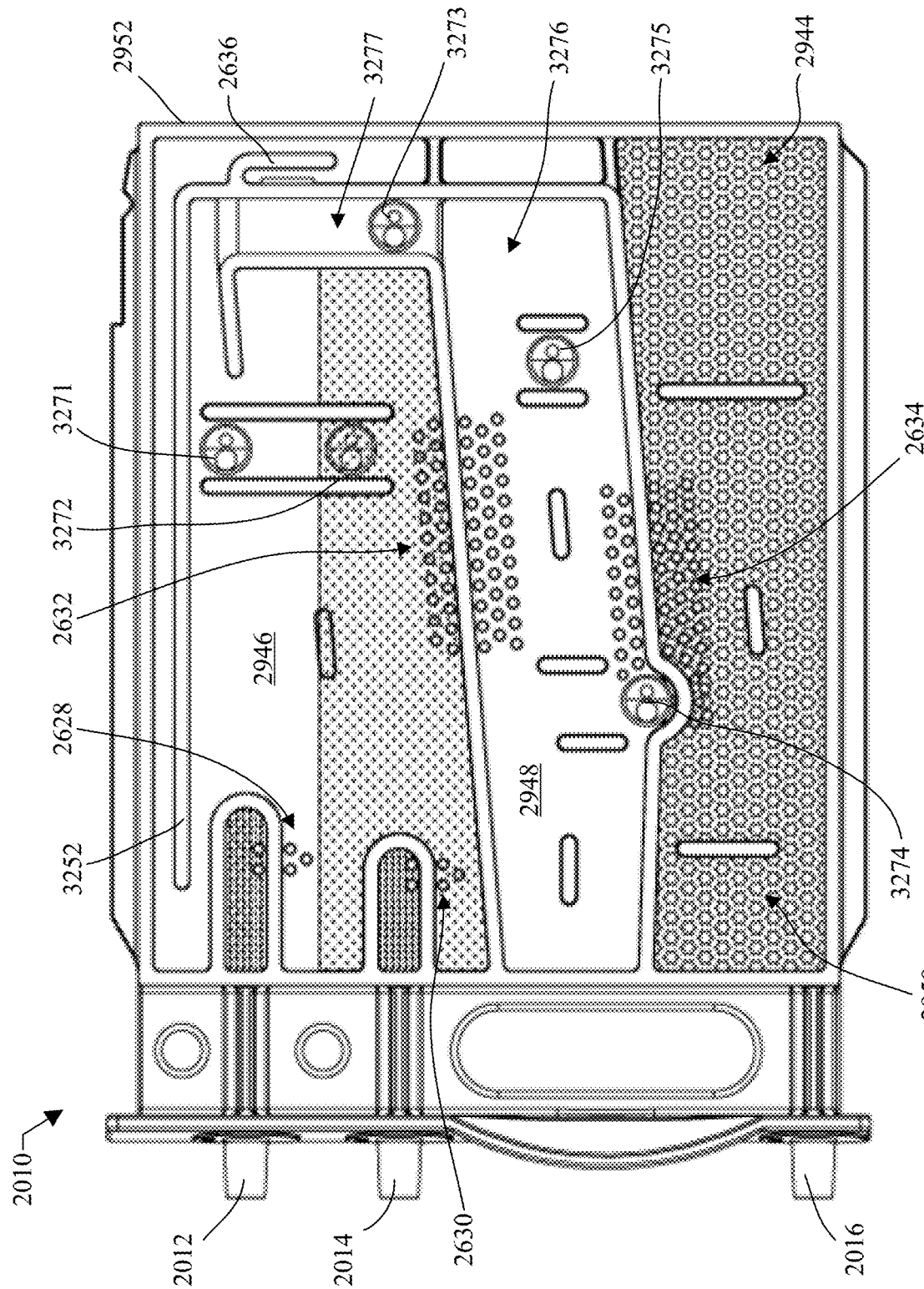
FIG. 34 illustrates a side view of the deficit cartridge of FIG. 20 when the deficit monitoring feature of the fluid management system is in a fill/evacuation cycle.

Referring to FIGS. 30 through 32, the deficit cartridge 2010 is aligned with one or more sensors 2742 (e.g., sensors 3062, 3064, 3066, 3068, 3070 shown in FIGS. 30-31) of the deficit module 104 such that the control system of the fluid management system 100 can use the sensors 2742 to detect a volume of fluid moving through the chamber 2944 of the deficit cartridge 2010 and/or detect any potential problems with fluid flow through the deficit cartridge (e.g., potential overflow of fluid within section 2946 of the chamber 2944). In the illustrated embodiment, the one or more sensors 2742 include a first fluid presence sensor 3062, a second fluid presence sensor 3064, a third fluid presence sensor 3066, a fourth fluid presence sensor 3068, and a fifth fluid presence sensor 3070. Referring to FIGS. 32 through 34, in the illustrated embodiment, the first and second fluid presence sensors 3062, 3064 are aligned with first and second areas 3271, 3272, respectively, within the fill section 2946. These fluid presence sensors 3062, 3064 are used by the control system to close one or both of the inlet valves 2628, 2630 if the fluid within the fill section 2946 reaches the first and second areas 3271, 3272. The third fluid presence sensor 3066 is aligned with a third area 3273 in the measure section 2948 of the chamber 2944 and is used by the control system to switch from Fill/Measure cycle to the Fill/Evacuation cycle and determine a volume of fluid within the measure section 2948 prior to switch to the Fill/Evacuation cycle. The fourth fluid presence sensor 3068 is aligned with a fourth area 3274 within the measure section 2948 and is used by the system to switch from the Fill/Evacuation cycle to the Fill/Measure cycle. The fifth fluid presence sensor 3070 is aligned with a fifth area 3275 within the measure section 2948 and is used by the system to provide more accurate real-time fluid volume measurement in measure section 2948 and to determine a volume of fluid in the measure section 2948 after the procedure is completed or the type of fluid being monitored for recording a fluid deficit is changed to provide a more accurate fluid deficit calculation for the fluid. While the illustrated embodiment shows the deficit module 104 having five fluid presence sensors for detecting fluid flow conditions and volume within the chamber 2944 of the deficit cartridge, it should be understood that any other suitable number of fluid presence sensors can be used by the deficit module to detect fluid flow conditions and volume. The target areas 3271-3275 may include walls partially surrounding them to mitigate the effects of fluid turbulence on the accuracy of the sensor readings and any flexing of the film 2980.

Referring to FIG. 29, in the illustrated embodiment, the deficit cartridge 2010 includes a rigid body 2978 and a film 2980. The rigid body 2978 partially defines the various sections 2946, 2948, 2950 and the channel 2952 and narrow portion 3277 of the chamber 2944, and the film 2980 is attached to the rigid body 2978 to enclose the chamber 2944. The rigid body 2978 can be, for example, an injection molded body or any other suitably rigid body. The film 2980 is configured to allow the one or more sensors of the deficit module 104 to detect characteristics of the fluid through the film without contacting the fluid. The film 2980 can be, for example, a plastic film. The film 2980 can be attached to the rigid body 2978 with mechanical fasteners or by gluing, laser welding, vibration welding, ultrasonic welding, or any other suitable means. In alternative embodiments, the deficit cartridge 2010 does not include film 2980, but rather is made of an injection molded vessel that is capable of having the one or more sensors of the deficit module 104 detect characteristics of the fluid through the vessel without contacting the fluid. In other alternative embodiments, vessel may be cast or machined out of a material that is capable of being cleaned and reused.

FIGS. 33 and 34 illustrate the Fill/Measure cycle and the Fill/Evacuation cycle for the deficit cartridge 2010. Referring to FIG. 33, during the Fill/Measure cycle, fluid returning from the surgical site is pulled from the surgical site into the fill section 2946 of the deficit cartridge 2010 through inlet ports 2012, 2014 via a vacuum pressure from a suction source that is attached to vacuum port 2016. The diaphragm operated valve 2632 is in the open position, which allows fluid to travel from the fill section 2946 to the measure section 2948 via gravity. The diaphragm operated valve 2634 is in the closed position, which prevents fluid from the measure section 2948 from moving into the evacuation section 2950. The Fill/Measure cycle continues until the fluid level in the measure section 2948 has reached a predetermined level as sensed by the fluid presence sensor 3066 (FIGS. 30-31) of the deficit module 104 that targets area 3273. In the illustrated embodiment, the targeted area 3273 is disposed in a narrow portion 3277 (FIG. 32) of the measure section 2948 that extends above from the main portion 3276 (FIG. 32) of the measure section 2948. The volume of fluid in the narrow portion 3277 is small compared to the volume of fluid in the main portion 3276 of the measure section 2948 and, therefore, variables including fluid flow rates and turbulence (which can affect the accuracy of the sensed fluid level) do not materially affect the overall accuracy of the measuring function. In certain embodiments, a ratio of the volume of the main portion 3276 to a volume of the narrow portion can be greater than or equal to 5 to 1, such as greater than or equal to 20 to 1, such as greater than or equal to 50 to 1, such as greater than or equal to 75 to 1, such as greater than or equal to 90 to 1, such as greater than or equal to 100 to 1. In an exemplary embodiment, the ratio of the volume of the main portion 3276 to the volume of the narrow portion can be about 100 to 1. The volume of fluid within the main portion 3276 and narrow portion 3277 of the measure section 2948 are known by the system 100, which allows the system to record the volume of fluid within the measure section for each time the Fill/Measure cycle occurs. The system 100 records the volume and then transitions to the Fill/Evacuation cycle.

Referring to FIG. 34, during the Fill/Evacuation cycle, the diaphragm operated valve 2632 is moved to the closed position, which prevents fluid from the fill section 2946 from moving into the measure section 2948. The diaphragm operated valve 2634 is moved to the open position, which allows the fluid that was measured in the measure section 2948 during the Fill/Measure cycle to move into the evacuation section 2950 via gravity. The fluid entering the evacuation section 2950 is then evacuated through the vacuum port 2016, via the attached suction source, and the fluid is moved to the facility's waste disposal system via indirect-to-drain or direct-to-drain methods. To evacuate fluid from the evacuation section, the evacuation cycle relies upon a vacuum pressure differential between the vacuum pressure provided by the suction source and the down-regulated vacuum pressure inside of the chamber 2944 (as regulated via the pressure regulation and sensing port 2636). When the fluid presence sensor 3068 (FIGS. 30-31) that targets area 3274 detects no remaining fluid in the measure section 2948, the system 100 transitions back to the Fill/Measure cycle. The alternation between the Fill/Measure cycle and the Fill/Evacuation cycle continues until the procedure is completed, and the control system determines the fluid deficit of the fluid based at least partially on the various volume measurement recordings taken during the various Fill/Measure cycles.

The movement of fluid from the fill section 2946 to the measure section 2948 and the evacuation section 2950 is accomplished with gravity, as opposed to external suction or pressure sources. In these embodiments, the valves may be sized to minimize resistance and thereby facilitate high flow rates with relatively low forces. The pneumatically-actuated diaphragm valves 2628, 2630 accomplish the allowance or stoppage of flow into the deficit cartridge 2010, and the pneumatically-actuated diaphragm valves 2632, 2634 accomplish the allowance and stoppage of flow between the sections, 2946, 2948, 2950, by setting the pneumatic control pressure by the pressure pumps 3515, 3517 (FIGS. 35-36) of the deficit module 104 to a more positive gauge pressure than the combination of 1) the highest pressure expected on either wetted side of the valve, and 2) any additional pressure required to account for the additional force from the spring coefficient of the valve membrane.

To guard against overflow conditions, the deficit module 104 may have a fluid presence sensor 3064 (FIGS. 30-31) that targets area 3272, and the control system may be configured to close the fluid return valve 2628 (e.g., the valve connected to the underbody drape and/or floor suction at the surgical site) if the fluid presence sensor 3064 detects fluid at the target area 3272. This ensures that the fill section 2946 does not overfill and flow into the measure section 2948 through narrow portion 3277 or the evacuation section 2950 through the channel 2952, and ensures that the remaining capacity of the fill section remains available to receive fluid returning from the surgical instrument at the surgical site so as not to interrupt the surgical procedure. The deficit module may also have a fluid presence sensor 3062 (FIGS. 30-31) that targets area 3271, and the control system may be configured to close the fluid return valve 2630 (e.g., the valve connected to a surgical instrument at the surgical site) if the presence sensor 3062 detects fluid at the target area 3271. In an alternative embodiment, the valve 2628 can be connected to the surgical instrument at the surgical site, and the valve 2630 can be connected to the underbody drape and/or floor suction at the surgical site.

To provide end of procedure fluid deficit accuracy (assuming the end of the surgical procedure does not coincide with the end of a Fill/Measure or Fill/Evacuation cycle), the deficit module 104 may include one or more midpoint fluid presence sensors (e.g., sensor 3070) that target one or more areas (e.g., area 3275) to provide more accurate real-time measurement of the fluid in measure section 2948 and to measure the fluid in the measure section 2948 at the end of a surgical procedure or after the type of fluid being used during the surgical procedure has been changed.

Figure 44:
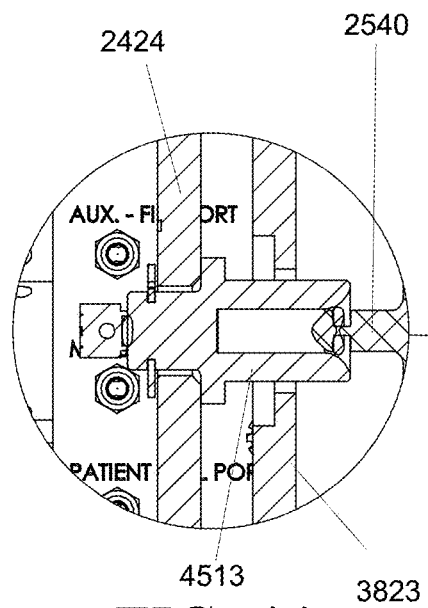
FIG. 44 illustrates a partial view of the deficit module shown in FIG. 43 showing an exemplary manifold connection assembly for connecting the deficit cartridge shown in FIG. 20, where the manifold connection assembly is in a disengaged position relative to the deficit cartridge.
Figure 43:
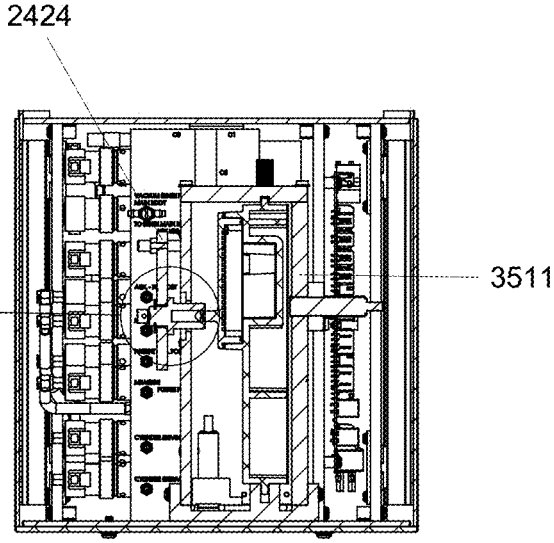
FIG. 43 illustrates a cross-sectional view of the deficit module of FIG. 20 taken along the line A-A shown in FIG. 42.
Figure 45:
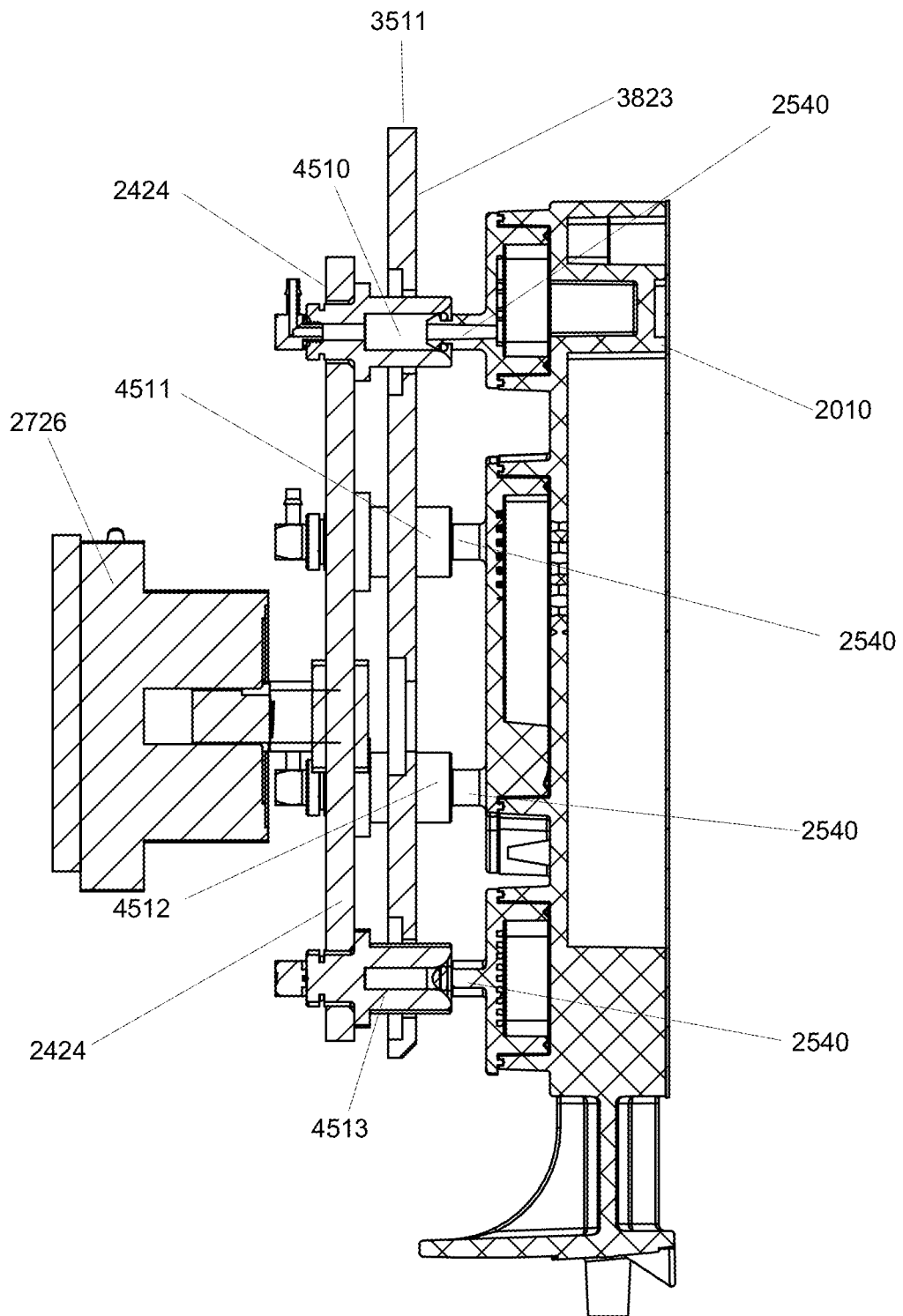
FIG. 45 illustrates the exemplary engagement mechanism shown in FIG. 44, where the manifold connection assembly is in the disengaged position relative to the deficit cartridge.
Figure 46:
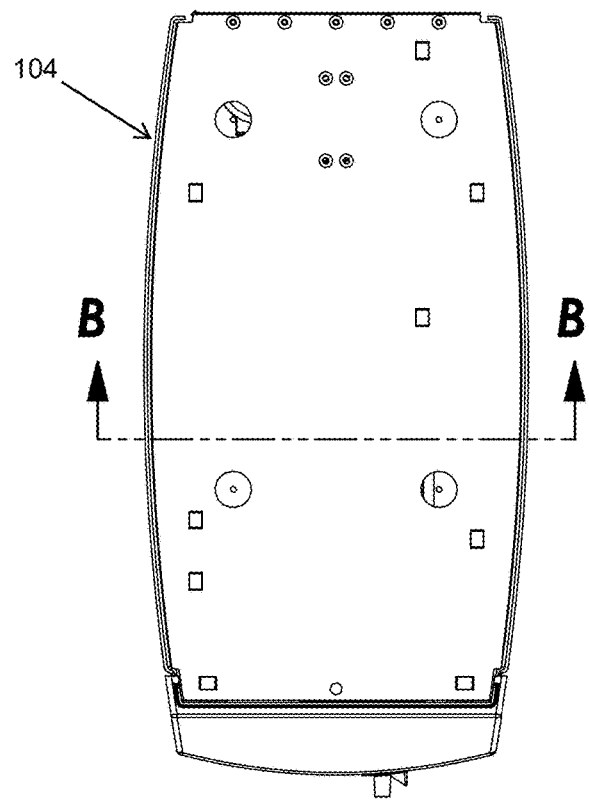
FIG. 46 illustrates a top view of the deficit module of FIG. 20.
Figure 48:
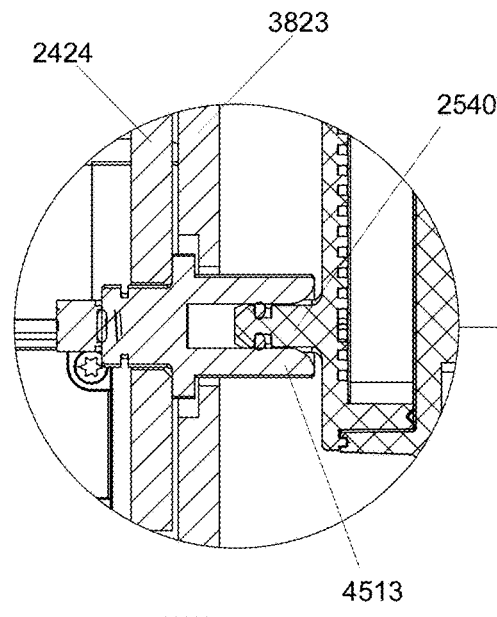
FIG. 48 illustrates a partial view of the deficit module shown in FIG. 43 showing the exemplary manifold connection assembly of FIG. 44, where the manifold connection assembly is in an engaged and connected position relative to the deficit cartridge.
Figure 47:
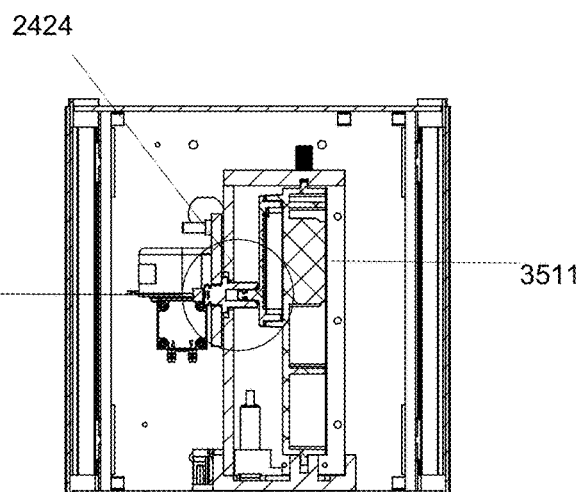
FIG. 47 illustrates a cross-sectional view of the deficit module of FIG. 20 taken along the line B-B shown in FIG. 46.
Figure 49:
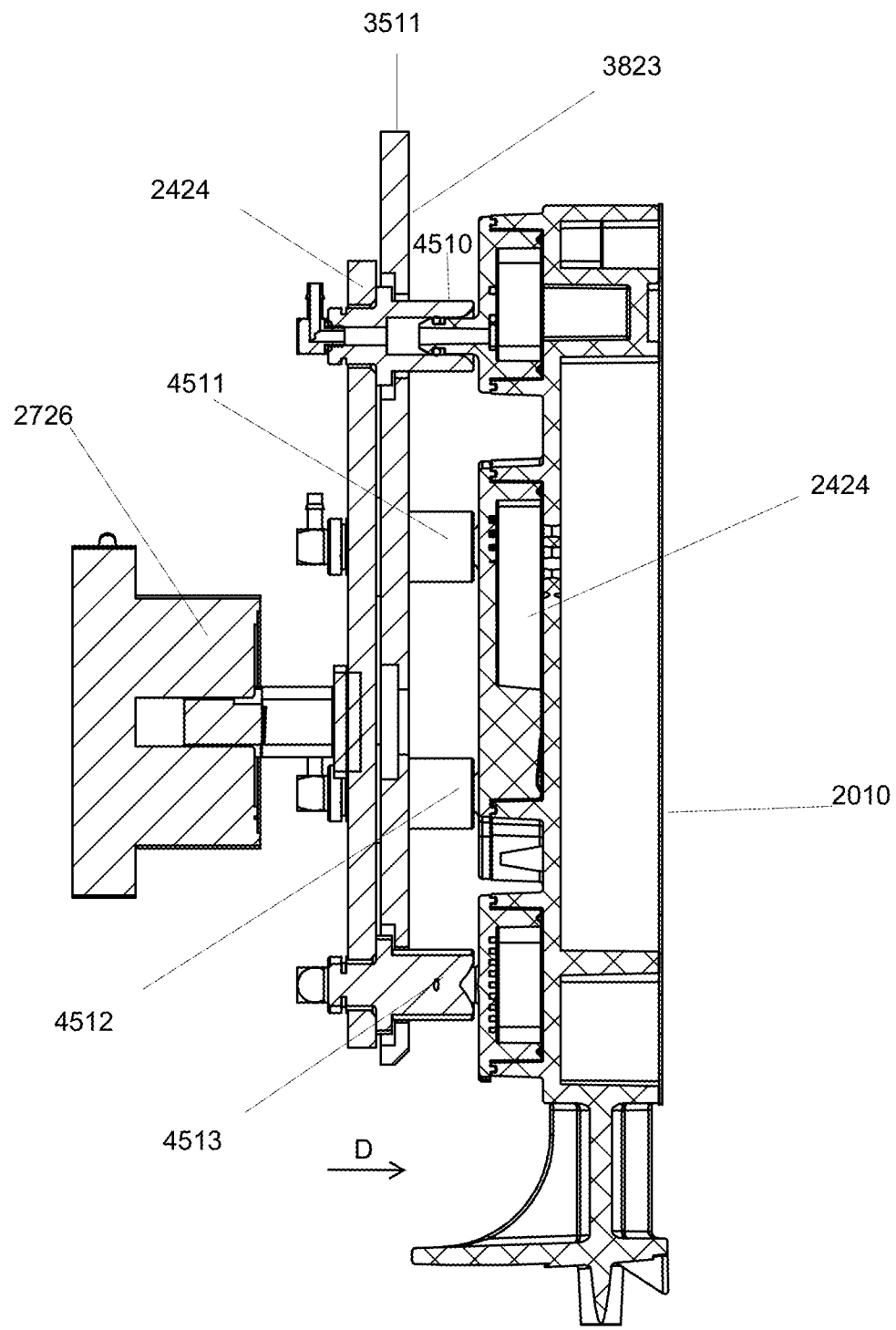
FIG. 49 illustrates the exemplary engagement mechanism shown in FIG. 44, where the manifold connection assembly is in the engaged and connected position relative to the deficit cartridge.

FIGS. 35 through 48 illustrate an exemplary embodiment of a deficit module 104 that can be used with the fluid management system 100 shown in FIG. 1 and the deficit cartridge 2010 shown in FIGS. 20-34. Referring to FIG. 35, the deficit module 104 may include a deficit cartridge receiving assembly 3511 for receiving the deficit cartridge 2010, one or more sensors 2742 for sensing characteristics of fluid moving through the deficit cartridge without contacting the fluid, a pump assembly 3514, a pump manifold assembly 3513, a manifold connection assembly 2424 for connecting the deficit cartridge 2010 to the pump assembly 3514 and a solenoid and pressure sensor (via the pump manifold assembly 3513), a pneumatic mechanism 2726 that moves the manifold connection assembly between an engaged position (e.g., as shown in FIGS. 47-49) and a disengaged position (e.g., as shown in FIGS. 43-45) with the deficit cartridge 2010, and a printed circuit board (PCB) 3519.

Figure 38:
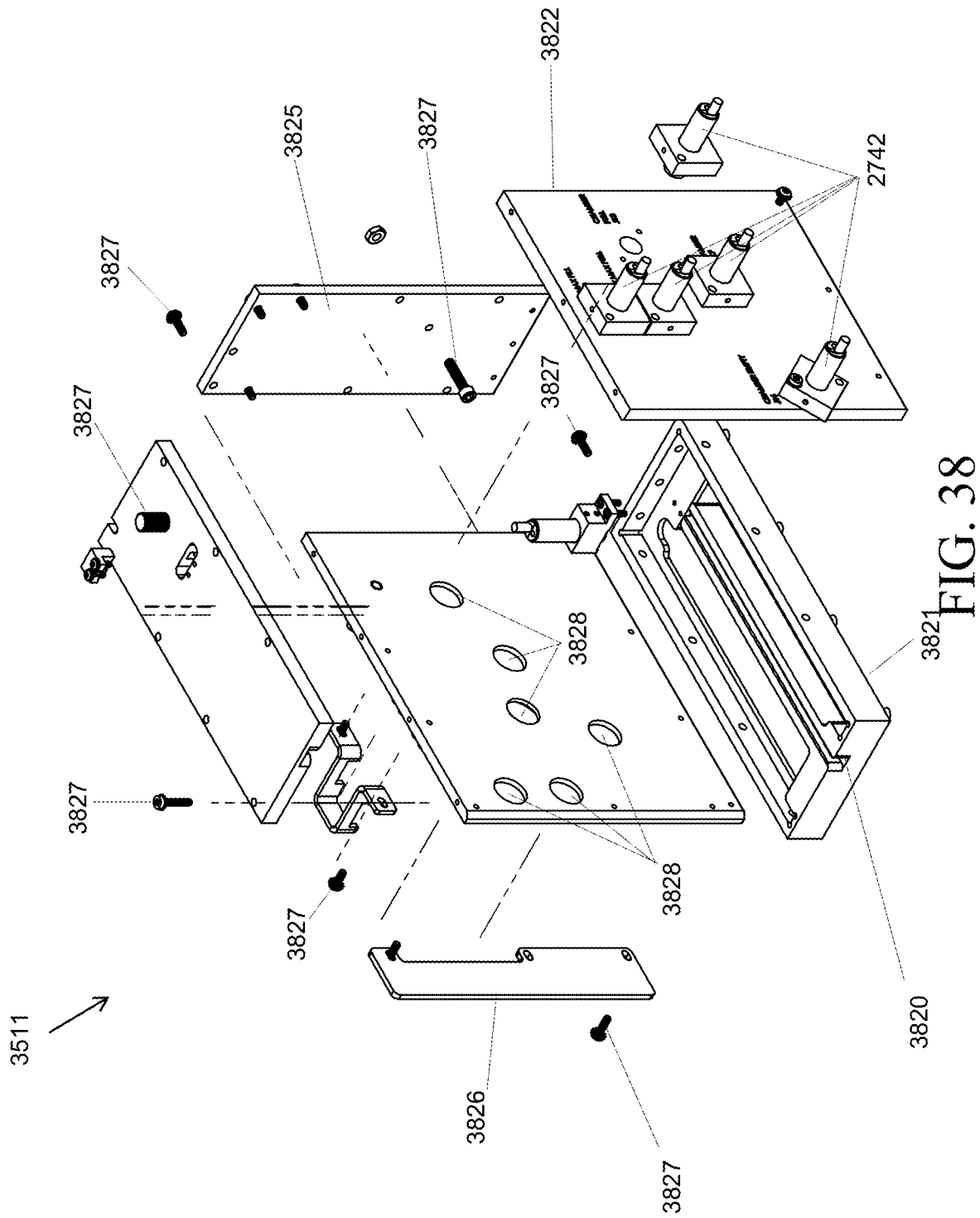
FIG. 38 illustrates an exploded perspective view of an exemplary deficit cartridge receiving assembly of the deficit module of FIG. 20 for receiving the deficit cartridge of FIG. 20.
Figure 39:
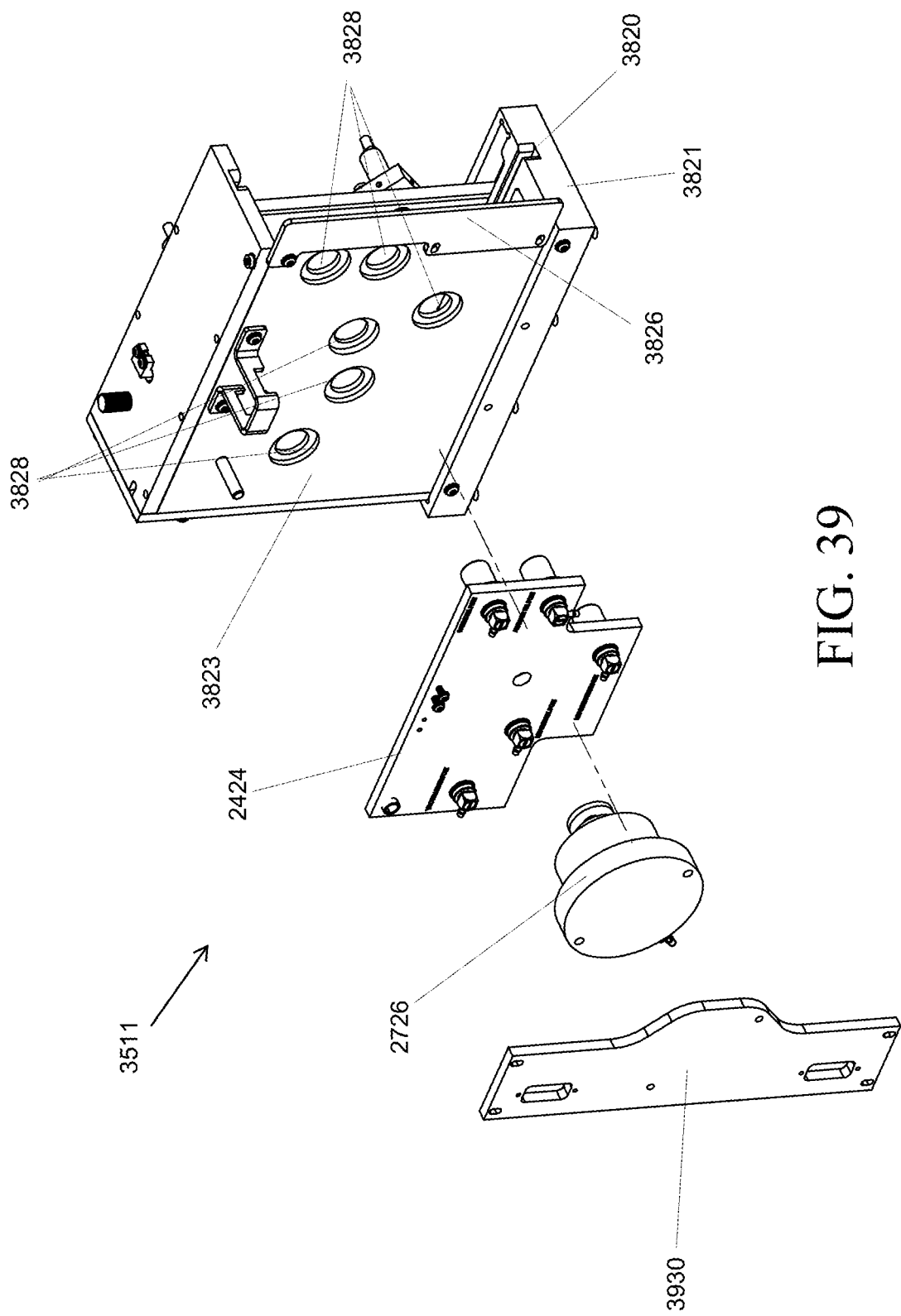
FIG. 39 illustrates a perspective view of an exemplary manifold connection assembly of the deficit module of FIG. 20 and the deficit cartridge receiving assembly of FIG. 38.
Figure 40:
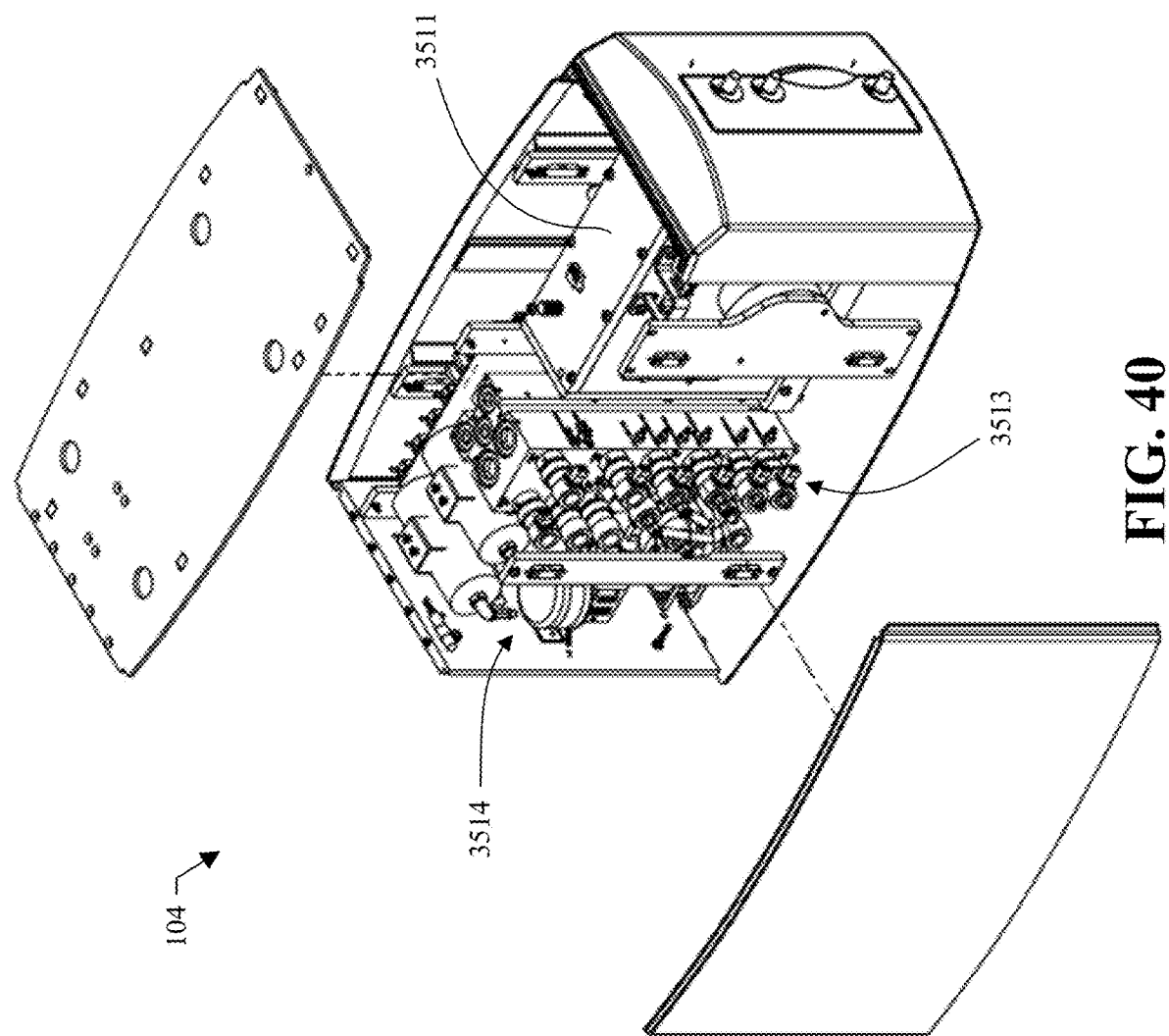
FIG. 40 illustrates a left side perspective view of the deficit module of FIG. 20.
Figure 41:
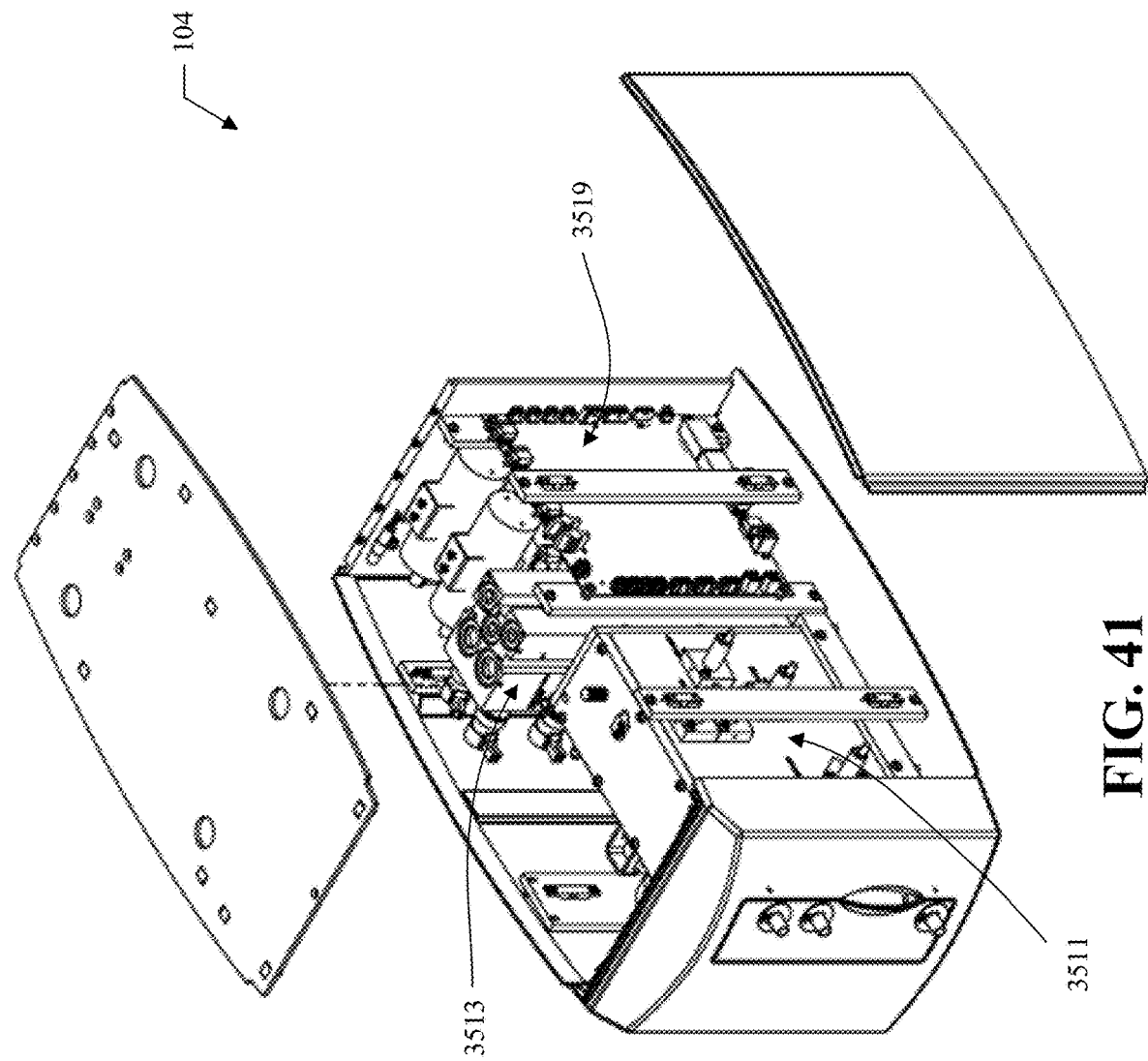
FIG. 41 illustrates a right-side perspective view of the deficit module of FIG. 20.
Figure 42:
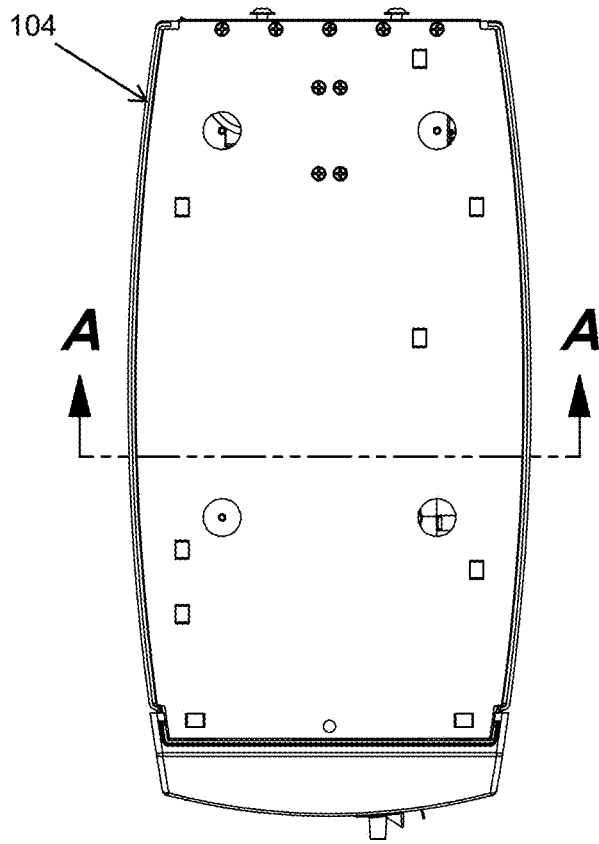
FIG. 42 illustrates a top view of the deficit module of FIG. 20.

Referring to FIGS. 38 and 39, the deficit cartridge receiving assembly 3511 includes a base 3821 having a slot or opening 3820 for receiving the deficit cartridge 2010 (FIGS. 30-34). The receiving assembly 3511 also includes one or more walls or components 3822-3826 that substantially separate the deficit cartridge 2010 from the remainder of the components within the interior of the deficit module 104 when the deficit cartridge 2010 is disposed within the receiving assembly 3511. The walls or components 3822-3826 and base 3821 can be connected by one or more fasteners 3827 to create the receiving assembly 3511. A first wall 3822 of the receiving assembly 3511 can be configured to hold the one or more sensors 2742 for sensing characteristics of fluid moving through the deficit cartridge 2010. In the illustrated embodiments, the one or more sensors 2742 are capacitive sensors that detect fluid presence. However, other fluid level or presence sensing technologies could be utilized including infrared sensors, laser sensors, optical sensors, electro-mechanical sensors (e.g. float with mechanical toggle switch actuation, piezo-electric pressure sensors, etc.), inductive sensors, ultrasonic sensors, or any other suitable sensors.

A second wall 3823 of the receiving assembly 3511 can include a plurality of openings 3828 for receiving connectors (e.g., connectors 4510-4513 shown in FIGS. 45 and 49) of the manifold connection assembly 2424 such that the pump assembly 3514 can be operatively connected to the diaphragm valves and pressure port of the deficit cartridge 2010, as discussed in more detail below with references to FIGS. 42-49. Referring to FIG. 39, the manifold connection assembly 2424 can be connected to or positioned adjacent to the wall 3823 of the receiving assembly 3511, and the pneumatic mechanism 2726 can be connected to the manifold assembly 2424 by one or more fasteners and to the deficit module 104 by a connection element or plate 3930.

Referring to FIGS. 35 and 36, in the illustrated embodiment, the pump assembly 3514 includes a positive pressure pump 3515 and a negative pressure pump 3517, where the pump assembly 3514 is connected to the pneumatic mechanism 2726 and the connectors of the manifold connection assembly 2424 via the pump manifold assembly 3513. The positive pressure pump 3515 provides pressure to the pneumatic cylinder 2726 to move the manifold connection assembly 2424 between the engaged position (e.g., as shown in FIGS. 47-49) and the disengaged position (e.g., as shown in FIGS. 43-45) with the deficit cartridge 2010. The positive pressure pump 3515 also expedites closing or augments closing force of the diaphragm valves of the deficit cartridge 2010. The negative pressure pump 3517 provides a vacuum pressure to the diaphragm valves of the deficit cartridge 2010 to move the diaphragm valves to the open position.

Figure 37:
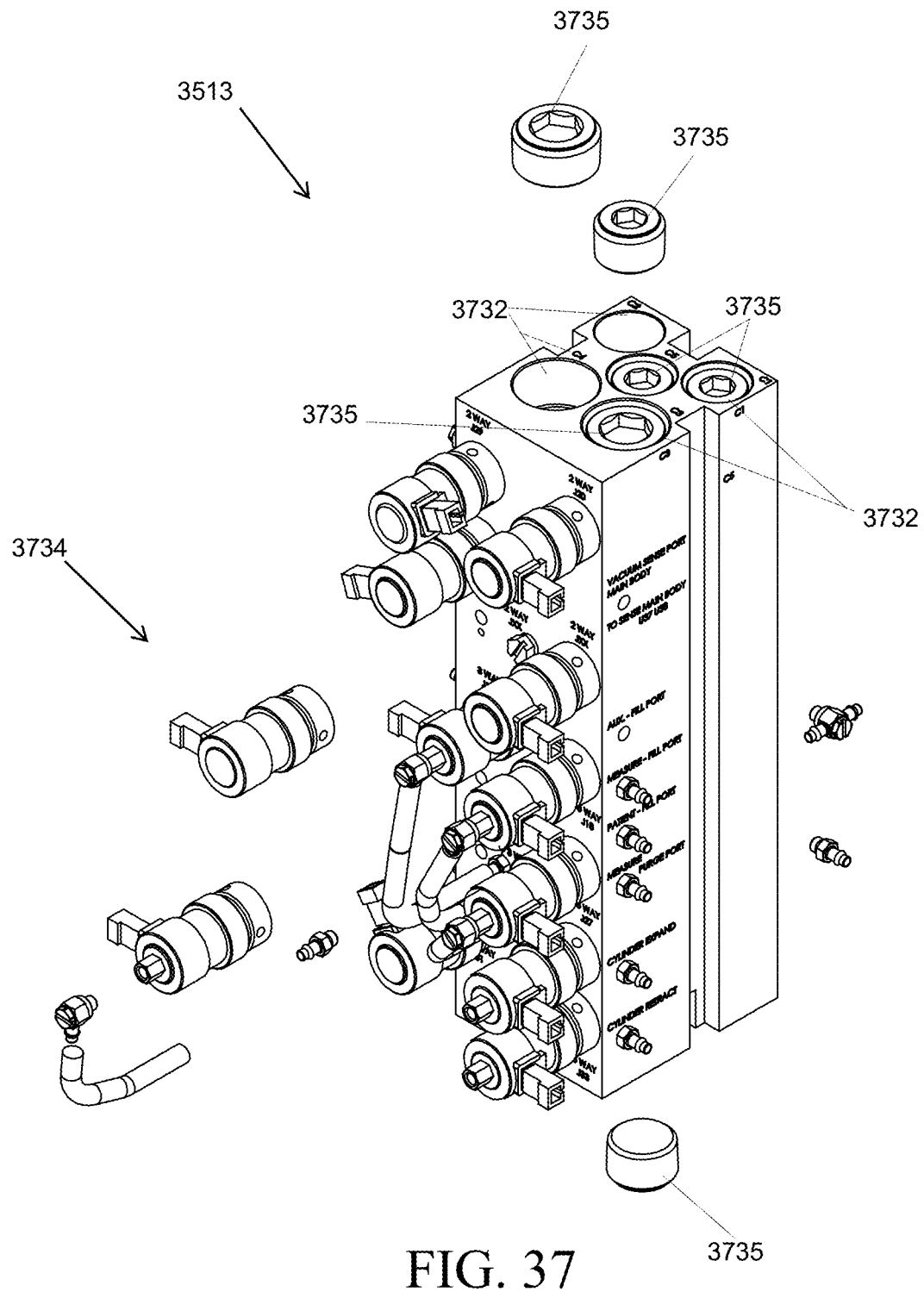
FIG. 37 illustrates a perspective view of an exemplary deficit pump manifold assembly for the deficit module of FIG. 20.

Referring to FIG. 37, in the illustrated embodiment, the pump manifold assembly 3513 includes a plurality of accumulators 3732 and solenoid valves 3734 for regulating pressure provided by the pumps 3515, 3517 and the opening and closing of the diaphragm valves of the deficit cartridge 2010. In certain embodiments, the accumulators 3732 vary the positive and negative pressures to: (1) allow for the use of smaller pressure pumps that can deliver the necessary flow rates; and (2) aid pressure regulation by reducing the impact of introducing air via a "bang-bang" control scheme (i.e., an open valve, close valve control scheme). In the illustrated embodiment, the pump manifold assembly 3513 includes five accumulators 3732 (e.g., holes that extend through the assembly 3515) that are capped off at the top and bottom by caps 3735). The solenoid valves 3734 of the pump manifold assembly 3513 may connect to the connectors of the manifold connection assembly 2424 via tubing.

Referring to FIGS. 42-49, the pneumatic mechanism 2726 is shown moving the manifold connection assembly 2424 between a disengaged position (FIGS. 43-45) with the deficit cartridge 2010 and an engaged position (FIGS. 47-49) with the deficit cartridge 2010. Referring to FIGS. 43-45, when in the disengaged position, the ports 2540 for the diaphragm valves and pressure port of the deficit cartridge 2010 are not engaged by the connectors 4510-4513. Referring to FIGS. 47-49, the manifold connection assembly 2424 is moved to the engaged position in the direction D (FIG. 49) by the pneumatic mechanism 2726 such that the connectors 4510-4513 engage a corresponding port 2540 of the deficit cartridge 2010. When the connectors 4510-4513 are engaging the ports 2540 of the deficit cartridge 2010, the pump assembly 3514 is operatively connected to the deficit cartridge 2010 such that the pump assembly 3514 can move the diaphragm valves of the deficit cartridge between the open and closed positions and the vacuum pressure supplied to the deficit cartridge 2010 can be sensed by a pressure sensor in the deficit module and down regulated by opening a solenoid to atmosphere.

Referring to FIGS. 35-49, in certain embodiments, insertion of the deficit cartridge 2010 into the receiving assembly 3511 of the deficit module 104 causes all of the internal connections between the deficit cartridge 2010 and the various components of the deficit module 104. For example, insertion of the deficit cartridge 2010 into the receiving assembly 3511 causes the pneumatic mechanism 2726 to move the manifold connection assembly to the engaged position with the deficit cartridge (e.g., as shown in FIGS. 47-49) and operatively connect the pump assembly 3514 to the deficit cartridge. Insertion of the deficit cartridge 2010 into the receiving assembly 3511 also causes the one or more non-contact sensors 2742 to be aligned with the chamber 2944 (FIG. 29) of the deficit cartridge 2010. These automatic connections between the deficit cartridge 2010 and the deficit module are advantageous because it limits the amount of connections a user has to make with respect to the deficit cartridge 2010. That is, after inserting the deficit cartridge 2010 into the deficit module 104, a user only needs to connect fluid return line(s) to inlet openings 2012, 2014 (FIG. 20) of the deficit cartridge 2010 and an evacuation line to a vacuum opening 2016 (FIG. 20) of the deficit cartridge.

Referring to FIG. 50, in certain embodiments, the system 100 may be used for gynecological, urological, and orthopedic procedures that are performed in operating rooms that are equipped with third party suction and fluid collection devices. In these embodiments, the system 100 can be configured to include a main unit 102 (e.g., any main unit 102 described in the present application) and a deficit module 104 (any deficit module 104 described in the present application), but not include the fluid suction and collection module 106. In this embodiment, a tubing set that includes deficit cartridge 2010 (FIGS. 20-34) can be used in combination with the main unit 102 and the deficit module 104 to determine a fluid deficit of a fluid during a surgical procedure.

Referring to FIG. 51, in some situations, gynecological, urological, and orthopedic procedures are performed in operating rooms in which the facility prefers or requires "direct-to-drain" disposal of fluids returning from the surgical site. In these situations, the facility often prefers or requires the volume of the fluid being returned from the surgical site be recorded. In some embodiments, the system 100 can be configured to include a fluid flow monitoring and evacuation module 5101 that includes features of the deficit module 104. The fluid flow monitoring and evacuation module 5101 can work in combination with the central suction system of the facility, main unit 102, and a tubing set that includes a deficit cartridge 2010 (FIGS. 20-34) or other similar cartridge to determine a fluid volume returning from the surgical site and entering a waste disposal system of the facility, as well as a fluid deficit for the surgical procedure. The fluid flow monitoring and evacuation module 5101 may communicate with the main unit 102 via Bluetooth or other wired or wireless means to measure, record, and display the return fluid volume and/or fluid deficit for the surgical procedure.

While the fluid flow monitoring and evacuation module 5101 is described as working in combination with the main unit 102 of the fluid management system 100, it should be understood that the fluid flow monitoring and evacuation module 5101 may also function as a stand-alone fluid flow monitoring and evacuation module capable of communicating with other equipment of the facility via Bluetooth or other wired or wireless means. After recording the fluid volume, module 5101 can then dispose of the fluid directly into a waste disposal system of the facility. In certain embodiments, the fluid flow monitoring and evacuation module 5101 can be a wall mounted unit or a cart mounted unit. In some embodiments, the fluid flow monitoring and evacuation module 5101 can include an integrated suction source to work in combination with, or in place of, the central suction system of the facility. As use of the deficit cartridge 2010 or other similar cartridge isolates the fluid returning from the surgical site from the components (e.g., sensors, pumps, etc.) of the fluid flow monitoring and evacuation module 5101, circulation of cleaning solution through the fluid flow monitoring and evacuation module after each procedure is not necessary, which enhances procedure efficiency.

The flow-based deficit monitoring feature of the system 100 (e.g., the combination of the deficit module 104 and the deficit cartridge 2010, or the fluid flow monitoring and evacuation module 5101) enables accurate and reliable fluid deficit monitoring that is cost-effective due to the single-use nature of the deficit cartridge 2010 and the elimination of canisters. This feature also enhances procedure efficiency as interruptions associated with setting up, connecting, changing, and discarding of the canisters will also be eliminated, as well as cleaning the deficit module and/or monitoring and evacuation module after each procedure. In alternative embodiments, the deficit cartridge 2010 may be configured for multi-procedure use.

In certain situations, the fluid management system 100 may be connected to an external pressure source (e.g., a suction source) that is used to pull fluid from the surgical site. As external suction sources are usually set to high vacuum levels in an operating room environment, down-regulation of the vacuum pressure provided by the external suction source may be necessary for proper operation of certain fluid outflow regulation, deficit monitoring, and/or collection functions. Down-regulation of a vacuum pressure provided by an external suction source can be accomplished via a manually or electronically-controlled regulator ("Regulator") provided it is isolated from the biohazardous fluid returning from the surgical site because replacing or cleaning the Regulator after every surgical procedure would be prohibitively expensive and/or unduly burdensome. However, isolating the Regulator by placing fluid collection canisters between it and the surgical site is not desirable due to the costs of the canisters, the complexity of setting them up, the need to change them during the procedure when they become full, and the need to dispose of them at the end of the procedure.

Figure 52:
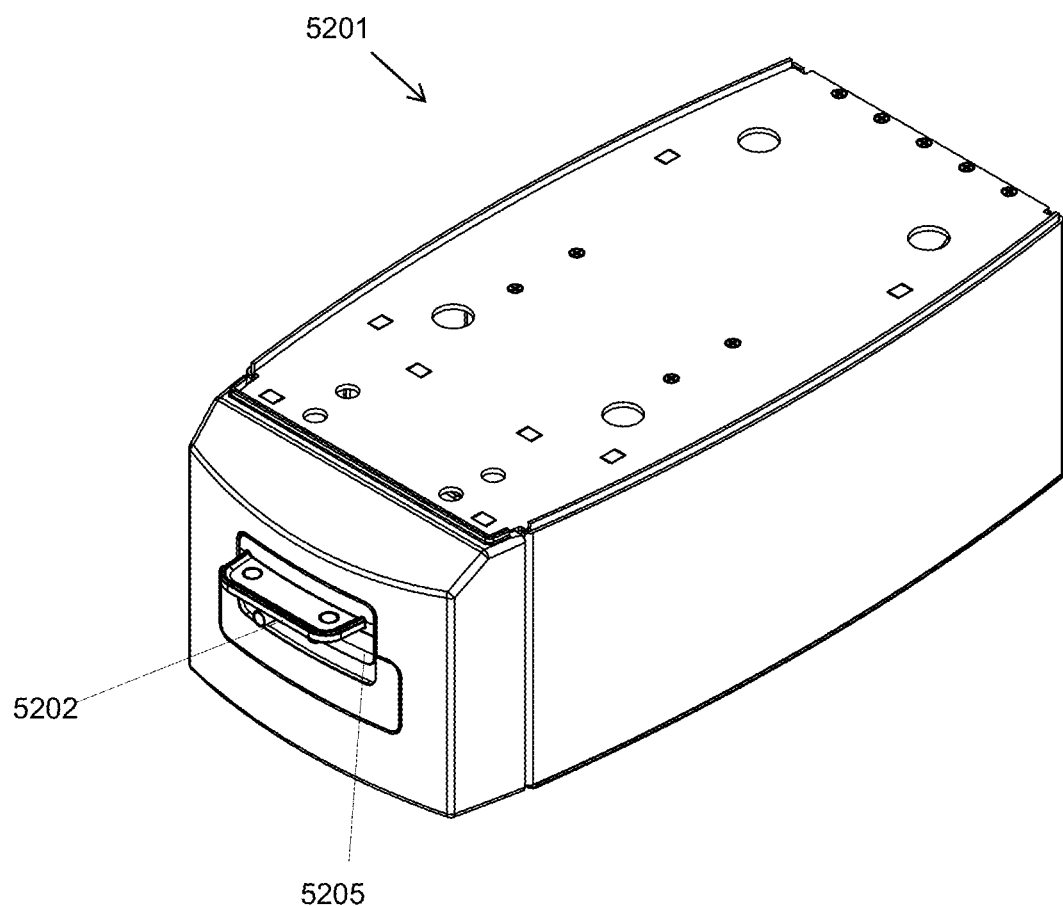
FIG. 52 illustrates a perspective view of an exemplary embodiment of an aspiration module and a pressure regulator for the fluid management system of FIG. 1, where the pressure regulator is inserted in the aspiration module.

Referring to FIG. 52, to overcome the problems associated with the use of a Regulator, the system 100 may utilize a single-use or multi-use pressure regulator 5205 that is cost-effective to manufacture and disposable. The pressure regulator 5205 does not need to be isolated from the biohazardous fluids returning from the surgical site because of its disposability. The pressure regulator 5205 can be used in combination with a pressure source (e.g., an air pump) and one or more pressure sensors of the fluid management system 100 to sense and regulate the vacuum pressure provided by an external suction source to control the rate of fluid outflow from a surgical site and, thereby, assist in efforts to provide good distention and visualization. The pressure pump and pressure sensors may be included in an aspiration module 5201 that is configured to be operatively connected to the control system of the fluid management system 100, or the pressure pump and pressure sensors may be integral to the main unit 102 of the fluid management system 100. In embodiments that include the use of the aspiration module 5201, inserting the pressure regulator 5205 into the aspiration module 5201 causes fluidic connections between the pressure regulator 5205 and the pressure sensing and gas bleed mechanisms and integrated pressure pump of the aspiration module 5201. After inserting the pressure regulator 5205 into the aspiration module 5201, the user can manually connect an external suction source and the fluid return lines from the surgical site to connection ports 5202 (e.g., openings 5315, 5317 shown in FIG. 53 and openings 5415, 5417 shown in FIGS. 54-55) of the pressure regulator 5205.

Figure 53:
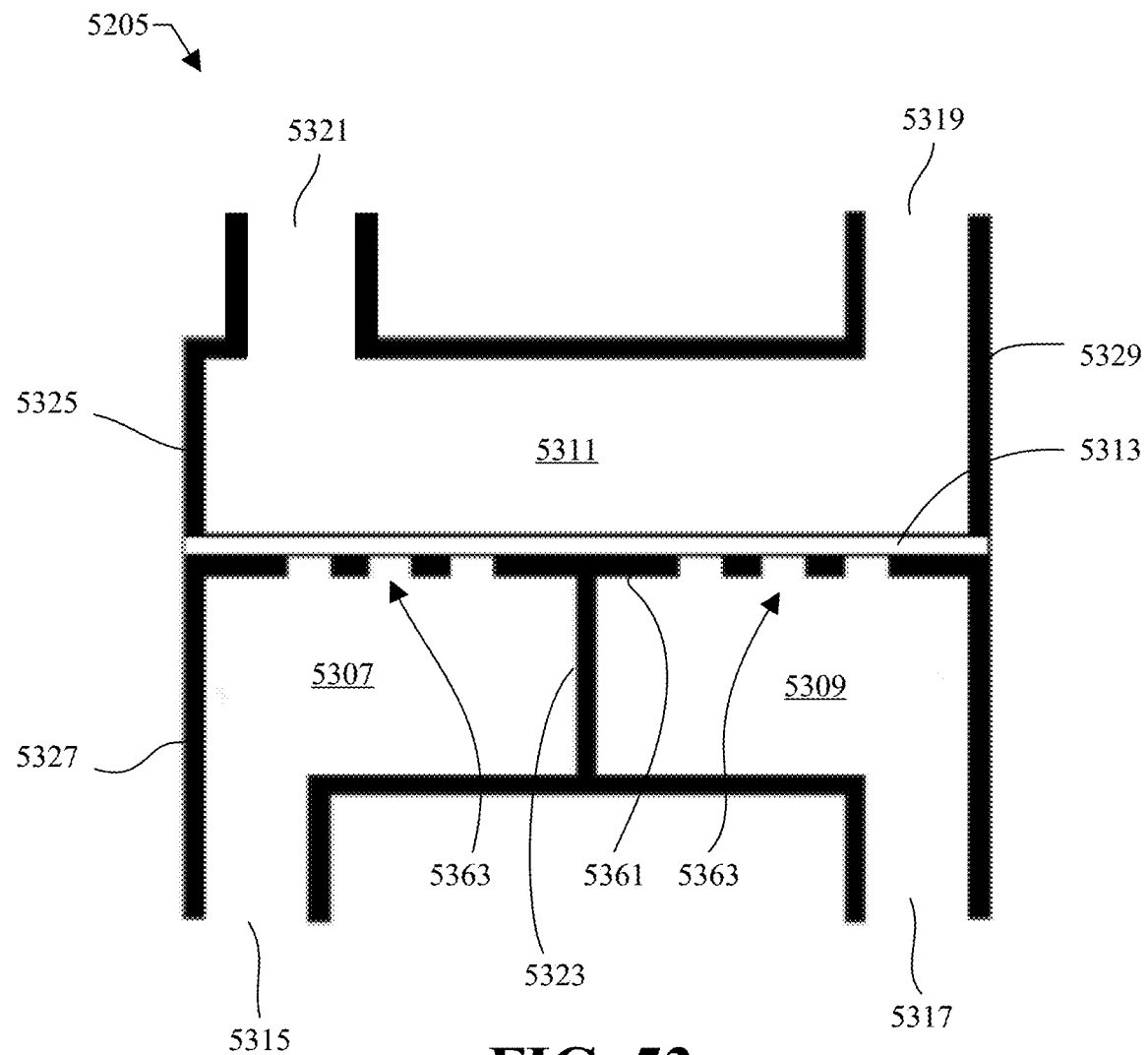
FIG. 53 illustrates a schematic view of an exemplary embodiment of the pressure regulator shown in FIG. 52.

Referring to FIG. 53, a first exemplary embodiment of the pressure regulator 5205 includes three chambers 5307, 5309, 5311 and a flexible membrane 5313. The first chamber 5307 includes an opening or port 5315 for fluidly connecting to the external suction source. The second chamber 5309 has an opening or port 5317 for fluidly connecting to the surgical site (via one or more fluid lines or tubes). The third chamber 5311 includes one or more ports for connecting to a pressure source (e.g., pressure source 7449 of aspiration module 5201 shown in FIG. 74) and a pressure sensor (e.g., pressure sensors 7451 of aspiration module 5201 shown in FIGS. 74-75). In the illustrated embodiment, the third chamber 5311 has a first opening 5319 for connecting to the pressure sensor and a second opening 5321 for connecting to the pressure source.

The flexible membrane 5313 is positioned to fluidly isolate (i.e., seal) the third chamber 5311 from both of the first chamber 5307 and the second chamber 5309, which allows the pressure source and pressure sensor of the fluid management system 100 (which are connected to the openings 5319, 5321 of the third chamber 5311) to be fluidly isolated from biohazardous fluid returning from the surgical site and moving through the first and second chambers 5307, 5309. In some embodiments, a hydrophobic filter (not shown) is disposed between the flexible membrane 5313 and the openings 5319, 5321 to provide further protection in preventing fluid from contacting the pressure source and pressure sensor of the fluid management system 100. For example, the hydrophobic filter can prevent fluid from contacting the pressure source and regulator if the flexible membrane 5313 tears or ruptures.

The first chamber 5307 is adjacent to the second chamber 5309 and separated from the second chamber 5309 by a substantially vertical extended member or wall 5323 and a substantially horizontal extended member or wall 5361. The wall 5361 includes openings 5363 that fluidly connect the first chamber 5307 to the second chamber 5309. The pressure source of the fluid management system 100 is configured to move the flexible membrane 5313 between an engaged position with the wall 5361 and one or more disengaged positions with the wall 5361, where the first and second chambers 5307, 5309 are fluidly isolated from each other when the flexible membrane is in the engaged position, and where the first and second chambers 5307, 5309 are fluidly connected to each other (via openings 5363) when the flexible membrane 5313 is in one of the disengaged positions. The size and spacing between of the openings 5363 prevent the membrane 5313 from rupturing due to over-extrusion through the openings when positive pressure is applied to stop flow across the valve. The size and spacing of the openings 5363 may vary based upon the elasticity and thickness of the material for flexible membrane 5313. The number of openings 5363 can ensure adequate flow, and, in some embodiments, the total combined surface area of the openings on either side of each valve may be roughly equivalent to, or greater than, the inner cross-sectional area of the tubing expected to be attached to the port 5315.

Figure 74:
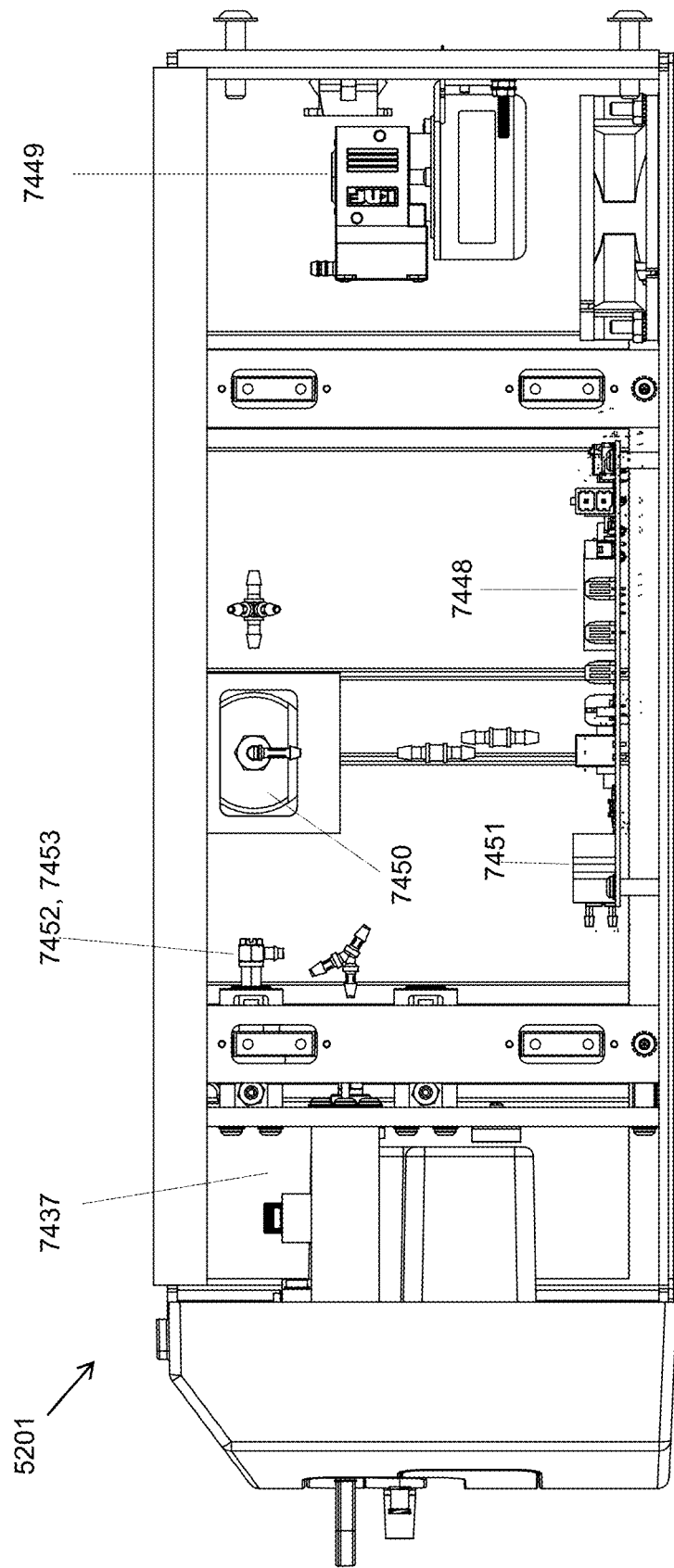
FIG. 74 illustrates a side cross-sectional view of an exemplary embodiment of the aspiration module shown in FIG. 52.

The fluid management system 100 is configured to provide pressure to the third chamber 5311 through opening 5319, and the system 100 is configured to sense and regulate the pressure within the third chamber 5311 by sensing pressure via the pressure sensor and opening 5321 and modulating the pressure provided by the pressure source to achieve the desired pressure setpoint (e.g., by modulating the air pump speed of pressure source 7449 of aspiration module 5201 shown in FIG. 74). The system 100 controls the pressure source to cause the flexible membrane 5313 to stretch away from the wall 5361 when a more positive pressure exists in the chamber 5309 than the greater of the pressure in the first chamber 5307 or the pressure in third chamber 5311 (in addition to the force required to displace the flexible membrane 5313). When a more positive pressure exists in the second chamber 5309 than in the first and third chambers 5307, 5311 (in addition to the force required to displace the flexible membrane 5313), fluid is able to displace the flexible membrane 5313 and create a fluidic connection between chambers 5307, 5309 via the holes 5363 through the wall 5361 and the displaced flexible membrane 5313 such that the desired regulated pressure (e.g., the lesser of the pressure in the first chamber 5307 or the pressure in the third chamber 5311, in addition to the force required to displace the flexible membrane 5313) is supplied to the surgical site through the opening 5317 of the second chamber 5309. In nominal conditions, the pressure of the external suction source present in the first chamber 5307 is the lower than the pressure of the other chambers 5309, 5311 of the pressure regulator 5205, the regulated pressure in the third chamber 5311 is greater than the pressure in the second chamber 5309, and the regulated pressure in the third chamber 5311 is adjustable to allow regulation of the pressure supplied to the surgical site through the opening 5317 of the second chamber 5309.

When the first chamber 5307 and the second chamber 5309 are fluidly connected, the biohazardous fluid moves from the surgical site, into the second chamber 5309 through opening 5317, through the opening between the flexible membrane 5313 and the wall 5361 via holes 5363 and into the first chamber 5307, and through the opening 5315 to a waste collection of the system 100 or the facility. When the valve is desired to be closed and flow stopped from the surgical site, the system 100 applies a pressure more positive in the third chamber 5311 than the maximum pressure expected in the second chamber 5309 (e.g., the pressure caused by the weight of the water column in the height difference between the valve inlet 5317 and the surgical site) and the pressure in the chamber 5307, in addition to the pressure required to displace the flexible membrane 5313. When the pressure in chamber 5311 is greater than the pressure in both chambers 5307 and 5309 (in addition to the pressure required to displace the flexible membrane), then the flexible membrane 5311 is held with sufficient force against wall 5361 to counteract the other system pressures such that flow is substantially halted. The flexible membrane 5313 seals the third chamber from the first and second chambers 5307, 5309 to prevent the biohazardous fluid from moving into the third chamber 5311 and contacting the pressure source and/or pressure sensors of the system 100.

Provided the pressure from the surgical site (as available in chamber 5309) is a more positive pressure than the gauge pressure supplied by the external suction source through the first chamber 5307, the gauge pressure supplied by the pressure source of the system 100 into the third chamber 5311, and the pressure required to stretch flexible membrane 5313, the regulated vacuum pressure supplied to the surgical site can be equal to the more-positive gauge pressure of the gauge pressure supplied by the external suction source (through the first chamber 5307) or the gauge pressure supplied by the pressure source of the system 100 (into the third chamber 5311) and the pressure required to stretch the flexible membrane 5313. That is, provided the flow rate from the surgical site is negligible with respect to the flow capacity of the external pressure source (supplied through the first chamber 5307), the pressure supplied to the surgical site (through chamber 5309) will be the pressure closest to absolute vacuum of the pressure supplied by the external pressure source (through the first chamber 5307) or the pressure supplied by the pressure source of the system 100 (into the third chamber 5311) and the pressure required to stretch the flexible membrane 5313.

In certain embodiments, the pressure required to stretch the flexible membrane 5313 may be modeled by a transfer function to determine a pressure setpoint for the pressure source of the system 100 (supplied into the third chamber 5311) that is required to achieve a desired regulated vacuum pressure in the second chamber 5309 that is supplied to the surgical site. The system 100 may be configured to vary the regulated vacuum pressure supplied to the surgical site, via the pressure sensor and pressure pump of the system 100, by varying the pressure supplied to the third chamber 5311. Also, the pressure supplied by the external suction source (through the first chamber 5307) and supplied to the second chamber 5309 may be regulated to a more positive pressure by regulating the pressure provided to the third chamber 5311 by the pressure source of the system 100 to a greater pressure than supplied by the external suction source. Because the regulated pressure setpoint is variable, this also enables the pressure regulator 5205 to serve as a simple 2-way valve to enable and disable flow on demand by regulating the pressure supplied to the third chamber 5311 with a pressure greater than the pressure in either the first chamber 5307 or second chamber 5309.

In certain embodiments, the flexible membrane 5313 is configured such that the pressure supplied by the pressure source in the third chamber 5311 causes the flexible membrane 5313 to stretch away from the wall 5361 and cause the regulated vacuum pressure supplied to the surgical site to be between about 10 mmHg and about 30 mmHg greater than the pressure provided by the pressure source of the system 100. The flexible membrane 5313 can be made of, for example, neoprene, silicone, natural rubber, nitrile, EPDM, other rubber compounds, or any other material that allows the flexible membrane to be moved between the engaged and disengaged positions.

The pressure regulator 5205 may have a housing 5325 that at least partially defines the three chambers 5307, 5309, 5311 and includes the openings 5315, 5317, 5319, 5321. The housing 5325 can be made of, for example, polycarbonate, any suitable type of plastic material, or any other suitable material. In certain embodiments, the housing 5325 has a first component 5327 that includes the first and second chambers 5307, 5309, and a second component 5329 that includes the third chamber 5311, where the flexible membrane 5313 is positioned between the first and second components 5327, 5329 to fluidly isolate the chambers of the first component 5327 from the chambers of the second component 5329. The first component 5327, the second component 5329, and the flexible membrane 5313 can be connected by a snap-fit connection, an adhesive connection, one or more fasteners, laser welding, ultrasonic welding, vibration welding, or any other suitable means.

Referring to the embodiment shown in FIG. 53, if the lowest desired regulated pressure supplied to the surgical site is a positive gauge pressure, the pressure supplied by the external pressure source could be a positive or negative gauge pressure. If the desired regulated pressure is a negative gauge pressure (i.e., a vacuum pressure), then the pressure supplied by the external suction source may be required to be a negative gauge pressure that is more negative than the lowest gauge pressure desired to be regulated because pressure supplied by the external pressure source is not being sensed. In other words, the pressure supplied by the external pressure source (through the first chamber 5307) is not required to be consistent (e.g., does not need to be regulated and may have pressure fluctuations) provided the highest gauge pressure supplied by the external pressure source is not a gauge pressure that is higher than the desired regulation pressure setpoint for the regulated source (e.g., the surgical site).

Figure 54:
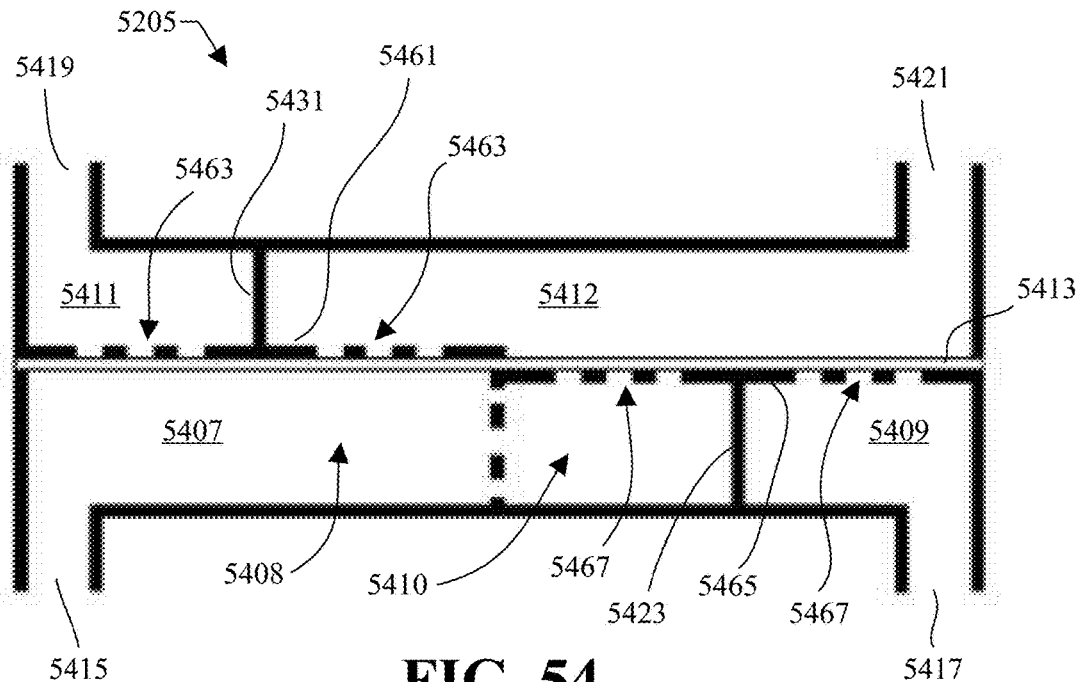
FIG. 54 illustrates a schematic view of another exemplary embodiment of the pressure regulator shown in FIG. 52.
Figure 55:
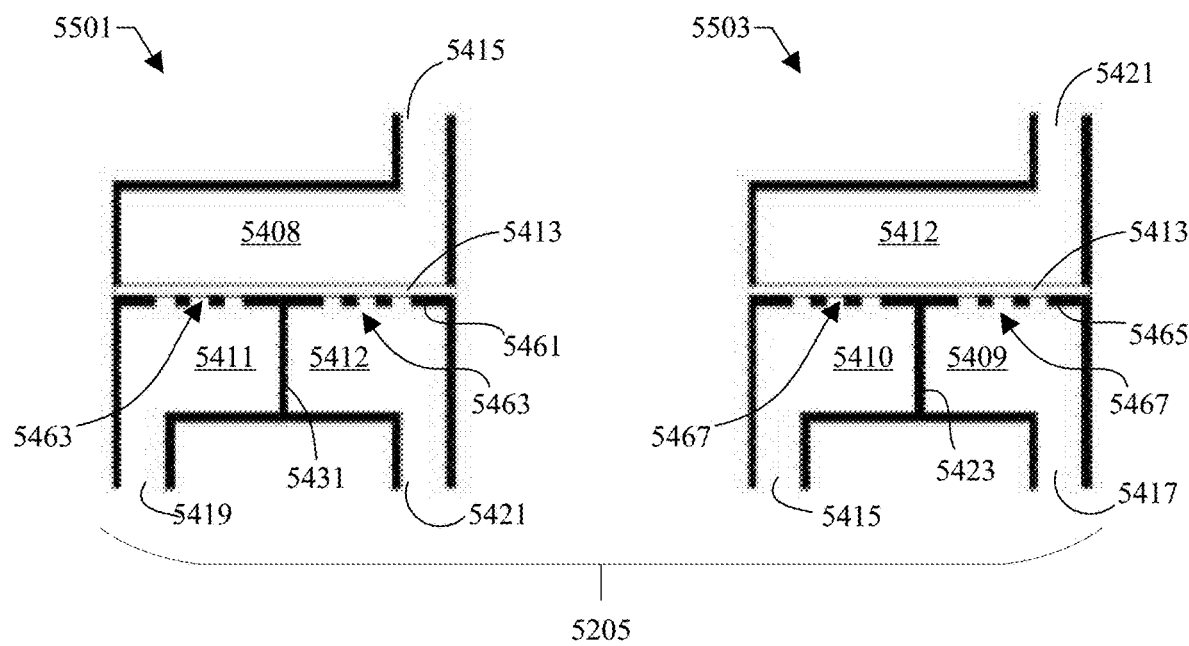
FIG. 55 illustrates a schematic view of the pressure regulator shown in FIG. 54 showing valves of the pressure regulator disposed in a series.
Figure 56:
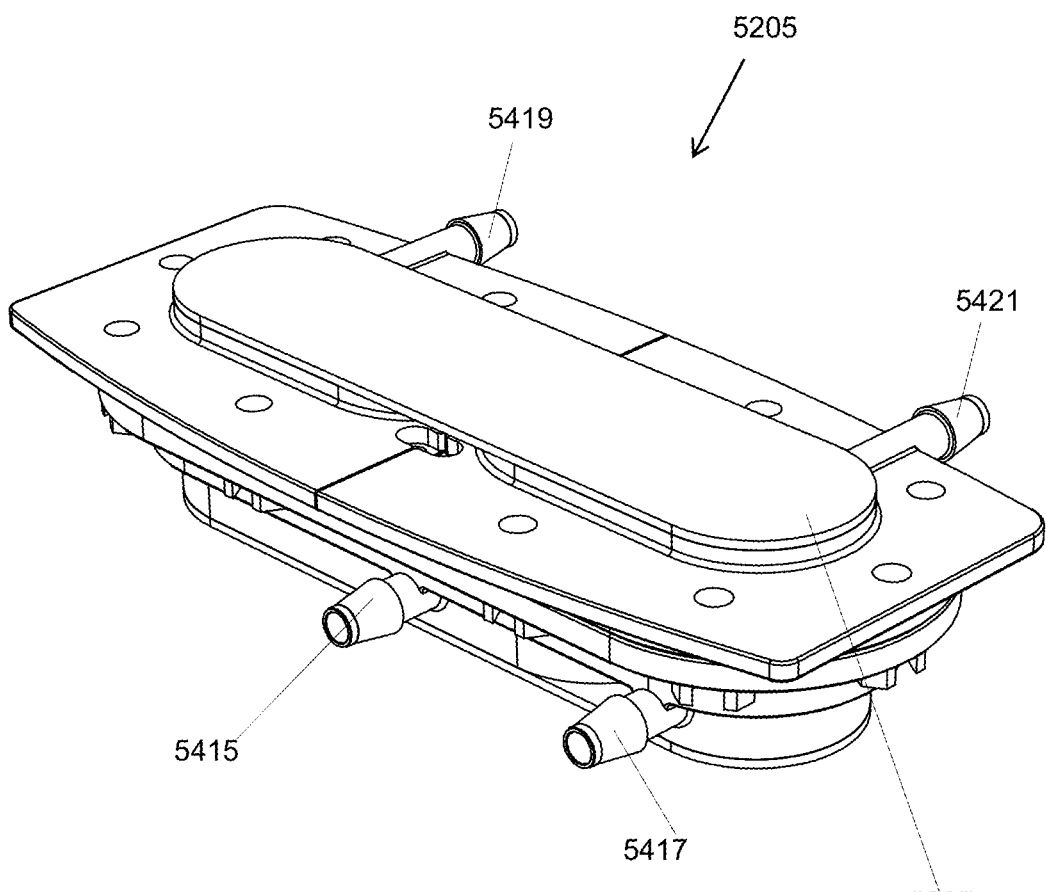
FIG. 56 illustrates a rear perspective of an exemplary embodiment of the pressure regulator shown in FIG. 54.
Figure 57:
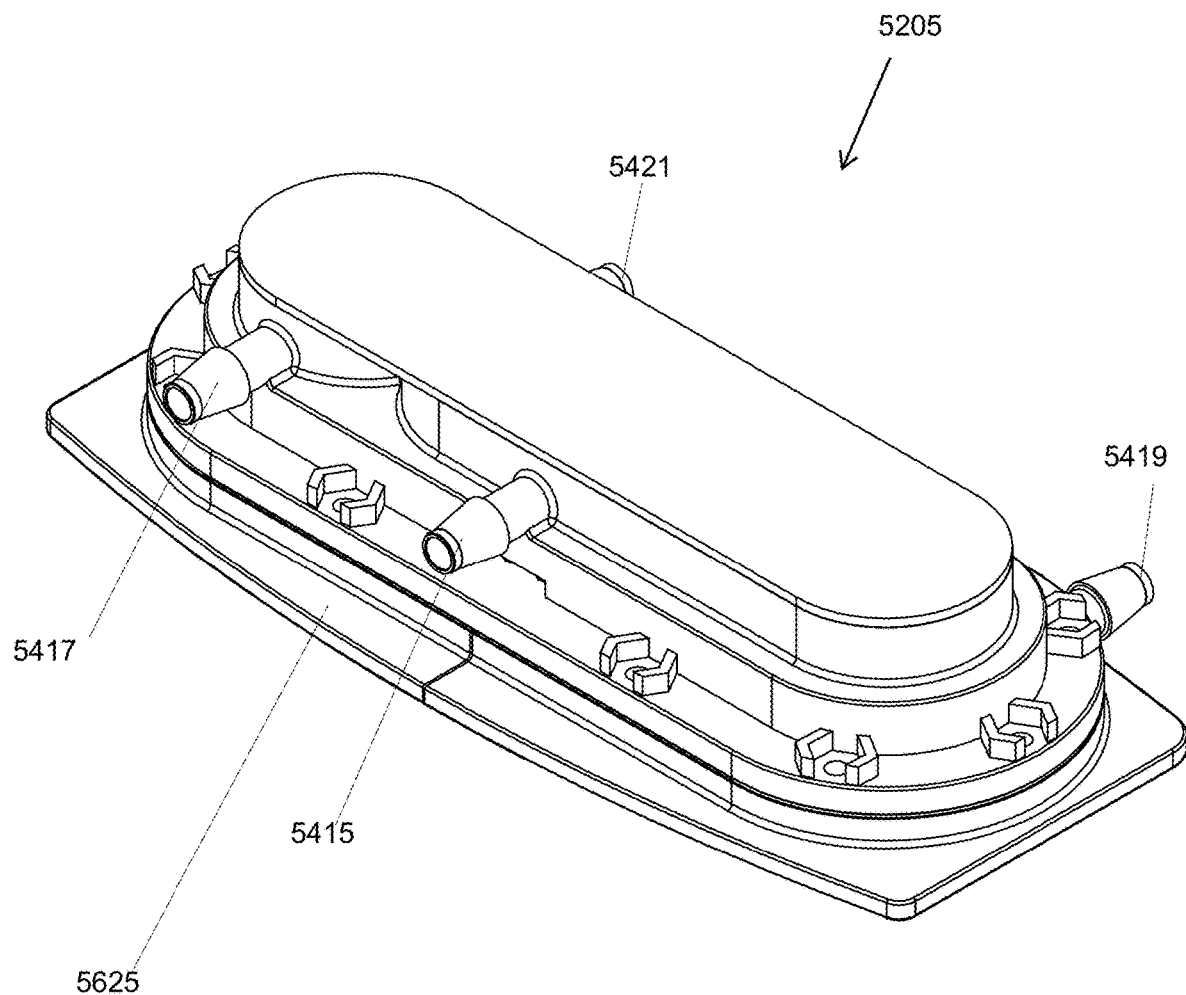
FIG. 57 illustrates a front perspective view of the pressure regulator shown in FIG. 56.

Although the embodiment of the pressure regulator 5205 shown in FIG. 53 is effective for regulating an external suction source that provides a vacuum level that is known to be more-negative than the desired regulated vacuum pressure provided to the surgical site, a second embodiment of the pressure regulator 5205 (shown in FIGS. 54-73) allows the fluid management system 100 to regulate an external suction source that is providing an unknown or variable vacuum level and sense when the vacuum level is sufficient to achieve the desired regulation setpoint. Referring to FIGS. 54 and 55, the second embodiment of the pressure regulator 5205 utilizes two valves of the first embodiment (FIG. 53) arranged in series.

Referring to FIG. 54, the second exemplary embodiment of the pressure regulator 5205 includes four chambers 5407, 5409, 5411, 5412 and a flexible membrane 5413. The first chamber 5407 includes an opening or port 5415 for fluidly connecting to the external suction source. The second chamber 5409 has an opening or port 5417 for fluidly connecting to the surgical site (via one or more fluid lines or tubes). The third chamber 5411 includes one or more ports 5419 for connecting to a pressure source (e.g., pressure source 7449 of aspiration module 5201 shown in FIG. 74), and the fourth chamber 5412 includes one or more openings 5421 for connecting to one or more pressure sensors (e.g., pressure sensors 7451 of aspiration module 5201 shown in FIGS. 74-75). Alternative embodiments can incorporate sensors from the same port connections of the pressure regulator 5205 for redundancy or improved regulation of the pressure source.

The flexible membrane 5413 is positioned to fluidly isolate (i.e., seal) each of the third and fourth chambers 5411, 5412 from both of the first and second chambers 5407, 5409, which allows the pressure source and pressure sensor of the fluid management system 100 to be fluidly isolated from biohazardous fluid returning from the surgical site and moving through the first and second chambers 5407, 5409. The first chamber 5407 is adjacent to the second chamber 5409 and separated from the second chamber 5409 by a vertical extended member or wall 5423 and a horizontal extended member or wall 5465. The wall 5465 includes openings 5467 that fluidly connect the first chamber 5307 to the second chamber 5309. The flexible membrane 5413 is movable from an engaged position and one or more disengaged positions with the wall 5465, where the first and second chambers 5407, 5409 are fluidly isolated from each other when the flexible membrane 5413 is in the engaged position, and where the first and second chambers 5407, 5409 are fluidly connected with each other (via openings 5467) when the flexible membrane 5413 is in the disengaged position. The third chamber 5411 is adjacent to the fourth chamber 5412 and separated from the first chamber 5412 by a vertical extended member or wall 5431 and a horizontal extended member or wall 5461. The wall 5461 includes openings 5463 that fluidly connect the third chamber 5411 to the fourth chamber 5413. The flexible membrane 5413 is also movable from an engaged position and one or more disengaged positions with the wall 5461, where the third and fourth chambers 5411, 5412 are fluidly isolated from each other when the flexible membrane 5413 is in the engaged position, and where the third and fourth chambers 5411, 5412 are fluidly connected with each other (via openings 5463) when the flexible membrane 5413 is in the disengaged position.

To better show that the embodiment of the pressure regulator 5205 shown in FIG. 54 utilizes two valves of the first embodiment of the pressure regulator shown in FIG. 53 in series, the first chamber 5407 is shown as having a first portion 5408 and a second portion 5410, but the pressure across both the first and second portions 5408, 5410, as supplied by the external suction source, is identical (as there is no barrier capable of sealing the first and second portions 5408, 5410 from each other). Referring to FIG. 55, the first valve 5501 of the pressure regulator 5205 utilizes the external suction source (via the first portion 5408 of the first chamber 5407) to regulate movement of the pressure supplied by the pressure source of the fluid management system from the third chamber 5411 to the fourth chamber 5412. The second valve 5503 utilizes the pressure in the fourth chamber 5412 (via the movement of pressure from the third chamber 5411 to the fourth chamber 5412) to regulate the movement of the pressure supplied by the external suction source from the second portion 5410 of the first chamber 5407 to the second chamber 5409 such that the pressure in the second chamber 5409 is substantially equal to the desired regulated vacuum pressure at the surgical site.

Referring to FIGS. 54 and 55, the pressure at the first portion 5408 of the first chamber 5407 causes the flexible membrane 5413 to be in either the engaged position or the disengaged position with the wall 5461. For example, if the vacuum pressure supplied by the external suction source is more negative than the pressure supplied by the pressure source of the system 100 into the third chamber 5411, the flexible membrane 5413 stretches away from the wall 5461 such that the third and fourth chambers 5411, 5412 are fluidly connected. When the third and fourth chambers 5411, 5412 are fluidly connected, the pressure in the fourth chamber 5412 is substantially equal to the pressure in the third chamber 5411. Comparatively, if the vacuum pressure supplied by the external suction source is more positive than the pressure supplied by the pressure source into the third chamber 5411, the flexible membrane is in the engaged position with the wall 5461 to fluidly isolate the fourth chamber 5412 from the third chamber 5411.

The fluid management system 100 senses the pressure within the fourth chamber 5412 via the one or more pressure sensors of the system 100, which allows the system 100 to determine if the pressure supplied by the external suction source is not supplying sufficient vacuum pressure to meet the desired regulated vacuum pressure at the surgical site. That is, if the external suction source is not supplying enough pressure to cause the flexible membrane 5413 to stretch away from the wall 5461, air will slowly bleed out of the fourth chamber 5412 via a small orifice or valve of the system 100 that may be constantly or periodically opened to a more positive gauge pressure to gradually bring the pressure in the fourth chamber 5412 closer to this more positive gauge pressure, and the pressure sensor of the system 100 will sense that the pressure in the fourth chamber 5412 is not equal to the pressure supplied by the pressure source to the third chamber 5411, which will cause the system to determine that the pressure supplied by the external suction source is not sufficient to meet the desired regulated vacuum pressure at the surgical site. The pressure sensed by the system 100 in the fourth chamber 5412, given enough time to bleed off pressure, can be used to determine the actual pressure present in the first chamber 5407 if it is less than the positive gauge pressure that is slowly bled into the fourth chamber 5412. If the system 100 determines that the external suction source is not supplying a sufficient vacuum pressure, the system 100 may be configured to notify the user to adjust the external pressure source (e.g., by increasing the suction setting of external pressure source, unclogging the line leading to the external pressure source, finding a leak in the line leading to the external pressure source, etc.) to ensure it is sufficient to down-regulate the vacuum pressure at the surgical site to the desired regulated vacuum pressure.

Referring to FIGS. 54 and 55, the second valve 5503 of the pressure regulator 5205 utilizes the pressure supplied by the pressure source of the fluid management system in the fourth chamber 5412 to regulate the movement of pressure supplied by the external suction source to the second chamber 5409 and, consequently, the surgical site. That is, the system 100 controls the pressure source to cause the flexible membrane 5413 to stretch away from the wall 5465 to fluidically connect the first and second chambers 5407, 5409 such that the desired regulated vacuum pressure is supplied to the surgical site through the opening 5417 of the second chamber 5409. The biohazardous fluid then moves from the surgical site, into the second chamber 5409 through opening 5417, through the openings 5467 between the flexible membrane 5413 the wall 5465 and into the first chamber 5407, and through the opening 5415 to a waste collection of the system 100 or the facility. The flexible membrane 5413 seals each of the third and fourth chambers 5411, 5412 from both of the first and second chambers 5407, 5409 to prevent the biohazardous fluid from contacting the pressure source and/or pressure sensors of the system 100.

Provided the pressure from the surgical site as available in chamber 5409 is a more positive pressure than both the gauge pressure supplied by the external suction source (through the first chamber 5407) and the gauge pressure supplied by the pressure source of the system 100 (into the third chamber 5411) and the pressure required to stretch flexible membrane 5413, the regulated vacuum pressure supplied to the surgical site can be equal to the more-positive gauge pressure of the gauge pressure supplied by the external suction source (through the first chamber 5407) or the gauge pressure supplied by the pressure source of the system 100 (into the third and fourth chambers 5411, 5412) and the pressure required to stretch the flexible membrane 5413. That is, provided the flow rate from the surgical site is negligible with respect to the flow capacity of the external pressure source (supplied through the first chamber 5407), the pressure supplied to the surgical site (through chamber 5409) will be the pressure closest to absolute vacuum of the pressure supplied by the external pressure source (through the first chamber 5407) and the pressure required to stretch the flexible membrane 5413 or the pressure supplied by the pressure source of the system 100 (into the third and fourth chambers 5411, 5412) and the pressure required to stretch the flexible membrane 5413.

In certain embodiments, the pressure required to stretch the flexible membrane 5413 may be modeled by a transfer function to determine a pressure setpoint for the pressure source of the system 100 (supplied into the third and fourth chambers 5411, 5412) that is required to achieve a desired regulated vacuum pressure in the second chamber 5409 that is supplied to the surgical site. The system 100 may be configured to vary the regulated vacuum pressure supplied to the surgical site, via the pressure sensor and pressure pump of the system 100, by varying the pressure supplied to the third and fourth chambers 5411, 5412. Also, the pressure supplied by the external suction source (through the first chamber 5407) and supplied to the second chamber 5409 may be regulated to a more positive pressure by regulating the pressure provided to the third and fourth chambers 5411, 5412 by the pressure source of the system 100 to a greater pressure than supplied by the external suction source. Because the regulated vacuum pressure setpoint is variable, this also enables the pressure regulator 5205 to serve as a simple 2-way valve to enable and disable flow on demand by regulating the pressure supplied to the third and fourth chambers 5411, 5412 with a pressure greater than the pressures in either the first chamber 5407 or second chamber 5409.

In certain embodiments, the flexible membrane 5413 is configured such that the pressure supplied by the pressure source in the third and fourth chambers 5411, 5412 causes the flexible membrane 5413 to stretch away from the wall 5423 and cause the regulated vacuum pressure supplied to the surgical site to be between about 10 mmHg and about 30 mmHg greater than the pressure provided by the pressure source of the system 100, such as about 20 mmHg greater than the pressure provided by the pressure source. The flexible membrane 5413 can be made of, for example, neoprene, silicone, natural rubber, nitrile, EPDM, other rubber compounds, or any other material that allows the flexible membrane to be moved between the engaged and disengaged positions.

In certain embodiments, the fourth chamber 5412 is pneumatically attached to a small orifice or valve of the fluid management system 100 that may be constantly or periodically opened to bleed off pressure to a gauge pressure that is greater than or equal to the maximum gauge pressure expected from either the pressure source of the fluid management system 100 or the external suction source. The opened orifice or valve bleeds off pressure at a negligible flow rate compared to the flow rate capability of the pressure source of the fluid management system to ensure that the pressure inside of the fourth chamber 5412 is the greater gauge pressure of the external pressure source or the desired regulated pressure in the second chamber 5409 and any additional force required to stretch or open the flexible membrane 5413.

The embodiment of the pressure regulator 5205 shown in FIGS. 54 and 55 allows for non-wetted, indirect sensing of the pressure source of the fluid management system 100 to help ensure that the external suction source is of sufficient pressure to regulate to the desired vacuum pressure of the system's pressure source to down-regulate the vacuum pressure in the second chamber 5409 and at the surgical site. Being able to indirectly sense the pressure supplied by the external suction source via the cost-effective single use pressure regulator 5205 is beneficial because it enables the system 100 to prompt the user to adjust the external suction source (by increasing the suction setting of the external suction source, unclogging the line leading to the external suction source, finding a leak in the line leading to the external suction source, etc.) to ensure it is sufficient to down-regulate the vacuum pressure at the surgical site to the desired regulated vacuum pressure or otherwise prevent operation of the system if the regulated vacuum pressure levels would be detrimental to the safety or efficacy of the intended use of the regulated vacuum pressure from the system.

Figure 58:
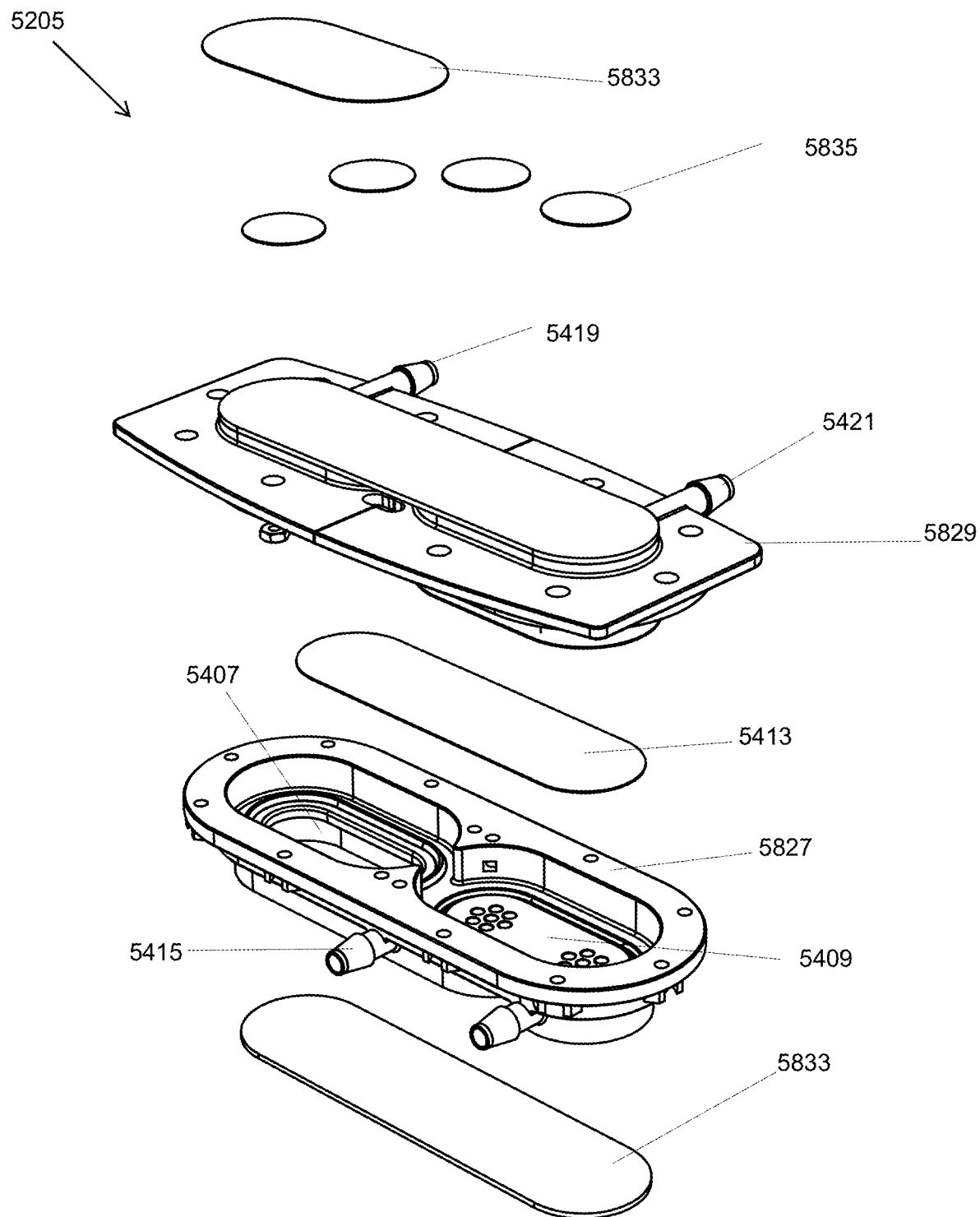
FIG. 58 illustrates an exploded perspective view of the pressure regulator shown in FIG. 56.
Figure 59:
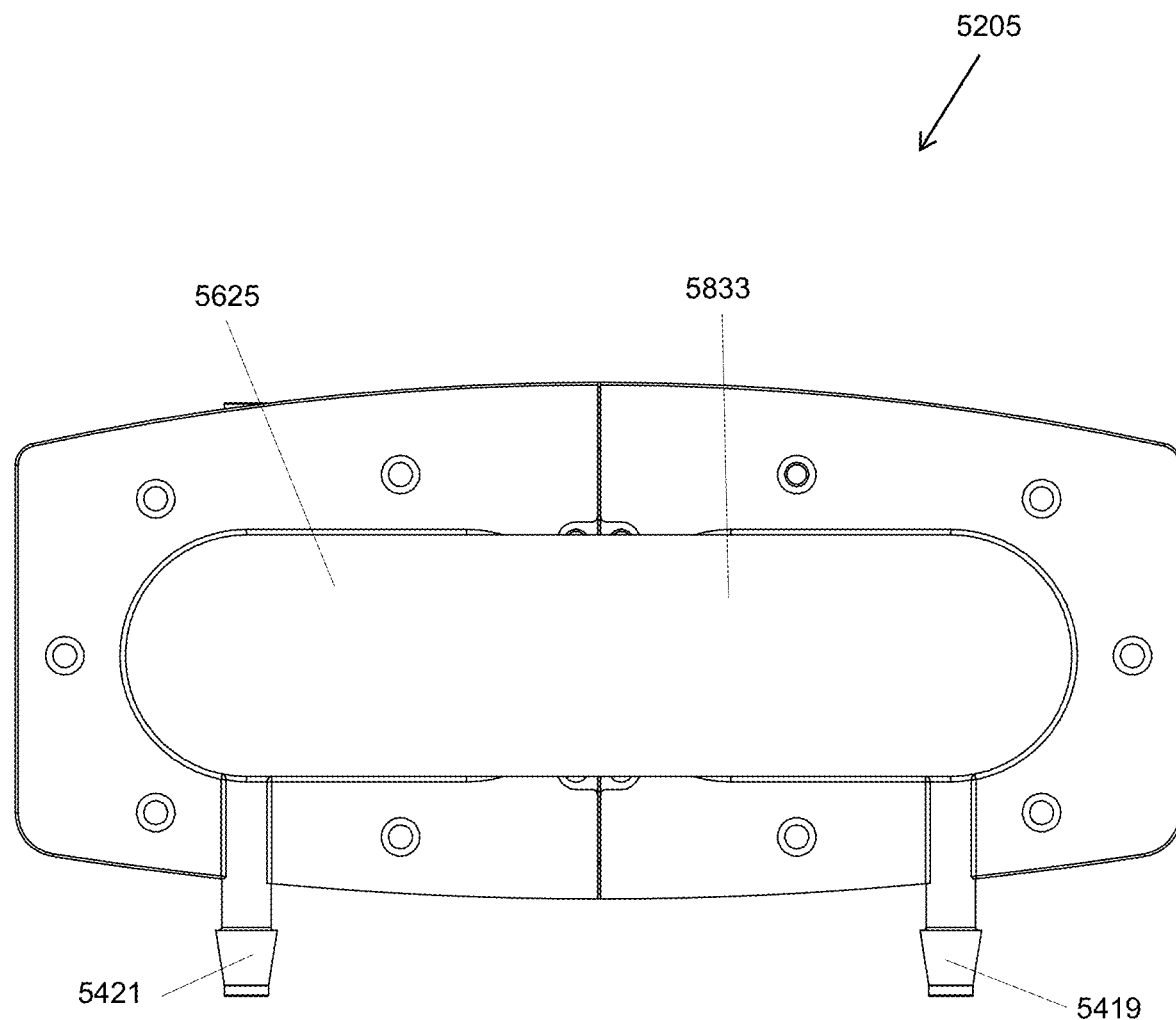
FIG. 59 illustrates a top view of the pressure regulator shown in FIG. 56.
Figure 60:
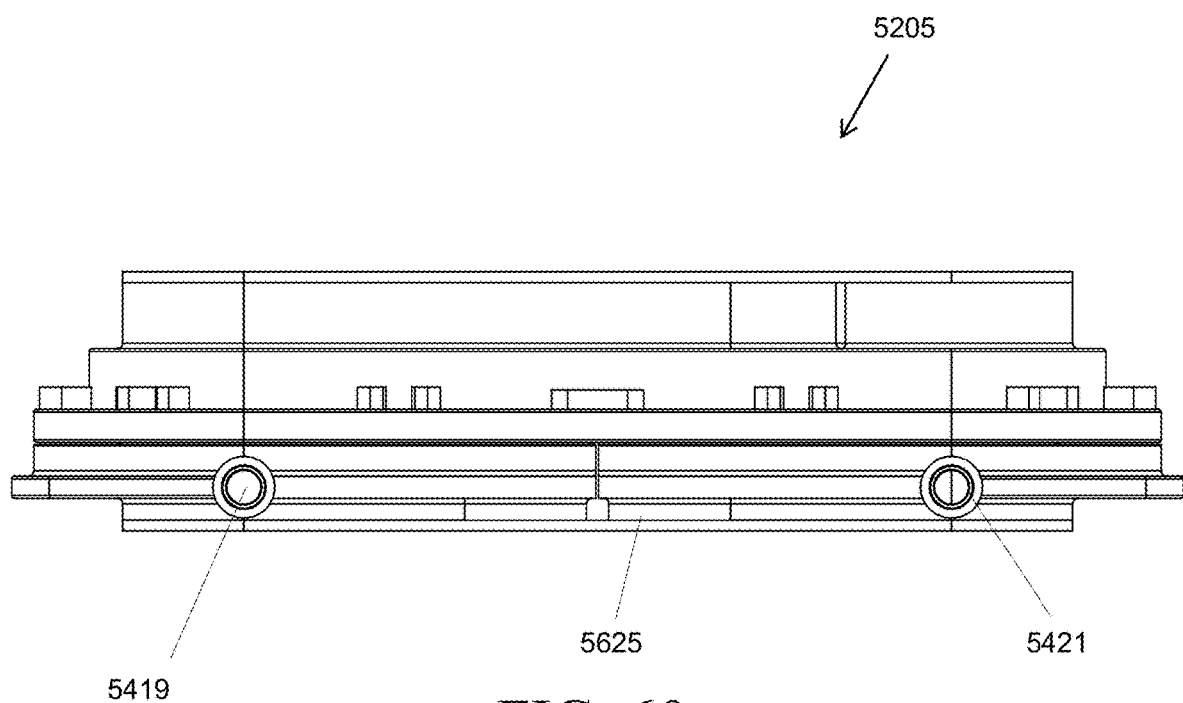
FIG. 60 illustrates a rear view of the pressure regulator shown in FIG. 56.
Figure 62:
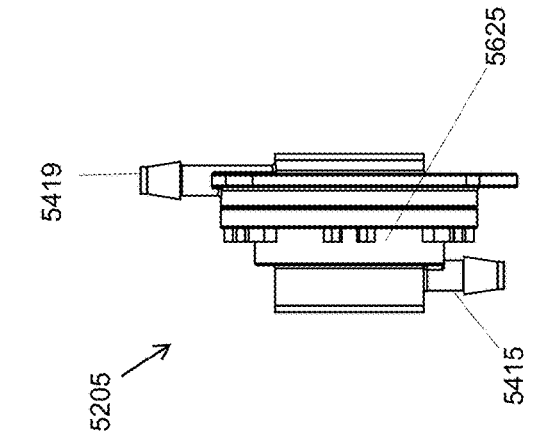
FIG. 62 illustrates a side view of the pressure regulator shown in FIG. 56.
Figure 61:
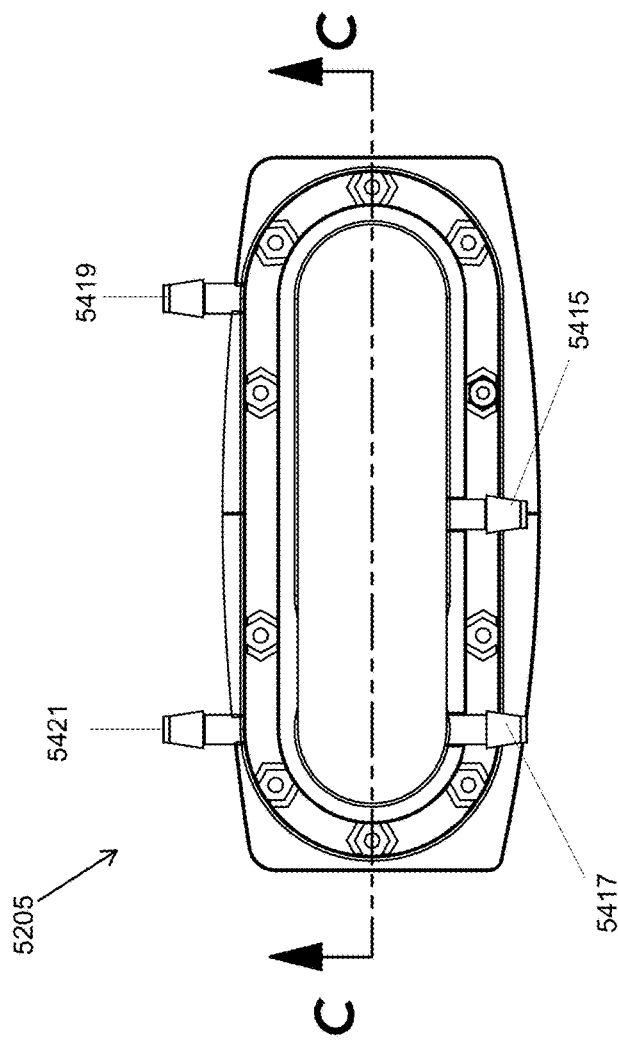
FIG. 61 illustrates a bottom view of the pressure regulator shown in FIG. 56.
Figure 63:
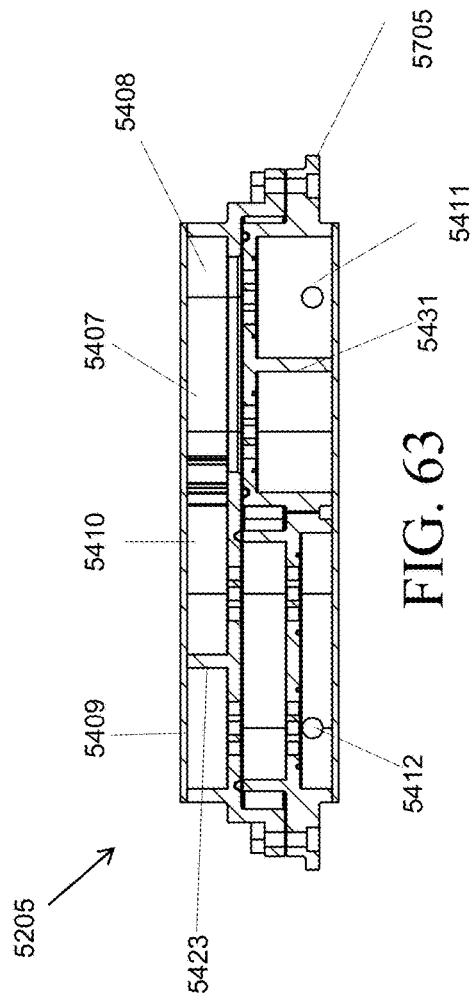
FIG. 63 illustrates a cross-sectional view of the pressure regulator shown in FIG. 56 taken along the lines C-C shown in FIG. 61.

FIGS. 56 through 64 show an embodiment of the pressure regulator 5205 shown in FIGS. 54 and 55. In the illustrated embodiment, the pressure regulator 5205 includes a housing 5625 that at least partially defines the four chambers 5407, 5409, 5411, 5412 and includes the openings 5415, 5417, 5419, 5421. The housing 5625 can be made of, for example, polycarbonate or any other suitable material. Referring to FIG. 58, in certain embodiments, the housing 5625 has a first component 5827 that includes the first and second chambers 5407, 5409, and a second component 5829 that includes the third and fourth chambers 5411, 5412. The first and second components 5827, 5829 can be, for example, injection molded pieces. The flexible membrane 5413 is positioned between the two components 5827, 5829 to fluidly isolate the chambers 5407, 5409 of the first component 5827 from the chambers 5411, 5412 of the second component 5829. In some embodiments, the pressure regulator 5205 may also include covers 5833 for covering the outer facing portions of the chambers for each component 5827, 5829. The first component 5827, the second component 5829, the flexible membrane 5413, and the covers 5833 can be connected by a snap-fit connection, an adhesive connection, one or more fasteners, ultrasonic welding, combinations thereof, or any other suitable means. In some embodiments, the pressure regulator 5205 may include one or more hydrophobic filters 5835 for helping maintain a bacterial barrier between the pressure source and pressure sensors of the fluid management system 100.

Figure 64:
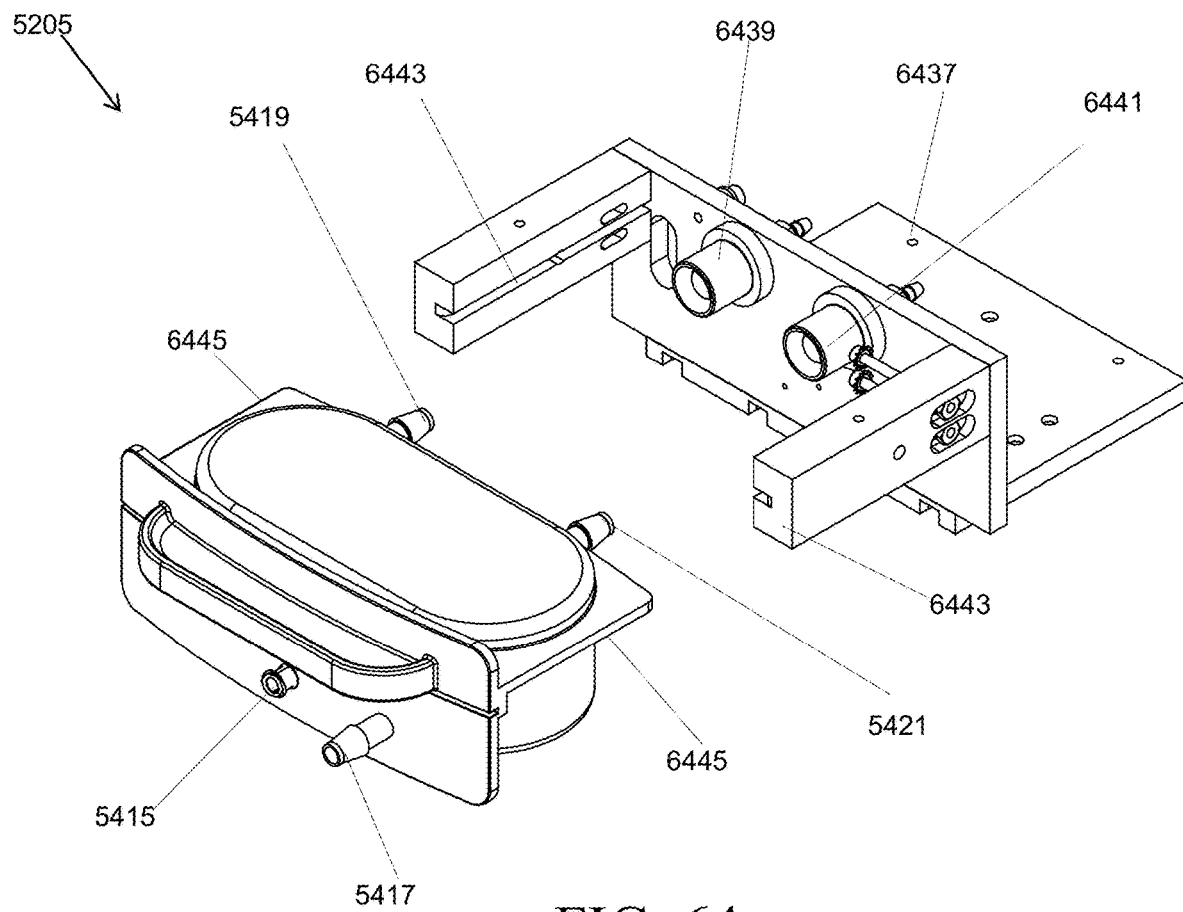
FIG. 64 illustrates a perspective view of an exemplary connection between the pressure regulator shown in FIG. 56 and an exemplary receiving mechanism for the aspiration module shown in FIG. 52.
Figure 65:
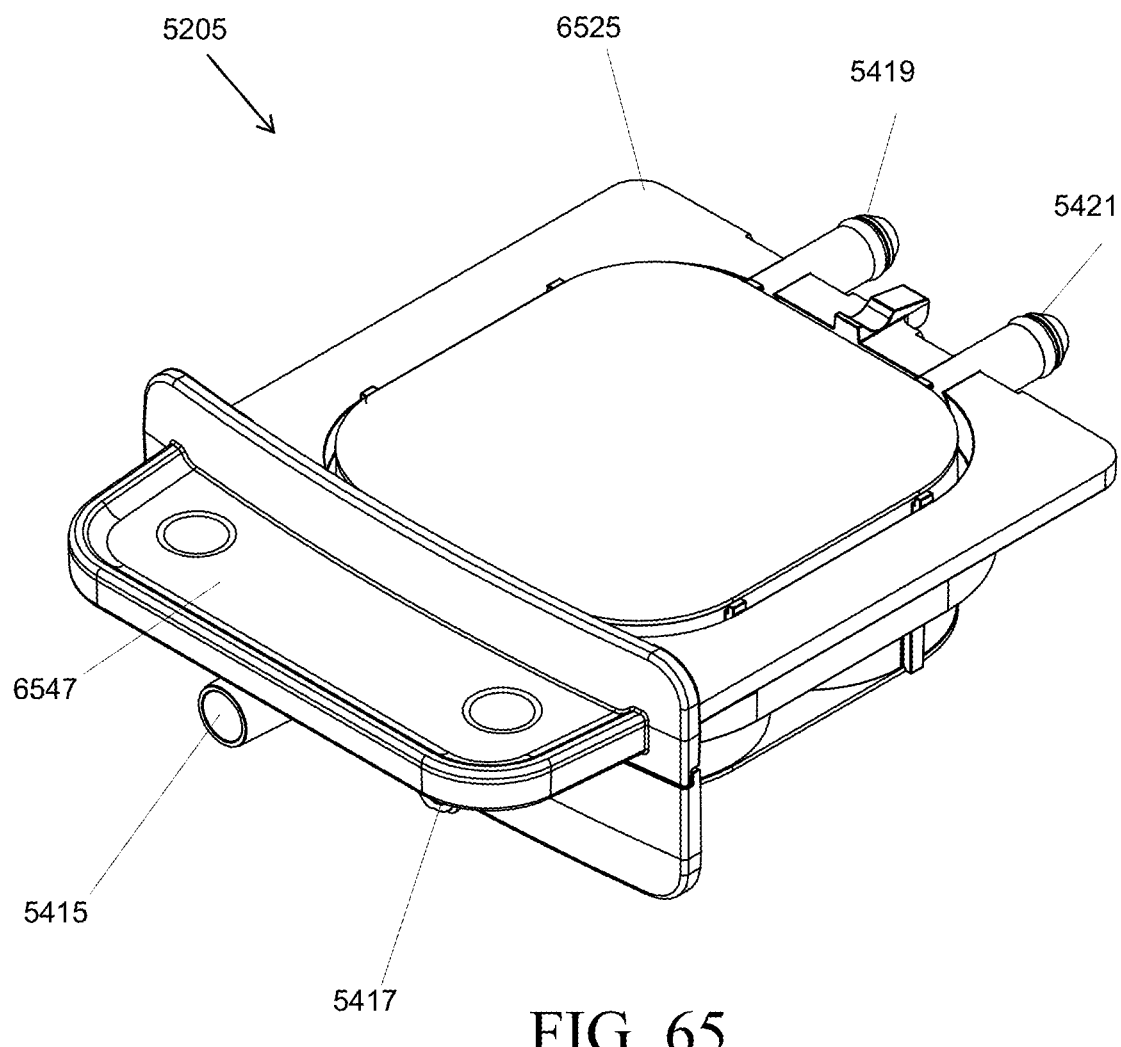
FIG. 65 illustrates a perspective view of another exemplary embodiment of the pressure regulator shown in FIG. 54.
Figure 66:
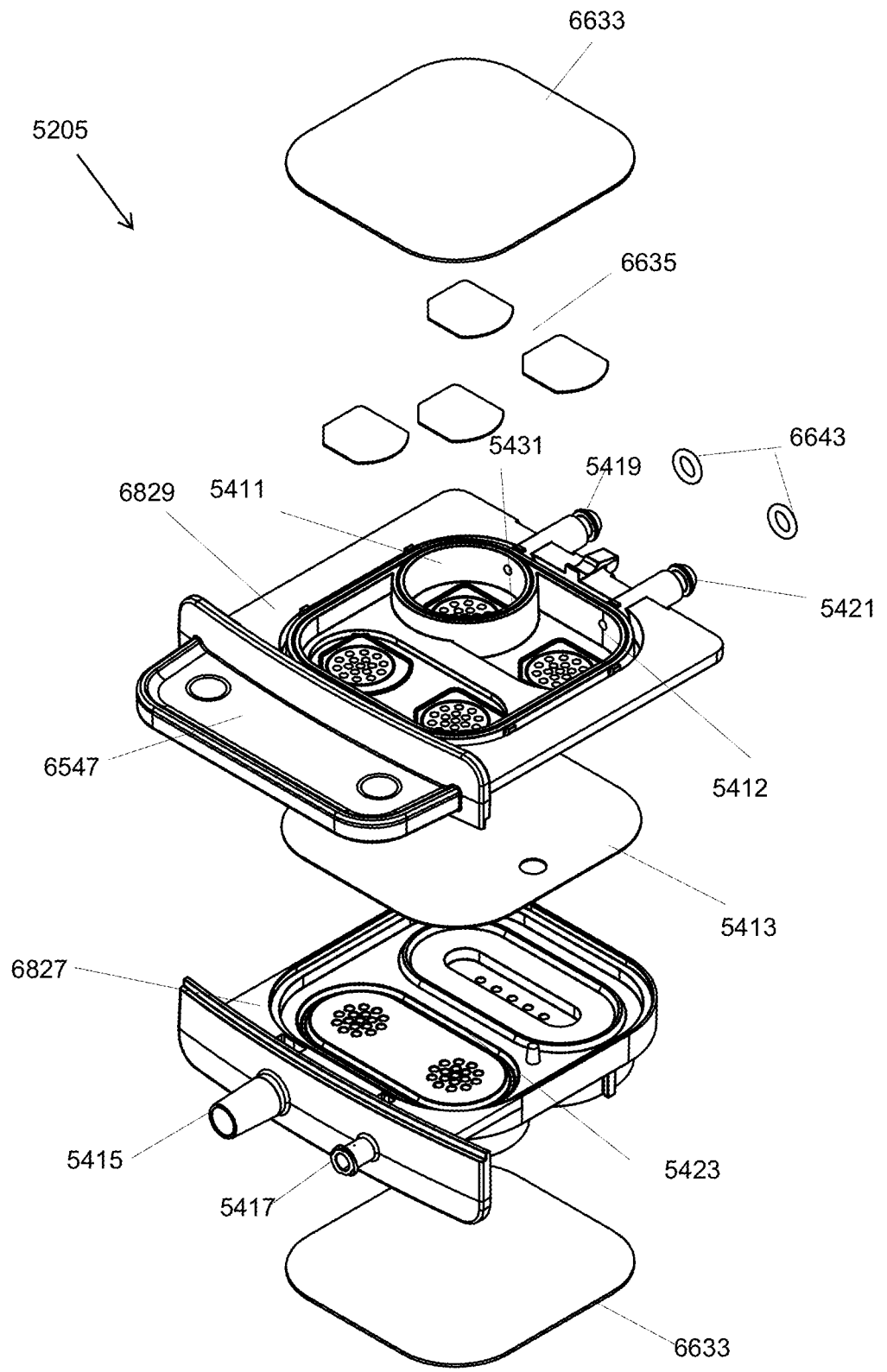
FIG. 66 illustrates an exploded perspective view of the pressure regulator shown in FIG. 65.
Figure 67:
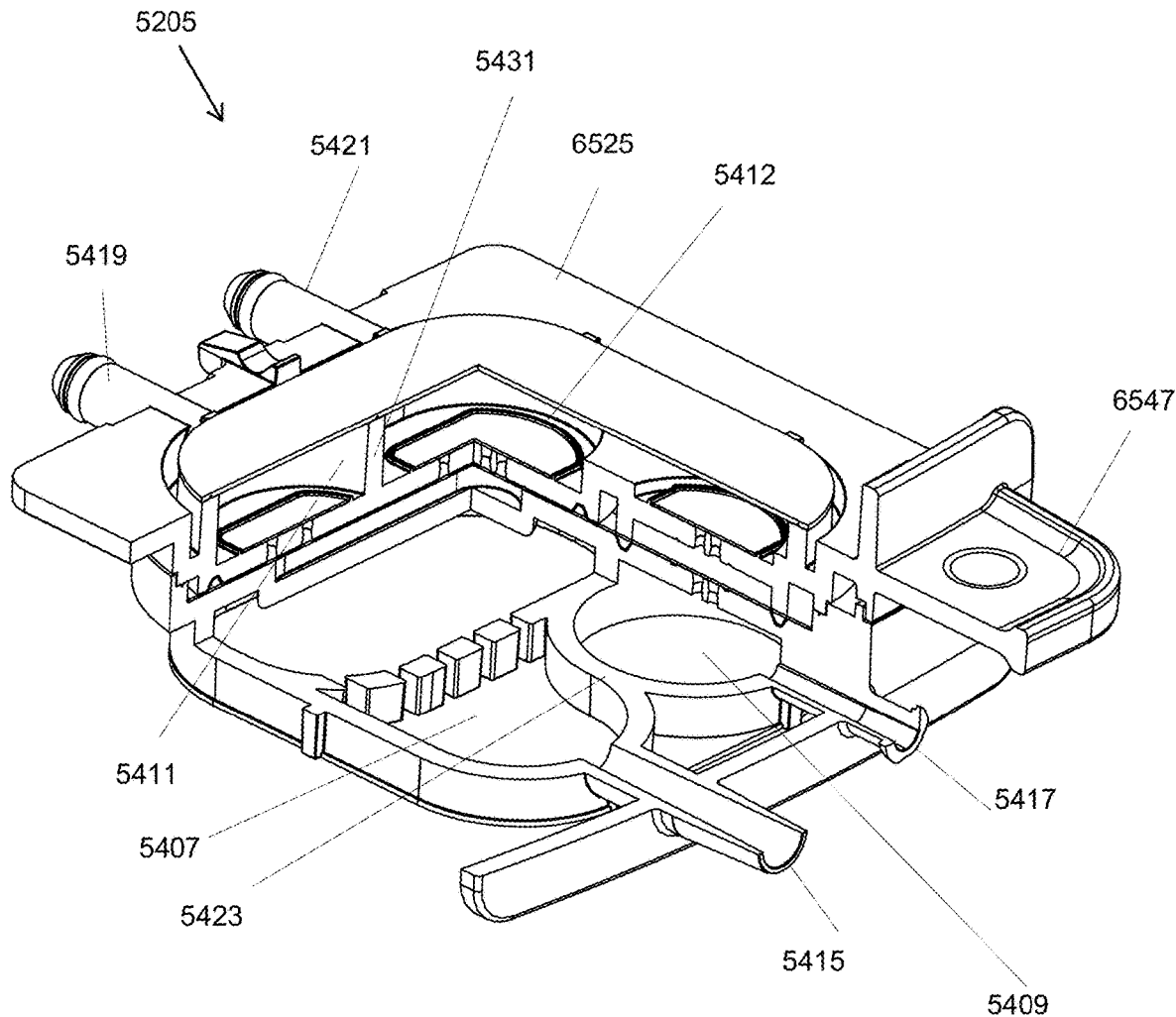
FIG. 67 illustrates a partial perspective view of the pressure regulator shown in FIG. 65.

Referring to FIG. 64, in certain embodiments, the pressure regulator 5205 shown in FIGS. 56-63 can be used in combination with an aspiration module (e.g., aspiration module 7404 shown in FIGS. 74-75) that includes a pressure pump (e.g., pressure pump 7449 shown in FIG. 74) and pressure sensors (e.g., pressure sensors 7451 shown in FIGS. 74-75) to sense and regulate the external suction source to control the rate of fluid outflow from a surgical site. When the pressure regulator is inserted into the aspiration module, the pressure regulator 5205 may be configured to connect to a receiving mechanism 6437 (FIG. 64) that automatically connects the port 5419 for the third chamber 5411 to a port 6439 that is operatively connected to the pressure pump of the aspiration module. The connection between the pressure regulator 5205 and the receiving mechanism may also automatically connect the port 5421 for the fourth chamber 5412 to a port 6441 that is operatively connected to sensors and or an air bleed mechanism of the aspiration module. The connection mechanism 6437 may include channels 6443 for receiving end portions 6445 of the pressure regulator 5205 to allow for a secure connection between the pressure regulator 5205 and the aspiration module. After inserting the pressure regulator into the aspiration module 5205, the user can manually connect the external suction source to the port 5415 for the first chamber 5407 and manually connect the fluid return lines from the surgical site to the port 5417 for the second chamber 5409.

FIGS. 65 through 73 show another embodiment of the pressure regulator 5205 shown in FIGS. 54 and 55. In the illustrated embodiment, the pressure regulator 5205 includes a housing 6525 that at least partially defines the four chambers 5407, 5409, 5411, 5412 and includes the openings 5415, 5417, 5419, 5421. The housing 6525 can be made of, for example, polycarbonate or any other suitable material. In certain embodiments, the housing 6525 has a first component 6829 that includes the first and second chambers 5407, 5409, and a second component 6827 that includes the third and fourth chambers 5411, 5412. The first and second components 6827, 6829 can be, for example, injection molded pieces. The flexible membrane 5413 is positioned between the two components 6827, 6829 to fluidly isolate the chambers 5407, 5409 of the first component 6827 from the chambers 5411, 5412 of the second component 6829. In some embodiments, the pressure regulator 5205 may also include covers 6633 for covering the outer facing portions of the chambers for each component 6827, 6829. The first component 6827, the second component 6829, the flexible membrane 5413, and the covers 6533, 6633 can be connected by a snap-fit connection, an adhesive connection, one or more fasteners, ultrasonic welding, combinations thereof, or any other suitable means. In some embodiments, the pressure regulator 5205 may include one or more hydrophobic filters 6635 for helping maintain a bacterial barrier between the pressure source and pressure sensors of the fluid management system 100. The pressure regulator 5205 can also include one or more sealing members 6643 (e.g., O-rings) for making fluid tight connections. In certain embodiments, the housing 6525 has a gripping member or handle 6547 that helps a user insert and remove the pressure regulator from the aspiration module or other component of the fluid management system 100.

Referring to FIGS. 72 and 73, in certain embodiments, the pressure regulator 5205 shown in FIGS. 65-71 can be used in combination with an aspiration module (e.g., aspiration module 7404 shown in FIGS. 74-75) that includes a pressure pump (e.g., pressure pump 7449 shown in FIG. 74) and pressure sensors (e.g., pressure sensors 7451 shown in FIGS. 74-75) to sense and regulate the external suction source to control the rate of fluid outflow from a surgical site. When the pressure regulator 5205 is inserted into the aspiration module, the pressure regulator 5205 may be configured to connect to a receiving mechanism 7237 that automatically connects the port 5419 for the third chamber 5411 to a port 6439 that is operatively connected to the pressure pump of the aspiration module. The connection between the pressure regulator 5205 and the receiving mechanism may also automatically connect the port 5421 for the fourth chamber 5412 to a port 7241 that is operatively connected to sensors and or an air bleed mechanism of the aspiration module. The connection mechanism 6437 may include channels (not shown) for receiving end portions of the pressure regulator 5205 to allow for a secure connection between the pressure regulator 5205 and the aspiration module (e.g., similar to as shown in the embodiment shown in FIG. 64). After inserting the pressure regulator into the aspiration module 5205, the user can manually connect the external suction source to the port 5415 for the first chamber 5407 and manually connect the fluid return lines from the surgical site to the port 5417 for the second chamber 5409.

Figure 75:
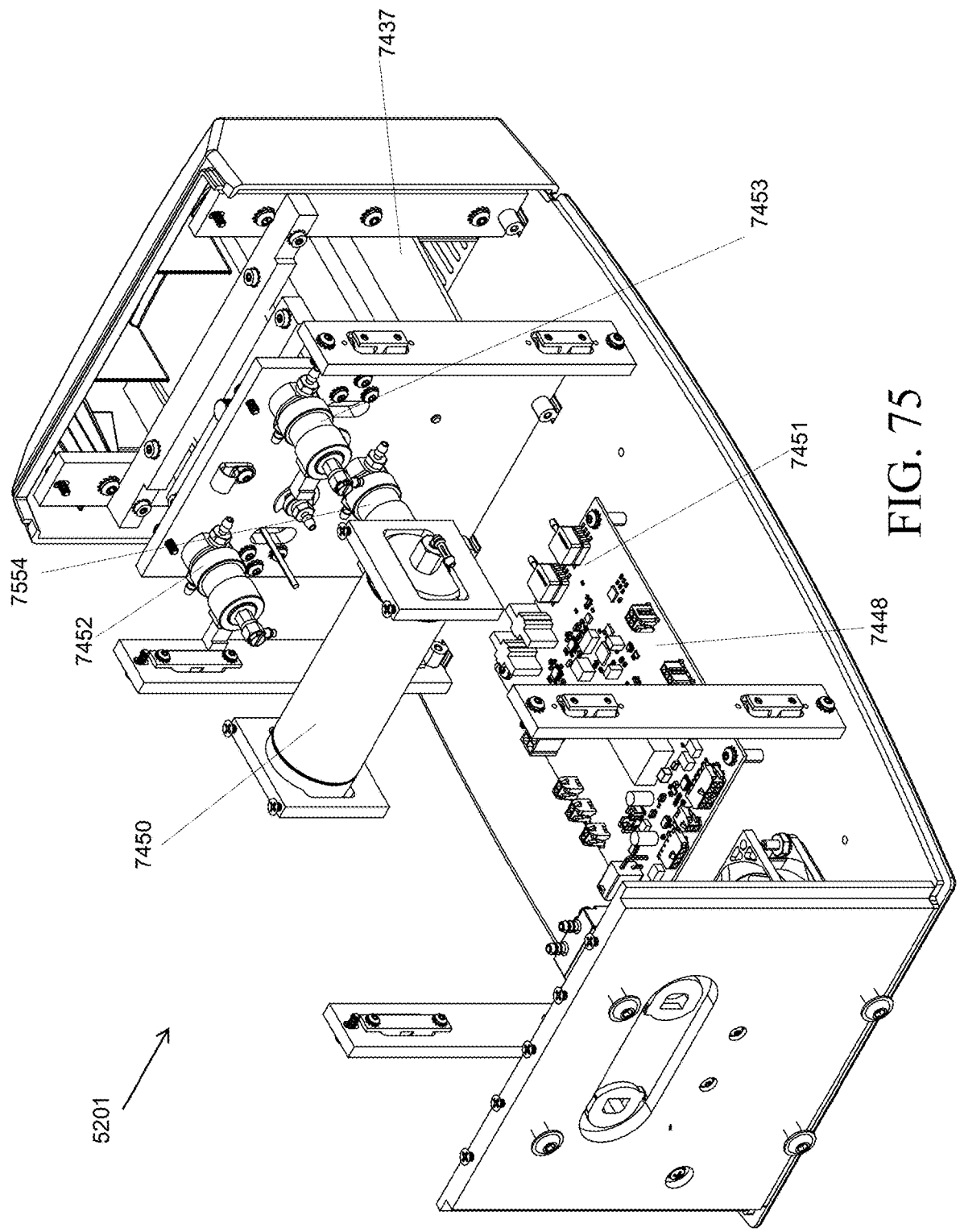
FIG. 75 illustrates a rear perspective view of the aspiration module shown in FIG. 74.

FIGS. 74 and 75 illustrate an exemplary embodiment of the aspiration module 5201 that can be used with the fluid management system 100 shown in FIG. 1 and the various embodiments of the pressure regulators 5205 shown in FIGS. 53-73. The aspiration module 5201 may include the receiving mechanism 7437 (e.g., receiving mechanism 6437 shown in FIG. 64 or receiving mechanism 7237 shown in FIG. 72) for receiving the pressure regulator 5205, an integrated pressure pump 7449, one or more valves 7452, 7453 for connecting the pressure pump to the pressure regulator 5205, and a printed circuit board (PCB) 7448 having one or more pressure sensors 7451.

The integrated pressure pump 7449 may be configured to supply a positive pressure or a negative pressure to the pressure regulator 5205 via opening 5419 (FIG. 54) of the pressure regulator. For example, the pump 7449 may be an air pump that includes two ports (not shown), and the aspiration module 5201 may include valves 7452, 7453 (e.g., three-way valves) connected to the opening 5419 of the pressure regulator 5205 and the ports of the pump 7449. A first port of the pump 7449 may be configured to pull air into the pump 7449, and a second port of the pump 7449 may be configured to push air out of the pump, which allows the pump 7449 to supply both positive and negative pressures for pressure regulation and stoppage of flow through the valves. For example, if the port which pulls air into the pump 7449 is left open to ambient and the port which pushes air out of the pump 7449 is connected to a substantially sealed vessel, then the pump 7449 will build up positive pressure inside the substantially sealed vessel. Conversely, if the port which pushes air out of the pump 7449 is left open to ambient and the port which pulls air into the pump 7449 is connected to a substantially sealed vessel, then the pump 7449 will build up vacuum pressure inside the substantially sealed vessel. In this embodiment, the valves 7452, 7453 are ported such that the pump ports can each be opened to ambient air pressure and connected to supply pressure to the aspiration module. Software of the control system may modulate the states of the valves 7452, 7453 to configure the pump to supply positive or vacuum pressure to the system based on the desired valve state and regulation setpoint. The pump 7449 can be fluidly connected to the valves 7452, 7453 by tubing. In other embodiments, the pump 7449 may be configured to supply either a positive pressure or a negative pressure to the pressure regulator, or the aspiration module 5201 may include separate positive and negative pressure pumps for supplying pressure to the pressure regulator 5205. In certain embodiments, an accumulator 7450 is fluidly positioned between pressure pump 7449 and the pressure regulator 5205 to aid in regulating the pressure provided to the pressure regulator 5205 by the pressure pump 7449.

The one or more pressure sensors 7451 may be used to monitor both the pressure supplied to third chamber 5411 (FIG. 54) of the pressure regulator 5205 by the pressure pump 7449 and a pressure within the fourth chamber 5412 (FIG. 54) of the pressure regulator 5205. In certain embodiments, the pressure sensors 7451 can be operatively connected to the accumulator 7450 by pneumatic tubing to monitor the pressure supplied to the pressure regulator 5205, and the pressure sensors 7451 can be operatively connected to the opening 5421 (FIG. 54) of the pressure regulator 5205 by pneumatic tubing to monitor the pressure within the fourth chamber 5412. The pressure sensors 7451 allow the fluid management system 100 to sense the pressure within the fourth chamber 5412 (FIG. 54) of the pressure regulator 5205 to determine if the pressure supplied by the external suction source that is connected to the first chamber 5407 (FIG. 54) is not supplying sufficient vacuum pressure to meet the desired regulated vacuum pressure at the surgical site.

Referring to FIG. 75, in certain embodiments, the aspiration module 5201 includes a valve 7554 that allows for the fourth chamber 5412 (FIG. 54) of the pressure regulator 5205 to be constantly or periodically opened to bleed off pressure to a gauge pressure that is greater than or equal to the maximum gauge pressure expected from either the pressure pump 7449 (FIG. 74) or the external suction source. The opened orifice or valve bleeds off pressure at a negligible flow rate compared to the flow rate capability of the pressure pump 7449 to ensure that the pressure inside of the fourth chamber 5412 (FIG. 54) is the greater gauge pressure of the external pressure source or the desired regulated pressure supplied to the surgical site.

Figure 76:
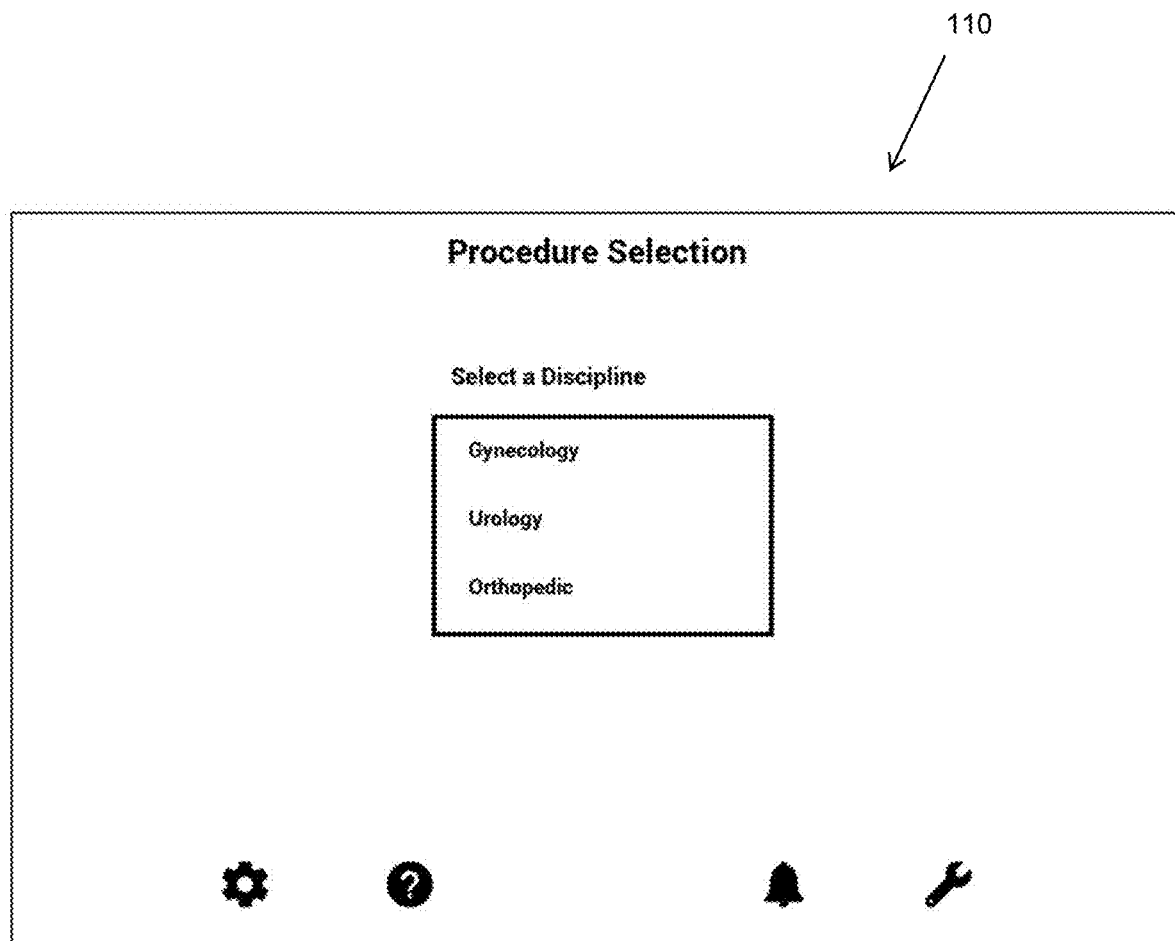
FIG. 76 illustrates an exemplary prompt by the fluid management system of FIG. 1 to a user via a user interface regarding the type of procedure to be performed.
Figure 77:
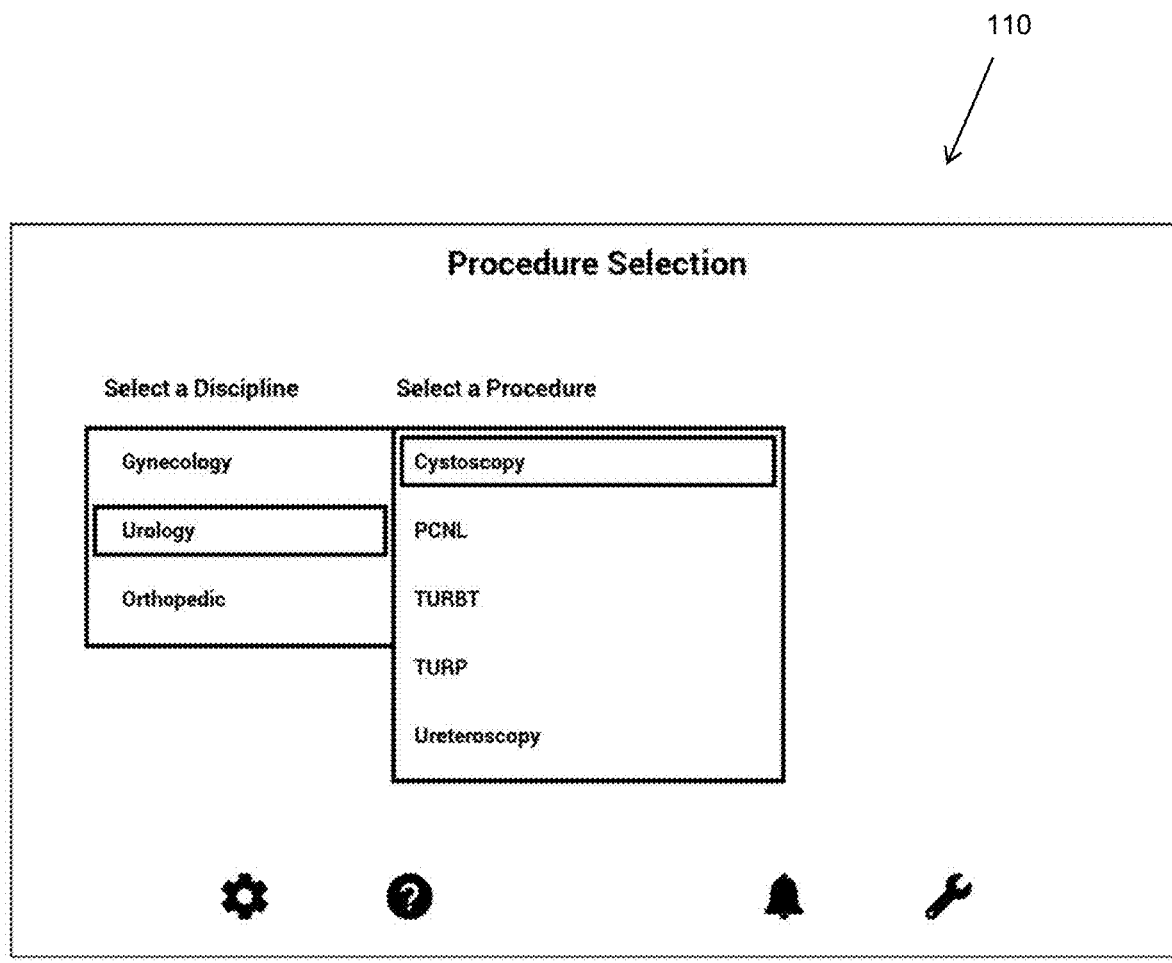
FIG. 77 illustrates another exemplary prompt by the fluid management system of FIG. 1 to a user via a user interface regarding the type of procedure to be performed.

Referring to the operation of the fluid management system 100 discussed in the present application, the control system may be configured to guide the user through the setup process using, for example, instructions, illustrations, animations, video, and/or system feedback via the user interface 110. Referring to FIGS. 76 and 77, in certain embodiments, the system 100 prompts a user (via the user interface 110) to select the surgical discipline and procedure that will be performed, which can cause the system 100 to set default operating parameters for the procedure, as well as safe, permissible adjustment ranges for those parameters (as stored in a memory of the system 100). For example, the system 100 may prompt a user to select a discipline of "Gynecology," "Urology," or "Orthopedic"; and, if the user selects "Urology," the system 100 may prompt the user to select one of the following procedures: "Cystoscopy," "PCNL," "TURBT," "TURP," or "Ureteroscopy." Based on the selection by the user, the system 100 may then set default operating parameters (e.g., pressure control mode or flow control mode, setpoint fluid pressure or flow rate, fluid warming condition enabled or disabled, fluid deficit monitoring enabled or disabled, etc.) for the procedure.

In certain embodiments, the system 100 may provide instructions to a user for installing the tubing sets to the various components of the system 100. For example, the system 100 may instruct the user to insert the cartridge assembly 419 (FIG. 4) that includes the fluid conditioner 420 (FIG. 4) and fluid warming cartridge 422 (FIG. 4) into the main unit 102, and then place or route the tubing that connects the fluid supply containers and the cartridge assembly 419 into or through the pump 212 (FIG. 2). The system 100 may then prompt the user to indicate whether fluid deficit monitoring will be performed during the procedure. In certain situations, the system 100 may require fluid deficit monitoring be performed based on an input from the user as to the type of procedure that is being performed. For example, if the user selects an operative hysteroscopy procedure, fluid deficit monitoring is required. For other gynecological and urological procedures, fluid deficit monitoring may be optional. If the user did not select an operative hysteroscopy procedure and did not elect to enable fluid deficit monitoring for the selected procedure, the system 100 may instruct the user to spike and hang the fluid bags. If the user selected an operative hysteroscopy, or selected another procedure and elected to enable fluid deficit monitoring feature for the selected procedure, the system 100 may prompt the user to indicate whether one or more fluid types will be used during the procedure and what the fluid types are, as illustrated FIGS. 78 through 80.

In various embodiments, the system 100 may be configured to monitor and display fluid deficit by fluid type. For example, in operative hysteroscopy, surgeons can utilize multiple fluid types during a procedure based on the type of procedure being performed and the surgical instruments employed. These fluids can differ in osmolality, electrolyte content, and viscosity. The amount of these fluids absorbed by the surgical patient depend on the fluid pressure, the length of the procedure, and the degree of surgical disruption of the venous sinuses in the endometrium and, importantly, the myometrium if the intrauterine fluid pressure is greater than the surgical patient's mean arterial pressure. Thus, the capability of monitoring and displaying fluid deficit by fluid type enhances the safety for the patient.

Figure 78:
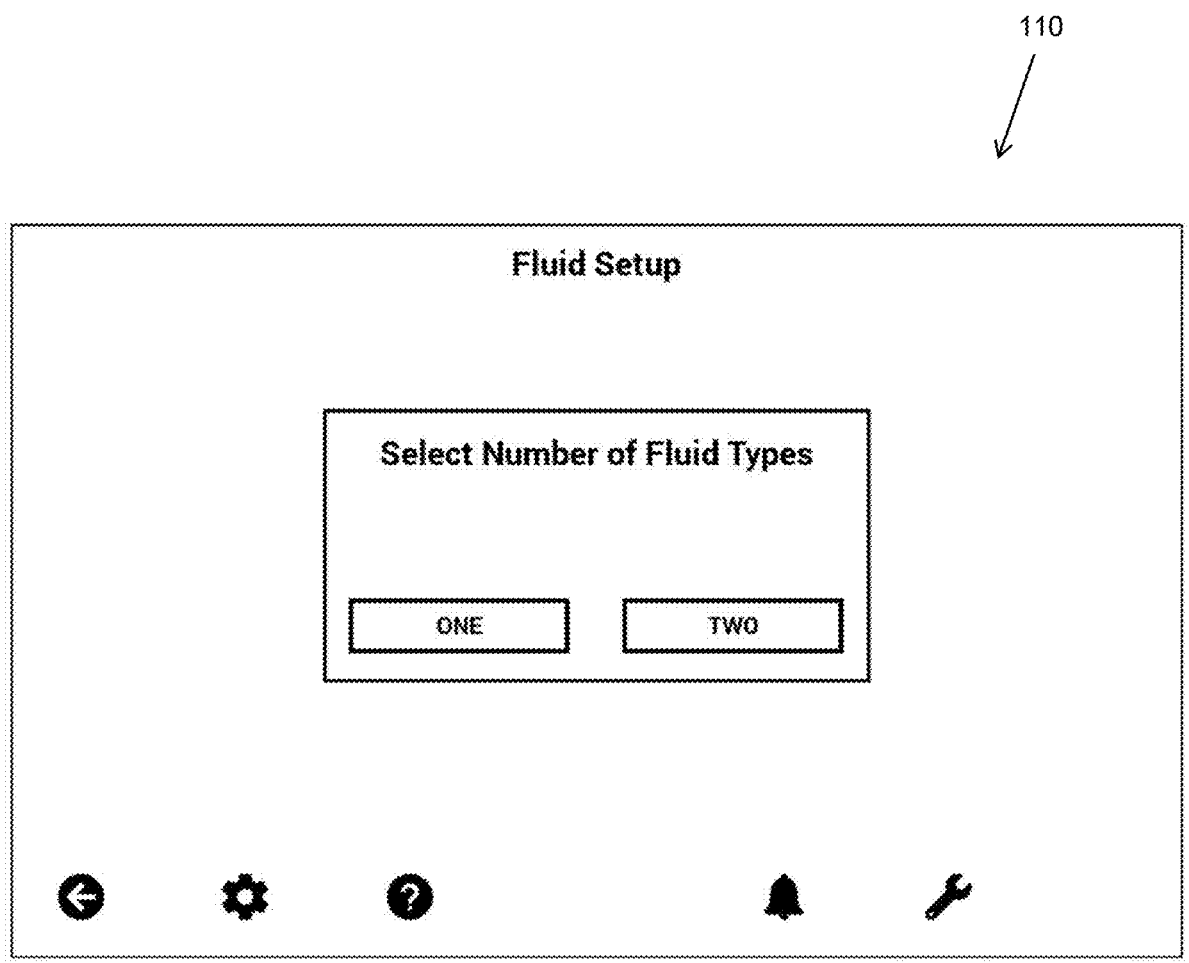
FIG. 78 illustrates an exemplary prompt by the fluid management system of FIG. 1 to a user via a user interface regarding the number of fluid types that will be used during a procedure.
Figure 79:
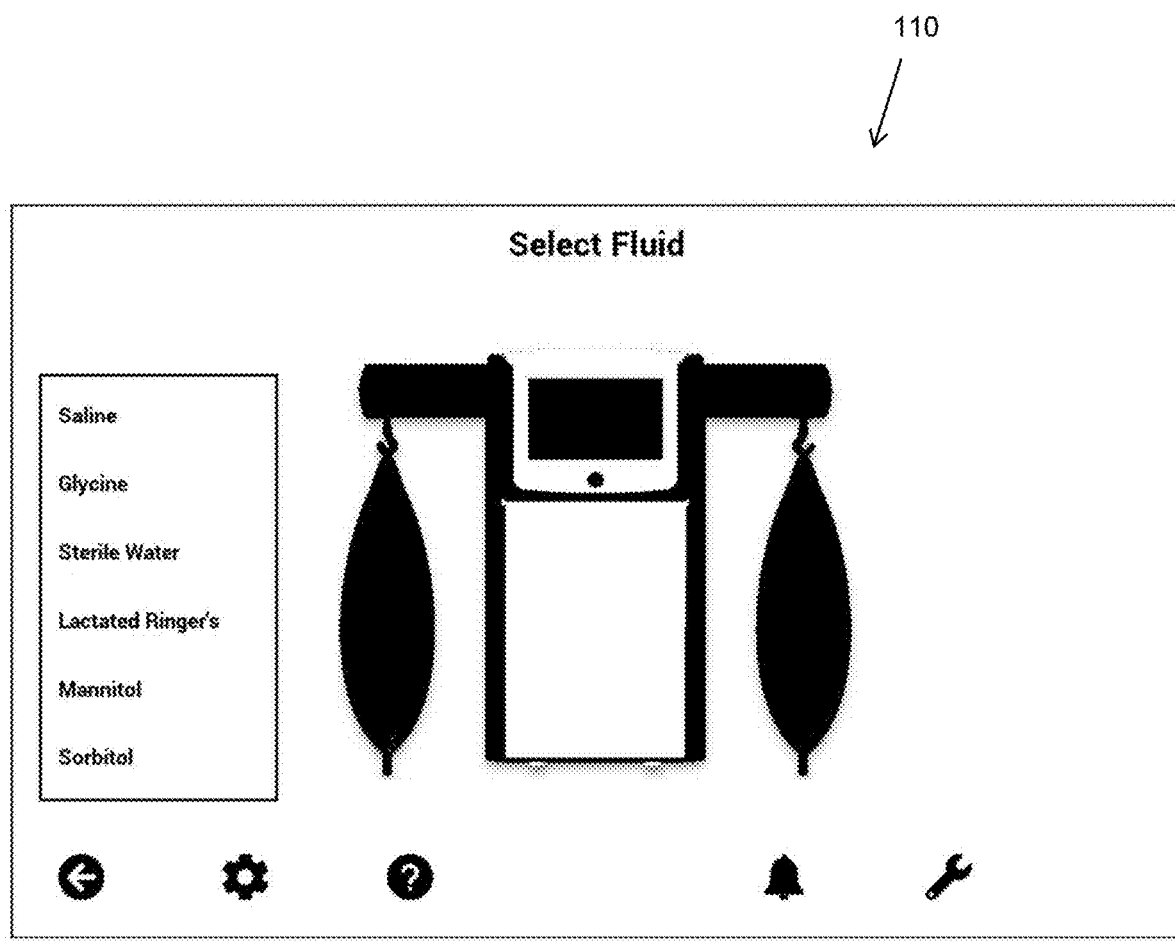
FIG. 79 illustrates another exemplary prompt by the fluid management system of FIG. 1 to a user via a user interface regarding the number of fluid types that will be used during a procedure.
Figure 80:
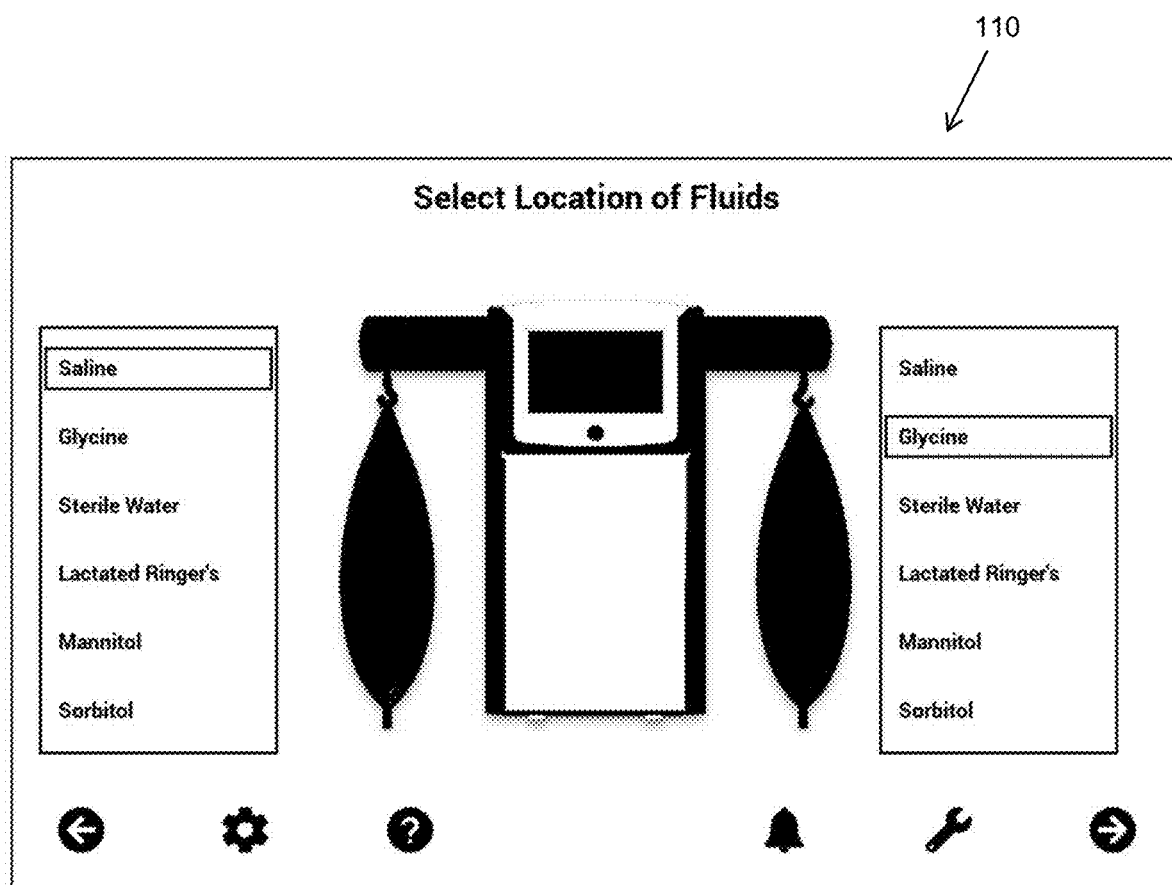
FIG. 80 illustrates another exemplary prompt by the fluid management system of FIG. 1 to a user via a user interface regarding the number of fluid types that will be used during a procedure.

Referring to FIGS. 78-80, after the user indicates the number of fluid types that will be used during the procedure, the system 100 may prompt the user (via the user interface 110) to select the specific fluids will be used during the procedure. The system 100 may then set the maximum allowable deficit limit for each specific fluid type (based on information stored in a memory of the control system or based on information inputted by a user). For example, the maximum allowable deficit limit for hypotonic, electrolyte-free fluids may be 1000 ml, and the maximum allowable deficit limit for isotonic, electrolyte containing fluids may be 2500 ml. The system 100 may also set a maximum total deficit limit for the procedure based on a sum of the fluid deficits for the selected fluid types. For example, the maximum total deficit limit for the procedure may be 2,500 ml.

In various embodiments, the system 100 will provide a user with instructions (via the user interface 110) for hanging the fluid supply containers. For example, with regards to a first fluid type selected by the user, the system 100 may instruct the user as to which hanging members 116 (FIGS. 1 and 2) to use, instruct the user to hang the fluid supply container(s) and then monitor the hanging member(s) 116 (FIGS. 1 and 2) to confirm that the fluid supply container(s) were disposed on the correct hanging members, or prompt the user to indicate which hanging member(s) 116 (FIGS. 1 and 2) will be used to hold the fluid supply container(s) and then monitor the weight of the hanging member(s) 116 (e.g., via load cells connected to the hanging members) to determine when the fluid container(s) are disposed on the corresponding hanging members 116. The system 100 can then repeat the above process for the fluid container(s) holding the second fluid type.

During the procedure, the system 100 may be configured to monitor and display the fluid deficit level for the first fluid type (via the user interface 110) by subtracting an amount of fluid returned from the surgical site (e.g., as determined using the deficit cartridge 2010 and deficit module 104 or by monitoring a weight of fluid collection containers hanging from member(s) 116 (FIGS. 1 and 2), etc.) from the volume of fluid pumped to the surgical site (e.g., as determined by monitoring the weight of the fluid supply containers, monitoring the amount of pump rotations of the pump 212, etc.).

In certain embodiments, the user can switch to the second fluid type via the user interface 110 (e.g., by pressing a "Change Fluid Type" button or other similar button). The system 100 may then instruct the user to close the tubing line(s) connecting the fluid supply containers for the first fluid type to the pump 212 (e.g., by closing clamp(s) on the tubing line(s)). The system 100 may also instruct the user to collect all residual fluid of the first fluid type from the surgical site, underbody drape, and the floor. Subsequently, the system 100 may instruct the user to fluidly connect the tubing lines of the fluid supply containers for the second fluid type (e.g., by opening clamp(s) on the tubing line(s)). In alternative embodiments, the system 100 may be configured to detect (via one or more processors of the control system) when a user switches to the second fluid type. In certain embodiments, the tubing lines may be automatically fluidly connected or disconnected by pinch valves.

After fluidly connecting the tubing lines for the second fluid type, the user may initiate a purge of the first fluid type from the system 100. In certain embodiments, the user will stop the pump, remove the scope and/or surgical instrument from the body cavity constituting the surgical site, and allow the cavity to drain the first fluid type into the underbody drape. When complete, the user will fluidly disconnect the first fluid type from the pump by closing the associated clamp(s), fluidly connect the second fluid type to the pump by opening the associated clamp(s), direct the scope and/or surgical instrument into the underbody drape and press a "Purge" or similar button on the user interface 110 of system 100 which will cause the system 100 to pump the volume of the second fluid type necessary to force the first fluid type from the cartridge assembly 419, fluid inflow tube, and scope and/or instrument. In certain embodiments, system 100 may pump the second fluid type necessary to cause the purge until the user presses a "Stop Purge" or similar button on the user interface 110 of system 100. After the purge has been completed and the underbody drape has emptied, system 100 will record the fluid deficit for the first fluid type, empty the deficit cartridge 2010 (FIGS. 33-34), and then indicate to the user via user interface 110 of system 100 that the procedure can proceed with the second fluid type. This process may be repeated to change back and forth between the first and second fluid types.

After the first fluid type is purged from the system 100, the system 100 may commence monitoring and display of the fluid deficit level for the second type of fluid. The system 100 may be configured to display the total fluid deficit, the deficit of the first fluid type, and/or the deficit of the second fluid type. In certain embodiments, a user may be able to elect, via a toggle switch or similar button on the user interface 100, whether the system 100 displays the total fluid deficit, the deficit of the first fluid type, the deficit of the second fluid type, and/or any combination thereof.

In some embodiments, if the user does not notify the system 100 of a fluid change (i.e., the change from the first fluid to the second fluid), the system 100 may stop the pump 212 to pause fluid flow. For example, the system 100 may prompt the user to indicate whether a change in fluid type was intended, and, if the user indicates that a change in fluid type was not intended, the system can instruct the user to check for any issues that may be affecting the weight on a hanging member associated with the other fluid type (e.g., such as leakage from the bag or an open or partially open clamp). If the user indicates that a change in fluid type was intended, the system 100 can instruct the user to initiate a purge of the system (as indicated above). The user may switch the fluids multiple times using the procedures described herein.

In certain embodiments, a user that initially indicated only one fluid would be used in the procedure, may during the procedure, indicate to system 100 via user interface 110 that a second fluid will be used by pressing a "Settings" button or icon or similar button or icon on the user interface 110 and then pressing an "Add Second Fluid" button or icon or similar button or icon. The system 100 may then instruct the user via user interface 110 to hang the second fluid type, purge the first fluid type, record the deficit for the first fluid type, and instruct the user to continue the procedure using the second fluid type as indicated above. The system can then track the deficit for the first fluid type, the second fluid type, and total deficit.

In certain embodiments, once the fluid containers have been placed on the hanging members 116, the system 100 may guide the user to complete the tubing installation process. For example, if the fluid suction and collection module 106 is utilized, but the deficit module 104 is not utilized, the instructions can include connecting the fluid lines returning from the surgical site, underbody drape, and the floor (if applicable) to the fluid suction and collection module 106. If the deficit module 104 is utilized, the instructions can include inserting the deficit cartridge 2010 into the deficit module 104, connecting the suction source to the deficit cartridge 2010 (e.g., via vacuum port 2016), and connecting the fluid return tubing lines (from the surgical site) to the deficit cartridge 2010 (e.g., via fluid inlet ports 2012, 2014). If the aspiration module 5201 is utilized, the instructions can include inserting the pressure regulator 5205 into the aspiration module 5201, connecting the suction source to the pressure regulator 5205 (e.g., via port 5315 shown in FIG. 53 or port 5415 shown in FIGS. 54-55), and connecting the fluid return tubing lines (from the surgical site) to the pressure regulator 5205 (e.g., via port 5317 shown in FIG. 53 or port 5417 shown in FIGS. 54-55). If the fluid flow and evacuation module 5101 (FIG. 51) is utilized, the instructions can include inserting the deficit cartridge 2010 (or similar single-use fluid volume monitoring cartridge) into the fluid flow monitoring and evacuation module 5101 and connecting the fluid return tubing lines (from the surgical site) to the deficit cartridge (e.g., via fluid inlet ports 2012, 2014).

Following the tubing installation process, the system 100 may instruct the user to complete a priming process. For example, the system 100 may instruct the user to fluidly disconnect the fluid conditioner 420 (FIG. 10) from the surgical instrument being used at the surgical site (e.g., by closing a clamp on the tubing that connects the fluid conditioner 420 to the surgical instrument). The system 100 may also instruct the user to fluidly connect at least one of the fluid supply containers to the pump 212 (e.g., by opening a clamp on the tubing that connects the fluid supply container to the pump 212). Subsequently, the system 100 may instruct the user to initiate priming of the tubing set (e.g., by pressing a "Prime" button or other similar button), which will cause the system 100 to pump fluid from the at least one fluid container and into the fluid conditioner 420 until the pressure sensors of the system 100 indicate that fluid in the fluid outlet chamber 1054 (FIG. 10) of the fluid conditioner 420 has reached a certain fluid pressure, and/or until a fluid presence sensor (e.g., fluid presence sensor 948 shown in FIG. 9) of the system 100 that targets the fluid outlet chamber 1054 indicates that the fluid has reached a certain level. After the system 100 determines that the pressure or fluid level in the outlet chamber 1054 is sufficient, the system 100 may stop the pump 212. The fluid pressure within the outlet chamber 1054 may then be reduced by reversing the pump 212 or opening a solenoid valve (e.g., solenoid valve 951 shown in FIG. 9) until the desired fluid pressure or fluid level in the outlet chamber 1054 of the fluid conditioner 420 has been achieved. The volume of fluid necessary to prime the tubing set may be known and added as a constant offset for the purposes of monitoring and displaying the volume of fluid pumped and the fluid deficit (if applicable).

Figure 81:
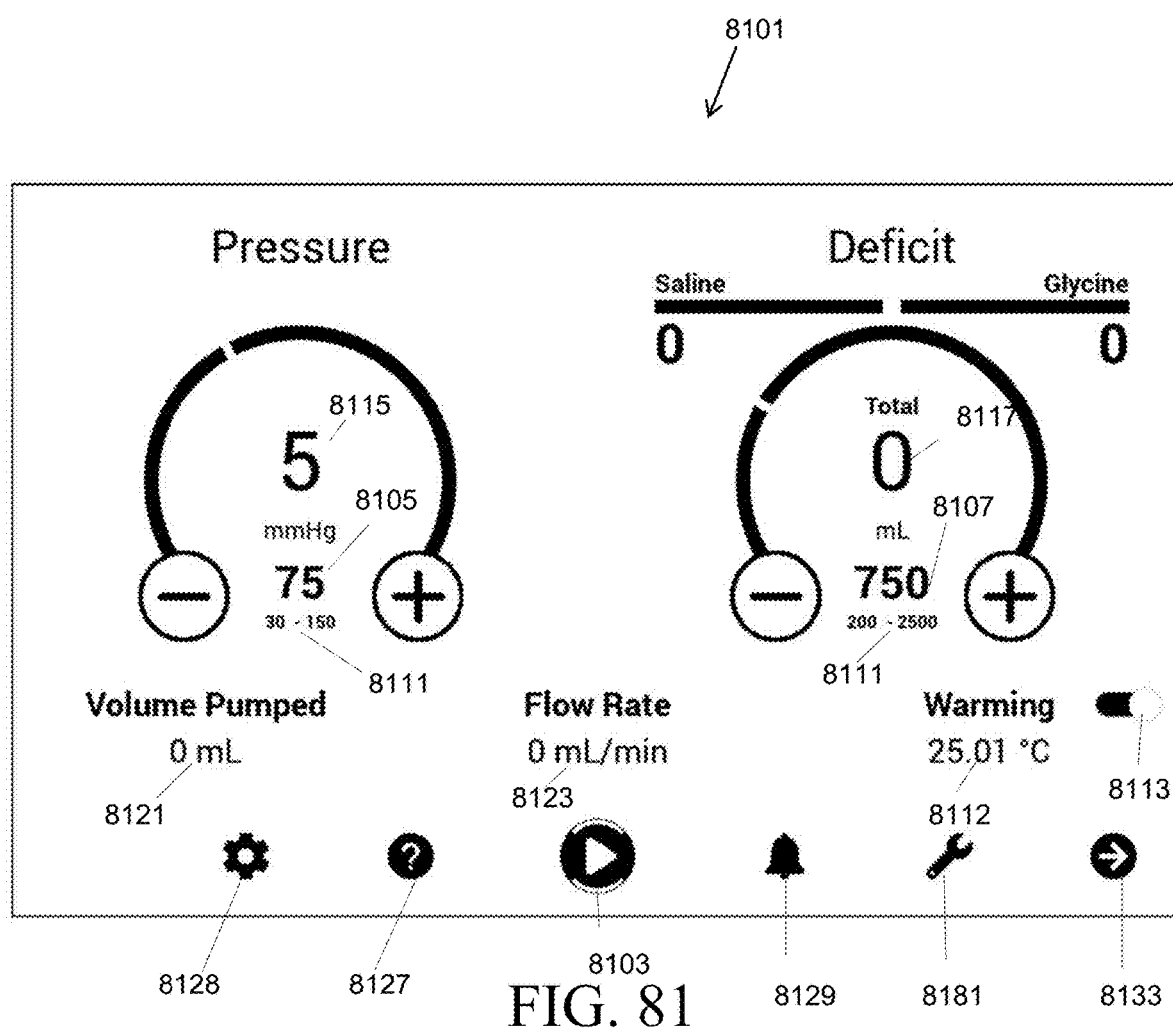
FIG. 81 illustrates an exemplary embodiment of a procedure run screen on a user interface of a fluid management system when the fluid management system is set to a pressure control mode.

Referring to FIG. 81, the system 100 may include a procedure run screen 8101 (via the user interface 110). In the illustrated embodiment, the procedure run screen 8101 is shown for a system that is in pressure control mode. In alternative embodiments, the system 100 may be in flow control mode or flex control mode. Each of these control modes are discussed in more detail below. The user may start a procedure by pressing the "Play", "Run", or similar icon or button 8103 in the navigation bar at the bottom of the screen 8101. The user may also, via adjustment control/buttons on the run screen 8101, change default operating settings, such as, for example, the fluid pressure setpoint condition 8105 (if the system 100 is in a pressure control mode), the fluid flow rate setpoint condition (not shown—if the system 100 is in a flow control mode), and the deficit alarm level 8107 (if the deficit monitoring function is required or has been elected). In certain embodiments, the system 100 may only allow a user to change the default operating settings to be within the safe, permissible adjustment ranges 8111 for the procedure. The procedure run screen 8101 may also allow a user to enable/disable the fluid warming function by using switch 8113 and display the fluid temperature 8112.

In addition to displaying an actual condition 8115 and setpoint condition 8105 for pressure (or for flow if the system 100 is in a flow control mode), and an actual condition 8117 and setpoint condition 8107 for fluid deficit (if applicable), the procedure run screen 8101 may also display other information. For example, the procedure run screen 8101 may display fluid inflow or volume pumped 8121 to the surgical site, the fluid flow rate 8123 (if the system 100 is in pressure control mode), and/or the fluid pressure (not shown—if the system 100 is in flow control mode). The procedure run screen 8101 may also have a navigation bar consisting of icons or buttons that can be used before or during the procedure, such as, for examples, a "Settings" button 8128, a "Help" or "Troubleshooting" button 8127, a "Notifications" button 8129, a "Maintenance" button 8181, and/or an "End Case" or "End Procedure" button 8133.

Figure 82:
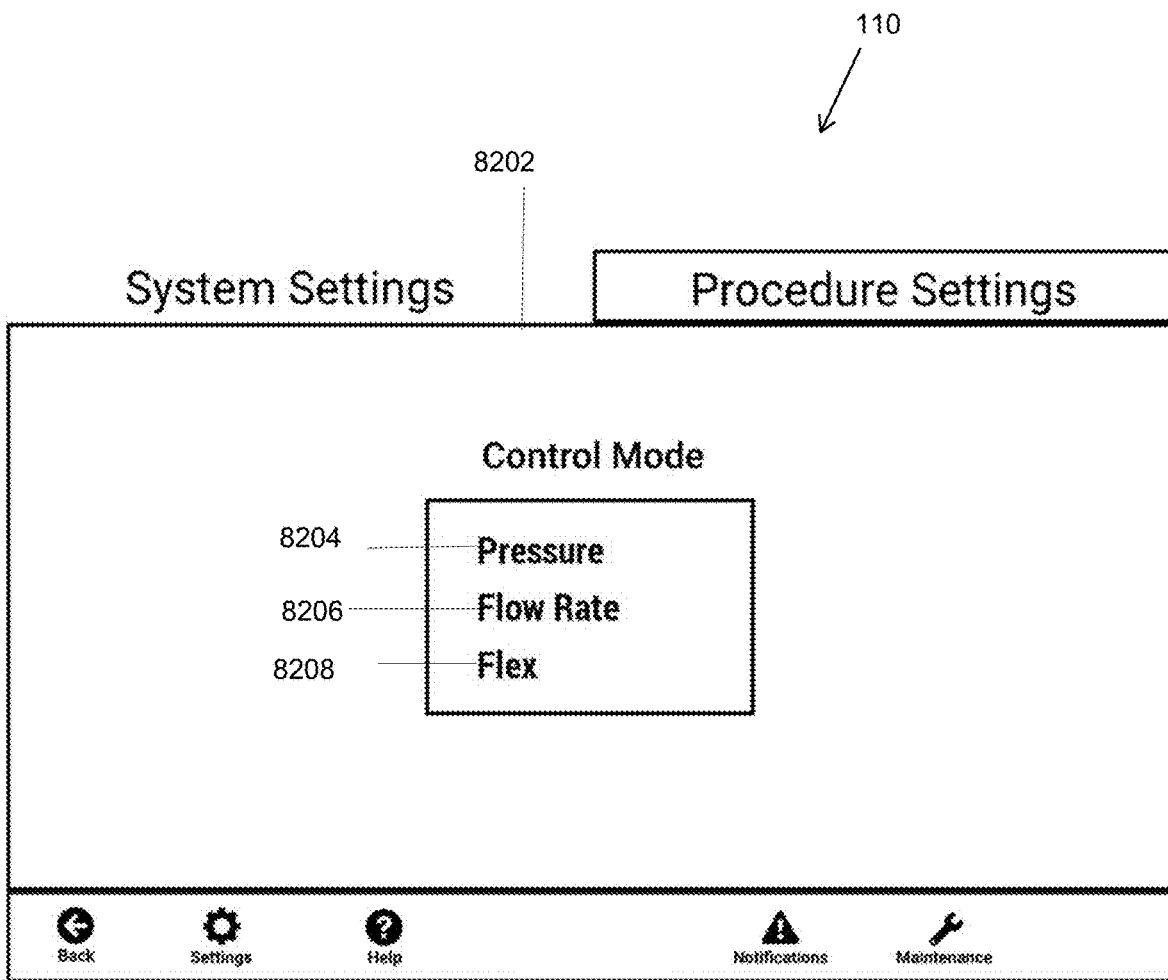
FIG. 82 illustrates an exemplary embodiment of a procedure settings screen on a user interface of a fluid management system.

In certain embodiments, pressing the "Settings" button 8128 brings up a settings screen (not shown) on the user interface 110 that allows the user to adjust, set, or enable other features of the system 100. For example, referring to FIG. 82, the system 100 may include a procedure settings screen 8202 that allows a user to set or adjust the control mode that the system 100 will follow for the procedure. In this embodiment, the system 100 may be set in a pressure control mode 8204, a flow control mode 8206, or a flex control mode 8208. In certain embodiments, the system 100 may default to one of the control modes (e.g., the pressure control mode 8204), but the user can change the type of control mode in the procedure settings screen 8202. If the system 100 is in flow control mode 8206, the system varies the speed of the pump 212 to achieve and maintain a user-selected fluid flow rate setpoint (e.g., as set by the user on the procedure run screen 8101) provided, however, that the maximum allowable fluid pressure for the procedure cannot be exceeded. In other words, the fluid pressure is varied to achieve the desired fluid flow rate.

Figure 81A:
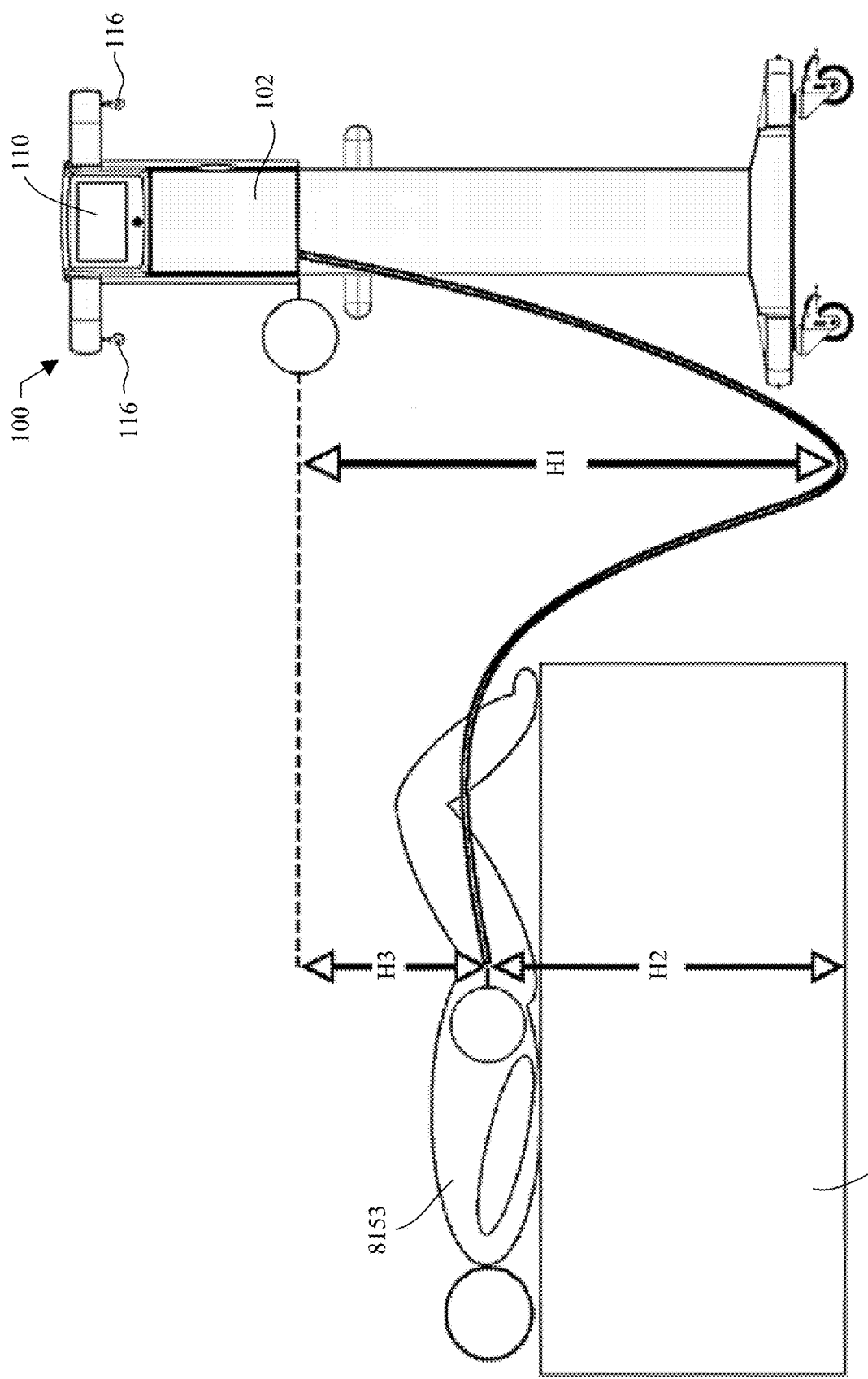
FIG. 81A illustrates a means of calculating a compensation height for calculating a pressure at a surgical scope or instrument.

If the system 100 is in pressure control mode 8204, the system 100 varies the speed of the pump 212 to achieve and maintain a user-selected fluid pressure setpoint (e.g., as set by the user on the procedure run screen 8101 shown in FIG. 81) provided, however, that the maximum allowable fluid flow rate for the procedure cannot be exceeded. In other words, the fluid flow rate is varied to achieve the desired fluid pressure. In some embodiments, the system 100 can control to the user-selected fluid pressure setpoint as the desired fluid pressure at the system. In some embodiments, the system 100 can control to the user-selected fluid pressure setpoint as the desired fluid pressure at the surgical scope or instrument. Referring to FIG. 81A, for ergonomic reasons corresponding to operating the graphical user interface 110, hanging fluid supply containers from hanging members 116, and inserting components (e.g., the cartridge assembly 419 and/or deficit cartridge 2010 described in the present application) into the main unit 102, a height H1 of main unit 102 may be higher than the surgical table 8151. In certain embodiments, the system 100 can compensate for the head pressure resulting from the difference H3 between the height H1 of the main unit 102 and the assumed or inputted height H2 of a patient 8153 in calculating the required system pressure. That is, the system 100 can equate the compensation height H3 to a pressure adjustment, and then subtract the pressure adjustment from the user-selected fluid pressure setpoint at the surgical scope or instrument. In some embodiments, the system 100 can control to the user-selected fluid pressure setpoint as the desired fluid pressure in the body cavity constituting the surgical site. In these embodiments, in addition to calculating the pressure adjustment based on the compensation height H3 described with reference to FIG. 81A, the system 100 may also take into account known restrictions of the tubing set and assumed or calibrated restrictions of the surgical scope or instrument to determine the required system pressure. Accordingly, in some embodiments, the user may elect for the system 100 to monitor and display (via the graphical user interface 110) the fluid pressure at the system, fluid pressure at the surgical scope or instrument, or fluid pressure in the body cavity constituting the surgical site.

Figure 83:
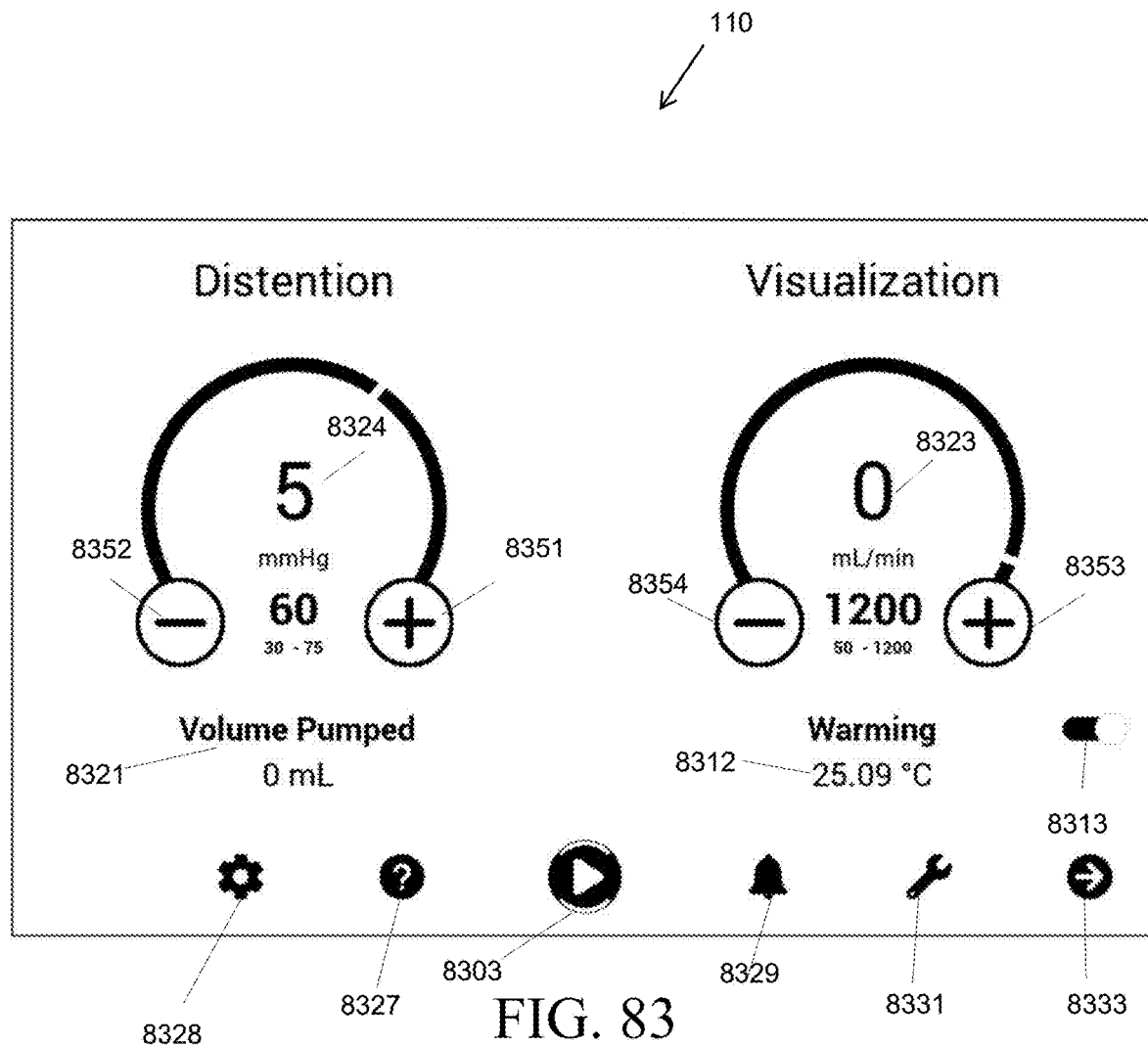
FIG. 83 illustrates an exemplary embodiment of a procedure run screen on a user interface of a fluid management system when the fluid management system is set to a "Surgical Site" control mode.

In endoscopic surgical procedures, good, steady distention and clear visibility are important to procedural efficacy and efficiency. Although fluid pressure and flow rate are the primary factors to achieve satisfactory surgical site distention and visibility, some users may lack a clear understanding of how fluid pressure and/or flow rate (as impacted by surgical site conditions and fluid inflow and outflow restrictions of the surgical instrument and the tubing sets delivering fluid to and from the surgical site) affect distention and visibility. Referring to FIG. 83, in an exemplary embodiment, the system 100 may alternatively be set to a flex control mode that allows a user to achieve desired surgical site conditions simply by making distention and visualization adjustments. That is, in this mode, the user is not concerned with whether the system 100 is operating fluid pressure control mode or the fluid flow rate control mode, nor is the user concerned with the setpoint pressure or flow rate. Instead, the user may provide feedback to the system 100 regarding the surgical site conditions via the user interface 110, and the system 100 determines whether to operate in pressure or flow control mode, as well as determines the proper setpoint for fluid pressure and/or flow rate for the procedure.

Referring to FIG. 83, if the user selects the flex control mode, the system 100 sets a default fluid pressure setpoint for the procedure and presents "Distention" controls or buttons 8351, 8352 and "Visualization" controls or buttons 8353, 8354 on the user interface 110. For example, the user may increase distention by pressing the "+" (increase) button 8351 or may decrease distention by pressing the "−" (decrease) button 8352, and the user may increase visualization by pressing the "+" (increase) button 8353 or may decrease visualization by pressing the "−" (decrease) button 8354. The user interface 110 may also display other information (similar to the procedure run screen 8101 shown in FIG. 81). For example, the user interface 110 may display fluid inflow or volume pumped 8321 to the surgical site, the fluid flow rate 8323, and/or the fluid pressure 8324. The user interface may also display the fluid temperature 8312 and allow a user to enable/disable the fluid warming function by using switch 8313. The user interface 110 may also have a navigation bar consisting of icons or buttons that can be used before or during the procedure, such as, for examples, a "Settings" button 8328, a "Help" or "Troubleshooting" button 8327, a "Notifications" button 8329, a "Maintenance" button 8331, and/or an "End Case" or "End Procedure" button 8333.

Figure 84:
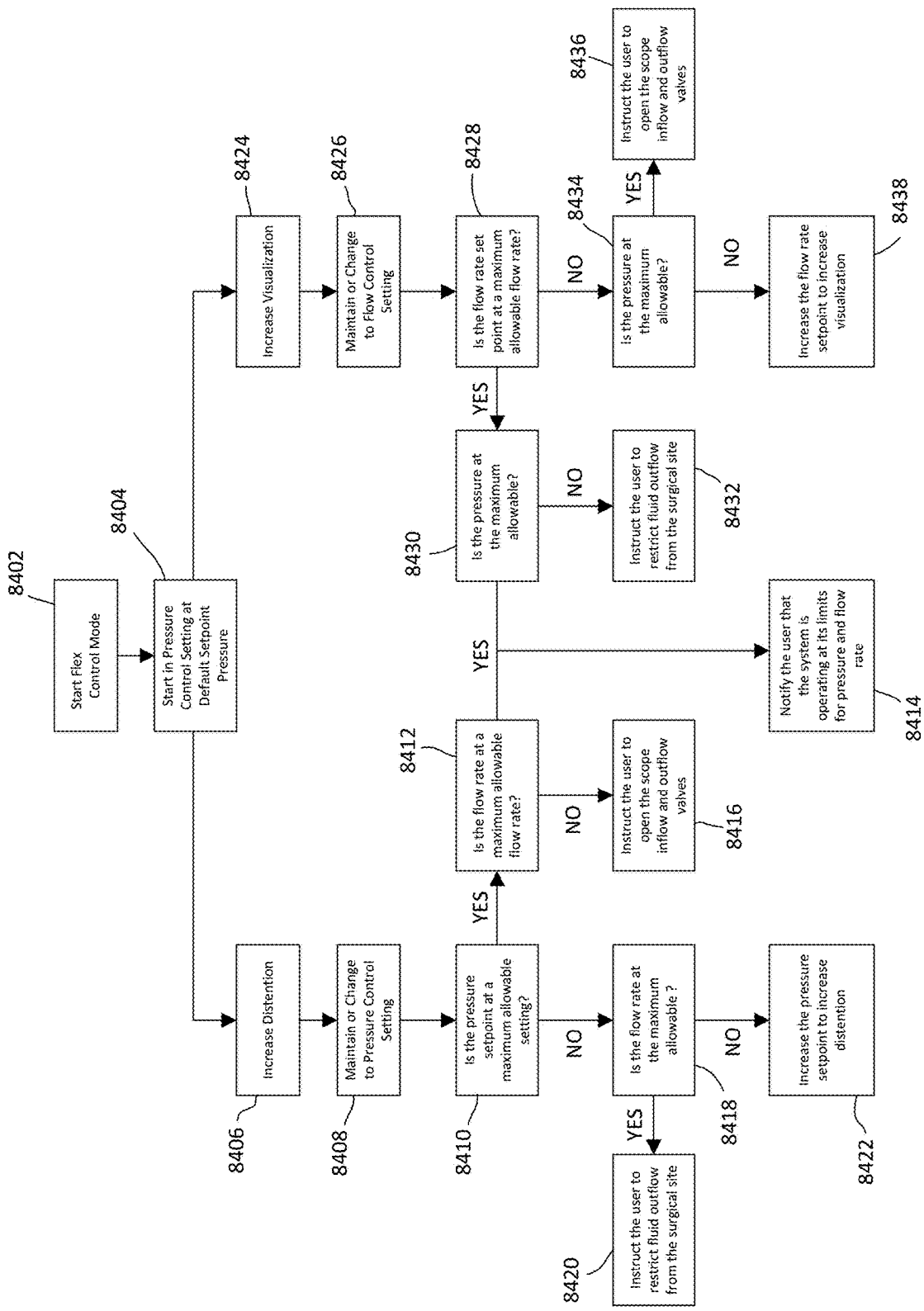
FIG. 84 illustrates a flow chart for a fluid management system that is operating in the surgical site control mode shown in FIG. 83.

Referring to FIG. 84, when the system is set to flex control mode (as shown at 8402), the system 100 may default to pressure control mode (as shown at 8404). In the illustrated embodiment, the adjustment of distention puts the system in fluid pressure control mode and adjusts the pressure setpoint for the procedure, and the adjustment of visualization puts the system in fluid flow rate control mode and adjusts the flow rate set point for the procedure.

If a user adjusts the distention (as shown at 8406), the system 100 maintains or transitions to the pressure control mode setting (as shown at 8408) such that the system 100 can adjust the setpoint pressure of the procedure to meet the desired distention by the user. In various embodiments, distention adjustment to the fluid pressure setpoint can never exceed the maximum allowable setpoint pressure for the procedure. If the user indicates that additional distention is desirable, but the pressure setpoint is at the maximum allowable level (as shown at 8410), the system 100 determines whether the flow rate for the system 100 is at the maximum allowable flow rate (as shown at 8412). If the flow rate is at the maximum allowable flow rate, the system 100 can notify the user (via the user interface 110) that the system 100 is operating at its pressure and flow rate limits for the procedure (as shown at 8414). If the flow rate is not at the maximum allowable flow rate, the system 100 can instruct the user to open the scope inflow and outflow valves to increase the fluid flow rate (as shown at 8416) and thereby increase the fluid moving through the surgical site. Going back to the step shown at 8410, if the setpoint pressure of the fluid is not at the maximum allowable pressure, the system 100 determines whether the flow rate for the system 100 is at the maximum allowable flow rate (as shown at 8418). If the flow rate is at the maximum allowable flow rate, the system 100 can instruct the user to restrict fluid outflow from the surgical site (as shown at 8420) by partially closing the scope outflow valve, partially closing a clamp on the outflow tubing, and/or using a fixed or variable restrictor component in the outflow tubing of the surgical instrument. If the flow rate is not at the maximum allowable flow rate, the system 100 can increase the pressure setpoint (as shown at 8422) to increase the distention.

If a user adjusts the visualization (as shown at 8424), the system 100 maintains or transitions to the flow control mode setting (as shown at 8426) such that the system 100 can adjust the setpoint flow rate of the procedure to meet the desired visualization by the user. In various embodiments, visualization adjustment to the fluid flow rate setpoint can never exceed the maximum allowable setpoint flow rate for the procedure. If the flow rate setpoint is at the maximum allowable level (as shown at 8428), the system 100 determines whether the fluid pressure for the system 100 is at the maximum allowable pressure (as shown at 8430). If the pressure is at the maximum allowable pressure, the system 100 can notify the user (via the user interface 110) that the system 100 is operating at its pressure and flow rate limits for the procedure (as shown at 8414). If the pressure is not at the maximum allowable flow rate, the system 100 can instruct the user to restrict fluid outflow from the surgical site (as shown at 8432), which allows the system 100 to increase the pressure of the fluid in the surgical site. The user can restrict outflow from the surgical site by, for example, partially closing an outflow valve of the surgical instrument, partially closing a clamp on the outflow tubing, and/or using a fixed or variable restrictor component in the outflow tubing of the surgical instrument. Going back to the step shown at 8428, if the setpoint flow rate of the fluid is not at the maximum allowable flow rate, the system 100 determines whether the fluid pressure for the system 100 is at the maximum allowable flow rate (as shown at 8434). If the pressure is at the maximum allowable pressure, the system 100 can instruct the user to open scope inflow and outflow valves (as shown at 8436) to increase the fluid flow rate through the surgical site. If the pressure is not at the maximum allowable pressure, the system 100 can increase the flow rate setpoint (as shown at 8438) to increase the visualization.

In other words, by utilizing the distention controls 8351, 8352, the user puts the system 100 in pressure control mode and adjusts the setpoint fluid pressure for the procedure up to the maximum allowable level for the procedure, while maintaining a maximum allowable flow rate which cannot be exceeded. By utilizing the visualization controls 8353, 8354, the user puts the system 100 in flow control mode and adjusts the setpoint fluid flow rate for the procedure up to the maximum allowable level for the procedure while maintaining a maximum allowable fluid pressure which cannot be exceeded. Accordingly, the system 100 provides the user more intuitive control over the surgical site conditions while at all times remaining within the safe pressure and flow rates for the procedure and displaying the actual fluid pressure and flow rate.

Figure 85:
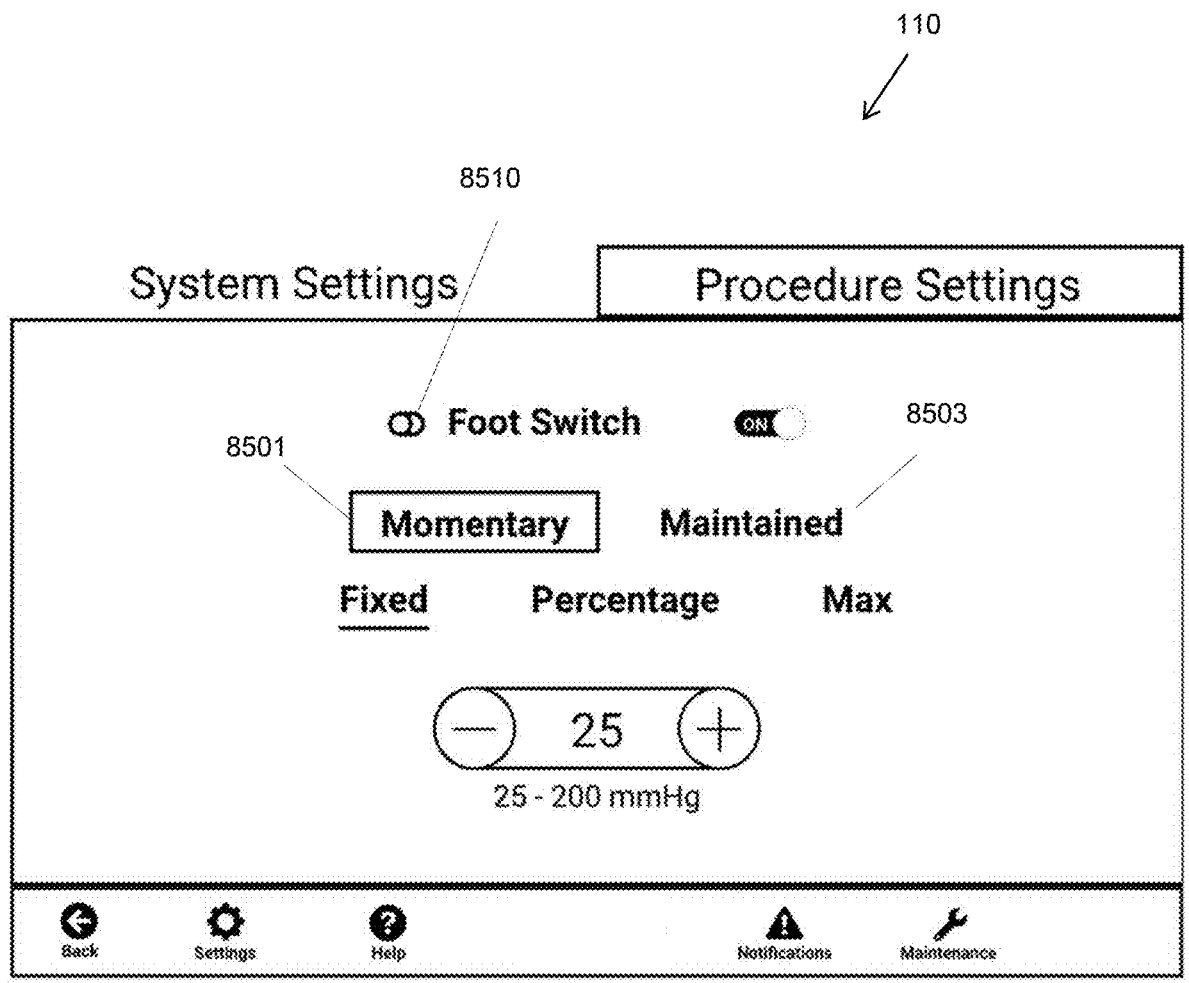
FIG. 85 illustrates an exemplary embodiment of a procedure settings screen on a user interface of a fluid management system that includes operating a bolus device.
Figure 86:
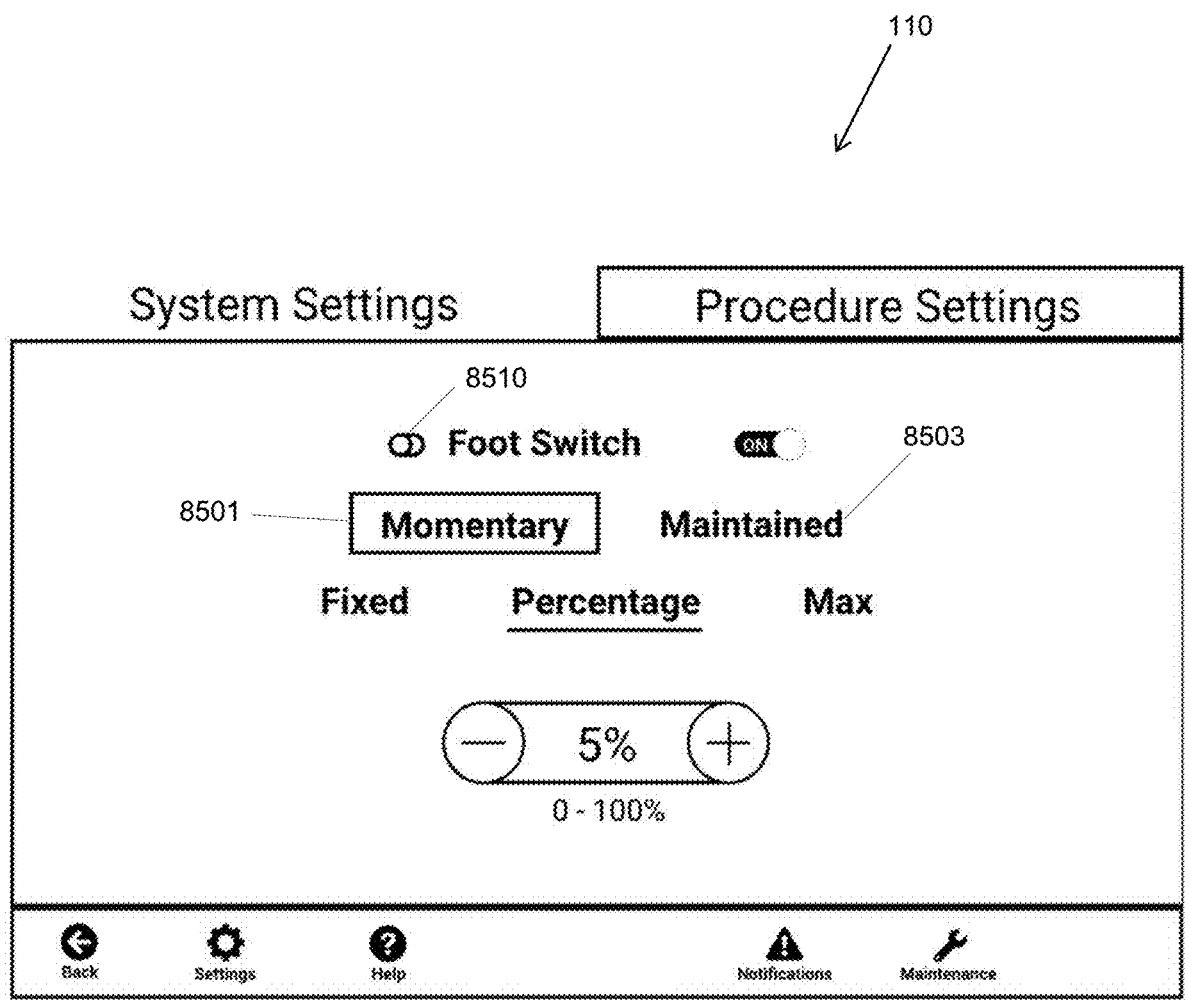
FIG. 86 illustrates the procedure settings screen of FIG. 85.
Figure 87:
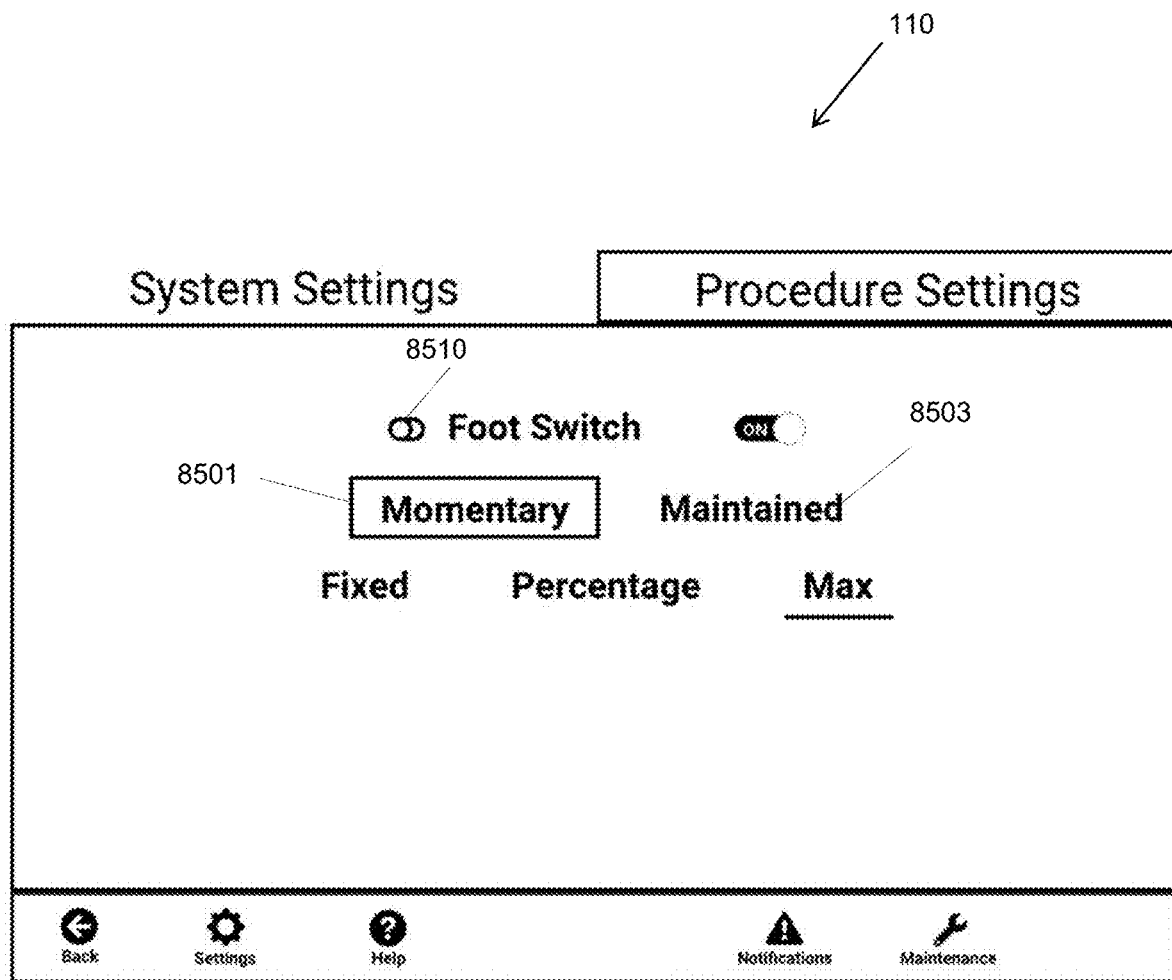
FIG. 87 illustrates the procedure settings screen of FIG. 85.

Referring to FIGS. 85 through 87, the system 100 may include a bolus feature or device that is used to temporarily increase the fluid pressure and/or flow rate to maintain or increase distention and/or to maintain or increase fluid flow for procedural and/or visualization purposes. The bolus feature or device may include a "Bolus" icon or button on one of the screens comprising the graphical user interface; pneumatic, electric, or wireless foot pedal; and/or other actuating device that allows a surgeon to temporarily increase the fluid pressure and/or flow rate for procedural and visualization purposes. The bolus device may be operatively connected to the pump 212 (FIG. 2) of the system 100 such that a surgeon can activate the bolus device to temporarily increase the pressure or flow rate by operation of the pump 212, and such that the pump returns to the normal setting for providing fluid at the setpoint pressure and flow rate after the surgeon deactivates the bolus device. Because the surgeon operates the bolus device, the bolus device can be provided when needed without requiring manual operation of a bolus device or the interaction of a circulating nurse with the system. The bolus feature also prevents the setpoint pressure and/or flow rate of the fluid management system to be changed for only a temporary increase in the pressure and/or flow rate.

The bolus device may interface with the system pneumatically, electrically, or wirelessly (e.g., via Bluetooth). The bolus device can be configured by the user via the user interface 110. For example, the user (via the user interface 110) may use a toggle switch 8510 to change the bolus device between an "On" and "Off" state. In certain embodiments, the user may elect to have the bolus device operate in a momentary mode 8501 where the increase is sustained for as long as the foot pedal is pressed. The user may alternatively elect to have the bolus device operate in a maintained mode 8503 where the foot pedal is pressed to activate the bolus device and pressed again to deactivate the bolus device. In another embodiment, the user may elect to have the bolus device operated in a timed mode (not shown) where the foot pedal is pressed to activate the bolus device, and the system 100 maintains the bolus device in the activate state for a desired amount of time. Whether the increase caused by the bolus device is to the fluid pressure or flow rate setpoint may depend, for example, on whether the system 100 is in pressure mode or flow control mode at the time of bolus activation. The user may elect to have the increase equal a set increment (e.g., a 25 mmHg pressure increase or a 50 ml/min flow rate increase), a percentage increase over setpoint (e.g., 20%), or the maximum allowable fluid pressure or fluid flow rate for the procedure. The increase in fluid pressure and fluid flow rate may be limited to the maximum allowable setpoint for the procedure.

The bolus device of the present application is beneficial because the fluid pressure or flow rate increase is known and safe. That is, the user sets the increase, the actual fluid pressure and flow rate are displayed on the user interface 110 of the system 100, and the increase never exceeds the max allowable safe limit for the procedure. In addition, the duration of the increase is appropriate as determined and controlled by the surgeon. Also, because the surgeon controls the bolus device via, for example, a foot pedal, the bolus device does not need to be operated by a circulating nurse, and the bolus device does not involve interacting with the system.

In an alternative embodiment, the system 100 may include a temporary adjustment feature or device that is used to temporarily increase or decrease the fluid pressure and/or flow rate, which allows a user to temporarily increase or decrease distention and/or visualization at the surgical site. This adjustment feature or device may include a "Temporary" icon or button representing a temporary adjustment on one of the screens comprising the graphical user interface in combination with a foot pedal or other type of actuating device. In certain embodiments, the actuating device includes a pneumatic, electric, or wireless foot pedal(s) such as a foot pedal with rocker action or a dual foot pedal arrangement that allows a surgeon to temporarily increase or decrease the fluid pressure and/or flow rate for procedural and visualization purposes. The adjustment device may be operatively connected to the pump 212 (FIG. 2) of the system 100 such that a surgeon can activate the device to temporarily increase or decrease the pressure or flow rate by operation of the pump 212, and such that the pump returns to the normal setting for providing fluid at the setpoint pressure and flow rate after the surgeon deactivates the adjustment device. Because the surgeon operates the adjustment device, the temporary adjustment to pressure and/or flow rate can be provided when needed without requiring manual operation of a device or the interaction of a circulating nurse with the system 100. The adjustment device may interface with the system pneumatically, electrically, or wirelessly (e.g., via Bluetooth) and can be configured by the user via the user interface 110 for mode (momentary or maintained) and adjustment type (fixed, percentage, or max).

Figure 88:
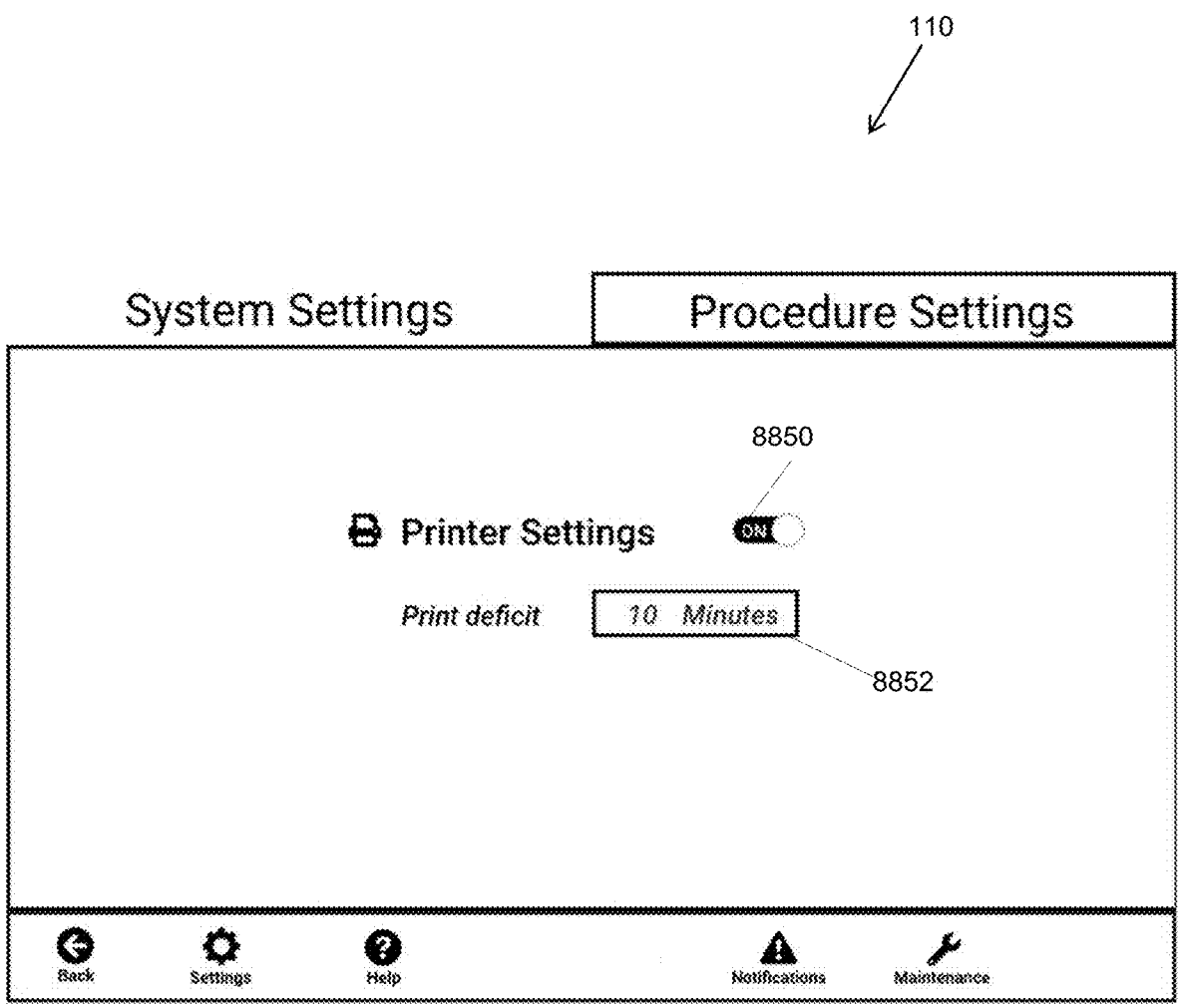
FIG. 88 illustrates an exemplary embodiment of a procedure settings screen on a user interface of a fluid management system that includes operating a printer of the fluid management system.

In certain embodiments, the system 100 may include a printer (e.g., printer 218 shown in FIG. 2) for printing out pertinent information regarding a surgical procedure during or after the procedure. Referring to FIG. 88, in situations in which the system 100 is tracking a fluid deficit for the procedure, the user may elect (via the user interface 110) to have the fluid deficit automatically recorded and printed out at set time intervals during the procedure (e.g., every 10 minutes). As illustrated in FIG. 88, the user interface 110 may include a toggle button to turn on or off the automatic recording and printing of fluid deficit at set time intervals during the procedure. This capability eliminates the need for the user to periodically check and manually record or print out the fluid deficit information. In some embodiments, the user may (via the user interface 110) request to have the fluid deficit recorded at set time intervals during the procedure and printed at the end of the procedure. In some embodiments, the user may (via the user interface 110) request that the deficit information from previous time intervals be displayed. In some embodiments, the system 100 may be configured to print the fluid deficit at volume intervals of the deficit monitoring (e.g., every 50 ml of volume for each fluid deficit individually and/or the total fluid deficit). In some embodiments, rather than printing to a printer of the system 100 itself, the system 100 may be configured to automatically communicate with a printer of the facility in which the system 100 is being used (e.g., via wire, Bluetooth, or WiFi) and print pertinent information at during or after the procedure, or at set time intervals during the procedure.

The system 100 can be configured to offer the user the ability to printout pertinent procedure information at the end of the procedure, including, but not limited to, the date, procedure type, start time, end time, fluid volume pumped, fluid deficit (if applicable), fluid deficit at set time intervals (if applicable), average fluid pressure, fluid warming enabled/disabled, and/or average fluid temperature. In some embodiments, the user may be able to elect to have different or additional information printed, including, but not limited to, facility information, physician information, patient information, fluid deficit by fluid type (if applicable), fluid deficit by time increment (if applicable), fluid pressure range, fluid flow range, notifications and alerts list, and alarms list. Additionally, the user may elect to transmit pertinent procedure information via the Bluetooth or Wi-Fi capabilities of the system 100 to a data collection and/or record retention system of the facility.

To avoid procedure interruption caused by depleted fluid supply bags, the system 100 may record the initial weight of the fluid supply bag hung on each hanging member 116 (FIG. 1), the current weight of the fluid supply bag on each hanging member 116, and the current fluid flow rate for the procedure. The system 100 may also be able to provide audible and/or visual indicators if the system 100 determines that a fluid bag may become depleted. The system 100 may also provide an audible and visible indication when the estimated time before a fluid bag will become depleted has fallen below a specified level.

Figure 89:
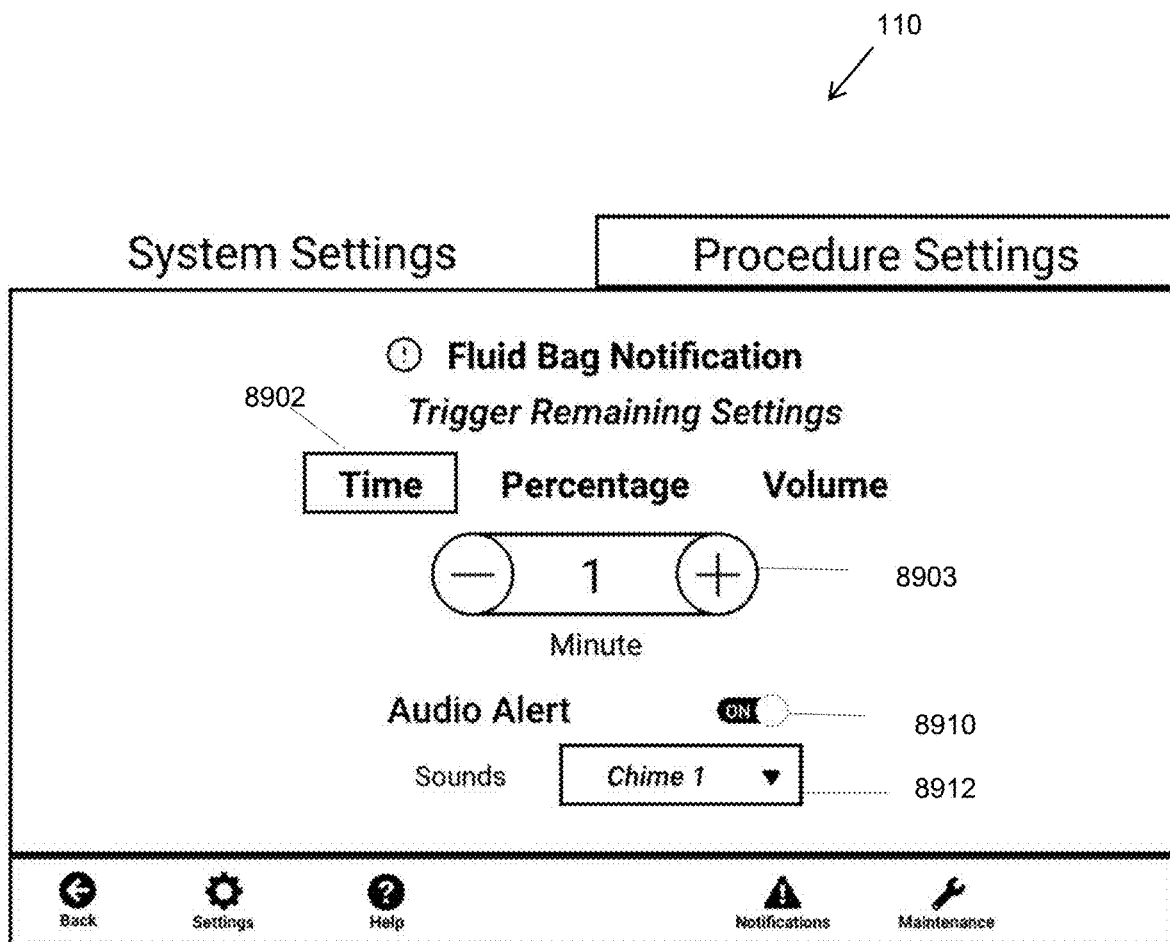
FIG. 89 illustrates an exemplary embodiment of a procedure settings screen on a user interface of a fluid management system that includes alert settings for notifying a user when a fluid supply container is becoming depleted, where the system is in a timed setting.
Figure 90:
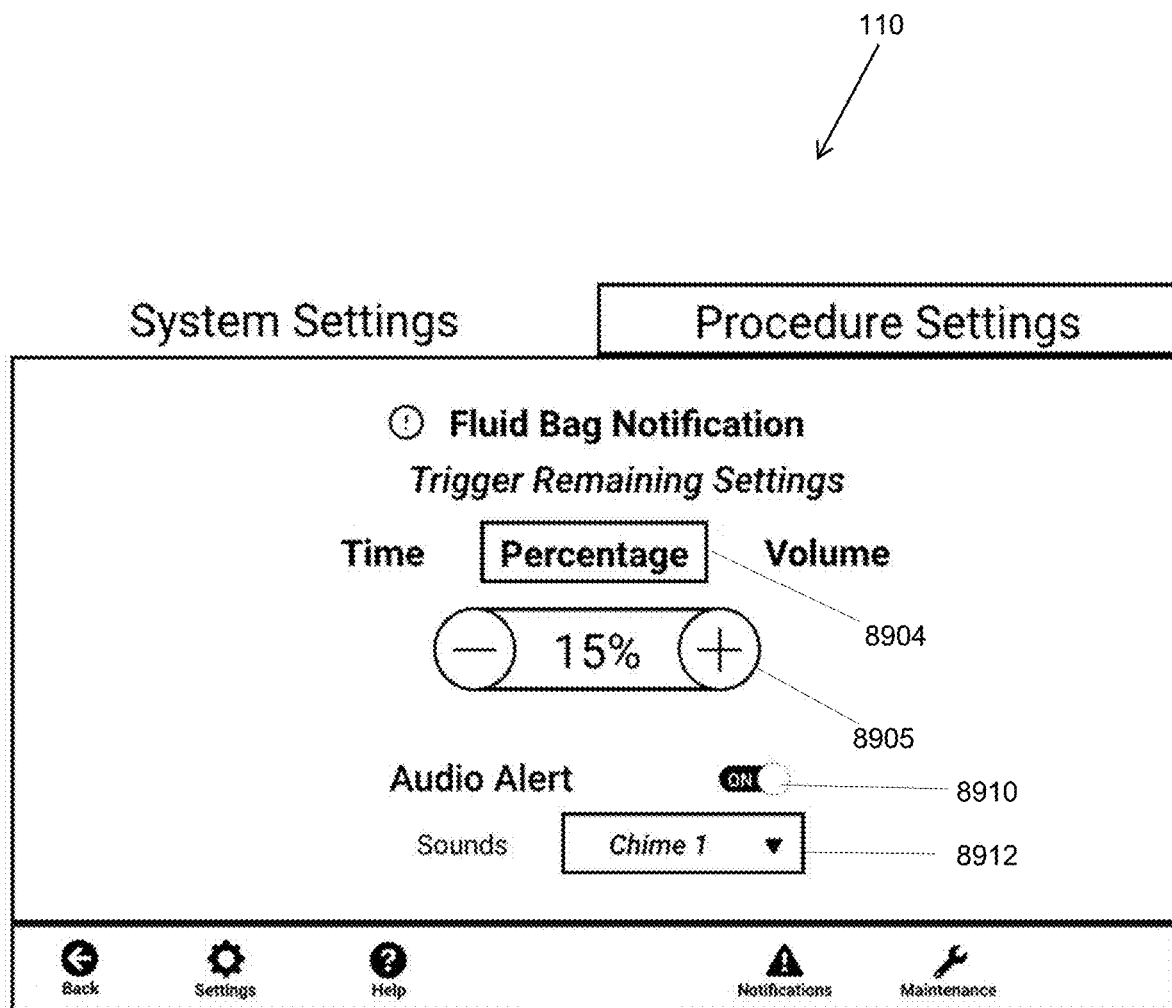
FIG. 90 illustrates the procedure settings screen of FIG. 89, wherein the system is in a percentage setting.
Figure 91:
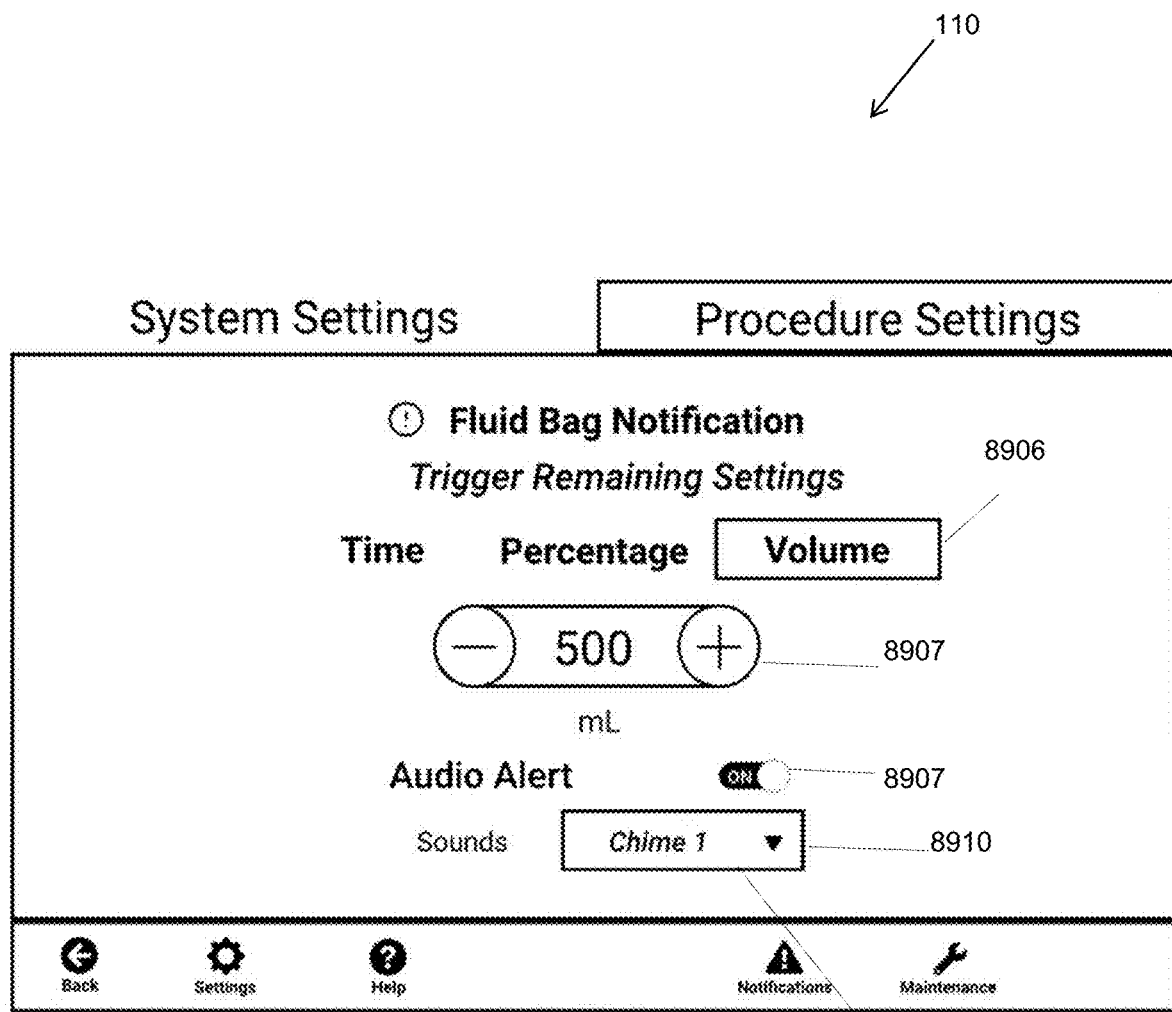
FIG. 91 illustrates the procedure settings screen of FIG. 89, wherein the system is in a volume setting.

Alternatively, referring to FIGS. 89 through 91, the user may elect to receive audible and/or visual indicators (via the user interface 110) if the percentage of fluid remaining (based on the initial volume of the fluid bag) falls below a specified level. Referring to FIG. 89, the system 100 can be set to a "Time" setting 8902 that notifies a user when the amount of time until a bag becomes depleted drops below a predetermined amount of time (as shown at 8903) based on the current or average fluid flow rate. The system 100 may, alternatively, be set to a "Percentage" setting 8904 that notifies a user when a percentage of the fluid supply remaining drops below a predetermine percentage (as shown at 8904). Alternatively, the system 100 may be set to a "Volume" setting 8906 that notifies a user when a volume of fluid remaining in the fluid supply container drops below a predetermined volume (as shown at 8907). Provided the above-mentioned levels are set appropriately, the user (typically a circulating nurse) has time to replace a fluid bag without an interruption to the procedure. To avoid confusion and ensure elevated levels of attention for alarm conditions, the user may mute or reduce the sound level of certain indicators, alerts, and alarms provided by switch or button 8910 and selection window 8912. In some embodiments, however, adjustment of the alerts/indicators is not possible for certain safety critical alarms.

Figure 92:
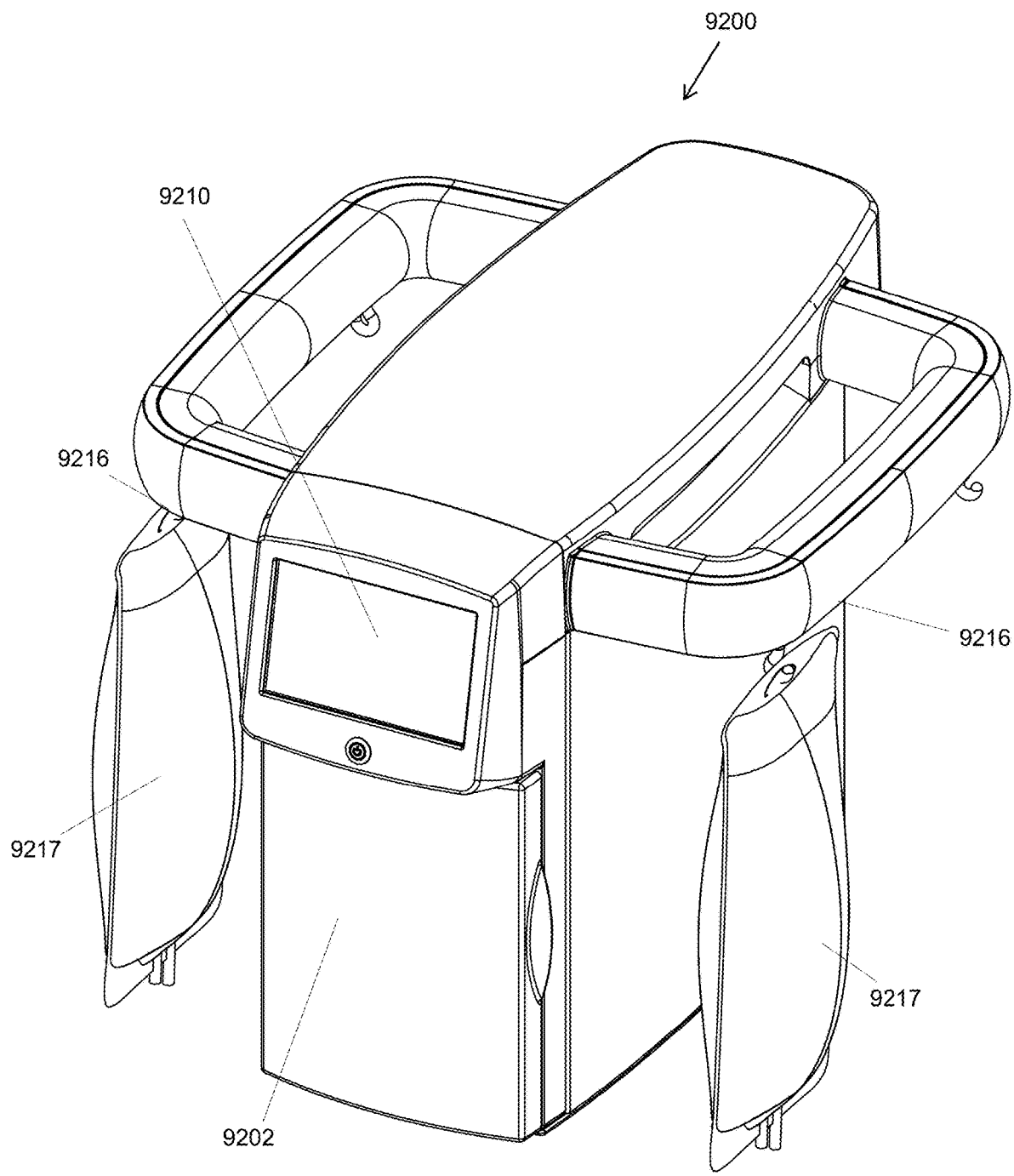
FIG. 92 illustrates an exemplary embodiment of a fluid management system for a physician's office environment, where fluid bags are attached to hanging members of the fluid management system.
Figure 93:
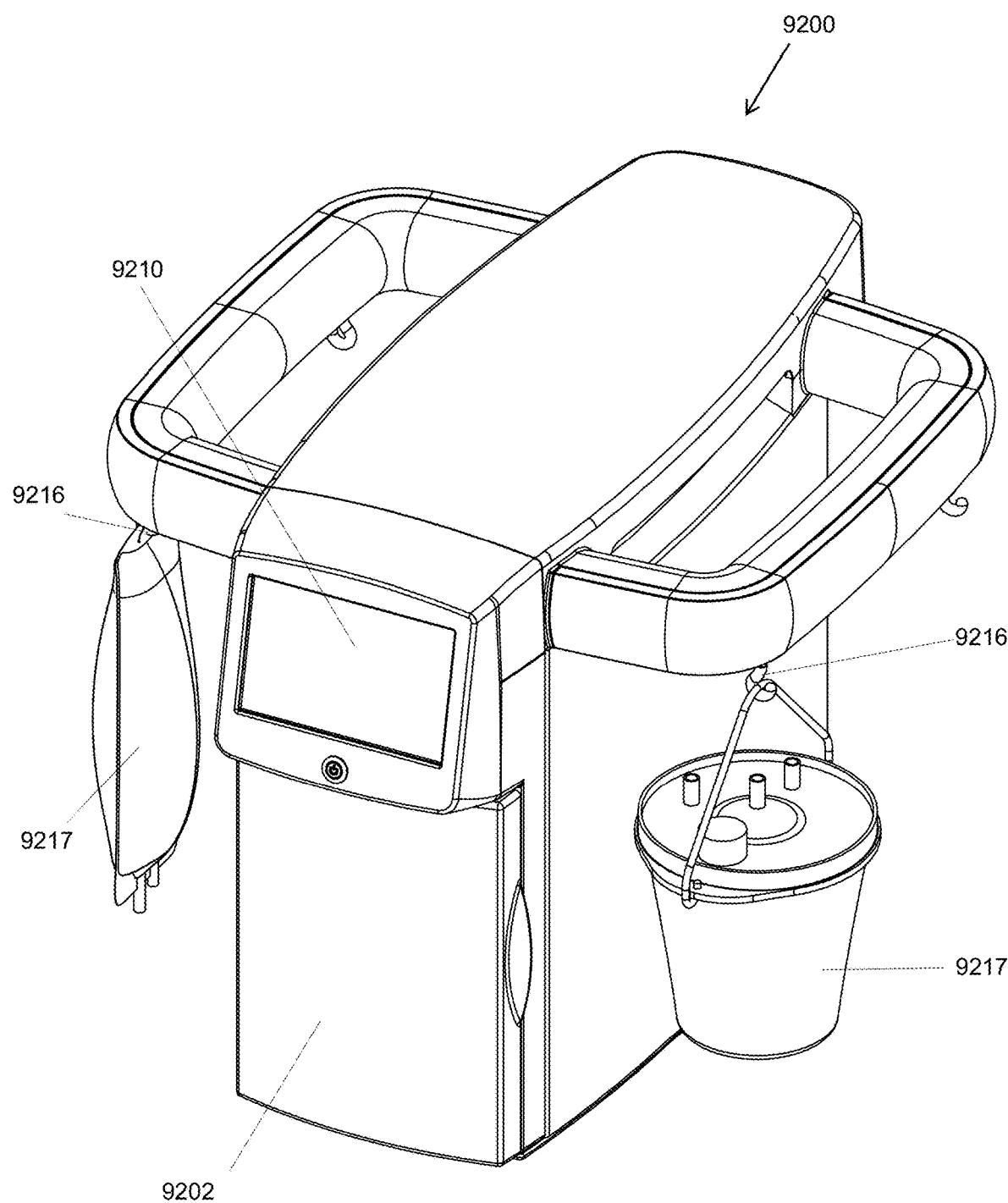
FIG. 93 illustrates the fluid management system of FIG. 92, where a fluid supply bag and a fluid return canister are attached to hanging members of the fluid management system.

Referring to FIGS. 92 and 93, an exemplary embodiment of a fluid management system 9200 for a physician's office environment where gynecological and urological procedures are performed is shown. The system 9200 includes a main unit 9202 that may include any or all of the features described above for the main unit 102 of the fluid management system 100 used in an operating room environment. For example, the main unit 9202 may include a control system that has one or more processors (not shown) for controlling various components of the system 9200 (e.g., a user interface, and various fluid pressure sensors, vacuum pressure sensors, fluid temperature sensors, fluid presence sensors, etc.). The processors may execute instructions (e.g., software code) stored in a memory (not shown) of the system 100 and/or execute instructions inputted into the system by a user. In some embodiments, the control system may have "Bluetooth" capability for connecting to remotely located components or modules of the system 9200 and "Wi-Fi" capability for connecting to the internet. The control system may include a touch-screen graphical user interface 9210 for receiving one or more inputs from a user and displaying information of the system 9202 (e.g., information regarding fluid deficit, fluid temperature, fluid pressure, distention, visualization, etc.).

The main unit 9202 may also include a pump (e.g., pump 212 shown in FIG. 2) for fluid pressurization, a vacuum pump for providing suction, a fluid conditioning assembly (e.g., fluid conditioning assembly 315 shown in FIG. 3) for receiving a fluid conditioner (e.g., fluid conditioner 420 shown in FIG. 10) and sensing one or more characteristics (e.g., fluid presence, fluid temperature, etc.) of fluid moving through the fluid conditioner, hanging members 9216 (e.g., hooks) for hanging fluid supply or collection containers 9217 (e.g., bags, canisters, vessels, etc.). In some embodiments, the main unit 9202 may include a heating assembly (e.g., heating assembly 314 shown in FIG. 3) for receiving a warming cartridge (e.g., warming cartridge 422 shown in FIGS. 14-18) such that system can be configured for fluid warming during the procedure, if applicable. The processor of the control system can be in circuit communication with the pump, sensors, fluid conditioning assembly, heating assembly (if applicable), and hanging members 9216; and the processor can be configured to control these components. In certain embodiments, the hanging members 9216 are operatively connected to load cells such that the control system can monitor a weight of the fluid containers 9217.

Although the system 100 for the operating room environment may include a cartridge assembly 419 (FIG. 4) that includes a fluid conditioner 420 and a fluid warming cartridge 422, the system 9200 for the physician's office may or may not include a fluid warming function. In embodiments that do not include a fluid warming function, the fluid conditioner 420 described with reference to the system 100 may also be used with the system 9200, but the fluid conditioner 420 may include a connector or tube 841 (FIG. 8), a pulse damping component, or a channel integral to the fluid conditioner 420 that connects the inlet chamber 1053 (FIG. 10) to the outlet chamber 1054 (FIG. 10), rather than the warming cartridge 422. If the system 9200 does include a fluid warming component, a warming cartridge (e.g., warming cartridge 422 shown in FIGS. 14-18) can be an accessory that attaches to the fluid conditioner 420 such that the system 9200 can perform fluid warming.

The system 9200 may be configured to perform deficit monitoring by a weight-based method, as compared to the flow-based deficit monitoring method described with the fluid management system 100. Flow-based deficit monitoring (as used with the system 100) is appropriate for the operating room environment due to the generally higher fluid volume usage associated with the longer, more complex surgical procedures performed there. However, the complexity and cost of the flow-based deficit monitoring feature may not be necessary in a physician's office environment, as the surgical procedures performed there are generally shorter and use less fluid. Accordingly, the system 9200 may be configured to include weight-based deficit monitoring. In certain embodiments, the hanging members 9216 are configured for the dual purpose of holding and monitoring the weight of the fluid containers 9217. That is, the processor of the system 9200 can be operatively connected to the load cells of the hanging members 9216, which allows the system 9200 to monitor the weight of the fluid containers 9217. At least one fluid container 9217 is for supplying fluid to the surgical site, and at least one fluid container 9217 is for fluid returning from the surgical site. The system 9200 monitors the weight of the hanging members 9216 to determine the fluid inflow volume to the surgical site (by based on the weight of the fluid supply container) and the fluid outflow volume returned from the surgical site (based on the weight of the fluid return container) to calculate the fluid deficit, which is the difference between the fluid inflow volume and the fluid outflow volume. The system 9200 can be configured to monitor and display the fluid volume and fluid deficit. The system 9200 can also be configured to provide a notification or alarm if the deficit level exceeds the default limit or the adjusted limit set by the user.

Similar to the system 100 described in the present application, the system 9200 may be configured to guide the user through the setup process using instructions, illustrations, animations, and/or system feedback via the user interface 9210. For example, the system 9200 may first prompt the user to select the surgical discipline and procedure that will be performed, which can cause the system 9200 to set the default operating parameters for the procedure as well as the safe, permissible adjustment ranges for those parameters.

If deficit monitoring is required or elected by the user, the system 9200 can prompt the user to indicate the type of fluid that will be utilized and will set the maximum deficit limit for that fluid. The system 9200 can then instruct the user to hang a fluid supply container and indicate when the container has been placed on the hanging member 9216 (with the system confirming placement by monitoring the weight of each hanging member). The system 9200 can also instruct the user to hang the fluid supply container 9217 on a specific hanging member 9216 (with the system 9200 confirming placement by monitoring the weight of the designated hanging member). The system 9200 may then instruct the user to connect the fluid return lines to a fluid return container 9217, connect the fluid return container 9217 to a suction source (e.g., an integrated suction source of the main unit 9200 or an external suction source), and then to hang the fluid return container on another hanging member 9216. When the system 9200 senses that the fluid return container 9217 has been hung, it may set and record the empty fluid container weight to zero such that the system 9200 can properly calculate the fluid deficit for the procedure. Alternatively, the system 9200 can instruct the user place fluid supply container 9217 on the hanging member 9216, and when the system 9200 senses that a fluid supply container is properly placed, the system 9200 can instruct the user to prepare and hang a fluid return container as discussed above. The system 9200 can properly assign hanging members for each of the fluid supply containers and fluid return containers by monitoring the weight changes of the respective hanging members during the process, or by comparing the respective weight on the hanging members after the process has been completed. Although the system 9200 can accommodate standard canisters that can hold up to 5 L of fluid, the packaging of the tubing sets intended for procedures performed in the physician office environment can also be used for the described fluid collection function.

If deficit monitoring is not required or elected, the system 9200 can prompt the user to place the fluid supply containers 9217 on the hanging members 9216, place or route the tubing connecting the fluid containers(s) with the fluid conditioner (e.g., fluid conditioner 420), into or through the pump 212, and insert the fluid conditioner into the main unit 9202.

Following the tubing installation process, the system 9200 can then instruct the user to complete the priming process as described above with reference to the system 100. When priming is complete, the user interface can transition to a procedure run screen (e.g., procedure run screen 8101) where the user may start and control the procedure.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

The invention claimed is:

1. A fluid management system, comprising:
   a pump for delivering fluid from a fluid supply container to a surgical site;
   a pressure regulator positioned between the surgical site and an external vacuum source, wherein the pressure regulator regulates a vacuum pressure provided by the external vacuum source to the surgical site, and wherein the fluid from the surgical site passes through the pressure regulator; and
   a pressure source providing a regulating pressure to the pressure regulator enabling the pressure regulator to regulate the vacuum pressure provided by the external vacuum source to the surgical site, wherein the pressure source is fluidly isolated from the fluid from the surgical site.

2. The fluid management system according to claim 1, further comprising a pressure sensor.

3. The fluid management system according to claim 2, further comprising an aspiration module, wherein the aspiration module includes the pressure sensor and the pressure source.

4. The fluid management system according to claim 2, wherein the pressure regulator comprises:
   a first chamber having an inlet opening for fluidly connecting to the external vacuum source;
   a second chamber having an outlet opening for supplying a regulated pressure to the surgical site;
   a third chamber having one or more openings for connection to the pressure source and the pressure sensor of the fluid management system; and
   a flexible membrane fluidly isolating the third chamber from both of the first and second chambers, wherein the flexible membrane is movable by the pressure source between a first position in which the flexible membrane fluidly isolates the first chamber from the second chamber and a second position in which the first and second chambers are fluidly connected.

5. The fluid management system according to claim 4, wherein the flexible membrane is made of at least one of neoprene, silicone, natural rubber, nitrile, and EPDM.

6. The fluid management system according to claim 4, wherein the flexible membrane is configured to move to the second position and allow the regulated pressure supplied through the outlet opening of the second chamber to be between about 10 mmHg and about 30 mmHg greater than a pressure provided by the pressure source through the pressure opening and into the third chamber.

7. A fluid management system, comprising:
   a pump for delivering fluid from a fluid supply container to a surgical site;
   a pressure source;
   a pressure sensor; and
   a pressure regulator removably connected to the fluid management system and an external vacuum source, wherein the pressure regulator is positioned between the surgical site and the external vacuum source, wherein the pressure regulator comprises:
      a first chamber having an inlet opening for fluidly connecting to the external vacuum source;
      a second chamber having an outlet opening for supplying a regulated pressure to the surgical site;
      a third chamber having one or more openings for connection to the pressure source and the pressure sensor; and
      a flexible membrane fluidly isolating the third chamber from both of the first and second chambers, wherein the flexible membrane is movable by the pressure source between a first position in which the flexible membrane isolates the first chamber from the second chamber and a second position in which the first and second chambers are fluidly connected.

8. The fluid management system according to claim 7, further comprising an aspiration module positioned between the surgical site and the vacuum source, wherein the aspiration module comprises the pressure source and the pressure sensor, and wherein the pressure regulator removably connects to the aspiration module.

9. The fluid management system according to claim 7, further comprising a control system comprising one or more processors and a memory storing instructions that when executed by the one or more processors, cause the control system to adjust a pressure provided by the pressure source based on the regulated pressure desired at the surgical site.

10. The fluid management system according to claim 7, wherein the pressure regulator further comprises a housing that defines the first, second, and third chambers.

11. The fluid management system according to claim 10, wherein the housing comprises a first component that forms the first and second chambers and a second component that forms the third chamber.

12. The fluid management system according to claim 10, wherein the housing is made of polycarbonate.

13. The fluid management system according to claim 7, wherein the flexible membrane is made of at least one of neoprene, silicone, natural rubber, nitrile, and EPDM.

14. The fluid management system according to claim 7, wherein the flexible membrane is configured to move to the second position and allow the regulated pressure supplied through the outlet opening of the second chamber to be between about 10 mmHg and about 30 mmHg greater than a pressure provided by the pressure source through the pressure opening and into the third chamber.

* * * * *